(12) United States Patent
Hoffmann et al.

(10) Patent No.: US 9,187,478 B2
(45) Date of Patent: *Nov. 17, 2015

(54) SUBSTITUTED NAPHTHYRIDINES AND THEIR USE AS MEDICAMENTS

(71) Applicant: Boehringer Ingelheim International GmbH, Ingelheim am Rhein (DE)

(72) Inventors: Matthias Hoffmann, Mittelbiberach (DE); Georg Dahmann, Warthausen-Birkenhard (DE); Dennis Fiegen, Biberach an der Riss (DE); Sandra Handschuh, Biberach an der Riss (DE); Jasna Klicic, Biberach an der Riss (DE); Guenter Linz, Mittelbiberach (DE); Gerhard Schaenzle, Biberach an der Riss (DE); Andreas Schnapp, Biberach an der Riss (DE); Stephen Peter East, Wallingford (GB); Michael Philip Mazanetz, Abingdon (GB); Robert John Scott, Abingdon (GB); Edward Walker, Didcot (GB)

(73) Assignee: Boehringer Ingellheim International GmbH, Ingelheim am Rhein (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/592,301

(22) Filed: Jan. 8, 2015

(65) Prior Publication Data
US 2015/0126503 A1    May 7, 2015

Related U.S. Application Data

(62) Division of application No. 13/013,973, filed on Jan. 26, 2011, now Pat. No. 8,969,568.

(30) Foreign Application Priority Data

Jan. 29, 2010   (EP) .................................. 10152159

(51) Int. Cl.
*C07D 471/02*      (2006.01)
*C07D 471/04*      (2006.01)
(Continued)

(52) U.S. Cl.
CPC ............ *C07D 471/04* (2013.01); *C07D 498/04* (2013.01); *C07D 519/00* (2013.01)

(58) Field of Classification Search
CPC ..................................................... C07D 471/04
USPC ........................................................ 546/122
See application file for complete search history.

(56) References Cited

U.S. PATENT DOCUMENTS 4,329,349 A    5/1982   Damon, II et al.
7,321,041 B2   1/2008   Cywin et al.

(Continued)

FOREIGN PATENT DOCUMENTS

EP    1396488 A1    3/2004
JP    56020588      2/1981
(Continued)

OTHER PUBLICATIONS

Ames, D.E., "Condensation of beta-Dicarbonyl Compounds with Halogenopyridinecarboxylic Acids. A Convenient sythesis of Some Naphthridine Derivatives". Journal of the Chemical Society, Perkin Transactions 1, Chemical Society, Letchworth; GB LNKD-DOI:10. 1029/P19720000705, Jan. 1, 1972, pp. 705-710.

(Continued)

*Primary Examiner* — Nizal Chandrakumar
(74) *Attorney, Agent, or Firm* — Michael P. Morris; Usha R. Patel

(57) ABSTRACT

The invention relates to new substituted naphthyridines of formula 1, as well as pharmacologically acceptable salts, diastereomers, enantiomers, racemates, hydrates or solvates thereof,

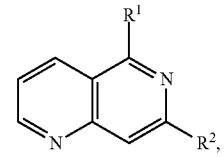

wherein
$R^1$ is selected from among —O—$R^3$ or —N$R^3R^4$,
$R^3$ is $C_{1-6}$-alkyl which is substituted by $R^5$ and $R^6$,
$R^5$ is selected from hydrogen, branched or linear $C_{1-6}$-alkyl, $C_{2-6}$-alkenyl, —$C_{1-6}$-alkylen-O—$C_{1-3}$-alkyl, $C_{1-3}$-haloalkyl,
$R^6$ is ring X

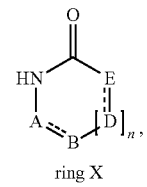

ring X wherein n is either 0 or 1,
and
=−= is a either a single or a double bond and
wherein A, B, D and E are each independently from one another selected from $CH_2$, CH, C, N, NH, O or S and wherein ring X is attached to the molecule either via position A, B, D or E, wherein said ring X may optionally be further substituted by one, two or three residues each selected individually from the group consisting of -oxo, hydroxy, —$C_{1-3}$-alkyl, —$C_{1-3}$-haloalkyl, —O—$C_{1-3}$-alkyl, —$C_{1-3}$-alkanol and halogen,
and wherein $R^4$, $R^2$, $R^7$, $R^8$, $R^9$, $R^{10}$, $R^{11}$ and Q may have the meanings as given in claim 1, as well as pharmaceutical compositions containing these compounds.

2 Claims, No Drawings

(51) Int. Cl.
   *C07D 519/00*   (2006.01)
   *C07D 498/04*   (2006.01)

(56) References Cited

U.S. PATENT DOCUMENTS

| | | | |
|---|---|---|---|
| 8,546,402 | B2 | 10/2013 | Sokoloff et al. |
| 8,604,049 | B2 | 12/2013 | Fiegen et al. |
| 8,912,173 | B2 | 12/2014 | Hoffmann et al. |
| 8,969,568 | B2 * | 3/2015 | Hoffmann et al. ............ 546/122 |
| 2003/0158195 | A1 | 8/2003 | Cywin et al. |
| 2003/0229090 | A1 | 12/2003 | Cywin et al. |
| 2005/0009784 | A1 | 1/2005 | Vu et al. |
| 2008/0176846 | A1 | 7/2008 | Chianelli et al. |
| 2008/0188467 | A1 | 8/2008 | Wong et al. |
| 2011/0201608 | A1 | 8/2011 | Hoffmann et al. |
| 2011/0263549 | A1 | 10/2011 | Fiegen et al. |
| 2012/0028939 | A1 | 2/2012 | Hoffmann et al. |
| 2014/0142135 | A1 | 5/2014 | Fiegen et al. |
| 2015/0065489 | A1 | 3/2015 | Hoffmann et al. |
| 2015/0126503 | A1 | 5/2015 | Hoffmann et al. |

FOREIGN PATENT DOCUMENTS

| | | | |
|---|---|---|---|
| WO | 0172711 | A1 | 10/2001 |
| WO | 02094790 | A1 | 11/2002 |
| WO | 03057695 | A1 | 7/2003 |
| WO | 2004080463 | A1 | 9/2004 |
| WO | 2005034869 | A2 | 4/2005 |
| WO | 2005120509 | A1 | 12/2005 |
| WO | 2008133753 | A2 | 11/2008 |
| WO | 2009040290 | A1 | 4/2009 |
| WO | 2010015518 | A2 | 2/2010 |
| WO | 2010015520 | A1 | 2/2010 |
| WO | 2011027289 | A1 | 3/2011 |
| WO | 2011092128 | A1 | 8/2011 |
| WO | 2012160030 | A1 | 11/2012 |
| WO | 2013013815 | A1 | 1/2013 |

OTHER PUBLICATIONS

Brun, E.M. et al., "New approach to condensed pyrid-2-ones". ARKIVOC (Gainesville, FL, U.S.) [online computer file], coden: AGFUAR URL: http://www.arkat-usa.org/ark/journal/2002/part(x)_general/2-615c/615c.pdf, vol. 2002, No. (x), Jan. 22, 2003, pp. 80-89.

Cywin, C.L. et al., "Discovery and SAR of Novel [1,6]Naphthyridines as Potent Inhibitors of Spleen Tyrosine Kinase (SYK)". Bioorganice & Medicinal Chemistry Letters, 13, 2003, 1415-1418.

International Search Report and Written Opinion for PCT/EP2009/059493 mailed May 19, 2010.

International Search Report for PCT/EP2011/050871 mailed Mar. 23, 2011.

Li, Jianke et al. "Synthesis of 5-hydroxyquinolines" Tetrahedron Letters (2010) 51, pp. 3876-3878.

Politanskaya, Larisa V. et al. "Regioselectivity and relative substrate activity of difluoroquinolines containing fluorine atoms in benzene ring in reaction with sodium methoxide" Journal of Fluorine Chemistry, (2005) vol. 126, pp. 1502-1509.

Ulanova, Marina et al. "Spleen tyrosine kinase (Syk) as a novel target for allergic asthma and rhinitis" (2005) Expert Opin. Ther. Targets, vol. 9 (5) pp. 901-921.

Weinblatt et al.; Treatment of Rheumatoid Arthritis With a Syk Kinase Inhibitor, A Twelve-Week, Randomized, Placebo-Controlled Trial; Arthritis & Rheumatism; Nov. 2008; vol. 58; No. 11; pp. 3309-3318.

Wong, Brian R. et al. "Targeting Syk as a treatment for allergic and autoimmune disorders" (2004) Expert Opin. Investig. Drugs vol. 13 (7), pp. 743-762.

Xie et al.; Pharmacophore modeling study based on known Spleen tyrosine kinase inhibitors together with virtual screening for identifying novel inhibitors; Bioorganic & Medicinal Chemistry Letters; 2009; No. 19; pp. 1944-1949.

* cited by examiner

SUBSTITUTED NAPHTHYRIDINES AND THEIR USE AS MEDICAMENTS

The invention relates to new substituted naphthyridines of formula 1,

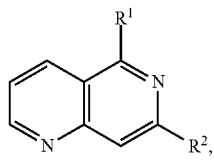

wherein
$R^1$ is selected from among —O—$R^3$ or —$NR^3R^4$
wherein $R^3$ is $C_{1-6}$-alkyl which is substituted by $R^5$ and $R^6$
wherein $R^5$ is selected from hydrogen, branched or linear $C_{1-6}$-alkyl, $C_{2-6}$-alkenyl, —$C_{1-6}$-alkylen-O—$C_{1-3}$-alkyl, $C_{1-3}$-haloalkyl,
wherein $R^6$ is ring X

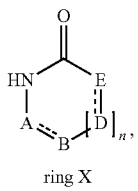

ring X wherein n is either 0 or 1,
wherein === is a either a single or a double bond and
wherein A, B, D and E are each independently from one another selected from $CH_2$, CH, C, N, NH, O or S and
wherein ring X is attached to the molecule either via position A, B, D or E,
wherein said ring X may optionally be further substituted by one, two or three residues each selected individually from the group consisting of -oxo, hydroxy, —$C_{1-3}$-alkyl, —$C_{1-3}$-haloalkyl, —O—$C_{1-3}$-alkyl, —$C_{1-3}$-alkanol and halogen,
$R^4$ is selected from the group consisting of hydrogen and $C_{1-6}$-Alkyl,
$R^2$ is selected from the group consisting of hydrogen; 5- to 10-membered aryl; 5- to 10-membered heteroaryl comprising 1, 2 or 3 heteroatoms each individually selected from among N, O and S; 5- to 10-membered, saturated or partially unsaturated heterocyclus comprising 1, 2 or 3 heteroatoms each individually selected from among N, O and S; 3- to 10-membered saturated or partially unsaturated cycloalkyl,
wherein—in case that $R^2$ is not hydrogen—said $R^2$ may optionally be substituted by 1, 2, 3 or 4 residues each individually selected from the group consisting of hydrogen, -oxo, halogen, $C_{1-6}$-alkyl, $C_{2-6}$-alkenyl, —$C_{1-6}$-alkylene-COOH, —COOH, —CO—$NR^9R^{10}$, —$C_{1-6}$-alkylene-CO—$NR^9R^{10}$, —$C_{1-6}$-alkylene-$NR^9R^{10}$, —$C_{1-6}$-alkylene-CO-Q, —CO-Q, —$C_{1-6}$-alkylene-CO—$NR^9$Q, —CO—$NR^9$Q, —$C_{1-6}$-alkylene-$NR^{11}$—CO—$NR^9R^{10}$, —$C_{1-6}$-alkylene-$NR^{11}$—CO-Q, —$C_{1-6}$-alkylene-$NR^{11}$—$SO_2R^9$, —$C_{1-6}$-alkylene-O—CO—$R^9$, —$C_{1-6}$-alkylene-O—CO—$NR^9R^{10}$, —$C_{1-6}$-alkylene-O—$R^9$, —$C_{1-6}$-alkylene-SO—$NR^9R^{10}$, —$C_{1-6}$-alkylene-$SO_2R^9$, —$C_{1-6}$-alkylene-$SOR^9$, —$C_{1-6}$-alkinylene-O—$R^9$, —$C_{1-6}$-alkinylene-Q, —$C_{1-6}$-alkinylene-$NR^9R^{10}$, $C_{5-10}$-aryl, -Q, —$C_{3-8}$-cycloalkyl, —O—$R^7$, —O—$C_{1-6}$-alkylene-$R^7$, —$C_{1-3}$-haloalkyl, cyanide, —$NR^{11}R^7$, —$NR^{11}(C_{1-6}$-alkylene-$R^7)$, —S(O)—$C_{1-6}$-alkyl, —$SO_2$—$C_{1-6}$-alkyl, —S—$C_{1-6}$-alkyl, —$SO_2$—$NR^9R^{10}$ and —$SO_2$—$NR^{11}$Q,
wherein $R^7$, $R^8$, $R^9$, $R^{10}$, $R^{11}$ and Q may have the meanings given in claim 1,
as well as the N-oxides of the aforementioned compounds, particularly the 1-naphthyridinyl-oxides of the aforementioned compounds, and the pharmacologically acceptable salts, diastereomers, enantiomers, racemates, hydrates or solvates thereof.

1. BACKGROUND TO THE INVENTION

1.1 SYK-Inhibitors

The present invention describes new substituted naphthyridines that inhibit the protein kinase Syk (spleen tyrosine kinase), the preparation and formulation thereof and their use for preparing a medicament.

Syk is an intracellular tyrosine kinase that has an important mediator function in the signal transduction of different receptors in B-cells, mast cells, monocytes, macrophages, neutrophils, T-cells, dendritic cells and epithelial cells. The receptors in which Syk performs an important function in signal transduction include for example the receptors for IgE (FcεRI) and IgG (FcγR1) on mast cells and B cells, the B-cell receptor (BCR) and the T-cell receptor (TCR) on B- and T-cells, the ICAM1 receptor (ICAM1R) on epithelial cells of the respiratory tract, the DAP12-receptor on natural killer cells, dendritic cells and osteoclasts, the dectin 1-receptor on a subpopulation of T-helper cells (Th-17 cells), as well as the integrin receptors for β1-, β2- and β3-integrins on neutrophils, monocytes and macrophages (Wong et al.; Expert Opin. Investig. Drugs (2004) 13(7), 743-762; Ulanova et al.; Expert Opion. Ther. Target (2005) 9(5); 901-921; Wang et al.; J. Immunol. (2006) 177, 6859-6870; Leibundgut-Landmann et al.; Nature Immunology (2007) 8, 630-638; Slack et al., European J. Immunol. (2007) 37, 1600-1612). The best description is of the molecular processes during the signal transduction of the FcεRI. In mast cells the binding of IgE to FcεRI causes the cross-linking of IgE-receptors and the recruiting and activation of Lyn (a tyrosine kinase from the Src family). Active Lyn phoshorylates so-called ITAM motifs, which are present in may of the receptors listed above, and thereby generates binding sites for the SH2-domain of Syk. As a result of the binding to the ITAM motif Syk is activated and then phosphorylates various substrates which are needed for the release of allergic and inflammatory mediators such as e.g. histamine and β-hexosamidase (BHA), as well as for the synthesis of lipid mediators, such as e.g. prostaglandins and leukotrienes.

In view of its central function in different signal transduction pathways Syk has been discussed as a therapeutic target for different diseases such as e.g. Allergic rhinitis, asthma, autoimmune diseases, rheumatoid arthritis, osteopenia, osteoporosis, COPD and various leukaemias and lymphomas (Wong et al.; Expert Opin. Investig. Drugs (2004) 13(7), 743-762; Ulanova et al.; Expert Opin. Ther. Target (2005) 9(5); 901-921; Sigh and Masuda. Annual Reports in Medicinal Chemistry (2007) Vol 42; 379-391; Bajpai et al.; Expert Opin. Investig. Drugs (2008) Vol 15 (5); 641-659; Masuda and Schmitz; PPT (2008) Vol 21; 461-467).

Allergic rhinitis and asthma are diseases associated with allergic reactions and inflammatory processes and involving different cell types such as e.g. Mast cells, eosinophils, T-cells and dendritic cells. After exposure to allergens has occurred, the high affinity immunoglobulin receptors for IgE (FcεRI) and IgG (FcγR1) are activated and induce the release of pro-inflammatory mediators and bronchoconstrictors. An inhibitor of the Syk kinase activity should thus be able to inhibit these steps.

Rheumatoid arthritis (RA) is an autoimmune disease in which the bones and ligaments structures surrounding the joints are progressively destroyed. In the pathophysiology of RA, B-cells play a significant role, as has been demonstrated for example by the therapeutic use of rituximab, a B cell-depleting antibody. In addition to the function of Syk in the signal transduction of the BCR (which after being stimulated also induces the release of pro-inflammatory mediators), Syk also plays an important part in the maturation and proliferation of B cells (Cheng et al. Nature (1995) 378, 303-306, Cornall et al., PNAS (2000) 97(4), 1713-1718). An inhibitor of the Syk kinase activity may thus offer a therapeutic option for the treatment of autoimmune diseases such as RA and diseases with an increased proliferation of B cells, such as e.g. B-cell lymphomas.

Chronic obstructive pulmonary disease (COPD) is characterised by a successive deterioration in lung function and chronic inflammation of the airways, which is initiated and produced by noxious substances of all kinds and contributes to the maintenance of the course of the disease. At a cellular level, in COPD there is in particular a multiplication of T-lymphocytes, neutrophils, granulocytes and macrophages. In particular, there is an increase in the number of CD8-positive lymphocytes, that is directly connected with the impairment of lung function. Another characteristic of COPD are acute deteriorations in lung function (exacerbations), characterised by viral (e.g. Rhinovirus), or bacterial (e.g. *Streptococcus pneumoniae, Haemophilus influenzae* and *Moraxella catarrhalis*) infections.

In view of the pro-inflammatory function of Syk in macrophages, T-cells and neutrophils as described above (see: Wong et al.; Expert Opin. Investig. Drugs (2004) 13(7), 743-762; and references cited therein) an inhibitor of the Syk kinase activity could be a new therapeutic approach to the treatment of the inflammatory processes that underlie COPD. It has also been shown that Syk in epithelial cells of the respiratory tract is involved in the ICAM1R-mediated uptake and subsequent replication of the Rhinovirus and that a siRNA against Syk blocks these steps (Wang et al.; J. Immunol. (2006) 177, 6859-6870; Lau et al.; J. Immunol. (2008) 180, 870-880). Thus, an inhibitor of the Syk kinase activity could also be used therapeutically in exacerbations caused by Rhinoviruses.

Various studies suggest that Syk is involved in the malignant transformation of lymphocytes (summarised in Sigh and Masuda. Annual Reports in Medicinal Chemistry (2007) Vol 42; 379-391). A TEL-Syk fusion protein with a constitutive Syk activity transformed B cells of a patient with myelodysplastic syndrome, a constitutively active ITK-Syk fusion protein was isolated from patients with T-cell lymphomas. Moreover, constitutively active Syk was found in B-cell lymphoma cells of patients. On the basis of these data it seems that Syk is a proto-oncogene in haematopoietic cells and represents a potential target for the treatment of certain leukaemias and lymphomas.

1.2 Prior Art

BE 835770 describes 5-amino-1,6-naphthyridine with an antimicrobial activity. U.S. Pat. Nos. 3,928,367, 4,017,500, 4,115,395 and 4,260,759 describe 5-amino-1,6-naphthyridines with an antifungal and antibacterial activity. WO 9918077 describes 5-piperazinyl-1,6-naphthyridines as serotonin antagonists. U.S. Pat. No. 7,321,041 describes substituted [1,6]-naphthyridines as SYK-inhibitors, although they have a completely different substitution pattern from the compounds according to the invention.

Surprisingly it has now been found that naphthyridines of formula 1 are particularly suitable for the treatment of respiratory complaints, allergic diseases, osteoporosis, gastrointestinal diseases, autoimmune diseases, inflammatory diseases and diseases of the peripheral or central nervous system, particularly for the treatment of asthma, allergic rhinitis, rheumatoid arthritis, allergic dermatitis and COPD.

2. DESCRIPTION OF THE INVENTION

The present invention therefore relates to compounds of formula 1,

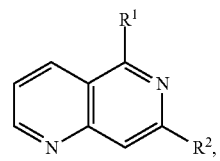

wherein
$R^1$ is selected from among —O—$R^3$ or —N$R^3R^4$
wherein $R^3$ is $C_{1-6}$-alkyl which is substituted by $R^5$ and $R^6$
wherein $R^5$ is selected from hydrogen, branched or linear $C_{1-6}$-alkyl, $C_{2-6}$-alkenyl, —$C_{1-6}$-alkylen-O—$C_{1-3}$-alkyl, $C_{1-3}$-haloalkyl,
wherein $R^6$ is ring X

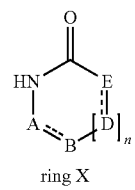

ring X wherein n is either 0 or 1,
wherein ═══ is a either a single or a double bond and
wherein A, B, D and E are each independently from one another selected from $CH_2$, CH, C, N, NH, O or S and
wherein ring X is attached to the molecule either via position A, B, D or E,
wherein said ring X may optionally be further substituted by one, two or three residues each selected individually from the group consisting of -oxo, hydroxy, —$C_{1-3}$-alkyl, —$C_{1-3}$-haloalkyl, —O—$C_{1-3}$-alkyl, —$C_{1-3}$-alkanol and halogen,
$R^4$ is selected from the group consisting of hydrogen and $C_{1-6}$-Alkyl,
$R^2$ is selected from the group consisting of hydrogen; 5- to 10-membered aryl; 5- to 10-membered heteroaryl comprising 1, 2 or 3 heteroatoms each individually selected from among N, O and S; 5- to 10-membered, saturated or partially unsaturated heterocyclus comprising 1, 2 or 3 heteroatoms each individually selected from among N, O and S; 3- to 10-membered saturated or partially unsaturated cycloalkyl, wherein—in case that $R^2$ is not hydrogen—said $R^2$ may optionally be substituted by 1, 2, 3 or 4 residues each individually selected from the group consisting of hydrogen, -oxo, halogen, $C_{1-6}$-alkyl, $C_{2-6}$-alkenyl, —$C_{1-6}$-alkylene-COOH, —COOH, —CO—$NR^9R^{10}$, —$C_{1-6}$-alkylene-CO—$NR^9R^{10}$, —$C_{1-6}$-alkylene-$NR^9R^{10}$, —$C_{1-6}$-alkylene-CO-Q, —CO-Q, —$C_{1-6}$-alkylene-CO—$NR^9Q$, —CO—$NR^9Q$, —$C_{1-6}$-alkylene-$NR^{11}$—CO—$NR^9R^{10}$, —$C_{1-6}$-alkylene-$NR^{11}$—CO-Q, —$C_{1-6}$-alkylene-$NR^{11}$—$SO_2R^9$, —$C_{1-6}$-alkylene-O—CO—$R^9$, —$C_{1-6}$-alkylene-O—CO—$NR^9R^{10}$, —$C_{1-6}$-alkylene-O—$R^9$, —$C_{1-6}$-alkylene-SO—$NR^9R^{10}$, —$C_{1-6}$-alkylene-$SO_2R^9$, —$C_{1-6}$-alkylene-$SOR^9$, —$C_{1-6}$-alkinylene-O—$R^9$, —$C_{1-6}$-alkinylene-Q, —$C_{1-6}$-alkinylene-$NR^9R^{10}$, $C_{5-10}$-aryl, -Q, —$C_{3-8}$-cycloalkyl, —O—$R^7$, —O—$C_{1-6}$-alkylene-$R^7$, —O—$C_{1-6}$-alkylene-O—$R^7$, —$C_{1-3}$-haloalkyl, cyanide, —$NR^{11}R^7$, —$NR^{11}(C_{1-6}$-alkylene-$R^7$), —S(O)—$C_{1-6}$-alkyl, —$SO_2$—$C_{1-6}$-alkyl, —S—$C_{1-6}$-alkyl, —$SO_2$—$NR^9R^{10}$ and —$SO_2$—$NR^{11}Q$; 5- to 10-membered heteroaryl comprising 1, 2 or 3 heteroatoms each individually selected from among N, O and S, —$NR^{11}$—CO—$R^7$ and —O—CO—$R^7$, wherein $R^7$ is selected from the group consisting of hydrogen; branched or linear $C_{1-6}$-alkyl; $C_{1-6}$-haloalkyl; —$C_{1-6}$-alkylene-COOH; —$C_{1-6}$-alkylen-CO—$NR^9R^{10}$; —$C_{1-6}$-alkylene-CO-Q; —$C_{2-6}$-alkylene-$NR^{11}$—CO—$NR^9R^{10}$; —$C_{2-6}$-alkylene-$NR^{11}$—CO-Q; —$C_{2-6}$-alkylene-$NR^{11}$—$SO_2R^9$; —$C_{2-6}$-alkylene-$NR^9R^{10}$; —$C_{2-6}$-alkylene-Q; —$C_{2-6}$-alkylene-O—CO—$R^9$, —$C_{2-6}$-alkylene-O—CO—$NR^9R^{10}$, —$C_{2-6}$-alkylene-SO—$NR^9R^{10}$, —$C_{2-6}$-alkylene-$SO_2$—$R^9$, —$C_{2-6}$-alkylene-SO—$R^9$, —$SO_2$—$R^9$, —SO—$R^9$, —$SO_2$—$NR^9R^{10}$, —$SO_2$—$NR^{11}Q$, —$SO_2$-Q, —$C_{1-6}$-alkylene-O—$R^9$; —CO—$NR^9R^{10}$, —CO—$NR^9Q$, —CO—$R^9$, —CO-Q, —$C_{1-6}$-alkylene-Q, —$C_{5-10}$-aryl, -Q; 3- to 8-membered saturated or partially unsaturated cycloalkyl; 5- to 10-membered heteroaryl comprising 1, 2 or 3 heteroatoms each individually selected from among N, O and S; —$C_{1-6}$-alkylene-heteroaryl wherein this heteroaryl is 5- to 10-membered and comprises 1, 2 or 3 heteroatoms each individually selected from among N, O and S;

whereby—in case that $R^7$ is not hydrogen—$R^7$ may optionally be substituted by 1, 2 or 3 residues $R^8$ that are individually selected from the group consisting of hydrogen; -oxo; hydroxy; —$C_{1-6}$-alkyl; —$C_{1-6}$-haloalkyl; —$NR^9R^{10}$, -Q, —$NR^9Q$, 3- to 6-membered saturated or partially unsaturated cycloalkyl;

whereby—in case that $R^8$ is not hydrogen—$R^8$ may optionally be substituted by 1, 2 or 3 residues selected from hydrogen, -oxo, -hydroxy, —$C_{1-6}$-alkyl, halogen, —$C_{1-6}$-haloalkyl, —O—$C_{1-6}$-alkyl, —$C_{1-3}$-alkylene-O—$C_{1-3}$-alkyl, wherein each of $R^9$, $R^{10}$ and $R^{11}$ is individually from one another selected from the group consisting of hydrogen, —$C_{1-6}$-alkyl, —$C_{3-8}$-cycloalkyl, —$C_{1-6}$-alkyl-$C_{3-8}$-cycloalkyl and phenyl, and wherein each Q is individually selected either from a 5- to 10-membered saturated or partially unsaturated heterocyclus comprising 1, 2 or 3 heteroatoms each individually selected from among N, O or S or from a 5- to 10-membered heteroaryl comprising 1, 2 or 3 heteroatoms each individually selected from among N, O and S;

whereby Q is attached to the rest of the molecule either via a carbon atom or via an nitrogen atom, the N-oxides of the aforementioned compounds, particularly the 1-naphthyridinyl-oxides of the aforementioned compounds, and the pharmaceutically acceptable salts of the aforementioned compounds.

A preferred object of the present invention relates to compounds of the above formula 1 with the above-mentioned definitions of the individual variables, wherein $R^4$ is hydrogen or methyl, the N-oxides of the aforementioned compounds, particularly the 1-naphthyridinyl-oxides of the aforementioned compounds, and the pharmaceutically acceptable salts, diastereomers, enantiomers, racemates, hydrates and solvates thereof.

Also preferred are compounds of formula 1 with the above-mentioned definitions of the individual variables, wherein $R^5$ is selected from hydrogen, -methyl, ethyl, n-propyl, isopropyl, n-butyl, isobutyl, tert-butyl, ethenyl, propenyl, -ethylene-O-Methyl, -propylene-O-Methyl, —$CF_3$, —$CHF_2$, —$CH_2F$, —$CF_2$—$CF_3$ and —$CH_2$—$CF_3$, the N-oxides of the aforementioned compounds, particularly the 1-naphthyridinyl-oxides of the aforementioned compounds, and the pharmaceutically acceptable salts, diastereomers, enantiomers, racemates, hydrates and solvates thereof.

A preferred object of the present invention relates to compounds of the above formula 1 with the above-mentioned definitions of the individual variables, wherein $R^3$ is methylene or ethylene which is substituted by $R^5$ and $R^6$, the N-oxides of the aforementioned compounds, particularly the 1-naphthyridinyl-oxides of the aforementioned compounds, and the pharmaceutically acceptable salts, diastereomers, enantiomers, racemates, hydrates and solvates thereof.

A further preferred object of the present invention relates to compounds of the above formula 1 with the above-mentioned definitions of the individual variables, wherein $R^3$ is methylene which is substituted by $R^5$ and $R^6$, the N-oxides of the aforementioned compounds, particularly the 1-naphthyridinyl-oxides of the aforementioned compounds, and the pharmaceutically acceptable salts, diastereomers, enantiomers, racemates, hydrates and solvates thereof.

Also preferred are compounds of formula 1 with the above-mentioned definitions of the individual variables, wherein $R^6$ is a ring X selected from

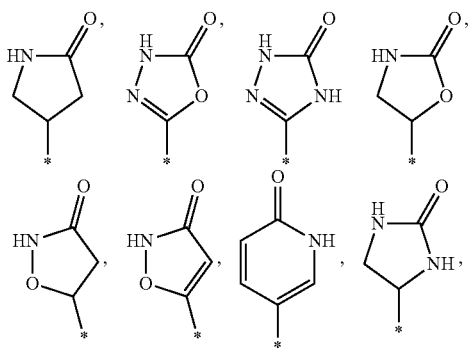

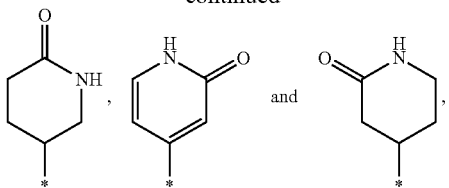

wherein each of said rings X may optionally be further substituted by one, two or three residues each selected individually from the group consisting of methyl, ethyl, propyl, isopropyl, —CF$_3$, F and -oxo, the N-oxides of the aforementioned compounds, particularly the 1-naphthyridinyl-oxides of the aforementioned compounds, and the pharmaceutically acceptable salts, diastereomers, enantiomers, racemates, hydrates and solvates thereof.

In another preferred aspect the present invention relates to compounds of formula 1 with the above-mentioned definitions of the individual variables, wherein R$^2$ is selected from the group consisting of hydrogen, phenyl, pyrrolyl, pyrrolidinyl, pyridine-2-yl, pyridine-3-yl, oxazolyl, isoxazolyl, benzo[1,3]dioxolyl, 1H-pyridine-2-one-yl, 2-H-pyridine-3-one-yl, furanyl, thiophenyl, pyrimidinyl, pyrazinyl, imidazolyl, thiazolyl, oxazolyl, quinolinyl, isoquinolinyl, purinyl, pyronyl, pyridonyl, thiopyranyl, pyranyl, tetrahydrothiopyranyl, tetrahydropyranyl, benzimidazolyl, indazolyl, pyrazolyl, triazolyl, tetrazolyl, benzoxazolyl, benzthiazolyl, isothioazolyl, oxadiazolyl, triazinyl, cumaronyl, benzothiophenyl, 3,4-dihydro-2H-benzo[1,4]oxazinyl, 1,2,3,4-tetrahydro-quinolinyl, 1,2,3,4-tetrahydro-isoquinolinyl, indolyl, 2,3-dihydro-1H-indolyl, cyclopropyl, cyclobutyl, cyclopenyl and cyclohexyl, wherein—in case that R$^2$ is not hydrogen—said R$^2$ may optionally be substituted as defined above, the N-oxides of the aforementioned compounds, particularly the 1-naphthyridinyl-oxides of the aforementioned compounds, and the pharmaceutically acceptable salts, diastereomers, enantiomers, racemates, hydrates and solvates thereof.

In a further preferred aspect the present invention relates to compounds of formula 1 with the above-mentioned definitions of the individual variables, wherein Q is selected from a five- to six-membered heterocyclus comprising one, two or three heteroatoms each individually from each other selected from the group consisting of N, O and S, which optionally may be substituted by hydrogen, oxo or C$_{1-3}$-Alkyl, the N-oxides of the aforementioned compounds, particularly the 1-naphthyridinyl-oxides of the aforementioned compounds, and the pharmaceutically acceptable salts, diastereomers, enantiomers, racemates, hydrates and solvates thereof.

Also preferred are compounds of formula 1 with the above-mentioned definitions of the individual variables, wherein Q is selected from the group consisting of

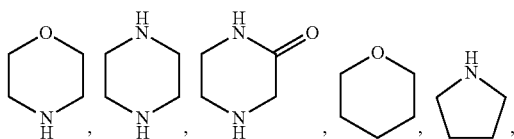

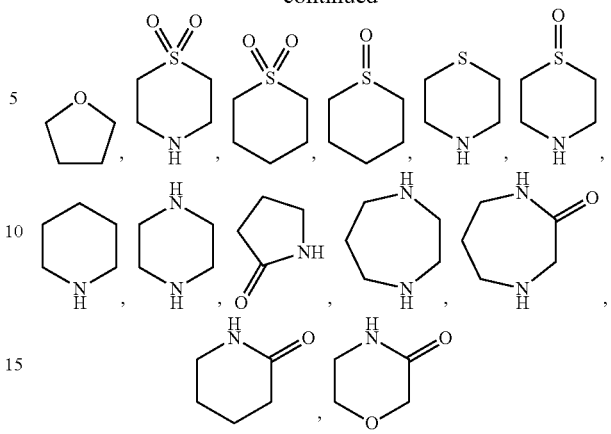

whereby Q is attached to the rest of the molecule either via a carbon atom or via an nitrogen atom, which optionally may be further substituted by a residue selected from hydrogen, oxo or C$_{1-3}$-Alkyl, the N-oxides of the aforementioned compounds, particularly the 1-naphthyridinyl-oxides of the aforementioned compounds, and the pharmaceutically acceptable salts, diastereomers, enantiomers, racemates, hydrates and solvates thereof.

In a further preferred aspect the present invention relates to compounds of formula 1 with the above-mentioned definitions of the individual variables, wherein R$^2$ is selected from the group consisting of hydrogen; 5- to 10-membered aryl; 5- to 10-membered heteroaryl comprising 1, 2 or 3 heteroatoms each individually selected from among N, O and S; 5- to 10-membered, saturated or partially unsaturated heterocyclus comprising 1, 2 or 3 heteroatoms each individually selected from among N, O and S; 3- to 10-membered saturated or partially unsaturated cycloalkyl, wherein—in case that R$^2$ is not hydrogen—said R$^2$ may optionally be substituted by 1, 2, 3 or 4 residues each individually selected from the group consisting of hydrogen, -oxo, F, Cl, Br, C$_{1-6}$-alkyl, -Q, —O—R$^7$, —O—C$_{1-6}$-alkylene-R$^7$, —O—C$_{1-6}$-alkylene-O— R$^7$, —C$_{1-3}$-haloalkyl, cyanide, wherein R$^7$ is selected from the group consisting of hydrogen; branched or linear C$_{1-6}$-alkyl; C$_{1-6}$-haloalkyl; —C$_{1-6}$-alkylene-NR$^9$R$^{10}$, -Q; 3- to 8-membered saturated or partially unsaturated cycloalkyl;

whereby—in case that R$^7$ is not hydrogen—R$^7$ may optionally be substituted by 1, 2 or 3 residues R$^8$ that are individually selected from the group consisting of hydrogen; -oxo; hydroxy; —C$_{1-6}$-alkyl; —C$_{1-6}$-haloalkyl; -Q, 3- to 6-membered saturated or partially unsaturated cycloalkyl;

whereby—in case that R$^8$ is not hydrogen—R$^8$ may optionally be substituted by 1, 2 or 3 residues selected from hydrogen, -oxo, -hydroxy, —C$_{1-6}$-alkyl, halogen, —C$_{1-6}$-haloalkyl, —O—C$_{1-6}$-alkyl, —C$_{1-3}$-alkylene-O—C$_{1-3}$-alkyl, wherein each of R$^9$ and R$^{10}$ is individually from one another selected from the group consisting of hydrogen, —C$_{1-6}$-alkyl, —C$_{3-8}$-cycloalkyl, —C$_{1-6}$-alkyl-C$_{3-8}$-cycloalkyl and phenyl, and wherein each Q is individually selected either from a 5- to 10-membered saturated or partially unsaturated heterocyclus comprising 1, 2 or 3 heteroatoms each individually selected from among N, O or S or from a 5- to 10-membered heteroaryl comprising 1, 2 or 3 heteroatoms each individually selected from among N, O and S;

whereby Q is attached to the rest of the molecule either via a carbon atom or via an nitrogen atom, the N-oxides of the aforementioned compounds, particularly the 1-naphthyridinyl-oxides of the aforementioned compounds, and the pharmaceutically acceptable salts, diastereomers, enantiomers, racemates, hydrates and solvates thereof.

In a further aspect the present invention relates to compounds of formula 1 with the above-mentioned definitions of the individual variables, wherein $R^2$ is selected from the group consisting of hydrogen; 5- to 10-membered aryl; 5- to 10-membered heteroaryl comprising 1, 2 or 3 heteroatoms each individually selected from among N, O and S; 5- to 10-membered, saturated or partially unsaturated heterocyclus comprising 1, 2 or 3 heteroatoms each individually selected from among N, O and S; 3- to 10-membered saturated or partially unsaturated cycloalkyl, wherein—in case that $R^2$ is not hydrogen—said $R^2$ may optionally be substituted by 1, 2, 3 or 4 residues each individually selected from the group consisting of $C_{1-6}$-Alkyl, $C_{2-6}$-alkenyl, $-C_{1-3}$-haloalkyl, cyanide, $-C_{1-6}$-alkylene-COOH, $-COOH$, $-CO-NR^9R^{10}$, $-C_{1-6}$-alkylene-CO-NR$^9$R$^{10}$, $-C_{1-6}$-alkylene-NR$^9$R$^{10}$, $-C_{1-6}$-alkylene-CO-Q, $-CO-Q$, $-C_{1-6}$-alkylene-CO-NR$^9$Q, $-CO-NR^9$Q, $-C_{1-6}$-alkylene-NR$^{11}$-CO-NR$^9$R$^{10}$, $-C_{1-6}$-alkylene-NR$^{11}$-CO-Q, $-C_{1-6}$-alkylene-NR$^{11}$-SO$_2$R$^9$, $-C_{1-6}$-alkylene-O-CO-R$^9$, $-C_{1-6}$-alkylene-O-CO-NR$^9$R$^{10}$, $-C_{1-6}$-alkylene-O-R$^9$, $-C_{1-6}$-alkylene-SO-NR$^9$R$^{10}$, $-C_{1-6}$-alkylene-SO$_2$R$^9$, $-C_{1-6}$-alkylene-SOR$^9$, $-C_{1-6}$-alkinylene-O-R$^9$, $-C_{1-6}$-alkinylene-Q, $-C_{1-6}$-alkinylene-NR$^9$R$^{10}$, $C_{5-10}$-aryl, -Q, $-C_{3-8}$-cycloalkyl, wherein each of $R^9$, $R^{10}$ and $R^{11}$ is individually from one another selected from the group consisting of hydrogen, $-C_{1-6}$-alkyl, $-C_{3-8}$-cycloalkyl, $-C_{1-6}$-alkyl-$C_{3-8}$-cycloalkyl and phenyl, and wherein each Q is individually selected either from a 5- to 10-membered saturated or partially unsaturated heterocyclus comprising 1, 2 or 3 heteroatoms each individually selected from among N, O or S or from a 5- to 10-membered heteroaryl comprising 1, 2 or 3 heteroatoms each individually selected from among N, O and S;

whereby Q is attached to the rest of the molecule either via a carbon atom or via an nitrogen atom, the N-oxides of the aforementioned compounds, particularly the 1-naphthyridinyl-oxides of the aforementioned compounds, and the pharmaceutically acceptable salts, diastereomers, enantiomers, racemates, hydrates and solvates thereof.

An other aspect the present invention relates to compounds of formula 1 with the above-mentioned definitions of the individual variables, wherein $R^2$ is selected from the group consisting of hydrogen; 5- to 10-membered aryl; 5- to 10-membered heteroaryl comprising 1, 2 or 3 heteroatoms each individually selected from among N, O and S; 5- to 10-membered, saturated or partially unsaturated heterocyclus comprising 1, 2 or 3 heteroatoms each individually selected from among N, O and S; 3- to 10-membered saturated or partially unsaturated cycloalkyl, wherein—in case that $R^2$ is not hydrogen—said $R^2$ may optionally be substituted by 1, 2, 3 or 4 residues each individually selected from the group consisting of $-NR^{11}R^7$, $-NR^{11}(C_{1-6}$-alkylene-$R^7)$, $-S(O)-C_{1-6}$-alkyl, $-SO_2-C_{1-6}$-alkyl, $-S-C_{1-6}$-alkyl, $-SO_2-NR^9R^{10}$ and $-SO_2-NR^{11}Q$, wherein $R^7$ is selected from the group consisting of hydrogen; branched or linear $C_{1-6}$-alkyl; $C_{1-6}$-haloalkyl; $-C_{1-6}$-alkylene-COOH; $-C_{1-6}$-alkylen-CO-NR$^9$R$^{10}$; $-C_{1-6}$-alkylene-CO-Q; $-C_{2-6}$-alkylene-NR$^{11}$-CO-NR$^9$R$^{10}$; $-C_{2-6}$-alkylene-NR$^{11}$-CO-Q; $-C_{2-6}$-alkylene-NR$^{11}$-SO$_2$R$^9$; $-C_{2-6}$-alkylene-NR$^9$R$^{10}$; $-C_{2-6}$-alkylene-Q; $-C_{2-6}$-alkylene-O-CO-R$^9$, $-C_{2-6}$-alkylene-O-CO-NR$^9$R$^{10}$, $-C_{2-6}$-alkylene-SO-NR$^9$R$^{10}$, $-C_{2-6}$-alkylene-SO$_2$-R$^9$, $-C_{2-6}$-alkylene-SO-R$^9$, $-SO_2-R^9$, $-SO-R^9$, $-SO_2-NR^9R^{10}$, $-SO_2-NR^{11}Q$, $-SO_2-Q$, $-C_{1-6}$-alkylene-O-$C_{1-3}$-alkylR$^9$; $-CO-NR^9R^{10}$, $-CO-NR^9Q$, $-CO-R^9$, $-CO-Q$, $-C_{1-6}$-alkylene-Q, $-C_{6-10}$-aryl, -Q, 5- to 10-membered: saturated or partially unsaturated heterocyclus comprising 1, 2 or 3 heteroatoms each individually selected from among N, O or S; 3- to 10-membered saturated or partially unsaturated cycloalkyl; $-C_{1-6}$-alkylene-NH$_2$; $-C_{1-6}$-alkylene-NH($C_{1-3}$-alkyl) and $-C_{1-6}$-alkylene-N($C_{1-3}$-alkyl)$_2$, whereby—in case that $R^7$ is not hydrogen—$R^7$ may optionally be substituted by 1, 2 or 3 residues $R^8$ that are individually selected from the group consisting of hydrogen; -oxo; hydroxy; $-C_{1-6}$-alkyl; $-C_{1-6}$-haloalkyl; $-NR^9R^{10}$, -Q, $-NR^9Q$, 3- to 6-membered saturated or partially unsaturated cycloalkyl;

whereby—in case that $R^8$ is not hydrogen—$R^8$ may optionally be substituted by 1, 2 or 3 residues selected from hydrogen, -oxo, -hydroxy, $-C_{1-6}$-alkyl, halogen, $-C_{1-6}$-haloalkyl, $-O-C_{1-6}$-alkyl, $-C_{1-3}$-alkylene-O-$C_{1-3}$-alkyl, wherein each of $R^9$, $R^{10}$ and $R^{11}$ is individually from one another selected from the group consisting of hydrogen, $-C_{1-6}$-alkyl, $-C_{3-8}$-cycloalkyl, $-C_{1-6}$-alkyl-$C_{3-8}$-cycloalkyl and phenyl, and wherein each Q is individually selected either from a 5- to 10-membered saturated or partially unsaturated heterocyclus comprising 1, 2 or 3 heteroatoms each individually selected from among N, O or S or from a 5- to 10-membered heteroaryl comprising 1, 2 or 3 heteroatoms each individually selected from among N, O and S;

whereby Q is attached to the rest of the molecule either via a carbon atom or via an nitrogen atom, the N-oxides of the aforementioned compounds, particularly the 1-naphthyridinyl-oxides of the aforementioned compounds, and the pharmaceutically acceptable salts, diastereomers, enantiomers, racemates, hydrates and solvates thereof.

In a further preferred aspect the present invention relates to compounds of formula 1 with the above-mentioned definitions of the individual variables, wherein in case that $R^7$ is not hydrogen—$R^7$ may optionally be substituted by 1, 2 or 3 residues $R^8$ that are individually selected from the group consisting of hydrogen; -oxo; methyl, ethyl, n-propyl, isopropyl, n-butyl, tertiär-butyl, isobutyl, -Q, whereby—in case that $R^8$ is not hydrogen—$R^8$ may optionally be substituted by 1, 2 or 3 residues selected from hydrogen, -oxo, methyl, ethyl, n-propyl, isopropyl, n-butyl, tertiär-butyl, isobutyl wherein each of $R^9$, $R^{10}$ and $R^{11}$ is individually from one another selected from the group consisting of hydrogen, $-C_{1-6}$-alkyl, and wherein each Q is individually selected either from a 5- to 7-membered saturated heterocyclus comprising 1, 2 or 3 heteroatoms each individually selected from among N, O or S, whereby Q is attached to the rest of the molecule either via a carbon atom or via an nitrogen atom, the N-oxides of the aforementioned compounds, particularly the 1-naphthyridinyl-oxides of the aforementioned compounds, and the pharmaceutically acceptable salts, diastereomers, enantiomers, racemates, hydrates and solvates thereof.

A further preferred object of the present invention relates to compounds of the above formula 1 with the above-mentioned definitions of the individual variables, wherein $R^1$ is selected from the group consisting of

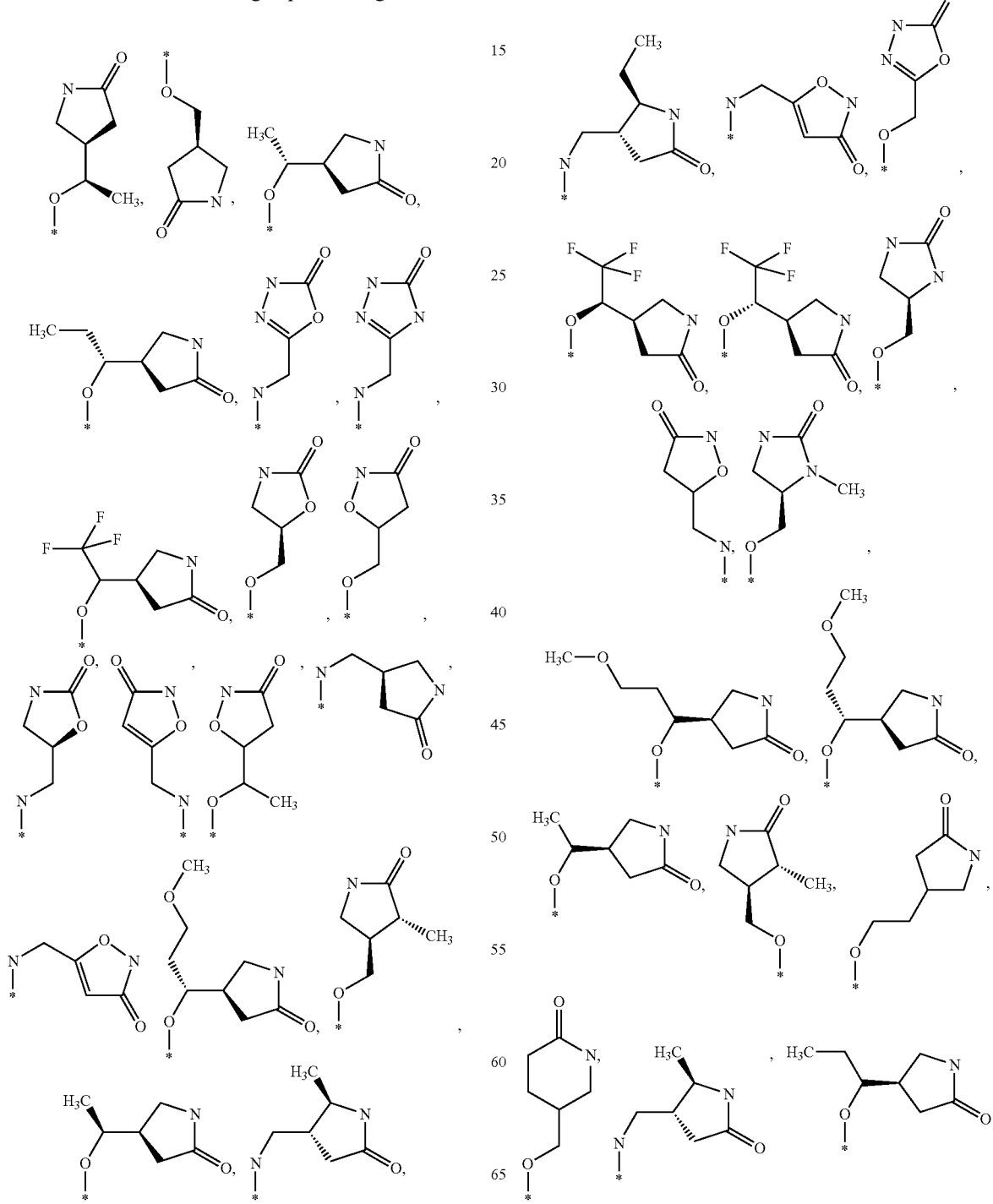

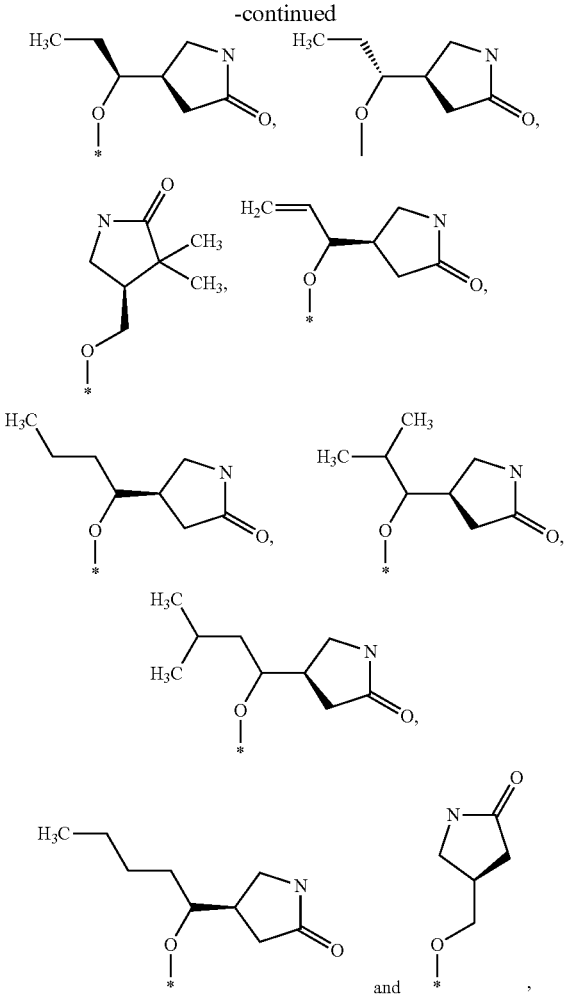
and wherein R² is selected from the group consisting of
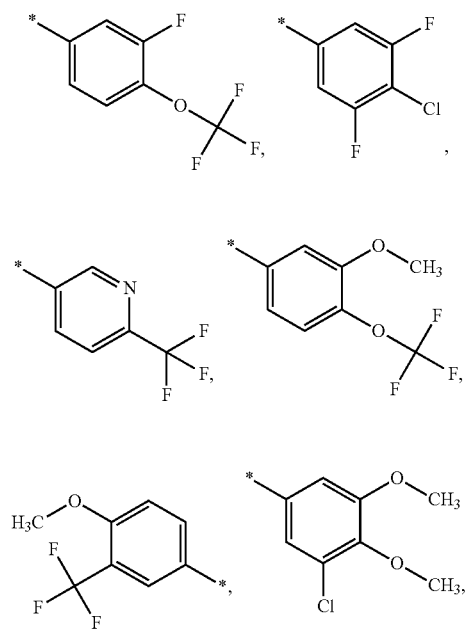
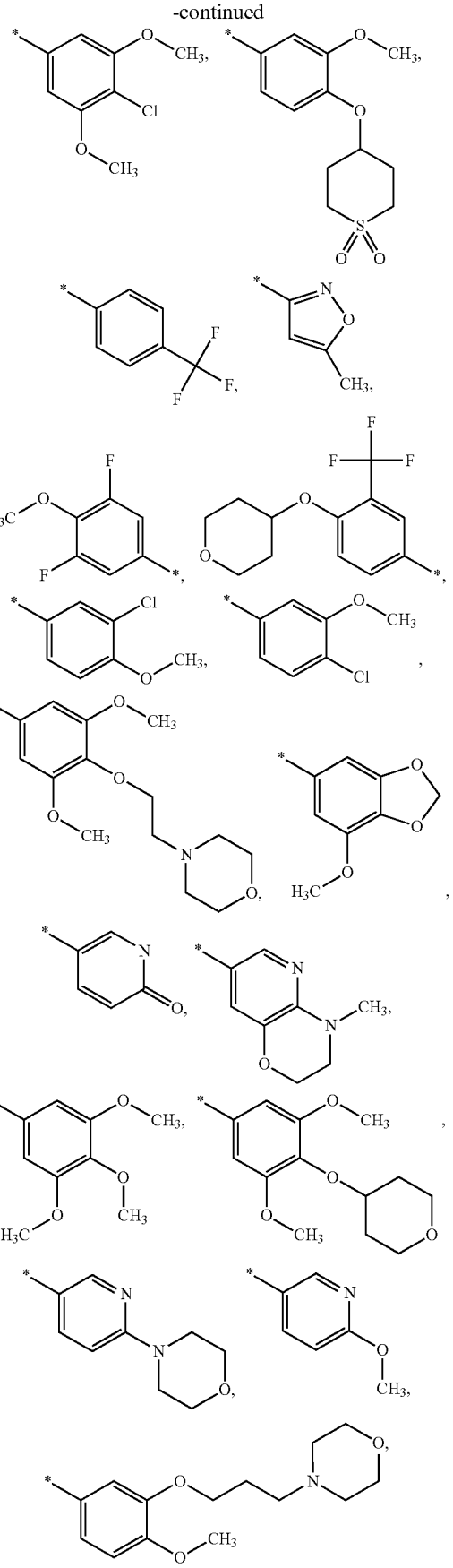

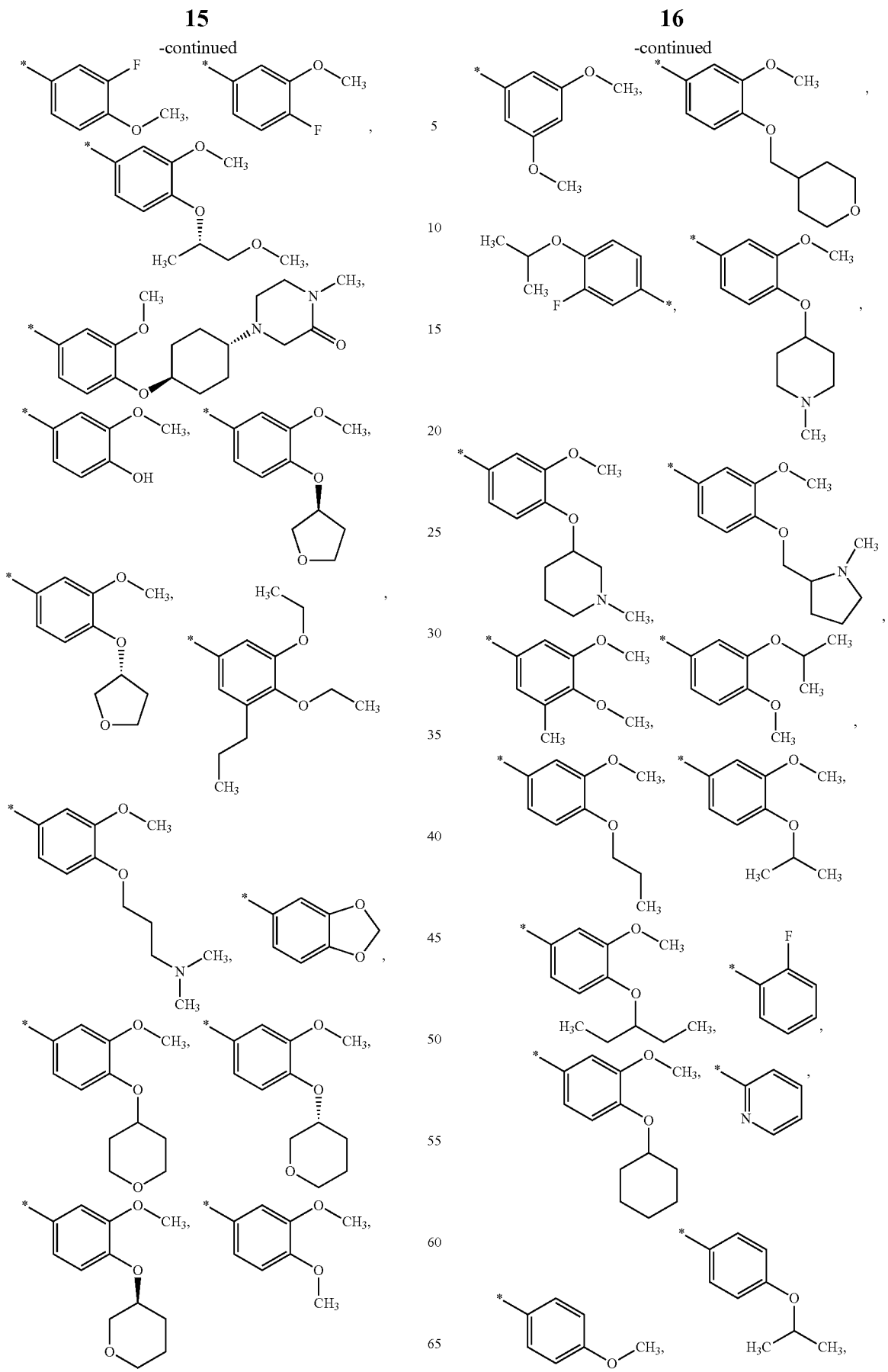

-continued

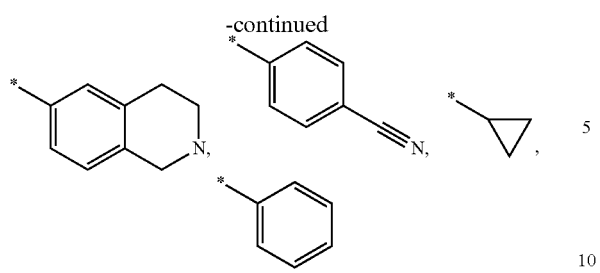

and hydrogen,
the N-oxides of the aforementioned compounds, particularly the 1-naphthyridinyl-oxides of the aforementioned compounds, and the pharmaceutically acceptable salts, diastereomers, enantiomers, racemates, hydrates and solvates thereof.

The invention further relates to the use of the above compounds of formula 1 with the above-mentioned definitions of the individual variables for preparing a medicament for the treatment of diseases which can be treated by inhibiting the SYK enzyme.

In another preferred aspect the invention relates to the use of the above compounds of formula 1 with the above-mentioned definitions of the individual variables for preparing a medicament for the treatment of diseases selected from among allergic rhinitis, asthma, COPD, adult respiratory distress syndrome, bronchitis, B cell lymphoma, T-cell lymphoma, capsule cell lymphoma, dermatitis and contact dermatitis, allergic dermatitis, allergic rhinoconjunctivitis, rheumatoid arthritis, anti-phospholipid syndrome, Berger's disease, Evans's syndrome, ulcerative colitis, allergic antibody-based glomerulonephritis, granulocytopenia, Goodpasture's syndrome, hepatitis, Henoch-Schönlein purpura, hypersensitivity vasculitis, immunohaemolytic anaemia, autoimmune haemolytic anemia, idiopathic thrombocytopenic purpura, Kawasaki syndrome, allergic conjunctivitis, lupus erythematodes, neutropenia, non-familial lateral sclerosis, Crohn's disease, multiple sclerosis, myasthenia gravis, osteoporosis, osteolytic diseases, osteopenia, psoriasis, Sjögren's syndrome, sclerodermy, urticaria/angiooedema, Wegener's granulomatosis and coeliac disease.

In a particularly preferred aspect the present invention relates to the use of the above compounds of formula 1 with the above-mentioned definitions of the individual variables for preparing a medicament for the treatment of diseases selected from among asthma, COPD, allergic rhinitis, adult respiratory distress syndrome, bronchitis, allergic dermatitis, contact dermatitis, idiopathic thrombocytopenic purpura, rheumatoid arthritis and allergic rhinoconjunctivitis.

The present invention relates in particular to the use of the above compounds of formula 1 with the above-mentioned definitions of the individual variables for preparing a medicament for the treatment of diseases selected from among asthma, COPD, allergic rhinitis, allergic dermatitis and rheumatoid arthritis.

Moreover the present invention preferably relates to pharmaceutical formulations which contain one or more compounds of formula 1 with the above-mentioned definitions of the individual variables.

The invention further relates to pharmaceutical formulations which contain one or more compounds of formula 1 with the above-mentioned definitions of the individual variables, in combination with an active substance selected from among anticholinergics, betamimetics, corticosteroids, PDE4-inhibitors, EGFR-inhibitors and LTD4-antagonists, CCR3-inhibitors, iNOS-inhibitors and HMG-CoA reductase inhibitors (statins).

In another preferred aspect the invention relates to the following intermediate products in the preparation of the above compounds according to formula 1 selected from formula 5

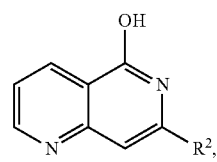

from formula 6

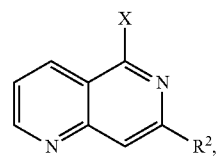

from formula 7a

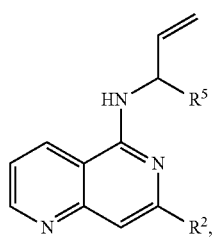

from formula 7b

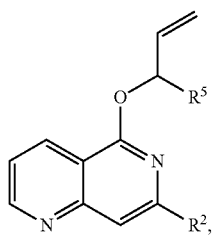

from formula 7c

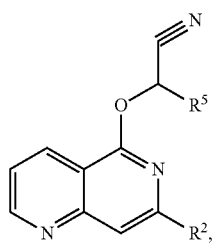

wherein X is Cl or triflate and
wherein $R^1$, $R^2$, $R^5$ are defined as stated above.

In another preferred aspect the invention relates to the N-oxides of formula 1 which are the compounds of formula 1'

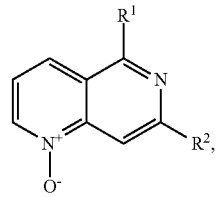

1' wherein R¹ and R² are defined as above.

3. TERMS AND DEFINITIONS USED

Unless stated otherwise, all the substituents are independent of one another. If for example a number of $C_{1-6}$-alkyl groups are possible substituents at a group, in the case of three substituents, for example, $C_{1-6}$-alkyl could represent, independently of one another, a methyl, an n-propyl and a tert-butyl.

Within the scope of this application, in the definition of possible substituents, these may also be presented in the form of a structural formula. An asterisk (*) in the structural formula of the substituent is to be understood as being the linking point to the rest of the molecule. Moreover, the atom of the substituent following the linking point is understood as being the atom in position number 1. Thus for example the groups N-piperidinyl (I), 4-piperidinyl (II), 2-tolyl (III), 3-tolyl (IV) and 4-tolyl (V) are represented as follows:

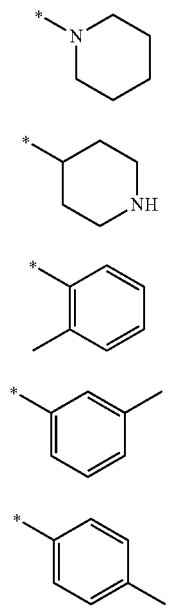

If there is no asterisk (*) in the structural formula of the substituent, each hydrogen atom may be removed at the substituent and the valency thus freed may serve as a binding site to the rest of a molecule. Thus, for example, VI

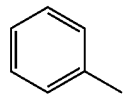

VI may represent 2-tolyl, 3-tolyl, 4-tolyl and benzyl.

Alternatively to the * within the scope of this application $X_1$ is also understood as being the linking point of the group $R^1$ to the structure of formula 1 and $X_2$ as being the linking point of the group $R^2$ to the structure of formula 1.

By the term "$C_{1-6}$-alkyl" (including those which are part of other groups) are meant branched and unbranched alkyl groups with 1 to 6 carbon atoms and by the term "$C_{1-3}$-alkyl" are meant branched and unbranched alkyl groups with 1 to 3 carbon atoms. "$C_{1-4}$-alkyl" accordingly denotes branched and unbranched alkyl groups with 1 to 4 carbon atoms. Alkyl groups with 1 to 4 carbon atoms are preferred. Examples of these include: methyl, ethyl, n-propyl, iso-propyl, n-butyl, iso-butyl, sec-butyl, tert-butyl, n-pentyl, iso-pentyl, neo-pentyl or hexyl. The abbreviations Me, Et, n-Pr, i-Pr, n-Bu, i-Bu, t-Bu, etc., may also optionally be used for the above-mentioned groups. Unless stated otherwise, the definitions propyl, butyl, pentyl and hexyl include all the possible isomeric forms of the groups in question. Thus, for example, propyl includes n-propyl and iso-propyl, butyl includes iso-butyl, sec-butyl and tert-butyl etc.

By the term "$C_{1-6}$-alkylene" (including those which are part of other groups) are meant branched and unbranched alkylene groups with 1 to 6 carbon atoms and by the term "$C_{1-4}$-alkylene" are meant branched and unbranched alkylene groups with 1 to 4 carbon atoms. Alkylene groups with 1 to 4 carbon atoms are preferred. Examples of these include: methylene, ethylene, propylene, 1-methylethylene, butylene, 1-methylpropylene, 1,1-dimethylethylene, 1,2-dimethylethylene, pentylene, 1,1-dimethylpropylene, 2,2-dimethylpropylene, 1,2-dimethylpropylene, 1,3-dimethylpropylene or hexylene. Unless stated otherwise, the definitions propylene, butylene, pentylene and hexylene include all the possible isomeric forms of the groups in question with the same number of carbons. Thus, for example, propyl includes also 1-methylethylene and butylene includes 1-methylpropylene, 1,1-dimethylethylene, 1,2-dimethylethylene.

If the carbon chain is substituted by a group which together with one or two carbon atoms of the alkylene chain forms a carbocyclic ring with 3, 5 or 6 carbon atoms, this includes, inter alia, the following examples of the rings:

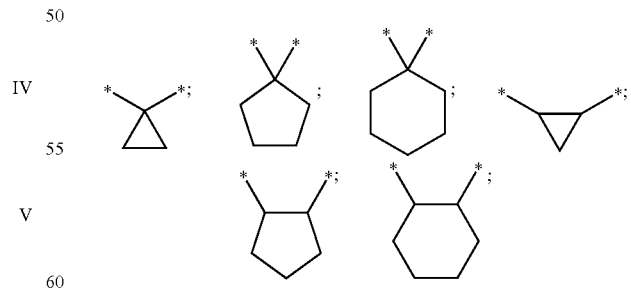

By the term "$C_{2-6}$-alkenyl" (including those which are part of other groups) are meant branched and unbranched alkenyl groups with 2 to 6 carbon atoms and by the term "$C_{2-4}$-alkenyl" are meant branched and unbranched alkenyl groups with 2 to 4 carbon atoms, provided that they have at least one double bond. Alkenyl groups with 2 to 4 carbon atoms are preferred. Examples include: ethenyl or vinyl, propenyl, butenyl, pentenyl or hexenyl. Unless stated otherwise, the definitions propenyl, butenyl, pentenyl and hexenyl include all the possible isomeric forms of the groups in question. Thus, for example, propenyl includes 1-propenyl and 2-propenyl, butenyl includes 1-, 2- and 3-butenyl, 1-methyl-1-propenyl, 1-methyl-2-propenyl etc.

By the term "$C_{2-6}$-alkenylene" (including those which are part of other groups) are meant branched and unbranched alkenylene groups with 2 to 6 carbon atoms and by the term "$C_{2-4}$-alkenylene" are meant branched and unbranched alkylene groups with 2 to 4 carbon atoms. Alkenylene groups with 2 to 4 carbon atoms are preferred. Examples of these include: ethenylene, propenylene, 1-methylethenylene, butenylene, 1-methylpropenylene, 1,1-dimethylethenylene, 1,2-dimethylethenylene, pentenylene, 1,1-dimethylpropenylene, 2,2-dimethylpropenylene, 1,2-dimethylpropenylene, 1,3-dimethylpropenylene or hexenylene. Unless stated otherwise, the definitions propenylene, butenylene, pentenylene and hexenylene include all the possible isomeric forms of the groups in question with the same number of carbons. Thus, for example, propenyl also includes 1-methylethenylene and butenylene includes 1-methylpropenylene, 1,1-dimethylethenylene, 1,2-dimethylethenylene.

By the term "$C_{2-6}$-alkynyl" (including those which are part of other groups) are meant branched and unbranched alkynyl groups with 2 to 6 carbon atoms and by the term "$C_{2-4}$-alkynyl" are meant branched and unbranched alkynyl groups with 2 to 4 carbon atoms, provided that they have at least one triple bond. Alkynyl groups with 2 to 4 carbon atoms are preferred. Examples include: ethynyl, propynyl, butynyl, pentynyl, or hexynyl. Unless stated otherwise, the definitions propynyl, butynyl, pentynyl and hexynyl include all the possible isomeric forms of the groups in question. Thus for example propynyl includes 1-propynyl and 2-propynyl, butynyl includes 1,2- and 3-butynyl, 1-methyl-1-propynyl, 1-methyl-2-propynyl etc.

By the term "$C_{2-6}$-alkynylene" (including those which are part of other groups) are meant branched and unbranched alkynylene groups with 2 to 6 carbon atoms and by the term "$C_{2-4}$-alkynylene" are meant branched and unbranched alkylene groups with 2 to 4 carbon atoms. Preferred are alkynylene groups with 2 to 4 carbon atoms. Examples include: ethynylene, propynylene, 1-methylethynylene, butynylene, 1-methylpropynylene, 1,1-dimethylethynylene, 1,2-dimethylethynylene, pentynylene, 1,1-dimethylpropynylene, 2,2-dimethylpropynylene, 1,2-dimethylpropynylene, 1,3-dimethylpropynylene or hexynylene. Unless stated otherwise, the definitions propynylene, butynylene, pentynylene and hexynylene include all the possible isomeric forms of the groups in question with the same number of carbons. Thus for example propynyl also includes 1-methylethynylene and butynylene includes 1-methylpropynylene, 1,1-dimethylethynylene, 1,2-dimethylethynylene.

By the term "aryl" (including those which are part of other groups) are meant aromatic ring systems with 6 or 10 carbon atoms. Examples include: phenyl or naphthyl, the preferred aryl group being phenyl. Unless otherwise stated, the aromatic groups may be substituted by one or more groups selected from among methyl, ethyl, iso-propyl, tert-butyl, hydroxy, fluorine, chlorine, bromine and iodine.

By the term "aryl-$C_{1-6}$-alkylene" (including those which are part of other groups) are meant branched and unbranched alkylene groups with 1 to 6 carbon atoms, which are substituted by an aromatic ring system with 6 or 10 carbon atoms. Examples include: benzyl, 1- or 2-phenylethyl or 1- or 2-naphthylethyl. Unless stated otherwise, the aromatic groups may be substituted by one or more groups selected from among methyl, ethyl, iso-propyl, tert-butyl, hydroxy, fluorine, chlorine, bromine and iodine.

By the term "heteroaryl-$C_{1-6}$-alkylene" (including those which are part of other groups) are meant—even though they are already included under "aryl-$C_{1-6}$-alkylene"—branched and unbranched alkylene groups with 1 to 6 carbon atoms, which are substituted by a heteroaryl.

A heteroaryl of this kind includes five- or six-membered heterocyclic aromatic groups or 5-10-membered, bicyclic heteroaryl rings which may contain one, two, three or four heteroatoms selected from among oxygen, sulphur and nitrogen, and contain so many conjugated double bonds that an aromatic system is formed. The following are examples of five- or six-membered heterocyclic aromatic groups or bicyclic heteroaryl rings:

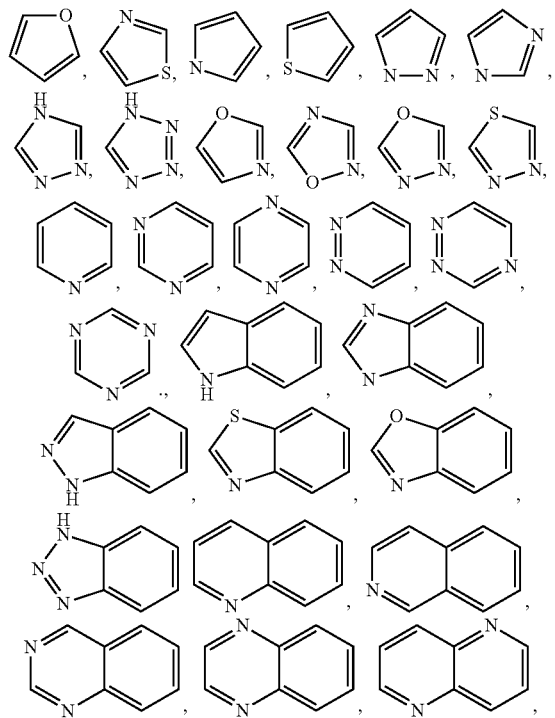

Unless otherwise stated, these heteroaryls may be substituted by one or more groups selected from among methyl, ethyl, iso-propyl, tert-butyl, hydroxy, fluorine, chlorine, bromine and iodine.

The following are examples of heteroaryl-$C_{1-6}$-alkylenes:

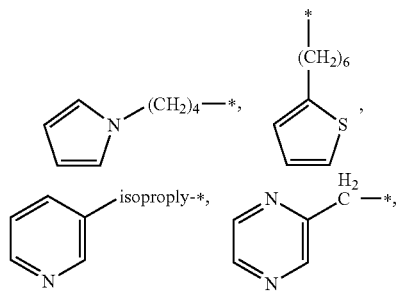

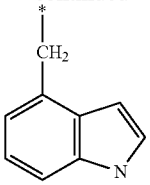

By the term "$C_{1-6}$-haloalkyl" (including those which are part of other groups) are meant branched and unbranched alkyl groups with 1 to 6 carbon atoms, which are substituted by one or more halogen atoms. By the term "$C_{1-4}$-alkyl" are meant branched and unbranched alkyl groups with 1 to 4 carbon atoms, which are substituted by one or more halogen atoms. Alkyl groups with 1 to 4 carbon atoms are preferred. Examples include: $CF_3$, $CHF_2$, $CH_2F$, $CH_2CF_3$.

By the term "$C_{3-7}$-cycloalkyl" (including those which are part of other groups) are meant cyclic alkyl groups with 3 to 7 carbon atoms. Examples include: cyclopropyl, cyclobutyl, cyclopentyl, cyclohexyl or cycloheptyl. Unless otherwise stated, the cyclic alkyl groups may be substituted by one or more groups selected from among methyl, ethyl, iso-propyl, tert-butyl, hydroxy, fluorine, chlorine, bromine and iodine.

By the term "$C_{3-10}$-cycloalkyl" are also meant monocyclic alkyl groups with 3 to 7 carbon atoms and also bicyclic alkyl groups with 7 to 10 carbon atoms, or monocyclic alkyl groups which are bridged by at least one $C_{1-3}$-carbon bridge.

By the term "heterocyclic rings" or "heterocycle" are meant, unless stated otherwise, five-, six- or seven-membered, saturated, partially saturated or unsaturated heterocyclic rings which may contain one, two or three heteroatoms, selected from among oxygen, sulphur and nitrogen, while the ring may be linked to the molecule through a carbon atom or through a nitrogen atom, if there is one. Although included by the term "heterocyclic rings" or "heterocycles", the term "saturated heterocyclic ring" refers to five-, six- or seven-membered saturated rings. Examples include:

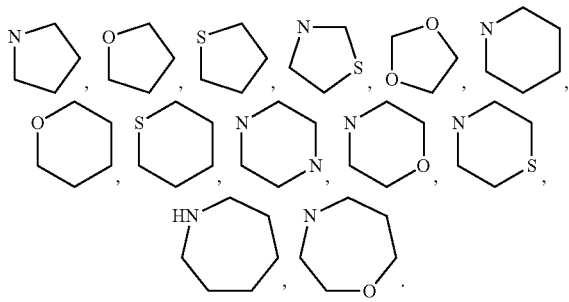

Although included by the term "heterocyclic rings" or "heterocyclic group", the term "partially saturated heterocyclic group" refers to five-, six- or seven-membered partially saturated rings which contain one or two double bonds, without so many double bonds being produced that an aromatic system is formed. Examples include:

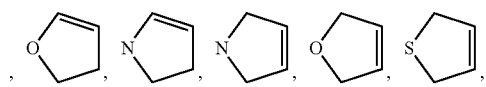

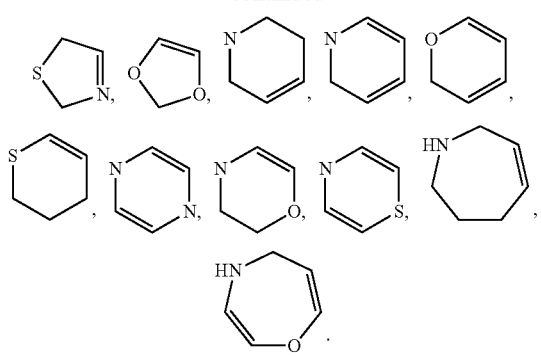

Although included by the term "heterocyclic rings" or "heterocycles", the term "heterocyclic aromatic rings", "unsaturated heterocyclic group" or "heteroaryl" refers to five- or six-membered heterocyclic aromatic groups or 5-10-membered, bicyclic heteroaryl rings which may contain one, two, three or four heteroatoms, selected from among oxygen, sulphur and nitrogen, and contain so many conjugated double bonds that an aromatic system is formed. Examples of five- or six-membered heterocyclic aromatic groups include:

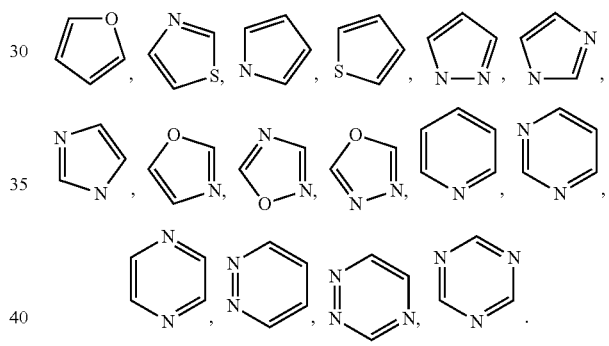

Unless otherwise mentioned, a heterocyclic ring (or heterocycle) may be provided with a keto group. Examples include:

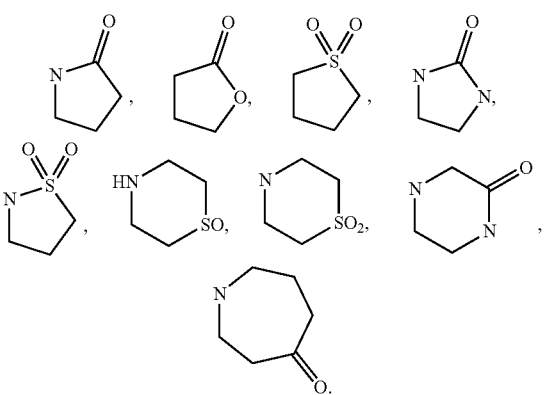

Although covered by the term "cycloalkyl", the term "bicyclic cycloalkyls" generally denotes eight-, nine- or ten-membered bicyclic carbon rings. Examples include

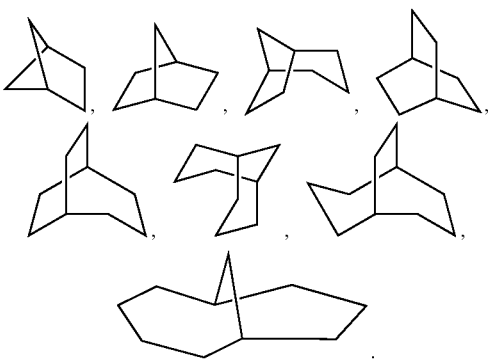

Although already included by the term "heterocycle", the term "bicyclic heterocycles" generally denotes eight-, nine- or ten-membered bicyclic rings which may contain one or more heteroatoms, preferably 1-4, more preferably 1-3, even more preferably 1-2, particularly one heteroatom, selected from among oxygen, sulphur and nitrogen. The ring may be linked to the molecule through a carbon atom of the ring or through a nitrogen atom of the ring, if there is one. Examples include:

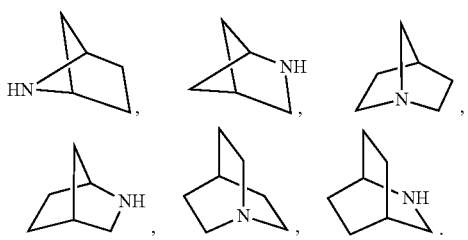

Although already included by the term "aryl", the term "bicyclic aryl" denotes a 5-10 membered, bicyclic aryl ring which contains sufficient conjugated double bonds to form an aromatic system. One example of a bicyclic aryl is naphthyl.

Although already included under "heteroaryl", the term "bicyclic heteroaryl" denotes a 5-10 membered, bicyclic heteroaryl ring which may contain one, two, three or four heteroatoms, selected from among oxygen, sulphur and nitrogen, and contains sufficient conjugated double bonds to form an aromatic system.

Although included by the term "bicyclic cycloalkyls" or "bicyclic aryl", the term "fused cycloalkyl" or "fused aryl" denotes bicyclic rings wherein the bridge separating the rings denotes a direct single bond. The following are examples of a fused, bicyclic cycloalkyl:

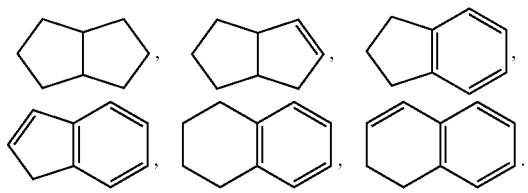

Although included by the term "bicyclic heterocycles" or "bicyclic heteroaryls", the term "fused bicyclic heterocycles" of "fused bicyclic heteroaryls" denotes bicyclic 5-10 membered heterorings which contain one, two, three or four heteroatoms, selected from among oxygen, sulphur and nitrogen and wherein the bridge separating the rings denotes a direct single bond. The "fused bicyclic heteroaryls" moreover contain sufficient conjugated double bonds to form an aromatic system. Examples include pyrrolizine, indole, indolizine, isoindole, indazole, purine, quinoline, isoquinoline, benzimidazole, benzofuran, benzopyran, benzothiazole, benzothiazole, benzoisothiazole, pyridopyrimidine, pteridine, pyrimidopyrimidine,

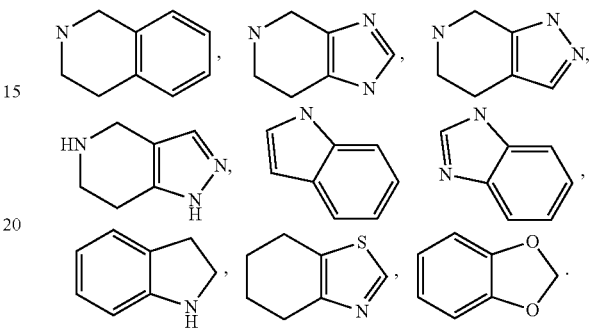

By the term "spiro group" (spiro) are meant 5-10 membered, spirocyclic rings which may optionally contain one, two or three heteroatoms, selected from among oxygen, sulphur and nitrogen, while the ring may be linked to the molecule through a carbon atom or if available through a nitrogen atom. Unless otherwise mentioned, a spirocyclic ring may be provided with an oxo, methyl or ethyl group. Examples of this include:

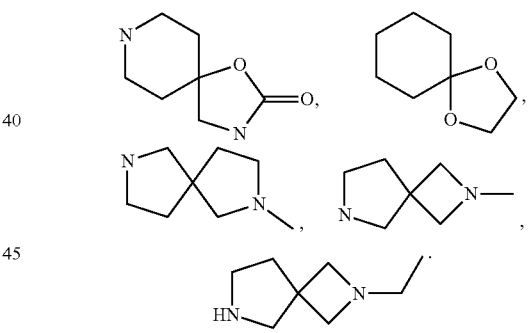

"Halogen" within the scope of the present invention denotes fluorine, chlorine, bromine or iodine. Unless stated to the contrary, fluorine, chlorine and bromine are regarded as preferred halogens.

Compounds of general formula 1 may have acid groups, mainly carboxyl groups, and/or basic groups such as e.g. Amino functions. Compounds of general formula 1 may therefore be present as internal salts, as salts with pharmaceutically usable inorganic acids such as hydrochloric acid, sulphuric acid, phosphoric acid, sulphonic acid or organic acids (such as for example maleic acid, fumaric acid, citric acid, tartaric acid or acetic acid) or as salts with pharmaceutically usable bases such as alkali metal or alkaline earth metal hydroxides or carbonates, zinc or ammonium hydroxides or organic amines such as e.g. diethylamine, triethylamine, triethanolamine, inter alia.

As mentioned previously, the compounds of formula 1 may be converted into the salts thereof, particularly for pharmaceutical use into the physiologically and pharmacologically acceptable salts thereof. These salts may be present on the one hand as physiologically and pharmacologically acceptable acid addition salts of the compounds of formula 1 with inorganic or organic acids. On the other hand, the compound of formula 1 when R is hydrogen may be converted by reaction with inorganic bases into physiologically and pharmacologically acceptable salts with alkali or alkaline earth metal cations as counter-ion. The acid addition salts may be prepared for example using hydrochloric acid, hydrobromic acid, sulphuric acid, phosphoric acid, methanesulphonic acid, acetic acid, fumaric acid, succinic acid, lactic acid, citric acid, tartaric acid or maleic acid. It is also possible to use mixtures of the above-mentioned acids. To prepare the alkali and alkaline earth metal salts of the compound of formula 1 wherein R denotes hydrogen, it is preferable to use the alkali and alkaline earth metal hydroxides and hydrides, of which the hydroxides and hydrides of the alkali metals, particularly sodium and potassium, are preferred, while sodium and potassium hydroxide are particularly preferred.

The compounds of general formula 1 may optionally be converted into the salts thereof, particularly for pharmaceutical use into the pharmacologically acceptable acid addition salts with an inorganic or organic acid. Examples of suitable acids for this purpose include succinic acid, hydrobromic acid, acetic acid, fumaric acid, maleic acid, methanesulphonic acid, lactic acid, phosphoric acid, hydrochloric acid, sulphuric acid, tartaric acid or citric acid. It is also possible to use mixtures of the above-mentioned acids.

The invention relates to the compounds in question, optionally in the form of the individual optical isomers, mixtures of the individual enantiomers or racemates, in the form of the tautomers as well as in the form of the free bases or the corresponding acid addition salts with pharmacologically acceptable acids—such as for example acid addition salts with hydrohalic acids—for example hydrochloric or hydrobromic acid—or organic acids—such as for example oxalic, fumaric, diglycolic or methanesulphonic acid.

The compounds according to the invention may optionally be present as racemates, but may also be obtained as pure enantiomers, i.e. In the (R) or (S) form.

The invention relates to the compounds in question, optionally in the form of the individual optical isomers, diastereomers, mixtures of diastereomers, mixtures of the individual enantiomers or racemates, in the form of the tautomers as well as in the form of the free bases or the corresponding acid addition salts with pharmacologically acceptable acids—such as for example acid addition salts with hydrohalic acids—for example hydrochloric or hydrobromic acid—or organic acids—such as for example oxalic, fumaric, diglycolic or methanesulphonic acid.

The invention relates to the respective compounds of formula 1 in the form of the pharmacologically acceptable salts thereof. These pharmacologically acceptable salts of the compounds of formula 1 may also be present in the form of their respective hydrates (e.g. Monohydrates, dihydrates, etc.) as well as in the form of their respective solvates. By a hydrate of the compound according to the formula 1 is meant, for the purposes of the invention, a crystalline salt of the compound according to formula 1, containing water of crystallisation.

By a solvate of the compound according to formula 1 is meant, for the purposes of the invention, a crystalline salt of the compound according to formula 1, which contains solvent molecules (e.g. Ethanol, methanol etc) in the crystal lattice.

The skilled man will be familiar with the standard methods of obtaining hydrates and solvates (e.g. recrystallisation from the corresponding solvent or from water).

4. METHODS OF PREPARATION

The compounds 1 claimed may be prepared by known methods (e.g. WO 03/057695). The Examples according to the invention were prepared according to Scheme 1-4.

Scheme 1

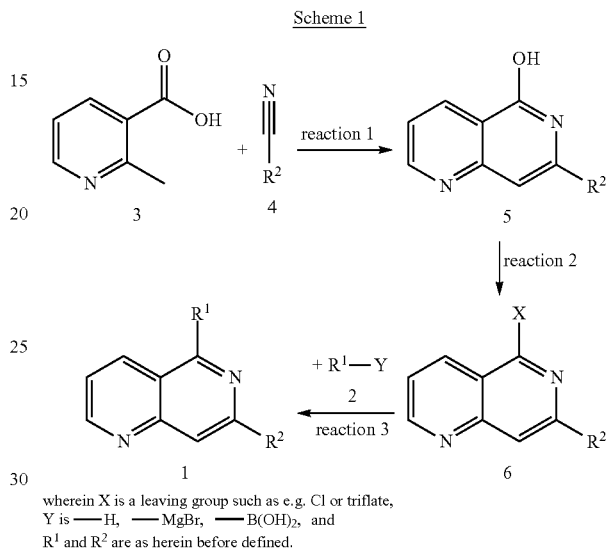

wherein X is a leaving group such as e.g. Cl or triflate,
Y is ——H, ——MgBr, ——B(OH)$_2$, and
R$^1$ and R$^2$ are as herein before defined.

Scheme 2

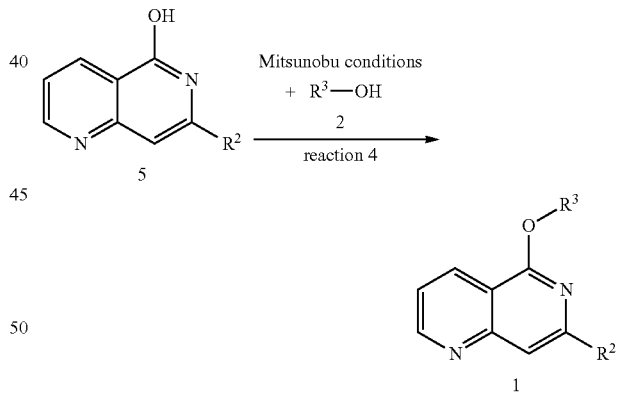

R$^2$ and R$^3$ are as herein before defined.

Scheme 3a

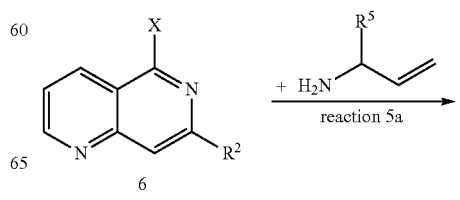

29
-continued
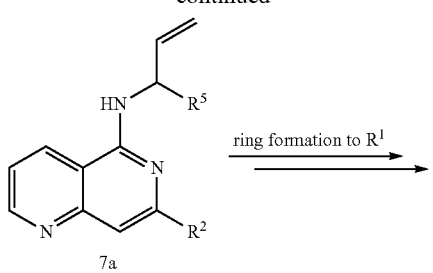
7a
ring formation to R¹ →
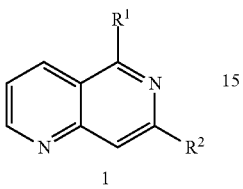
1
with X being Cl or triflate
R⁵, R² and R¹ being defined as above
Scheme 3b
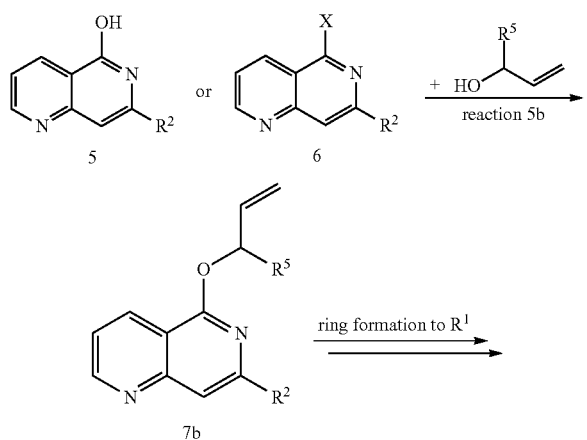
with X being Cl or triflate
R⁵, R² and R¹ being defined as above
Scheme 3c
30
-continued
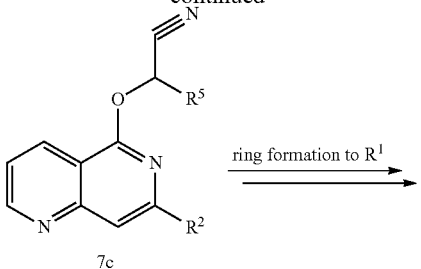
7c
ring formation to R¹ →
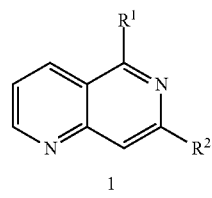
1
with X being Cl or triflate
R⁵, R² and R¹ being defined as above
Scheme 3d
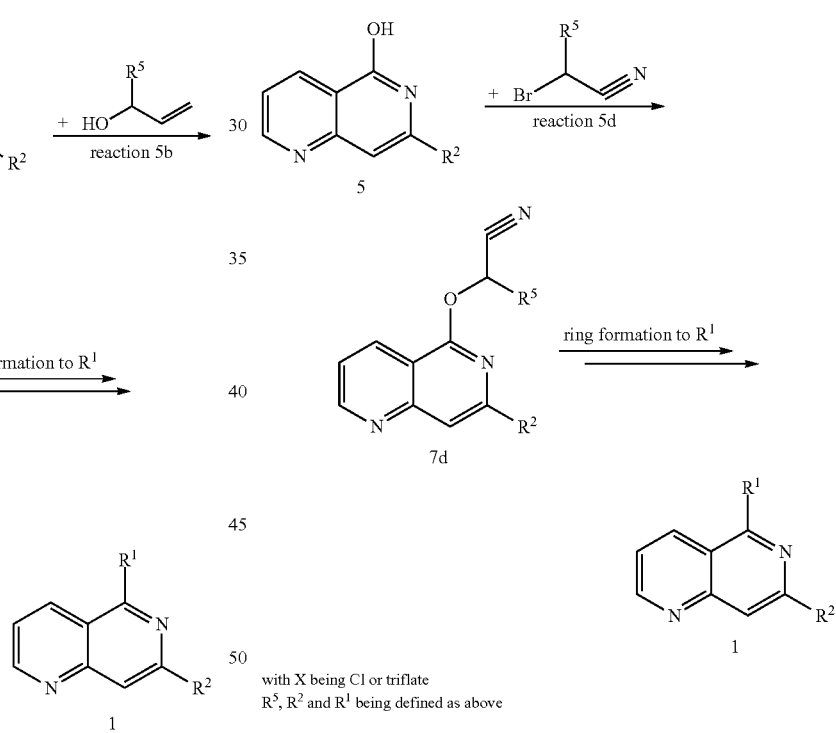
with X being Cl or triflate
R⁵, R² and R¹ being defined as above
Scheme 4
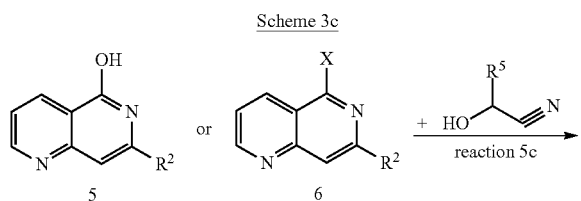
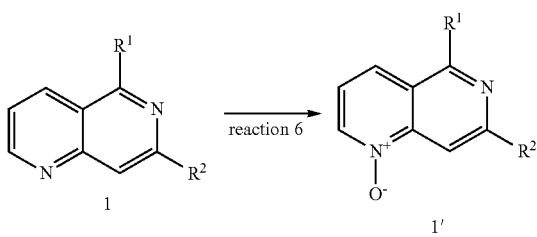

Optionally the groups R¹ or R² (Scheme 1-4) may subsequently be changed e.g. by reductive amination, alkylation, nuclophilic substitution or amide linking.

4.1. Intermediate Products

4.1.1. Synthesis of Compounds 4 from Scheme 1 (Nitrile Derivatives)

Synthesis of 4-trifluoromethoxy-3-fluoro-benzonitrile (4.1) (for Example 1 and 4)

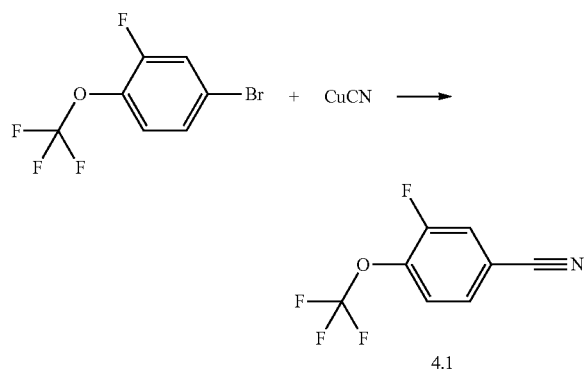

49 g 1-Bromo-3-fluoro-4-trifluoromethoxybenzene was stirred into 100 mL dimethylacetamide together with 20 g copper(I)cyanide at 140° C. overnight. Additional 10 g copper cyanide was added and heating was continued at 150° C. for 4 h. Further 12 g copper cyanide was added and stirring continued at 150° C. overnight. After cooling, the mixture was filtered through Celite/Cellulose and washed with ethyl acetate. The filtrate was added to ice water and filtered again through Celite/Cellulose. The filtrate was extracted with ethyl acetate (×3), dried over magnesium sulfate and concentrated to provide a brown oil which was distilled at 7 mbar and 60° C. to yield two product fractions with 23.5 g and 12 g (content 80%) yield.

Analysis: HPLC-MS (method E): $R_t$: 1.29 min.

The following were prepared using an analogous procedure and the appropriate aryl bromides:

3,5-Difluoro-4-chlorobenzonitrile (4.2) for Examples 2, 8
3-Methoxy-4-chlorobenzonitrile (4.3) for Example 17

Synthesis of 3-chloro-4,5-dimethoxy-benzonitrile (4.4) (for Example 6, 7, 9)

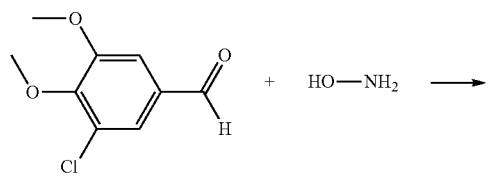

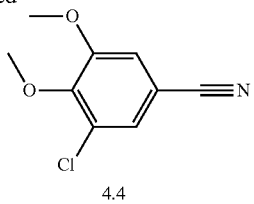

10 g 3-Chloro-4,5-dimethoxybenzaldehyde, 7.3 g sodium formate in 50 mL formic acid was stirred at 95° C. Hydroxylamine hydrochloride was added in portions and the mixture stirred for 4 h at 95° C. and 3 h at 120° C. The formic acid was almost distilled off and the residue was suspended in water. This was added to 700 mL almost saturated sodium chloride solution and the precipitate isolated, washed with water and dried.

Yield: 9 g (91% of theory)
Analysis: HPLC-MS (method E): $R_t$: 1.23 min.

The following were prepared analogously from the appropriate benzaldehyde:

7-Methoxy-benzo[1,3]dioxole-5-carbonitrile (4.5) for Example 21
3,4,5-Triethoxybenzonitrile (4.6) for Example 56

Synthesis of 4-(tetrahydro-pyran-4-yloxy)-3-trifluoromethyl-benzonitrile (4.7) (for Example 15)

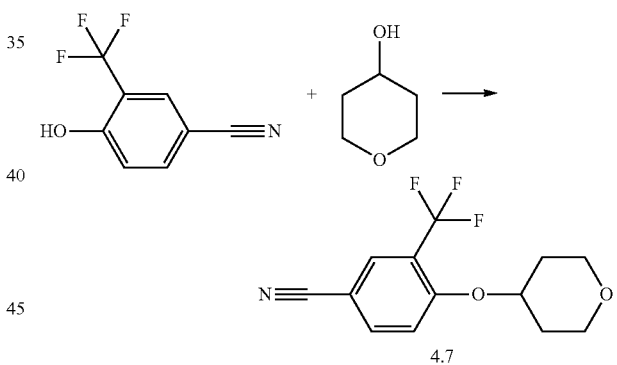

2 g 4-Hydroxy-3-trifluoromethyl-benzonitrile, 5.6 g triphenylphosphine and 1.2 g tetrahydro-4H-pyran-4-ol was suspended in 15 mL tetrahydrofuran at 0° C. before 4.92 g di-tert-butylazodicarboxylate (DBAD) as a solution in 5 mL tetrahydrofuran was added over 15 min. The reaction was warmed to ambient temperature. Additional 2.8 g triphenylphosphine, 0.55 g (5.3 mmol) tetrahydro-4H-pyran-4-ol and 2.46 g di-tert-butylazodicarboxylate (DBAD) in tetrahydrofuran were added and the reaction was stirred overnight. After this time, the reaction was diluted with water and extracted with ethyl acetate (×2). The organic phase was separated and then it was washed with 2N sodium hydroxide, water and saturated sodium chloride, dried over sodium sulfate, filtered and the filtrate was concentrated under reduced pressure. The residue was purified with silica gel chromatography (SiO₂: heptane/ethyl acetate) to provide the title compound.

Yield: 2.77 g (96% of theory)

Analysis: $^1$H NMR (500 MHz, chloroform-d) in ppm 1.88 (2 H, m), 2.02-2.11 (2 H, m), 3.63-3.73 (2 H, m), 3.95 (2 H, m), 4.78 (1 H, m), 7.07 (1 H, d), 7.78 (1 H, m), 7.89 (1 H, m).

Synthesis of 3,5-dimethoxy-4-(2-morpholine-4-yl-ethoxy)-benzonitrile (4.8) (for Example 18, 19, 20)

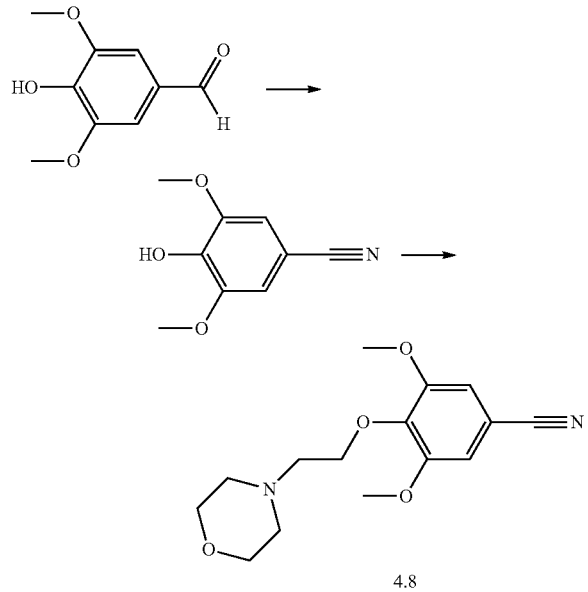

Step 1

18.5 g Syringealdehyde, 14.5 g sodium formate in 100 mL formic acid was stirred at 85° C. 7.5 g Hydroxylamine hydrochloride was added in portions and the mixture stirred for 1 h at 85° C. The mixture was poured onto 1000 mL of almost saturated sodium chloride solution and the precipitate isolated, washed with water and petroleum ether and dried.

Yield: 16.06 g (90% of theory)
Analysis: HPLC-MS (method D): $R_t$: 1.20 min.

Step 2

6.06 g 3,5 Dimethoxy-4-hydroxy-benzonitrile was dissolved in 20 mL dimethylacetamide, 5.2 g potassium carbonate and 6.7 g N-(2-chloroethyl)morpholine hydrochloride was added and the mixture was stirred at 100° C. for 6 h. The solvent was distilled off and the residue was co-evaporated twice with toluene. The residue was suspended in dichloromethane, filtered and the filtrate was concentrated.

Yield: 6.95 g (67% of theory)
Analysis: HPLC-MS (method D): $R_t$: 1.13 min.

Synthesis of 3,5-dimethoxy-4-(4-tetrahydropyranyl)-benzonitrile (4.9) (for Example 44)

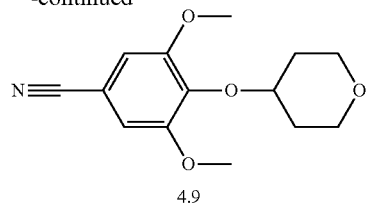

15 g 3,5 Dimethoxy-4-hydroxy-benzonitrile (for synthesis see: benzonitrile for Example 18), 28 g triphenylphosphine and tetrahydro-4H-pyran-4-ol was suspended in 150 mL tetrahydrofuran at 0° C. before 25 g di-tert-butylazodicarboxylate (DBAD) was added. The reaction was stirred overnight at ambient temperature. After this time the solvent was distilled off and the residue was dissolved in ethyl acetate. The organic phase was extracted with 2N sodium hydroxide (×2), 4N hydrochloric acid (×3), saturated sodium chloride solution, dried and concentrated. The residue was purified with silica gel chromatography (SiO$_2$: cyclohexane/ethyl acetate 5:1) and the appropriate fractions were combined and concentrated. The residue was dissolved in formic acid and stirred at 50° C. for 2 h, concentrated and dissolved in ethyl acetate. The organic phase was washed with 2N hydrochloric acid and saturated sodium chloride solution, dried and concentrated.

Yield: 21.3 g (94% of theory)
Analysis: HPLC-MS (method D): $R_t$: 1.42 min.

Synthesis of 4-methoxy-3-(3-morpholine-4-yl-propoxy)-benzonitrile (4.10) (for Example 47)

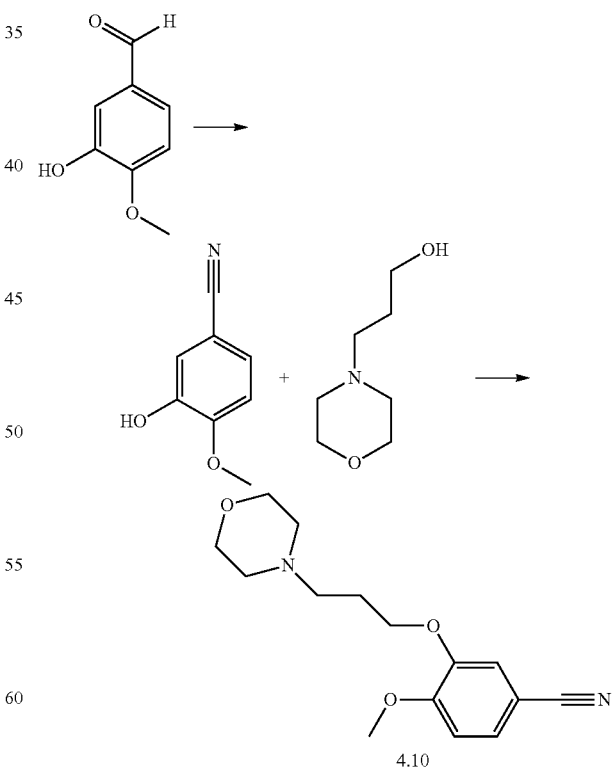

Step 1

14.2 g Isovanillin, 15 g sodium formate in 75 mL formic acid was stirred at 85° C. 9 g Hydroxylamine hydrochloride was added in portions and the mixture stirred for 4 h at 85° C. The mixture was poured on to an almost saturated sodium chloride solution and the precipitate was isolated, washed with water and petroleum ether and dried.

Yield: 14.2 g (93% of theory)

Analysis: HPLC-MS (method D): $R_t$: 1.18 min

Step 2

5 g 3-Morpholine-4-yl-propan-1-ol was dissolved in dichloromethane, cooled to 0° C., 3.25 mL methanesulfonylchloride was added and the mixture was stirred for 2 h at ambient temperature. Then 7 g potassium carbonate and 3-hydroxy-4-methoxybenzonitrile were added and the reaction was stirred at 45° C. for 3 h. The mixture was concentrated and 70 mL dimethylacetamide was added and stirred at 120° C. for 3 h. After this time, the mixture was diluted with dichloromethane and extracted with water, the organic phase was dried over magnesium sulfate and concentrated.

Yield: 8.6 g (85% content, 77% of theory)

Synthesis of 3-methoxy-4-(4-(methyl-3-oxo-piperazine-1-yl)-cyclohexyloxy)-benzonitrile (4.11) (for Example 52)

4-(4-hydroxy-cyclohexyl)-1-methyl-piperazine-2-one:

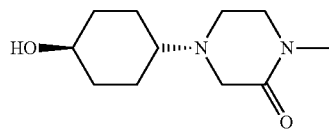

4-(4-Hydroxy-cyclohexyl)-1-methyl-piperazine-2-one may be synthesised according to the following literature: Himmelsbach, Frank; Jung, Birgit; Lotz, Ralf; Ostermeier, Markus WO2008095847

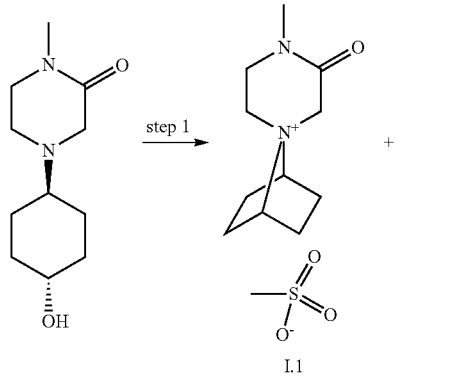

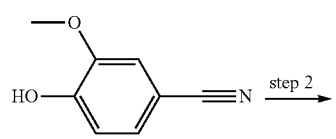

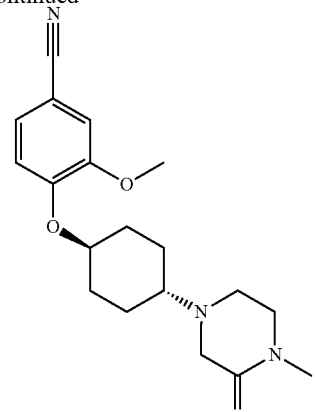

4.11

Step 1

5 g 4-(4-Hydroxy-cyclohexyl)-1-methyl-piperazine-2-one was dissolved in 50 mL acetonitrile and concentrated by approximately 50%. The suspension was diluted with 25 mL tetrahydrofuran, cooled to 0° C. and 6.16 mL of triethylamine and 1.87 mL methanesulfonylchloride was added dropwise. The mixture was stirred for 2 h at ambient temperature. The precipitate was filtered and the filtrate was stirred at reflux for 4 h. After cooling the precipitate was removed by filtration, washed with ethyl acetate, dried and concentrated.

Yield: 4.15 g of 1.1 (71% of theory)

Step 2

2 g 4-Hydroxy-3-methoxy-benzonitrile, 4.15 g intermediate 1.1 and 2.8 g potassium carbonate was suspended in 20 mL dimethylacetamide and stirred at 120° C. for 3 h. After cooling the mixture was diluted with dichloromethane, washed with water and the organic phase was dried over magnesium sulfate and concentrated.

Yield: 4.54 g (95% content, 94% of theory)

Synthesis of 3-methoxy-4-(4-methoxy-benzyloxy)-benzonitrile (4.12) (for Example 53, 54, 55, 61, 62, 10, 116)

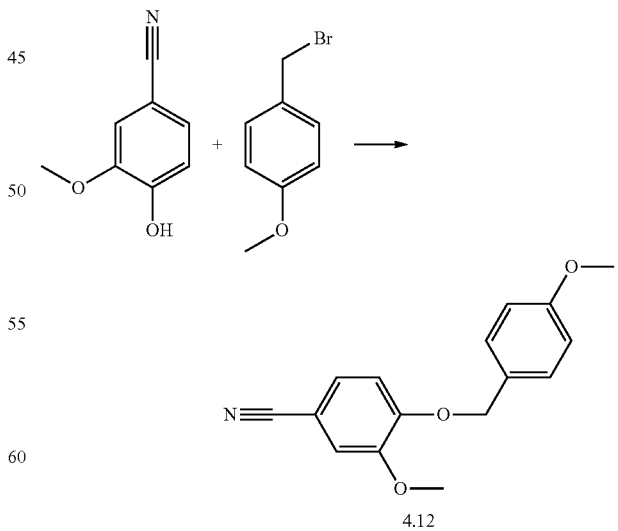

3.73 g 4-Hydroxy-3-methoxybenzonitrile was dissolved in dimethylformamide and 3.8 g potassium carbonate was added before the mixture was stirred for 15 min. 5 g para- Methoxybenzylbromide was added and stirring was continued for 1 h. The mixture was diluted with dichloromethane and water. The phases were separated and the water phase extracted again with dichloromethane. The combined organic phases were dried over magnesium sulfate and concentrated.

Yield: 6.66 g (90% content, 89% of theory)

Synthesis of 4-(3-dimethylamino-propoxy)3-methoxy-benzonitrile (4.13) (for Example 57)

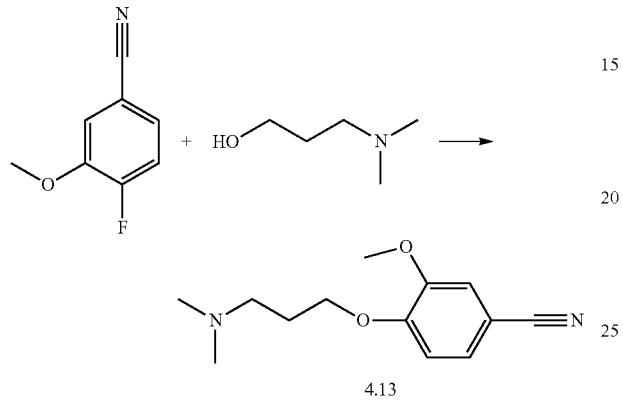

4.13

15 g 4-Fluoro-3-methoxybenzonitrile and 12 mL 3-dimethylamino-1-propanol was dissolved 150 mL tetrahydrofuran. 21.7 g Potassium hexamethyldisilazide was added and the mixture was stirred at 65° C. for 6 h. the mixture was concentrated to 50 mL and the residue diluted in ethyl acetate, washed with water and saturated sodium chloride solution and the organic phase dried over magnesium sulfate.

Yield: 15.5 g (content 90%, 60% yield)

Synthesis of 3-Methoxy-4-(tetrahydro-pyran-4-yloxy)-benzonitrile (4.14) (for Example 59, 60, 63-65)

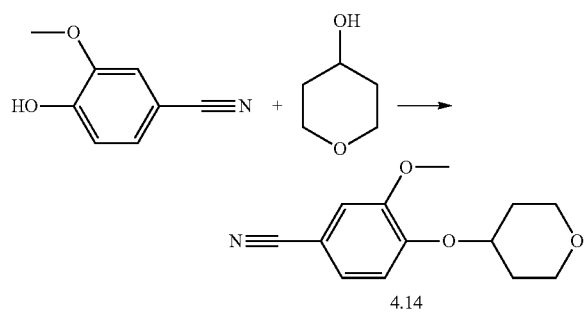

4.14

8 g 3-Methoxy-4-hydroxy-benzonitrile, 28.1 g triphenylphosphine and 5.48 g tetrahydro-4H-pyran-4-ol was suspended in 1 L tetrahydrofuran at 0° C. before 24.7 g di-tert-butylazodicarboxylate (DBAD) was added over 30 min. The reaction was warmed to ambient temperature and stirred for 2 d. After this time, the reaction was diluted with water and ethyl acetate. The organic phase was separated and then it was washed with 1N sodium hydroxide, water and saturated sodium chloride, dried over sodium sulfate, filtered and the filtrate was concentrated under reduced pressure. The residue was purified on silica gel chromatography (SiO$_2$: heptane/ethyl acetate 8:2 to 7:3) to provide the title compound.

Yield: 10.2 g (81% of theory)

Analysis: HPLC-MS (Method C): R$_t$: 1.72 min, (M+H)$^+$: 234.

Synthesis of 3-methoxy-4-(1-methyl-piperidine-3-yloxy)-benzonitrile and 3-methoxy-4-(1-methyl-pyrrolidin-2-ylmethoxy)-benzonitrile (4.15 and 4.16) (for Examples 105, 106)

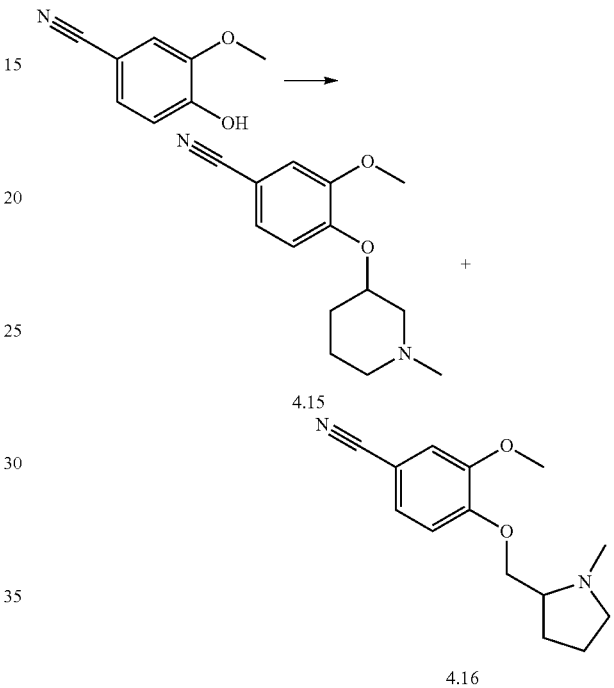

4.0 g 4-Hydroxy-3-methoxy-benzonitrile, 14.1 g triphenylphosphine and 3.09 g tetrahydro-4H-pyran-4-ol was suspended in 250 mL tetrahydrofuran at 0° C. before 12.4 g di-tert-butylazodicarboxylate (DBAD) as a solution in 250 mL tetrahydrofuran was added over 1 h. The reaction was warmed to ambient temperature overnight. After this time, additional 7.04 g triphenylphosphine, 1.55 g (tetrahydro-4H-pyran-4-ol and 6.18 g di-tert-butylazodicarboxylate (DBAD) in tetrahydrofuran was added and the reaction was stirred overnight. After this time, the reaction was diluted with water and extracted with ethyl acetate. The organic phase was separated and then it was washed with 1N sodium hydroxide (×2), water and saturated sodium chloride, dried over sodium sulfate, filtered and the filtrate was concentrated under reduced pressure. The crude product was re-dissolved in tert-butyl methyl ether and washed with 3N hydrochloric acid (×3). The combined acidic aqueous was washed with tert butyl methyl ether and then made basic to pH ~9-10 with 5N sodium hydroxide and extracted with ethyl acetate (×3). The combined organic fractions were separated and then it was washed with saturated sodium chloride, dried over sodium sulfate, filtered and the filtrate was concentrated under reduced pressure. The residue was purified with silica gel chromatography (SiO$_2$: methanol/dichloromethane: 5% to 10%) and then again by silica gel chromatography (SiO$_2$: 7N aqueous ammonia in methanol/dichloromethane: 1% to 10%) to provide the title compounds as a mixture that were used for the next step.

Yield: 4.89 g (74% of theory)

Analysis: HPLC-MS (Method B): R$_t$: 1.10 min (M+H)$^+$=247

Synthesis of 3,4-dimethoxy-5-methyl-benzonitrile (4.17) (for Example 107, 108)

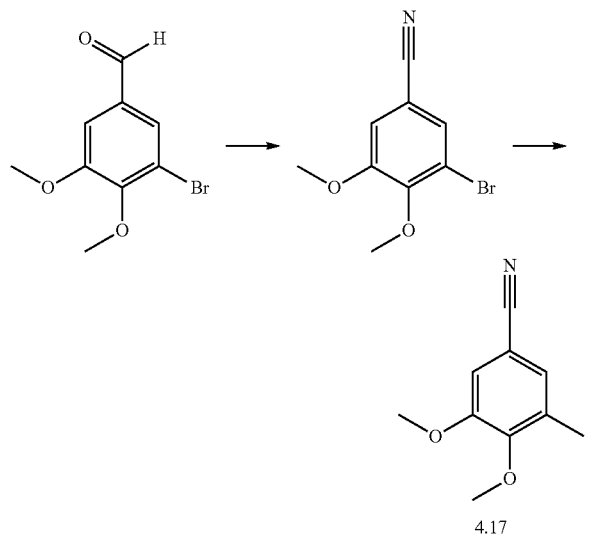

Step 1

11 g 3-Bromo-4,5-dimethoxybenzaldehyde, 6.5 g sodium formate were dissolved in 50 mL of formic acid and stirred at 95° C. 3.6 g Hydroxylamine hydrochloride was added in portions and the mixture stirred for 4 h at 95° C., 2 days at 50° C. and 3 h at 120° C. The mixture was poured on to 700 mL of an almost saturated sodium chloride solution/ice mixture and the precipitate isolated, washed with water and dried to provide 3-bromo-4,5 dimethoxybenzonitrile.

Yield: 11 g (100% of theory)
Analysis: HPLC-MS (method E): $R_t$: 1.26 min

Step 2

50 mg [1,1'-Bis(diphenylphosphino)ferrocene]dichloropalladium (II) and 5 mL tetrahydrofuran was stirred for 10 min at ambient temperature before 500 mg 3-bromo-4,5 dimethoxybenzonitrile, 0.1 mL trimethylboroxine and 0.85 g cesium carbonate as a solution in 1 mL water were added. The suspension was stirred at 100° C. for 4 h and then diluted with water and ethyl acetate. The phases were separated and the water phase was extracted with additional ethyl acetate (×2). The organic phases were combined, dried over magnesium sulfate and concentrated. The residue was purified with silica gel chromatography (SiO$_2$: cyclohexane/ethyl acetate 9:1 to 7:3) to provide 4.17.

Yield: 300 mg (82% of theory)
Analysis: HPLC-MS (method E): $R_t$: 1.19 min

Synthesis of 4-methoxy-3-(isopropyl)-benzonitrile (4.18) (for Example 109)

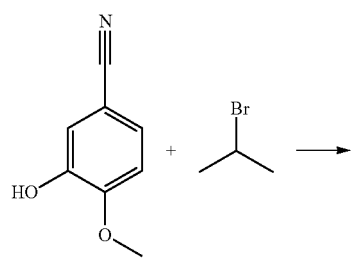

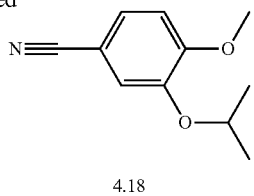

8 g Potassium carbonate and 2.7 g 3-hydroxy-4-methoxybenzonitrile (for synthesis see Example 47) was dissolved in 25 mL dimethylformamide. 2.15 mL 2-Bromopropane was added and the mixture stirred at 85° C. for 3 h. The mixture was concentrated, diluted in ethyl acetate and washed with water (×2) and saturated sodium chloride solution, dried over magnesium sulfate and concentrated.

Yield: 3.7 g (90% content, 96% of theory)
Analysis: HPLC-MS (method D): $R_t$: 1.49 min

Synthesis of 3-Methoxy-4-(tetrahydro-pyran-4-yl-methoxy)-benzonitrile (For Example 102)

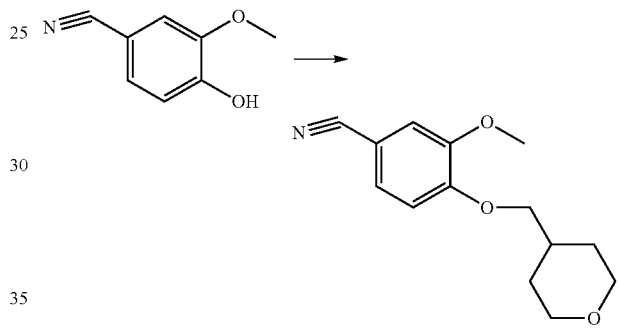

1.0 g 4-Hydroxy-3-methoxybenzonitrile, 1.1 g potassium carbonate and 2.0 g 4-(iodomethyl)-tetrahydropyran were placed in 20 mL acetone and heated to reflux overnight. After this time, 1.1 g potassium carbonate was added and the reaction was heated at reflux for a further 2 h before more 0.93 g potassium carbonate was introduced and reflux was continued for a further 3 h. The mixture was then cooled to ambient temperature and concentrated under reduced pressure. The material that remained was partitioned between diethyl ether and water and the aqueous phase was removed and extracted with additional diethyl ether. The combined organic fractions were dried, filtered and the filtrate was concentrated under reduced pressure. Purification by silica gel chromatography (SiO$_2$: ethyl acetate/heptanes: 10% to 30%) provided the title compound.

Yield: 307 mg (19% of theory)
Analysis: HPLC-MS (Method B): $R_t$: 1.85 min.

Synthesis of 3-fluoro-4-isopropoxy-benzonitrile (For Example 103)

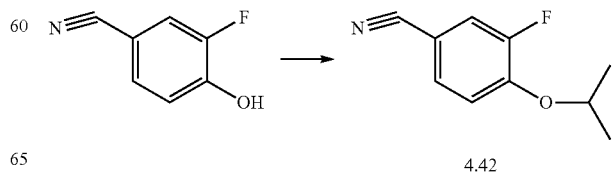

5.0 g 3-Fluoro-4-hydroxy-benzonitrile, 7.3 mL isopropyl iodide and 6.05 g potassium carbonate were placed in 54 mL acetone and heated to reflux where the reaction was maintained for 24 h. After this time, the mixture was cooled to ambient temperature and concentrated under reduced pressure. The material that remained was partitioned between ethyl acetate and water and the aqueous phase was removed and extracted with additional ethyl acetate. The combined organics were dried, filtered and the solvent was removed from the filtrate under reduced pressure to give the title compound that was used without further purification.

Yield: 4.75 g (73% of theory)

Analysis: HPLC-MS (Method B): $R_t$: 2.01 min $(M+H)^+$=180.

Synthesis of 3-Methoxy-4-(1-methyl-piperidine-4-yloxy)-benzonitrile (For Example 104)

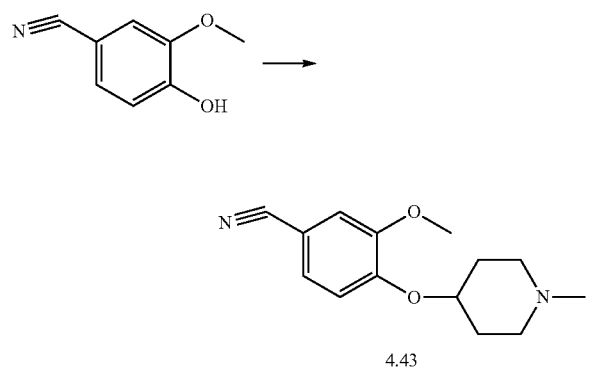

4.43

2.04 g 4-Hydroxy-3-methoxy-benzonitrile, 1.57 g 1-methyl-piperidine-4-ol and 7.17 g triphenylphosphine were placed in 125 mL tetrahydrofuran at 0° C. before 6.30 g di-tert-butylazodicarboxylate (DBAD) as a solution in 125 mL tetrahydrofuran was added over 15 min. The reaction was stirred for 5 min at 0° C. and then warmed to ambient temperature where it was maintained overnight. After this time additional 0.31 g 1-methyl-piperidine-4-ol, 1.79 g triphenylphosphine and 1.58 g di-tert-butylazodicarboxylate (DBAD) were added and the reaction was stirred for a further 3 h at ambient temperature. The mixture was then diluted with ethyl acetate and water and the organic phase was separated, washed with 1N sodium hydroxide (x2), water, saturated sodium chloride solution, dried over sodium sulfate, filtered and the filtrate was concentrated under reduced pressure. The material that remained was dissolved in tert-butyl dimethyl ether and washed with 3N hydrochloric acid. The aqueous phase was then made basic with 5N sodium hydroxide and extracted with ethyl acetate (x3). The combined organic fractions were washed water, saturated sodium chloride solution, dried over sodium sulfate, filtered and the filtrate was concentrated under reduced pressure. Purification on silica gel chromatography ($SiO_2$: dichloromethane/methanol 5% then dichloromethane/7N ammonia in methanol 5%) provided the title compound.

Yield: 2.48 g (73% of theory)

Analysis: HPLC-MS (Method B): $R_t$: 1.11 min. $(M+H)^+$=247

Synthesis of 4-isopropoxy-3-methoxy-benzonitrile (For Example 111-113)

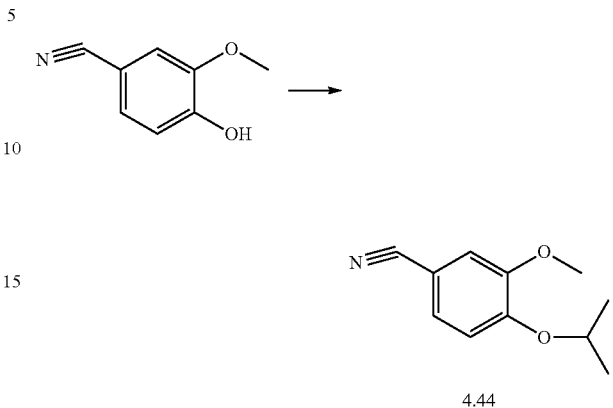

4.44

25 g 4-Hydroxy-3-methoxy-benzonitrile, 27.8 g potassium carbonate and 33.5 mL isopropyl iodide were placed in 250 mL acetone and heated to reflux where they were maintained for 22 h. After this time the mixture was cooled to ambient temperature and concentrated under reduced pressure. The crude product was partitioned between ethyl acetate and water and the aqueous phase was separated and extracted with additional ethyl acetate. The combined organic fractions were dried, filtered and the solvent was removed from the filtrate under reduced pressure to give the title compound which was used without further purification.

Yield: 30.5 g (95% of theory)

Analysis: HPLC-MS (Method B): $R_t$: 1.90 min. $(M+H)^+$=192.

6-Cyano-3,4-dihydro-1H-isoquinoline-2-carboxylic tert-butyl ester (4.19) (for Example 120)

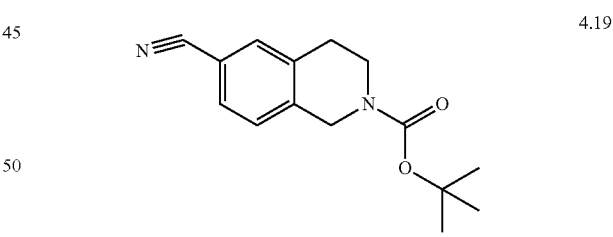

4.19

6-Cyano-3,4-dihydro-1H-isoquinoline-2-carboxylic tert-butyl ester may be synthesised according to the following literature: Subramanian, L. R. Introduction of the cyano group by substitution of oxygen functions. Science of Synthesis (2004), 19 197-213.

The following benzonitriles are commercially obtainable:

6-Trifluormethyl-nicotinonitrile (4.36) for Example 3

4-Methoxy-3-trifluormethylbenzonitrile (4.37) for Example 5

4-Trifluoromethylbenzonitrile (4.20) for Example 11

5-Methyl-3-isoxazolecarbonitrile (4.21) for Example 12

3,5-Difluoro-4-methoxybenzonitrile (4.38) for Example 13, 14

4-Methoxy-3-chlorobenzonitrile (4.22) for Example 16

6-Methoxy-nicotinonitrile (4.23) for Example 22, 46

3,4,5-Trimetoxybenzonitrile (4.24) for Examples 24-43

4-Methyl-3,4-dihydro-2H-benzo[1,4]oxazine-6-carbonitrile (4.25) for Example 23

6-Morpholino-nicotinonitrile (4.26) for Example 45

4-Methoxy-3-fluoro-benzonitrile (4.27) for Example 48

4-Fluoro-3-methoxybenzonitrile (4.39) for Example 49

Benzo[1,3]dioxole-5-carbonitrile (4.28) for Example 58

3,4-Dimethoxybenzonitrile (4.29) for Examples 66-78, 80-86, 88-101

2,3-Dimethoxybenzonitrile (4.40) for Example 79

3,5-Dimethoxybenzonitrile (4.47) for Example 87

3-Methoxy-4-propoxy-benzonitrile (4.30) for Example 110

2-Fluoro-benzonitrile (4.31) for Example 115

Pyridine-2-carbonitrile (4.32) for Example 117

4-Methoxybenzonitrile (4.45) for Example 118

4-Isopropoxybenzonitrile (4.46) for Example 119

Terephthalonitrile (4.33) for Example 121, 122

Cyclopropylnitrile (4.34) for Example 123

Benzonitrile (4.35) for Examples 124, 125, 126

4.1.2. Synthesis of $R^1$ Derivatives with Formula 2

Synthesis of (R)-4-(hydroxymethyl)-1-((R)-1-phenylethyl)pyrrolidin-2-one (2.1) (for Example 11, 23, 78, 120)

5 g (1'R,3R)-1-(1'Phenylethyl)-5-oxo-3-pyrrolidine carboxylic acid was dissolved in 50 mL tetrahydrofuran, then the solution was cooled to 0° C. 16.5 mL borane dimethyl sulfide (2 M in tetrahydrofuran) was added dropwise over 30 min and the reaction solution was slowly warmed to 25° C. and stirred for a further 2 h at 25° C. The reaction mixture was concentrated, diluted in dichloromethane and washed with sodium bicarbonate solution. The water phase was extracted with dichloromethane (×2) and the combined organic phases were dried over magnesium sulfate and concentrated.

Yield: 5.5 g (content 80%, 94% of theory)

Analysis: HPLC-MS (method D): $R_t$=1.20 min $(M+H)^+$=220

Synthesis of (R)-4-(hydroxymethyl)pyrrolidine-2-one (2.2) (for Example 5, 6, 10, 12, 13, 15-18, 32, 44, 47-55, 57, 58, 60-62, 79, 102, 103-107 109-111, 114, 116, 118, 119, 124)

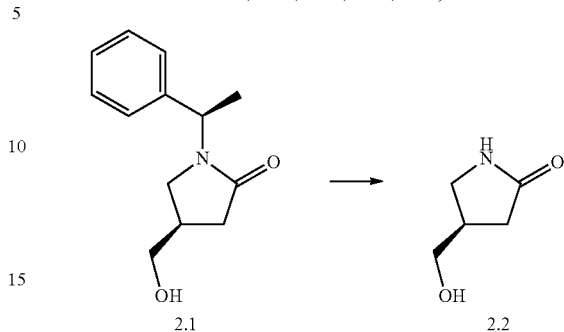

2 g (R)-4-(hydroxymethyl)-1-((R)-1-phenylethyl)pyrrolidine-2-one (2.1) was placed in 5 mL trifluoroacetic acid and stirred at 150° C. for 60 min in the microwave. Additional 10 mL trifluoroacetic acid was added and the mixture heated again to 150° C. for 60 min in the microwave. The mixture was concentrated, diluted with water and warmed to 60° C. for 30 min. The water phase was extracted with dichloromethane and the water phase was freeze-dried.

Yield: 1.6 g (content 65%, 99% of theory)

Synthesis of (R)-4-((R)-1-hydroxyethyl)pyrrolidine-2-one (2.3) (for Examples 1-4, 7-9, 14, 19, 21, 22, 35, 37, 45, 46, 56, 63, 85, 87, 108, 112, 115, 117, 121, 123, 126, 127) and (R)-4-((S)-1-hydroxyethyl)pyrrolidine-2-one (2.4) for Examples (84, 125)

Step 1

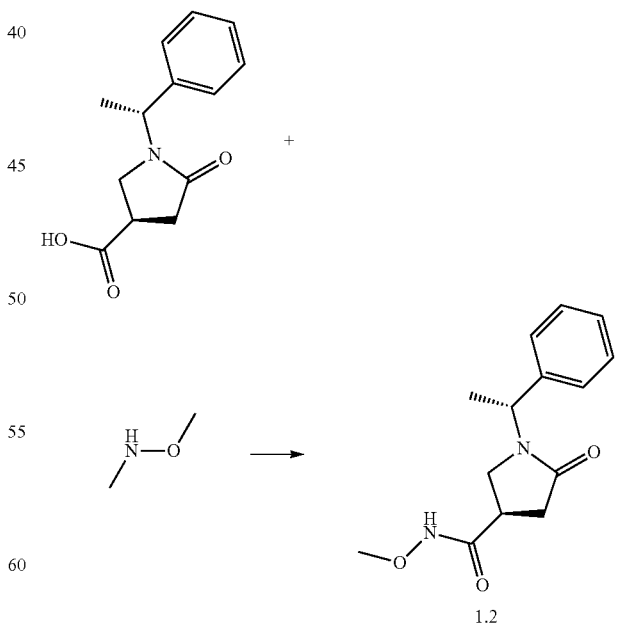

20 g (1'R,3R)-1-(1'-Phenylethyl)-5-oxo-3-pyrrolidinecarboxylic acid and N,O-dimethylhydroxylamine hydrochloride was dissolved in 100 mL dimethylformamide at 0° C. 13.9 g Hydroxybenzotriazole, 19.8 g 1-ethyl-3-(3-dimethylaminopropyl)carbodiimide (EDC) and 20 mL N-methylmorpholine were added and the mixture stirred at 0° C. for 2 h and overnight at ambient temperature. The reaction mixture was diluted with ethyl acetate and the organic phase was washed with 10% citric acid solution, 5% sodium bicarbonate and saturated sodium chloride solution. The organic phase was dried and concentrated.

Yield: 23.8 g of 1.2 (95% of theory)

Analysis (method E): $R_t$: 1.12 min, $(M+H)^+$: 277

Step 2

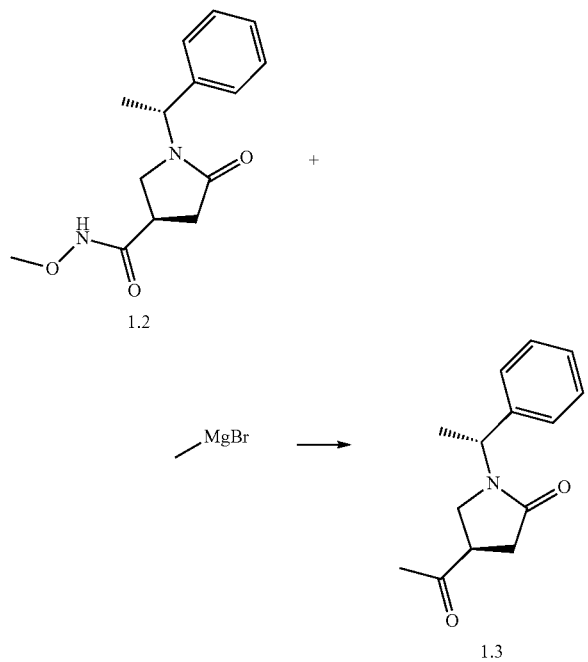

The reaction was carried out under a nitrogen atmosphere.

11.95 g (R)—N-methoxy-5-oxo-1-((R)-1-phenylethyl)pyrrolidine-3-carboxamide (I.2) were placed in 100 mL tetrahydrofuran at −10° C. 30 mL Methylmagnesium bromide in diethyl ether solution was added within 15 min (white suspension, temperature at +10° C.) and the mixture was stirred at −10° C. for 2 h and then warmed to ambient temperature. The mixture was diluted with ethyl acetate and washed with 1N hydrochloric acid, saturated sodium bicarbonate and saturated sodium chloride solution.

Yield: 9.45 g of 1.3 (95% of theory)

Step 3

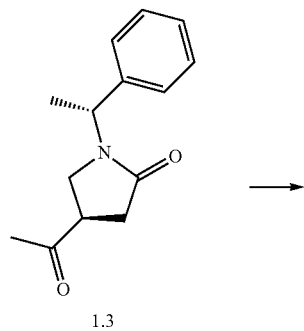

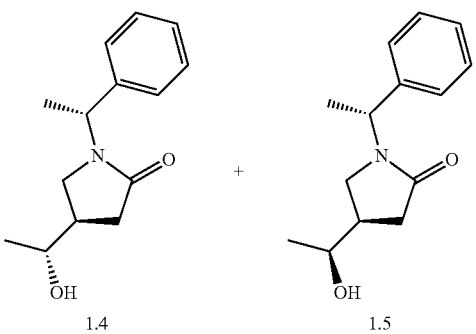

Reaction was carried out under argon atmosphere.

8.5 g (26.8 mmol) (R)-4-acetyl-1-((R)-1-phenylethyl)pyrrolidine-2-one (I.3) were placed in 40 mL dichloromethane at −50° C. and 40.5 mL (40.5 mmol) lithium 9-BBN hydride in tetrahydrofuran was added dropwise. During the addition the temperature increased to −30° C. The mixture was then stirred at −45° C. for 1 h. After this time, phosphate buffer was added and the mixture was warmed to ambient temperature, diluted with dichloromethane and extracted with water. The organic phase was dried over magnesium sulfate, concentrated and purified via prep RP-HPLC (X-bridge C18).

Yield: 2.60 g of 1.4 (30% of theory)

Analysis (method E): $R_t$: 1.08 min, $(M+H)^+$: 234

Yield: 2.60 g of 1.5 (30% of theory)

Analysis (method E): $R_t$: 1.12 min, $(M+H)^+$: 234

Step 4

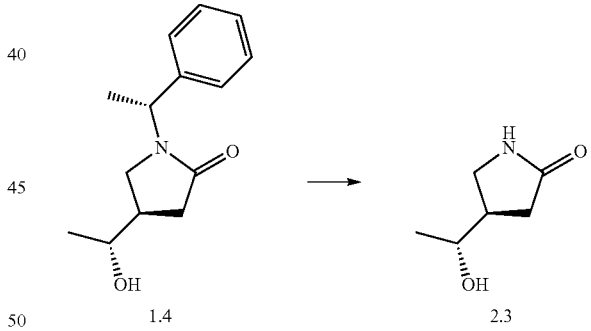

2.1 g (R)-4-((R)-1-hydroxyethyl)-1-((R)-1-phenylethyl)pyrrolidin-2-one (I.4) was placed in 15 mL trifluoroacetic acid at 150° C. in the microwave for 90 min. The solution was concentrated, diluted with water and stirred at 50° C. for 30 min. The water phase was extracted with dichloromethane and the water phase was freeze-dried. Yield (2.3): 1.17 g (content 90%, 91% of theory)

(R)-4-((S)-1-hydroxyethyl)pyrrolidine-2-one (2.4) (for Examples 84 and 125) was synthesised analogously from (I.5)

Synthesis of (R)-4-(1-hydroxyethyl)pyrrolidine-2-one (2.5) (for Example 83) was prepared analogously from (I.4) and (I.5) (synthesis as for (R)-4-(1-hydroxyethyl)pyrrolidine-2-one)

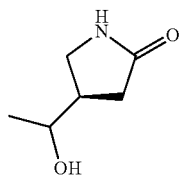

2.5

Synthesis of (R)-4-((R)-1-hydroxypropyl)pyrrolidine-2-one (2.6) (for Examples 20, 41, 65, 94, 113) was prepared analogously to the synthesis of (R)-4-((R)-1-hydroxyethyl)pyrrolidine-2-one (2.3)

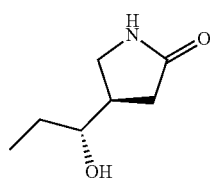

2.6

Synthesis of (R)-4-((S)-1-hydroxypropyl)pyrrolidine-2-one (2.7) (for Example 93) was prepared analogously to the synthesis of (R)-4-((S)-1-hydroxyethyl)pyrrolidine-2-one) (2.4)

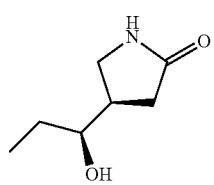

2.7

Synthesis of (R)-4-(1-hydroxypropyl)pyrrolidine-2-one (2.8) (for Example 92) was prepared analogously to the synthesis of (R)-4-(1-hydroxyethyl)pyrrolidine-2-one (2.5)

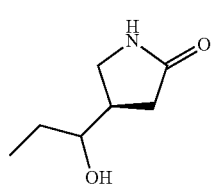

2.8

Synthesis of (R)-4-(1-hydroxyallyl)pyrrolidine-2-one (2.9) (for Example 97) was prepared analogously to the synthesis of (R)-4-(1-hydroxyethyl)pyrrolidine-2-one (2.5)

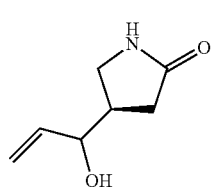

2.9

Synthesis of (R)-4-(1-hydroxybutyl)pyrrolidine-2-one (2.10) (for Example 98) was prepared analogously to the synthesis of (R)-4-(1-hydroxyethyl)pyrrolidine-2-one (2.5)

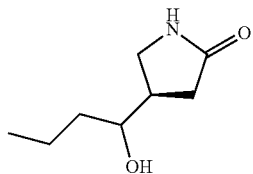

2.10

Synthesis of (R)-4-(1-hydroxy2-methylpropyl)pyrrolidine-2-one (2.11) (for Example 99) was prepared analogously to the synthesis of (R)-4-(1-hydroxyethyl)pyrrolidine-2-one (2.5)

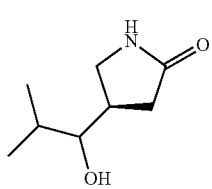

2.11

Synthesis of (R)-4-(1-hydroxy-3-methylbutyl)pyrrolidine-2-one (2.12) (for Example 100) was prepared analogously to the synthesis of (R)-4-(1-hydroxyethyl)pyrrolidine-2-one (2.5)

2.12

Synthesis of (R)-4-(1-hydroxy-pentyl)pyrrolidine-2-one (2.13) (for Example 101) was prepared analogously to the synthesis of (R)-4-(1-hydroxyethyl)pyrrolidine-2-one (2.5)

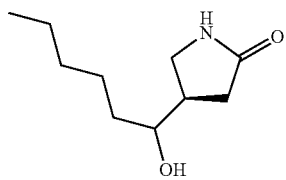

2.13

Synthesis of
5-Aminomethyl-3H-[1,3,4]oxadiazole-2-one (2.33)
(for Example 24, 67)

Step 1

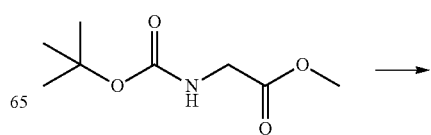

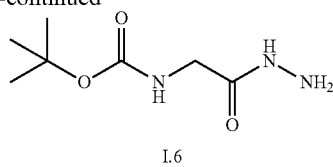

I.6

2.0 g of tert-Butoxycarbonylamino-acetic acid methyl ester and 6.35 g hydrazine hydrate (80%) were heated in a sealed tube at 100° C. for 3 h and then the reaction mixture was cooled to ambient temperature and stirred overnight. After this time, the mixture was extracted with dichloromethane (×3) and the combined organic fractions were dried over sodium sulfate, filtered and the filtrate was concentrated under reduced pressure to provide the title compound which was used without further purification.

Yield: 0.965 g (48% of theory)

Analysis: $^1$H NMR (250 MHz, chloroform-d) in ppm 1.45 (9H, s), 3.81 (4H, d, J=6.09 Hz), 5.13-5.53 (1H, m), 7.60-8.00 (1H, m)

Step 2

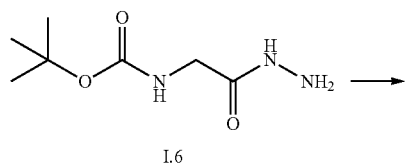

I.6

0.50 g Hydrazinocarbonylmethyl-carbamic acid tert-butyl ester (I.6) was placed in 26 mL tetrahydrofuran and 2.6 mL N,N-dimethylformamide at ambient temperature before 643 mg (carbonyl diimidazole and 0.74 mL triethylamine were introduced. The reaction was heated to reflux where it was maintained for 6 h. After this time, additional 643 mg carbonyl dimidazole and 0.74 mL triethylamine were added and the reaction was left at reflux overnight. The mixture was then cooled to ambient temperature and concentrated under reduced pressure. The crude product was re-dissolved in dichloromethane and washed with water, dried over sodium sulfate, filtered and the filtrate was concentrated under reduced pressure. Purification by silica gel chromatography twice (SiO$_2$: heptanes/ethyl acetate: 1:1 to 0:1 and then 3:1 to 0:1) provided the title compound.

Yield: 112 mg (20% of theory)

Analysis: $^1$H NMR (500 MHz, dimethyl sulfoxide-d6) in ppm 1.38 (9 H, s), 4.02 (2 H, d), 7.46 (1 H, t), 11.23-13.05 (1 H, m)

Step 3

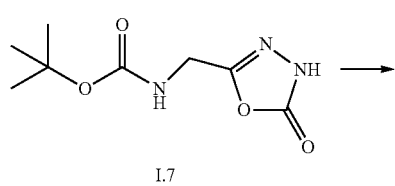

I.7

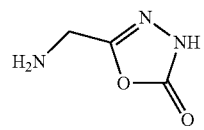

2.33

122 mg (5-Oxo-4,5-dihydro-[1,3,4]oxadiazol-2-ylmethyl)-carbamic acid tert-butyl ester (I.7) was placed in 20 mL dichloromethane at 0° C. before 0.39 mL trifluoroacetic acid was introduced dropwise. The reaction was stirred at 0° C. for 5 min and then warmed to ambient temperature where it was left for 30 min. After this time the solvent was removed under reduced pressure and used without further purification.

Yield: 60 mg (100% of theory)

Synthesis of
5-Aminomethyl-2,4-dihydro-[1,2,4]triazole-3-one
(2.34) (for example 25, 68)

Step 1

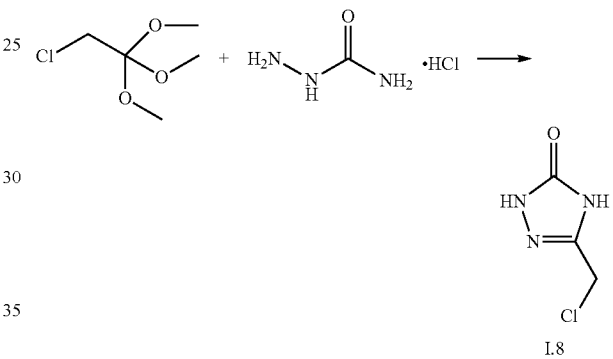

I.8

4.0 g Semicarbazide hydrochloride, 9.67 mL 2-chloro-1,1,1-trimethoxyethane and 40 mL methanol were combined and stirred at ambient temperature for 3 d. After this time additional 3.5 mL 2-chloro-1,1,1-trimethoxyethane was added to complete the reaction. The mixture was then concentrated under reduced pressure and the crude product was partitioned between ethyl acetate and 1N hydrochloric acid. The organic phase separated and it was washed with additional 1N hydrochloric acid (×2). The combined aqueous extracts were extracted with ethyl acetate (×5) and all of the organic fraction were then combined, dried over sodium sulfate, filtered and the filtrate was concentrated under reduced pressure. The solid that remained was triturated with ethyl acetate to give the title compound which was used without further purification.

Yield: 2.97 g (62% of theory)

Analysis: $^1$H NMR (500 MHz, dimethyl sulfoxide-d6) in ppm 4.49 (2 H, s), 11.55 (1 H, br. s.), 11.70 (1 H, br. s.)

Step 2

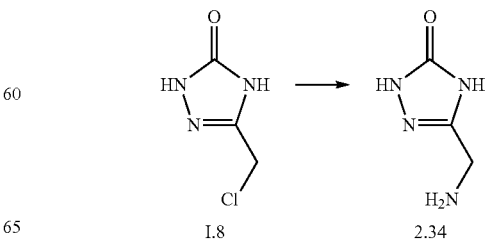

I.8     2.34

200 mg 5-Chloromethyl-2,4-dihydro-[1,2,4]triazol-3-one was placed in 25 mL of a 7N solution of ammonia in methanol at ambient temperature. The reaction was stirred overnight and then concentrated under reduced pressure. The product was used without further purification.

Yield: 171 mg (100% of theory)

Synthesis of (4R)-4-(2,2,2-trifluoro1-hydroxyethyl)pyrrolidine-2-one (2.14) (for Examples 26, 69)

Step 1

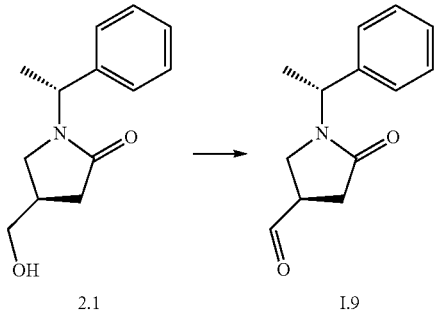 [SMILES: C[C@H](c1ccccc1)N1C[C@H](CO)CC1=O ; C[C@H](c1ccccc1)N1C[C@H](C=O)CC1=O]

2.2 g 2.1 was dissolved in 50 mL dichloromethane. 5.5 g Dess-Martin periodinane was added and the mixture was stirred at ambient temperature for 3 h. 0.22 mL Water was added and stirring continued for 30 min. Then 15 g polymer bound thiosulfate (1.5 mmol/g, washed with dichloromethane) and dichloromethane was added and the mixture stirred for 75 minutes. The mixture was filtered over Alox B (activity 3) with 250 mL dichloromethane/methanol 9:1. The filtrate was concentrated and used for the next step without further purification.

Yield: 2.05 g (94% of theory)
Step 2

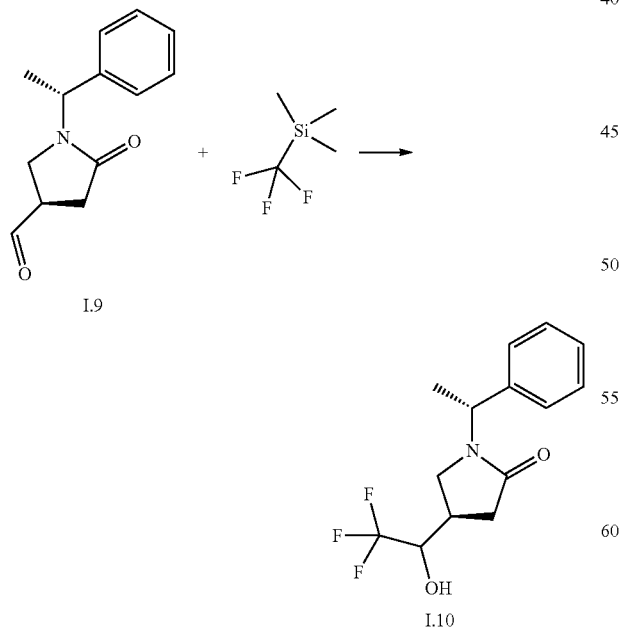

0.9 g I.9 was placed in 18 mL toluene. 0.79 mL. Trimethyl(trifluoromethyl)silane was added and the solution cooled to −60° C. 0.414 mL Tetrabutylammonium fluoride (1 M in tetrahydrofuran) was added and the reaction mixture was allowed to warm to ambient temperature overnight and then concentrated. The mixture was separated via RP-HPLC and the appropriate fractions combined and freeze-dried to provide intermediate I.10.

Yield: 390 mg (28% of theory)
Step 3

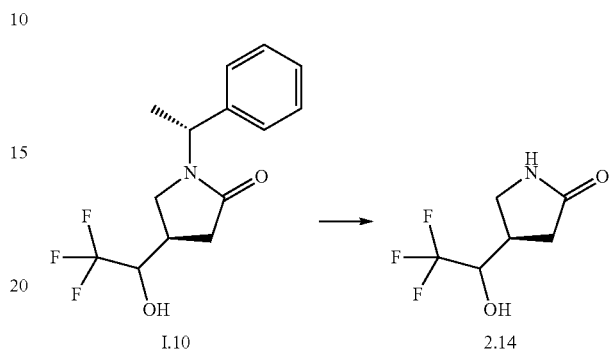

0.37 g I.10 was placed in 5 mL trifluoroacetic acid and stirred at 150° C. in the microwave for 90 min. The mixture was concentrated and used without further purification.

Yield: 460 mg (content 50%, 98% of theory)

(R)-4-((R)-2,2,2-trifluoro-1-hydroxyethyl)pyrrolidin-2-one (2.15) and (R)-4-((S)-2,2,2-trifluoro-1-hydroxyethyl)pyrrolidin-2-one (2.16) were synthesized analogously to the described method above. The diastereomers were separated via RP-HPLC as phenethyl protected pyrrolidines (For Example 70, 71)

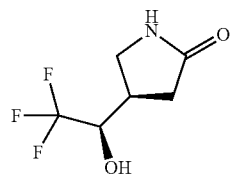

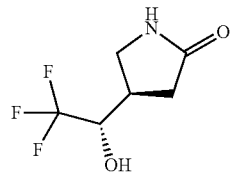

(R)-5-(hydroxymethyl)oxazolidine-2-one (2.17) (for Example 27, 72)

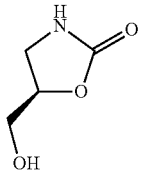

(R)-5-(Hydroxymethyl)oxazolidine-2-one may be synthesised according to the following literature: Sciotti, Richard J.; Pliushchev, Marina; Wiedeman, Paul E.; Balli, Darlene; Flamm, Robert; Nilius, Angela M.; Marsh, Kennan; Stolarik, DeAnne; Jolly, Robert; Ulrich, Roger; Djuric, Stevan W. Bioorganic & Medicinal Chemistry Letters (2002), 12(16), 2121-2123.

(R)-5-(aminomethyl)oxazolidine-2-one (2.19) (for Examples 29, 75)

Step 1

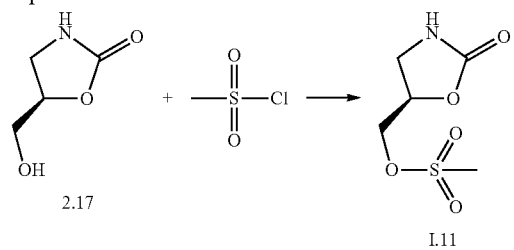

50 mg (R)-5-(Hydroxymethyl)oxazolidine-2-one (2.17) was placed in 1 mL pyridine and 63 mg methanesulfonylchloride in 0.5 mL dichloromethane was added over 10 min at −10° C. The mixture was stirred at −10° C. for 4 h. Then 0.15 mL silver nitrate (1 m in water) was added and the mixture concentrated in vacuo. The residue was suspended in dichloromethane and methanol (95:5) and filtered over silica with 12 mL dichloromethane/methanol 95:5.

Yield: 98 mg (content 80%, 94% of theory)

Step 2

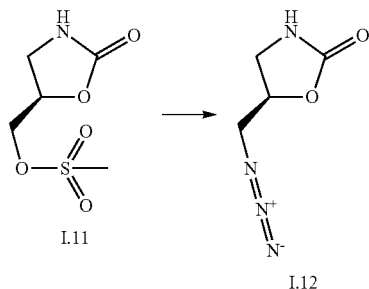

93 mg (R)-(2-Oxooxazolidine-5-yl)methylmethansulfonate (I.11) was dissolved in 1.5 mL dimethylformamide together with 90 mg sodium azide and the mixture was stirred at 70° C. for 2 days. 15 mL Water was added and the mixture extracted with dichloromethane (×5) and with ethyl acetate (×2). The combined organic phases were dried over magnesium sulfate and concentrated.

Yield: 64 mg (content 85%, 100% of theory)

Step 3

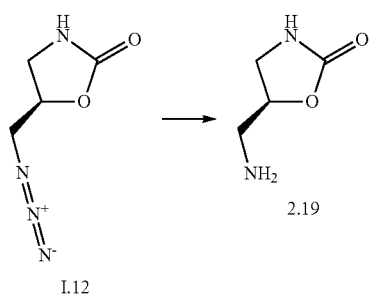 [SMILES: [N-]=[N+]=NC[C@H]1CNC(=O)O1 ; NC[C@H]1CNC(=O)O1]

60 mg (R)-5-(Azidomethyl)oxazolidine-2-one (I.12) was dissolved in 1 mL ethyl acetate and 4 mL ethanol, palladium on charcoal was added and the mixture was stirred at ambient temperature for 27 h under 40 psi hydrogen atmosphere. The reaction mixture was filtered and concentrated.

Yield: 42 mg (content 80%, 81% of theory).

(R)-4-(1-aminoethyl)pyrrolidine-2-one (2.20) (for Example 33, 80)

Step 1

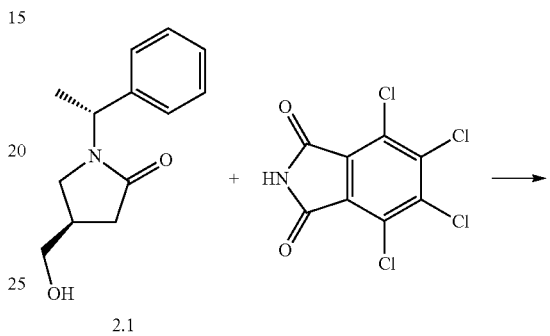

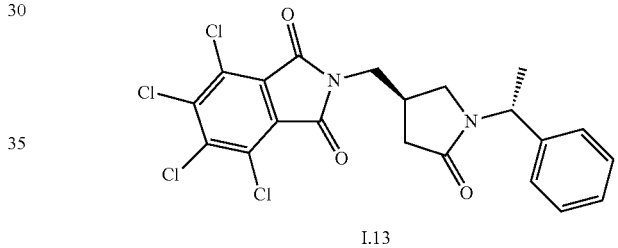

0.5 g (R)-4-(1-Hydroxyethyl)pyrrolidine-2-one (2.1), 1.3 g tetrachlorophthalimide and 1.2 g triphenylphosphine were dissolved in 15 mL tetrahydrofuran. A solution of 1.05 g DBAD in dichloromethane was added and the mixture stirred at ambient temperature for 2 h. The solvents are removed and the crude products separated via silica gel chromatography (SiO$_2$:gradient:cyclohexane→cyclohexane/ethyl acetate 3:7). The appropriate fractions were combined and concentrated.

Yield: 1.08 g (97% of theory)

Analysis (method E): R$_t$: 1.63 min, (M+H)$^+$: 485/487/489/491

Step 2

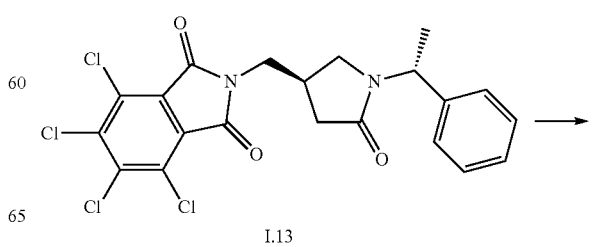

-continued

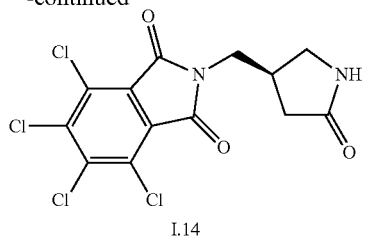

I.14

0.5 g I.13 was dissolved in 10 mL trifluoroacetic acid and stirred at 150° C. in the microwave for 40 min. The mixture was diluted with toluene and concentrated in vacuo. The residue was suspended in 50 mL dichloromethane and extracted with water. The precipitate was isolated and dried.

Yield: 210 mg (54% of theory)

Analysis (method E): $R_t$: 1.36 min, (M+H)$^+$: 383

Step 3

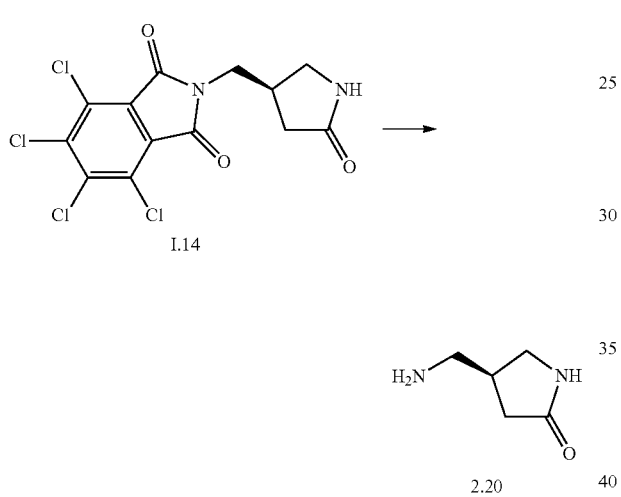

I.14

2.20

200 mg I.14 was suspended in 1 mL dimethylformamide, 1 mL tetrahydrofuran and 4 mL methylamine solution (40% in water) and stirred at 40° C. overnight. The mixture was concentrated half, 20 mL water and dioxane was added and the mixture stirred at ambient temperature for 30 min. The solid was filtered off and the filtrate was concentrated. The crude was dissolved in methanol and dichloromethane and purified via chromatography (amino phase: dichloromethane/methanol 80:20) and the appropriate fractions combined and concentrated.

Yield: 100 mg (content 60%, 100% of theory)

(R)-4-((R)-1-hydroxyethyl)pyrrolidine-2-one (2.21) (for Example 39) was prepared analogously from (R)-4-((R)-1-hydroxyethyl)pyrrolidine-2-one (2.3)

2.21

(R)-4-((R)-1-hydroxy-3-methoxypropyl)pyrrolidine-2-one (2.22) (for Example 34, 82)

Step 1

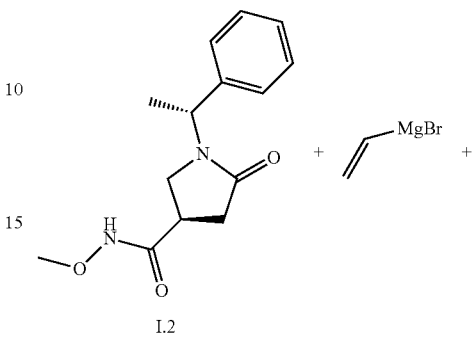

I.2

MeOH →

I.15

The reaction was carried out under a nitrogen atmosphere.

5 g (R)—N-methoxy-5-oxo-1-((R)-1-phenylethyl)pyrrolidine-3-carboxamide (I.2) (18.1 mmol) were placed in 100 mL tetrahydrofuran at −66° C. 40 mL (40 mmol) vinylmagnesium bromide in tetrahydrofuran was added slowly and the mixture was stirred at −65° C. for 16.5 h. 33.75 mL methanol, 2.6 mL concentrated sulfuric acid was added at −50° C. and then the mixture was warmed to −30° C. over 6 h and then stirred overnight at ambient temperature. After this time the mixture was concentrated and the crude product was used without further purification.

Yield: 5.77 g (85% content, 98% of theory)

Analysis (method E): $R_t$: 1.10 and 1.12 min, (M+H)$^+$: 276

Step 2

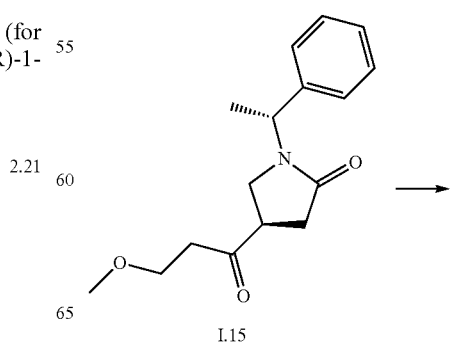

I.15

-continued

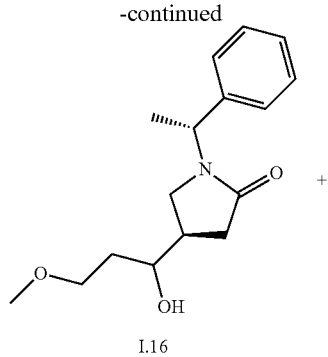
I.16

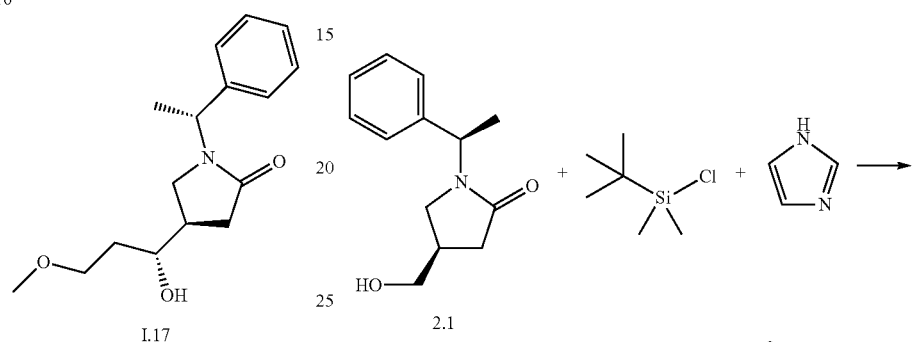

4.0 g I.15 was dissolved in ethanol and 1 g sodium borohydride was added and the mixture stirred at ambient temperature for 2 h. 200 mL Dichloromethane was added and the organic phase was extracted with 100 mL water (×2) and with 50 mL saturated sodium chloride solution. Yield (I.16) and (I.17): 2 g (55% of theory) mixture of diastereomers.

The mixture was separated via RP-HPLC (X-bridge C-18).

Yield: 170 mg (4.7% of theory) intermediate 1.17

Step 3

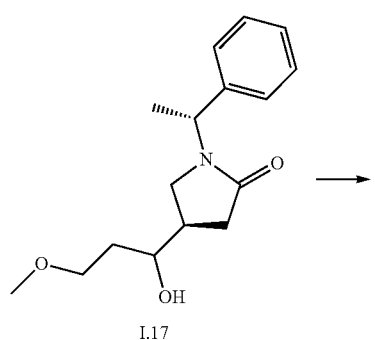
I.17

→

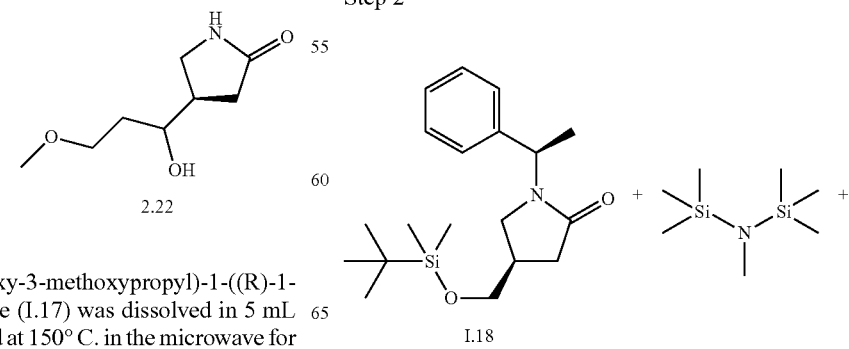

110 mg (4R)-4-(1-hydroxy-3-methoxypropyl)-1-((R)-1-phenylethyl)pyrrolidine-2-one (I.17) was dissolved in 5 mL trifluoroacetic acid and stirred at 150° C. in the microwave for 45 min. Water was added and the mixture was concentrated at 60° C. Co-evaporation with toluene and dichloromethane provided the title compound.

Yield: 69 mg (100% of theory)

((R)-1-hydroxy-3-methoxypropyl)pyrrolidine-2-one (2.23) (for Example 81) was synthesized analogously from the phenethyl protected pyrrolidine-2-one from 1.16

Synthesis of (3R,4R)-4-Hydroxymethyl-3-methyl-pyrrolidine-2-one (for Examples 36, 86, 122) (2.24) and (3R,4R)-4-Hydroxymethyl-3,3-dimethyl-pyrrolidine-2-one (for Examples 42, 95) (2.25)

Step 1

2.9 g (R)-4-Hydroxymethyl-1-((R)-1-phenyl-ethyl)-pyrrolidine-2-one (2.1) was placed in 50 mL dichloromethane at ambient temperature, then 0.99 g imidazole and 1.99 g tert-butyldimethylsilyl chloride were added. The reaction was stirred for 16 h before additional 0.20 g tert-butyldimethylsilyl chloride was added. After a further 3 h the reaction mixture was poured onto water/ice mixture and shaken. The mixture was extracted with ethyl acetate (×2) and the organic fractions were separated, dried over sodium sulfate, filtered and the solvent was removed from the filtrate under reduced pressure. The crude material was used without further purification.

Yield: 4.61 g (99% of theory)

Analysis: HPLC-MS (Method B): R$_t$=2.89 min (M+H)$^+$=334.

Step 2

MeI →

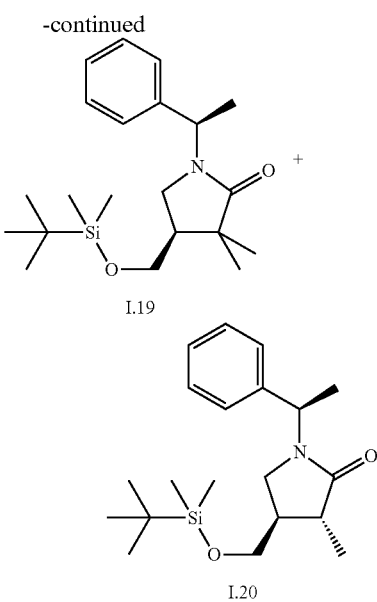

1.0 g (R)-4-(tert-Butyl-dimethyl-silanyloxymethyl)-1-((R)-1-phenyl-ethyl)-pyrrolidine-2-one (I.18) was placed in tetrahydrofuran at −78° C. under an atmosphere of nitrogen before 8.99 mL lithium hexamethyldisilazide as a solution in tetrahydrofuran was added dropwise. The reaction was stirred for 15 min at −78° C. before methyl iodide in 2 mL tetrahydrofuran was introduced and then the reaction was stirred for a further 15 min at −78° C. After this time the mixture was warmed to ambient temperature and stirred for 16 h. A solution of ammonium chloride was added to the mixture and the tetrahydrofuran was removed under reduced pressure. The mixture that remained was extracted with dichloromethane (×3) and the combined organic fractions were washed with water, dried over sodium sulfate, filtered and the solvent was removed from the filtrate under reduced pressure. Purification by chromatography on silica gel provided the two title compounds (R)-4-(tert-Butyl-dimethyl-silanyloxymethyl)-3,3-dimethyl-1-((R)-1-phenyl-ethyl)-pyrrolidine-2-one:

Yield: 48 mg of 1.19 (4% of theory)

Analysis: HPLC-MS (Method B): $R_t$=2.64 min $(M+H)^+$=384.

(3R,4R)-4-(tert-Butyl-dimethyl-silanyloxymethyl)-3-methyl-1-((R)-1-phenyl-ethyl)-pyrrolidine-2-one:

Yield: 471 mg of 1.20 (45% of theory)

Analysis: HPLC-MS (Method B): $R_t$=2.57 min $(M+H)^+$=348. [based on the $^1$H NMR spectrum it was estimated that the ~8% of the 3S diastereoisomer was present]

Step 3

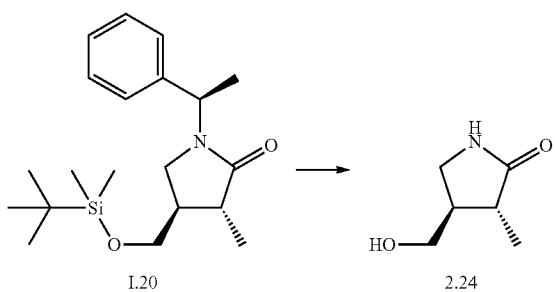

470 mg (3R,4R)-4-(tert-Butyl-dimethyl-silanyloxymethyl)-3-methyl-1-((R)-1-phenyl-ethyl)-pyrrolidine-2-one (I.20) (containing ~8% of the 3S isomer) was placed in 1 mL trifluoroacetic acid at ambient temperature. The mixture was heated at 160° C. under microwave irradiation for 30 min. After this time the mixture was concentrated under reduced pressure and the crude material was re-dissolved in 20 mL 7M ammonia as a solution in methanol and stirred at ambient temperature for 1 h. The solvent was then removed under reduced pressure. Purification by chromatography on silica gel (7M ammonia in methanol/dichloromethane: 1-10%) provided the title compound which was used without further purification.

Yield: 79 mg (45% of theory)

Analysis: $^1$H NMR (500 MHz, $d_4$-methanol) in ppm 1.18 (3 H, d), 2.16-2.29 (2 H, m), 3.13 (1 H, dd), 3.42 (1 H, dd), 3.56-3.61 (1 H, m), 3.63-3.69 (1 H, m) [based on the $^1$H NMR spectrum it was estimated that the ~7% of the 3S diastereoisomer was present].

Using an analogous procedure from (R)-4-(tert-Butyl-dimethyl-silanyloxymethyl)-3,3-dimethyl-1-((R)-1-phenyl-ethyl)-pyrrolidine-2-one (I.19), (R)-4-hydroxymethyl-3,3-dimethyl-pyrrolidine-2-one (2.25) was prepared (for Examples 42, 95)

Synthesis of (4R,5R)-4-(aminomethyl)-5-methylpyrrolidine-2-one (2.26) (for Example 38, 90)

Step 1

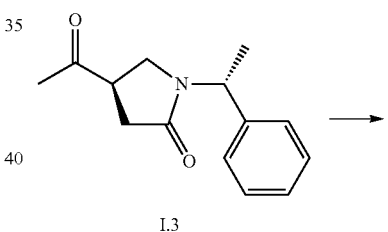

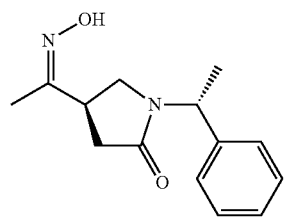

3 g (R)-4-Acetyl-1-((S)-1-phenylethyl)pyrrolidine-2-one (I.3) was dissolved in 15 mL pyridine and 2.2 g hydroxylamine hydrochloride was added and the mixture stirred at 90° C. for 2.5 h and maintained at ambient temperature overnight. Then 88 mL 2N hydrochloric acid was added slowly (slightly exothermic) and the mixture extracted with 100 mL dichloromethane (×2). The organic phase was dried over magnesium sulfate and concentrated.

Yield: 2.94 g (91% of theory)

Analysis (method D): $R_t$: 1.30 min, $(M+H)^+$: 247

Step 2

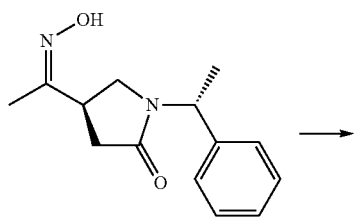

I.21

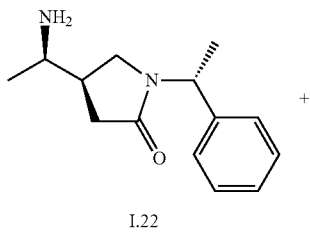

I.22

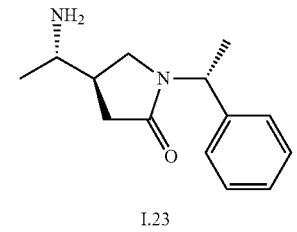

I.23

780 mg (R)-4-{1-[(Z)-Hydroxyimino]-ethyl}-1-((S)-1-phenyl-ethyl)-pyrrolidine-2-one (I.21) was dissolved in 25 mL methanol, Raney nickel was added and the mixture was hydrogenated for 14 h at 15 psi hydrogen pressure at ambient temperature. Then the mixture was filtered and concentrated to yield 660 mg as diastereomeric mixture and was purified via RP-HPLC.

Yield: 49 mg I.22
Analysis (method D): $R_t$: 1.09 min, $(M+H)^+$: 233
Yield: 67 mg I.23
Analysis (method D): $R_t$: 1.12 min, $(M+H)^+$: 233
Yield: 120 mg (mixed fractions 1.22 and 1.23)

Step 3:

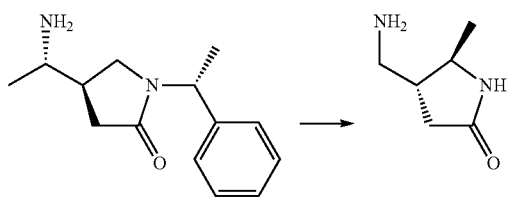

I.23     2.26

20 mg (R)-4-((S)-1-aminoethyl)-1-((S)-1-phenylethyl) pyrrolidine-2-one (I.22) was dissolved in trifluoroacetic acid and stirred for 90 min in the microwave at 150° C. The mixture was concentrated and used without further purification.

Yield: 40 mg (content 25%, 91%)

Synthesis of (4R,5R)-4-(aminomethyl)-5-ethylpyrrolidine-2-one (2.27) (for Example 43, 96) was synthesized analogously to (4R,5R)-4-(aminomethyl)-5-methylpyrrolidine-2-one (2.26)

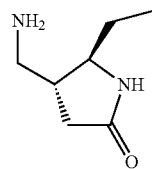

2.27

Synthesis of (R)-4-Hydroxymethyl-1-((R)-1-phenyl-ethyl)-imidazolidine-2-one (2.28) (for Examples 74 and 77)

Step 1

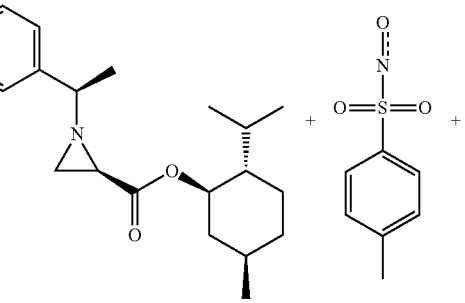

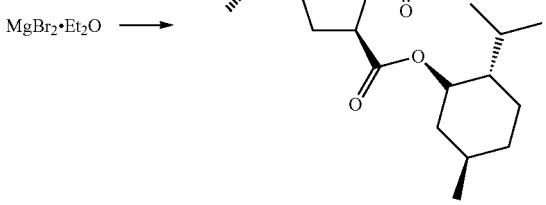

I.24

(R)-2-Oxo-1-((R)-1-phenyl-ethyl)-3-(toluene-4-sulfonyl)-imidazolidine-4-carboxylic acid (1R,2S,5R)-2-isopropyl-5-methyl-cyclohexyl ester may be synthesised according to the following literature procedure: Kim, M S; Kim, Y-U; Hahm, H S; Jang, J W; Lee, W K; Ha, H J Chem. Commun. (2005), 3062-3064.

Step 2

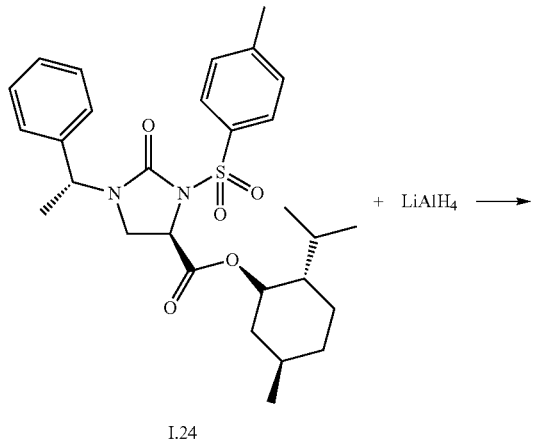

I.24

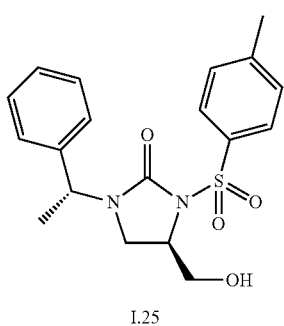

I.25

2.26 g (R)-2-Oxo-1-((R)-1-phenyl-ethyl)-3-(toluene-4-sulfonyl)-imidazolidine-4-carboxylic acid (1R,2S,5R)-2-isopropyl-5-methyl-cyclohexyl ester (I.24) was placed in 20 mL tetrahydrofuran at 0° C. under nitrogen, then 1.12 mL lithium aluminium hydride (2.3M in tetrahydrofuran) was added. The reaction was stirred for 1 h 45 min and then a 10 mL of a saturated solution of sodium sulfate was added. The mixture was extracted with ethyl acetate (×2), dried over sodium sulfate, filtered and the solvent was removed under reduced pressure. Purification by silica gel chromatography (dichloromethane/ethyl acetate 100:0 to 70:30) gave the title compound.

Yield: 637 mg (40% of theory)

Analysis: HPLC-MS (Method B): R$_t$=1.88 min (M+H)$^+$=375.

Step 3

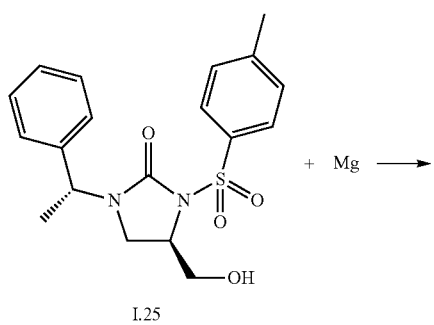

I.25

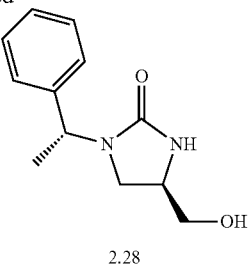

2.28

537 mg (R)-4-Hydroxymethyl-1-((R)-1-phenyl-ethyl)-3-(toluene-4-sulfonyl)-imidazolidine-2-one (I.25) was placed in 9.45 mL methanol at ambient temperature, then 348 mg magnesium turnings were added. The reaction was shaken for 24 h and then filtered. The solvent was removed from the filtrate under reduced pressure and the crude material was then partitioned between ethyl acetate and water. The organic layer was separated, dried over sodium sulfate, filtered and the solvent was removed from the filtrate under reduced pressure to give the title compound.

Yield: 174 mg (55% of theory)

Analysis: HPLC-MS (Method B): R$_t$=1.41 min (M+H)$^+$=220.

Synthesis of (4-(2-hydroxyethyl))pyrrolidine-2-one (2.29) (for Example 88)

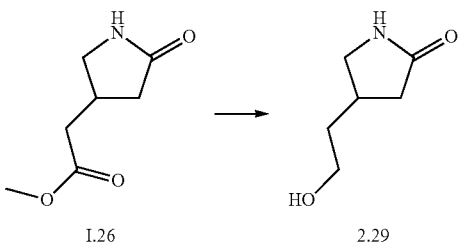

Step 1

100 mg Methyl 2-(5-oxopyrrolidine-3-yl)acetate (I.26) was placed in tetrahydrofuran and 30 mg lithium borohydride was added and the mixture stirred at ambient temperature overnight. The suspension was diluted with saturated sodium chloride solution and extracted with ethyl acetate (×3). The water phase was freeze dried.

Yield: 250 mg (content 30%, 99% of theory)

Methyl 2-(5-oxopyrrolidin-3-yl)acetate (I.26) may be synthesised according to the following literature:Kwak, Hyo-Shin; Koo, Ki Dong; Lim, Dongchul; Min, Kyeongsik; Park, Heuisul; Choi, Deog-Young; Choi, Jae-Ung; Park, Hyunjung; Park, Mijeong WO 2009038412.

5-(Hydroxymethyl)piperidine-2-one (2.30) (for Example 89)

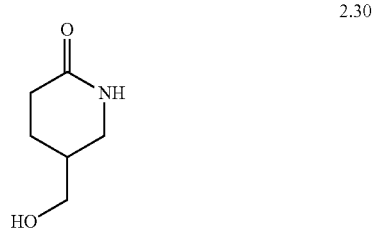

2.30

5-(Hydroxymethyl)piperidine-2-one may be synthesised according to the following literature: Lerchner, Andreas; Carreira, Erick M. Chemistry A European Journal (2006), 12(32), 8208-8219.

The following R1 derivatives are commercially obtainable:

5-Aminomethyl-1H-Pyridine-2-one (2.31) (for Example 40, 64, 91)

Muscimol (5-aminomethyl-isoxazole-3-one) (2.32) (For Example 30, 59)

4.2. Synthesis of compounds with formula 5: Reaction 1 of Scheme 1

Synthesis of 7-(3-fluoro-4-trifluoromethoxy-phenyl)-[1.6]naphthyridine-5-ol (5.1) (For Example 1

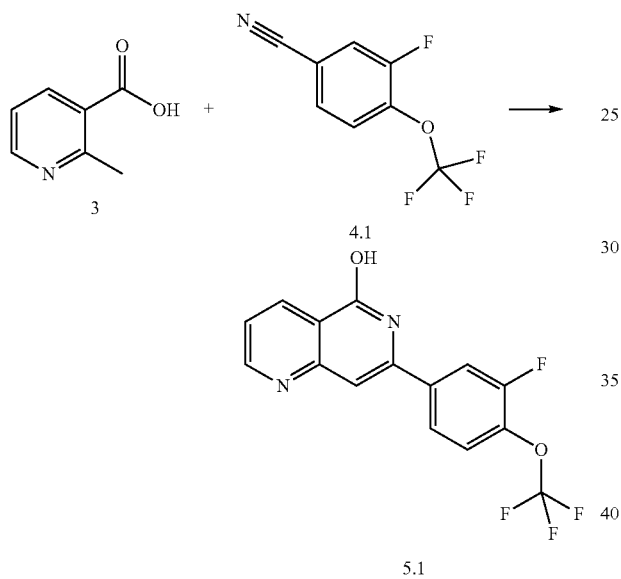

The reaction was carried out under an argon atmosphere.

300 mg 2-methyl-nicotinic acid was suspended in 10 mL of tetrahydrofuran, and cooled to −70° C. with a bath of ethanol/dry ice. 3.3 mL lithium diisopropylamide (2.0 M in tetrahydrofuran/n-heptane/ethylbenzene) was added dropwise over 10 min and the mixture was stirred for 1.5 h at 0° C. After this time, it was cooled again to −70° C. and 0.9 g 3-fluoro-4-trifluoromethoxy-benzonitrile (4.1) was added quickly. Then the reaction mixture was stirred for 2 h at −70° C. and then warmed overnight to ambient temperature. The solvent was distilled off, diluted with ethyl acetate, 10 mL phosphate buffer and 5 mL 2N aqueous hydrochloric acid solution (pH 6-7). The formed precipitate was collected and dried. The resulting liquid phase was separated and the water phase extracted twice with ethyl acetate. The organic phase was dried over magnesium sulfate, concentrated and the residue suspended in ether and ethyl acetate. The precipitate was collected, dried and combined with the first precipitate.

Yield: 300 mg (42% of theory)

Analysis (method E): $R_t$: 1.30 min, (M+H)$^+$: 325

Synthesis of 7-(3,4,5-trimethoxy-phenyl)-[1.6]naphthyridine-5-ol (5.2) (For Examples 24-43)

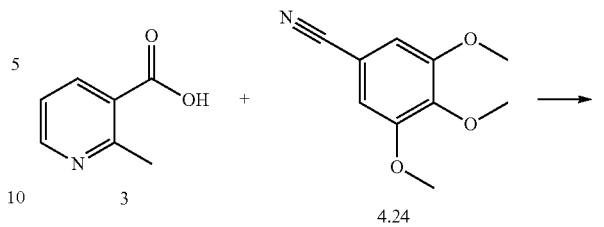

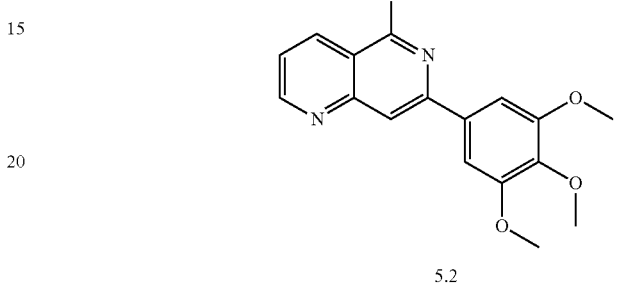

The reaction was carried out under an argon atmosphere.

7 g 2-Methyl-nicotinic acid was suspended in 150 mL of tetrahydrofuran, and cooled to −70° C. with a bath of ethanol/dry ice. 80 mL lithium diisopropylamide (2.0 M in tetrahydrofuran/n-heptane/ethylbenzene) was added dropwise over 10 min and the mixture was stirred for 2 h at 0° C. Then it was cooled to −73° C. and a solution of 10 g 3,4,5-trimethoxy-benzonitrile (4.24) in 50 mL tetrahydrofuran was added. Then the reaction mixture was warmed overnight to ambient temperature. 30 mL Water was added and the solvent was distilled off before 200 mL ethyl acetate was added and the precipitate that formed was collected.

Yield: 7.3 g (46% of theory)

Analysis (method D): $R_t$: 1.15 min, (M+H)$^+$: 313

Synthesis of 7-[3-methoxy-4-(1-methyl-piperidine-3-yloxy)-phenyl]-[1,6]naphthyridine-5-ol and 7-[3-methoxy-4-(1-methyl-pyrrolidine-2-ylmethoxy)-phenyl]-[1,6]naphthyridine-5-ol (for Examples 105, 106)

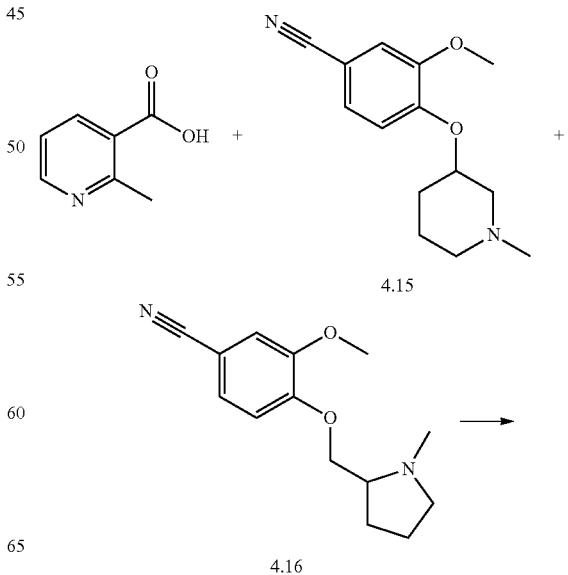

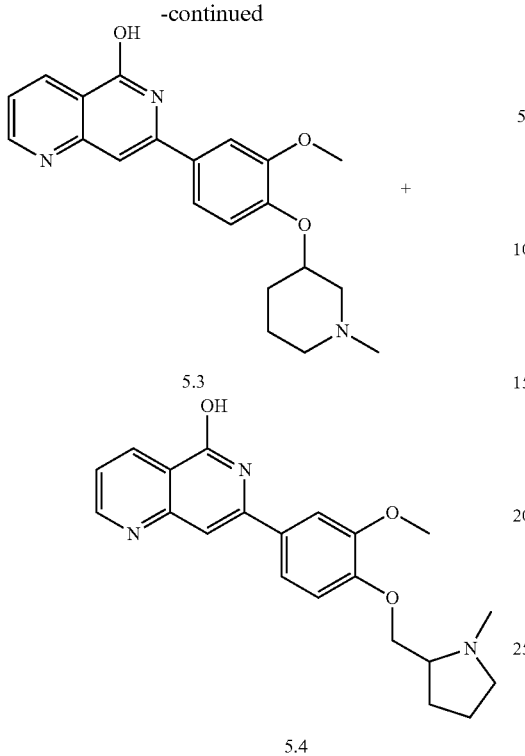

5.3

5.4

3.54 g 2-Methyl-nicotinic acid was placed in 50 mL tetrahydrofuran and cooled to −78° C. under nitrogen. 39.7 mL (as a 2 mol/L solution tetrahydrofuran/n-heptane/ethylbenzene) lithium diisopropylamide was added dropwise and the mixture was stirred for 1 h at −78° C. and then warmed to ambient temperature where it was maintained for a further 1 h. After this time the mixture was re-cooled to −78° C. and a mixture of 4.89 g 3-methoxy-4-(1-methyl-piperidine-3-yloxy)-benzonitrile (4.15) and 3-methoxy-4-(1-methyl-pyrrolidine-2-ylmethoxy)-benzonitrile (4.16) in 50 mL tetrahydrofuran was introduced dropwise. The reaction mixture was stirred for 1 h at −78° C. and then warmed to ambient temperature overnight. After this time 15 mL water was added and the solvent was removed under reduced pressure Purification by chromatography on silica gel (dichloromethane: methanol:aqueous ammonia: 240:1:1 to 240:7:2) provided the title compounds which were used as a mixture in the next step.

Yield: 4.25 g (59% of theory)

Analysis: HPLC-MS (Method B): $R_t$: 1.17 min $(M+H)^+=366$

Synthesis of 7-(4-Cyanophenyl)-[1,6]naphthyridine-5-ol (5.5) (For Example 121, 122)

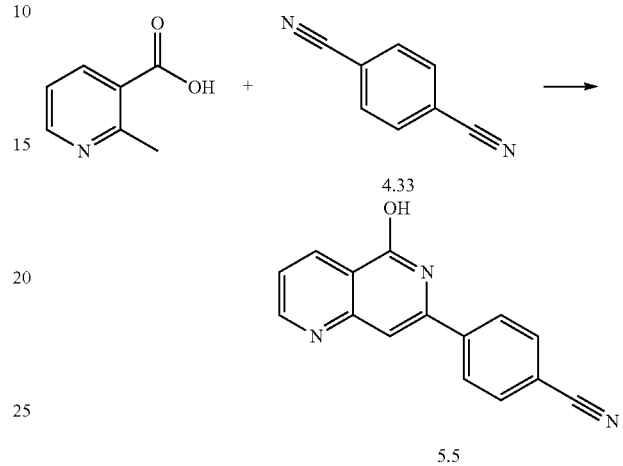

4.33

5.5

1 g 2-methyl-nicotinic acid was suspended in 30 mL of tetrahydrofuran and cooled to −78° C. under nitrogen before 14.6 mL lithium diisopropylamide (as a 2.0 M in tetrahydrofuran/n-heptane/ethylbenzene) was added dropwise and the mixture was stirred for 2 h at −78° C. and then warmed to ambient temperature where it was maintained for a further 2 h. After this time the mixture was cooled to −78° C. and it was added dropwise into a solution of 1.87 g terephthalonitrile (4.33) in 30 mL tetrahydrofuran. The reaction mixture was stirred for 2 h and then warmed to ambient temperature overnight. After this time 20 mL water was added and the solvent was removed under reduced pressure before 20 mL ethyl acetate was introduced and the precipitate that was formed was collected by filtration. The solid material that was collected (title compound) was used without further purification.

The following compounds were prepared analogously to the methods described (see Table 1).

TABLE 1

Further [1,6]-naphthyridin-5-ol derivatives

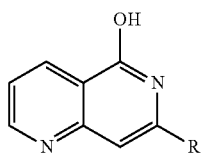

5.6–5.47

| Nitrile number | Product number | R² | Analytical data | Conditions |
|---|---|---|---|---|
| 4.2 For Example 2 | 5.6 | 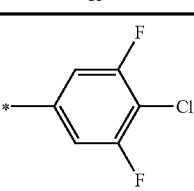 | HPLC-MS (method E) $R_t$ min = 1.24 $(M + H)^+$ 293 | 2 h −70° C., overnight to 25° C. |

TABLE 1-continued

Further [1,6]-naphthyridin-5-ol derivatives

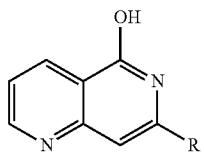

5.6–5.47

| Nitrile number | Product number | R² | Analytical data | Conditions |
|---|---|---|---|---|
| 4.36 For Example 3 | 5.7 | (5-pyridyl with 2-CF₃) | HPLC-MS (Method B) R_t min = 1.49 (M + H)⁺ 292/294 | 30 min −78° C., overnight to 25° C. |
| 4.37 For Example 5 | 5.8 | (phenyl with CF₃ and OMe) | HPLC-MS (Method C) R_t min = 1.76 (M + H)⁺ 321 | 2 h −78° C., 2 d to 25° C. |
| 4.4 For Examples 6, 7, 9 | 5.9 | (phenyl with 2 OMe and Cl) | HPLC-MS (method E) R_t min = 1.15 (M + H)⁺ 317 | overnight −70° C. |
| 4.12 For Examples 10, 50–51, 53–55, 61–62, 114, 116 | 5.10 | (phenyl-OMe-O-CH₂-phenyl-OMe) | HPLC-MS (method D) R_t min = 1.35 (M + H)⁺ 389 | −74° C. to −44° C. in 2 h, −30° C. overnight |
| 4.20 For Example 11 | 5.11 | (4-CF₃-phenyl) | HPLC-MS (method D) R_t min = 1.28 (M + H)⁺ 291 | 2 h −78° C., overnight to 25° C. |
| 4.21 For Example 12 | 5.12 | (3-methylisoxazol-5-yl) | HPLC-MS (Method B) R_t min = 1.40 (M + H)⁺ 228 | overnight to 25° C. |
| 4.38 For Example 13, 14 | 5.13 | (3,5-difluoro-4-methoxyphenyl) | HPLC-MS (Method B) R_t min = 1.65 (M + H)⁺ 289 | 2 h −78° C., overnight to 25° C. |
| 4.7 For Example 15 | 5.14 | (phenyl with CF₃ and O-tetrahydropyranyl) | HPLC-MS (Method B) R_t min = 1.81 (M + H)⁺ 391 | 2 h −78° C., overnight to 25° C. |

TABLE 1-continued

Further [1,6]-naphthyridin-5-ol derivatives

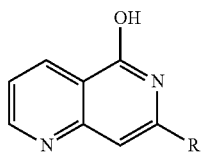

5.6–5.47

| Nitrile number | Product number | R² | Analytical data | Conditions |
|---|---|---|---|---|
| 4.22 For Example 16 | 5.15 | 3-Cl, 4-OMe phenyl | HPLC-MS (method D) R$_t$ min = 1.20 (M + H)$^+$ 287/289 (Cl) | 2 h −75° C., over weekend to 25° C. |
| 4.3 For Example 17 | 5.16 | 3-OMe, 4-Cl phenyl | HPLC-MS (method D) R$_t$ min = 1.27 (M + H)$^+$ 287/289 (Cl) | 2 h −75° C., overnight to 25° C. |
| 4.8 For Examples 18, 19, 20 | 5.17 | 3,5-diOMe, 4-(2-morpholinoethoxy) phenyl | HPLC-MS (method D) R$_t$ min = 1.05 (M + H)$^+$ 412 | 2 h −75° C., overnight to 25° C. |
| 4.5 For Example 21 | 5.18 | 4-OMe benzo[1,3]dioxole | HPLC-MS (method E) R$_t$ min = 0.96 (M + H)$^+$ 297 | −65° C. to 25° C. overnight |
| 4.23 For Examples 22, 46 | 5.19 | 6-OMe pyridin-3-yl | HPLC-MS (Method B) R$_t$ min = 1.25 (M + H)$^+$ 254 | 2 h −78° C., to 25° C. overnight |
| 4.25 For Example 23 | 5.20 | 4-methyl-3,4-dihydro-2H-pyrido[3,2-b][1,4]oxazin-7-yl | HPLC-MS (method D) R$_t$ min = 0.97 (M + H)$^+$ 295 | −60° C. to 25° C. overnight |
| 4.24 For Examples 24-43 | 5.2 | 3,4,5-triOMe phenyl | HPLC-MS (method E) R$_t$ min = 1.15 (M + H)$^+$ 313 | See description |

TABLE 1-continued

Further [1,6]-naphthyridin-5-ol derivatives 5.6–5.47

| Nitrile number | Product number | R² | Analytical data | Conditions |
|---|---|---|---|---|
| 4.14 For Example 44 | 5.21 | (2,6-dimethoxyphenyl with tetrahydropyranyloxy) | HPLC-MS (method D) R$_t$ min = 1.12 (M + H)⁺ 383 | −70° C. overnight |
| 4.26 For Example 45 | 5.22 | (pyridinyl-morpholine) | HPLC-MS (method D) R$_t$ min = 0.99 (M + H)⁺ 309 | −60° C. to 25° C. overnight |
| 4.10 For Example 47 | 5.23 | (methoxyphenyl-O-propyl-morpholine) | HPLC-MS (method D) R$_t$ min = 1.05 (M + H)⁺ 396 | −65° C. to 25° C. overnight |
| 4.27 For Example 48 | 5.24 | (3-fluoro-4-methoxyphenyl) | HPLC-MS (method D) R$_t$ min = 1.05 (M + H)⁺ 396 | 2 h −75° C. to 25° C. over weekend |
| 4.39 For Example 49 | 5.25 | (2-methoxy-3-fluorophenyl) | HPLC-MS (method D) R$_t$ min = 1.18 (M + H)⁺ 271 | −75° C. to 25° C. overnight |
| 4.11 For Example 52 | 5.26 | (methoxyphenyl-O-cyclohexyl-methylpiperazinone) | HPLC-MS (method D) R$_t$ min = 1.05 (M + H)⁺ 463 | −65° C. to 25° C. overnight |
| 4.6 For Example 56 | 5.27 | (2,3,4-triethoxyphenyl) | HPLC-MS (method E) R$_t$ min = 1.27 (M + H)⁺ 355 | −65° C. to 25° C. overnight |

TABLE 1-continued

Further [1,6]-naphthyridin-5-ol derivatives 5.6–5.47

| Nitrile number | Product number | R² | Analytical data | Conditions |
|---|---|---|---|---|
| 4.13 For Example 57 | 5.28 | | HPLC-MS (method D) R,min = 1.03 (M + H)⁺ 354 | −75° C. to 25° C. overnight |
| 4.28 For Example 58 | 5.29 | | HPLC-MS (method D) R,min = 1.10 (M + H)⁺ 267 | −73° C. to 25° C. overnight |
| 4.14 For Examples 59, 60, 63, 64, 65 | 5.30 | | HPLC-MS (Method B) R,min = 1.15 (M + H)⁺ 353 | 2 h −78° C. to 25° C. 2 d |
| 4.29 For Examples 66-78, 80-86 88-94, 96, 97-101 | 5.31 | | HPLC-MS (method D) R,min = 1.09 (M + H)⁺ 283 | −80° C. to 25° C. overnight |
| 4.40 For Example 79 | 5.32 | | HPLC-MS (Method B) R,min = 1.44 (M + H)⁺ 283 | 30 min −78° C. to 25° C. over weekend |
| 4.46 For Example 87 | 5.33 | | HPLC-MS (Method B) R,min = 1.89 (M + H)⁺ 283 | −60° C. to 25° C. overnight |
| 4.41 For Example 102 | 5.34 | | HPLC-MS (Method B) R,min = 1.59 (M + H)⁺ 367 | 30 min −78° C. to 25° C. overnight |
| 4.42 For Example 103 | 5.35 | | HPLC-MS (Method B) R,min = 1.82 (M + H)⁺ 299 | −60° C. to 25° C. overnight |

TABLE 1-continued

Further [1,6]-naphthyridin-5-ol derivatives 5.6–5.47

| Nitrile number | Product number | R² | Analytical data | Conditions |
|---|---|---|---|---|
| 4.43 For Example 104 | 5.36 | *-C₆H₄-O-(1-methylpiperidin-4-yl) | HPLC-MS (Method B) R, min = 1.10 (M + H)⁺ 366 | 1 h −78° C. to 25° C. 3 h |
| 4.17 For Examples 107, 108 | 5.37 | 3,4-dimethoxy-5-methylphenyl | HPLC-MS (method E) R, min = 1.07 (M + H)⁺ 297 | −70° C. overnight |
| 4.18 For Example 109 | 5.38 | 3-isopropoxy-4-methoxyphenyl | HPLC-MS (method D) R, min = 1.22 (M + H)⁺ 311 | −75° C. to 25° C. overnight |
| 4.30 For Example 110 | 5.39 | 3-methoxy-4-propoxyphenyl | HPLC-MS (Method D) R, min = 1.25 (M + H)⁺ 311 | −75° C. to 25° C. overnight |
| 4.44 For Examples 111, 112, 113 | 5.40 | 3-methoxy-4-isopropoxyphenyl | HPLC-MS (Method B) R, min = 1.66 (M + H)⁺ 311 | −60° C. to 25° C. overnight |
| 4.31 For Example 115 | 5.41 | 2-fluorophenyl | HPLC-MS (Method B) R, min = 1.50 (M + H)⁺ 241 | 2 h −78° C. to 25° C. overnight |
| 4.32 For Example 117 | 5.42 | pyridin-2-yl | HPLC-MS (method E) R, min = 0.82 (M + H)⁺ 224 | −65° C. to 25° C. overnight |
| 4.45 For Example 118 | 5.43 | 4-methoxyphenyl | HPLC-MS (Method B) R, min = 1.44 (M + H)⁺ 253 | 30 min −78° C. to 25° C. overnight |

TABLE 1-continued

Further [1,6]-naphthyridin-5-ol derivatives

[Structure: 1,6-naphthyridin-5-ol with R substituent at 7-position]

5.6–5.47

| Nitrile number | Product number | R² | Analytical data | Conditions |
|---|---|---|---|---|
| 4.46 For Example 119 | 5.44 | [4-isopropoxyphenyl] | HPLC-MS (Method B) $R_t$ min = 1.44 $(M + H)^+$ 253 | 30 min −78° C. to 25° C. overnight |
| 4.19 For Example 120 | 5.45 | [2-Boc-1,2,3,4-tetrahydroisoquinolin-7-yl] | $^1$H-NMR (400 MHz, CDCl$_3$): δ = 10.35 (1H), 8.97 (1H), 8.62 (1H), 7.60 (2H), 7.42 (1H), 7.30 (1H), 7.06 (1H), 4.65 (2H), 3.71 (2H), 2.95 (2H), 1.52 (9H) | −69° C. to 25° C. overnight |
| 4.33 For Examples 121, 122 | 5.5 | [4-cyanophenyl] | HPLC-MS (Method B) $R_t$ min = 1.50 $(M + H)^+$ 248 | see description |
| 4.34 For Example 123 | 5.46 | [cyclopropyl] | HPLC-MS (method E) $R_t$ min = 0.45 $(M + H)^+$ 187 | −69° C. to 25° C. overnight |
| 4.35 For Examples 124, 125, 126 | 5.47 | [phenyl] | HPLC-MS (method D) $R_t$ min = 1.07 $(M + H)^+$ 223 | −60° C. to 25° C. overnight |

Synthesis of 7-(3-methoxy-4-trifluoromethoxy-phenyl)-[1,6]naphthyridine-5-ol (5.48) (For Example 4)

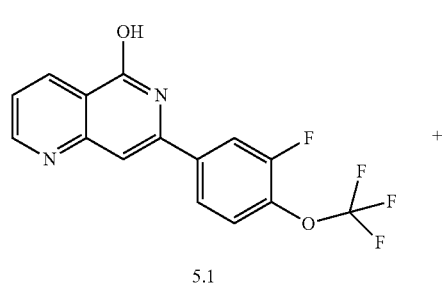

5.1

+

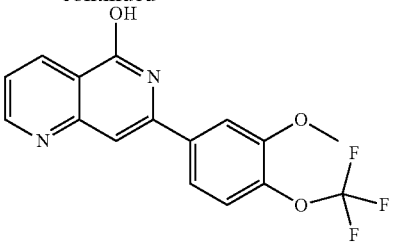

5.48

1.5 g 7-(3-Fluoro-4-trifluoromethoxy-phenyl)-[1,6]naphthyridine-5-ol (5.1) and 5 g sodium methoxide were dissolved in methanol and heated to 160° C. overnight in a sealed flask. Then additional 5 g sodium methoxide was added and the mixture heated to 170° C. for 3 h and overnight at 160° C. The solvent was distilled off and the residue extracted with water and dichloromethane. The precipitate that formed was collected and the organic phase and two additional dichloromethane extracts were combined and the solvent distilled off. The residue and the precipitate was combined and dried.

Yield: 1400 mg (content 90%, 81% of theory)

Analysis: HPLC-MS (method E): $R_t$=1.25 min $(M+H)^+$=337

7-(3,5-Dimethoxy-4-chloromethoxy-phenyl)-[1,6]naphthyridine-5-ol (5.49) was prepared in an analogous manner from 7-(3,5-difluoro-4-chloromethoxy-phenyl)-[1,6]naphthyridine-5-ol (5.6) (for Example 8).

4.3. Synthesis of compounds with formula 6: Reaction 2 of Scheme 1

4.3.1. Synthesis of [1,6]naphthyridine-5-yl-trifluoromethanesulfonic acid ester derivatives Synthesis of 7-(3,4,5-trimethoxy-phenyl)-[1,6]naphthyridine-5-yl-trifluoromethanesulfonic acid ester (6.6) (For Example 24, 25, 29, 30, 33, 38, 39, 40, 43)

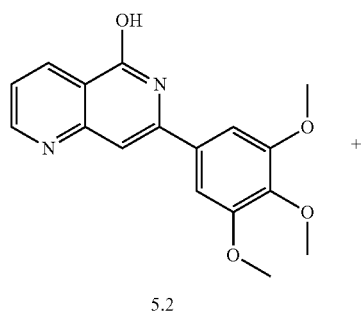

5.2

+

-continued 6.1

0.5 g 5.2 were placed in 10 mL dichloromethane, then 0.7 mL pyridine were added. At 0° C. a solution of 0.66 mL trifluoromethanesulfonic acid anhydride in 5 mL dichloromethane was added dropwise over 1 min. After the addition the reaction mixture was stirred overnight at ambient temperature. The reaction mixture was mixed with ice water and extracted with dichloromethane. The organic phase was concentrated to give 6.1.

Yield: 0.8 g (content 89%, 100% of theory)

Analysis (method E): $R_t$: 1.53 min, $(M+H)^+$: 445

The following compound was prepared analogously to the method described above (see Table 3).

TABLE 2

Further trifluoromethanesulfonic acid ester 6.2-6.9

| Adduct number | Product number | R² | Analytical data | Conditions |
|---|---|---|---|---|
| 5.31 | 6.2 For Examples 67, 68, 75, 76, 80, 90, 91, 96 |  | HPLC-MS (method E) $R_t$ min = 1.73 $(M+H)^+$ 415 | 3 h at 25° C. |

TABLE 2-continued

Further trifluoromethanesulfonic acid ester 6.2-6.9

| Adduct number | Product number | R² | Analytical data | Conditions |
|---|---|---|---|---|
| 5.17 | 6.3 For Example 18 | (2,6-dimethoxy-4-yl phenyl with O-CH₂CH₂-morpholine) | HPLC-MS (method D) R$_t$ min = 1.46 (M + H)⁺ 544 | 1 h at 25° C. |
| 5.19 | 6.4 For Example 46 | (6-methoxypyridin-3-yl) | HPLC-MS (method E) R$_t$ min = 1.55 (M + H)⁺ 386 | overnight at 25° C. |
| 5.22 | 6.5 For Example 45 | (6-morpholinopyridin-3-yl) | HPLC-MS (method D) R$_t$ min = 1.39 (M + H)⁺ 441 | 4 h at 25° C. |
| 5.30 | 6.6 For Examples 59, 64 | (3-methoxy-4-(tetrahydropyran-4-yloxy)phenyl) | HPLC-MS (Method B) R$_t$ min = 2.41 (M + H)⁺ 485 | 2.5 h at 25° C. |
| 5.41 | 6.7 For Example 115 | (2-fluorophenyl) | HPLC-MS (method E) R$_t$ min = 1.60 (M + H)⁺ 373 | 4 h at 25° C. |
| 5.46 | 6.8 For Example 123 | cyclopropyl | HPLC-MS (method E) R$_t$ min = 1.53 (M + H)⁺ 319 | overnight at 25° C. |
| 5.26 | 6.9 For Example 52 | (3-methoxy-4-((4-(4-methyl-3-oxopiperazin-1-yl)cyclohexyl)oxy)phenyl) | HPLC-MS (method D) R$_t$ min = 1.45 (M + H)⁺ 595 | overnight at 25° C. |

4.3.2. Synthesis of 5-chloro-[1,6]naphthyridine derivatives

Synthesis of 5-chloro-7-(4-(trifluoromethoxy)phenyl)-1,6-naphthyridine (6.1) (For Example 1

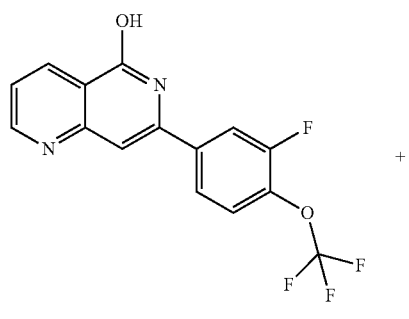

5.1

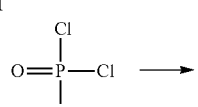

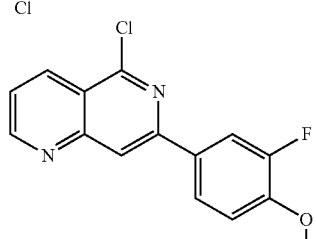

6.10

200 mg 7-(3-fluoro-4-trifluormethoxy-phenyl)[1,6]-naphthyridine-5-ol (5.1) and 10 µL N,N-diethylaniline were stirred into 4 mL phosphorus oxychloride overnight at 120° C. The reaction mixture was evaporated down, followed by co-evaporation with toluene (×3) and the residue purified via silica gel chromatography (ethyl acetate dichloromethane/methanol 4:1).

Yield: 226 mg (content 90%) (=96% of theory)
Analysis (method E): $R_t$: 1.64 min, (M+H)$^+$: 343/345 (Cl)

Synthesis of 5-chloro-7-(3,4,5-trimethoxy-phenyl)-[1,6]-naphthyridine (6.11) (For Examples 26, 27, 28, 31, 32, 34, 35, 36, 41, 42)

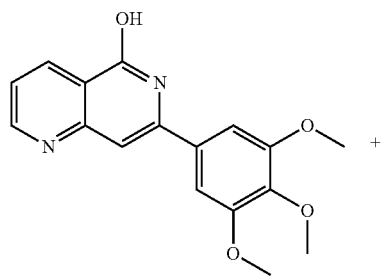

5.2

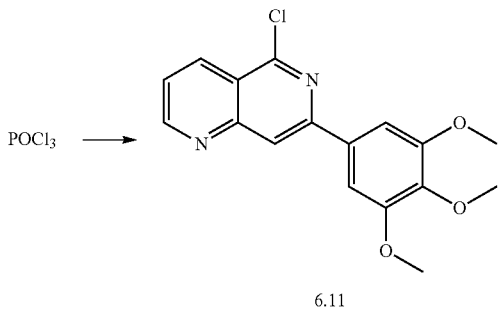

6.11

565 mg 7-(3,4,5-Trimethoxy-phenyl)-[1,6]-naphthyridine (5.2) and 15 µL N,N-diethylaniline were stirred into 4 mL phosphorus oxychloride overnight at 100° C. and at ambient temperature over 2 days. The reaction mixture was evaporated down, and a small amount of ethyl acetate was added. Upon scratching a precipitate were formed. Methyl-tert-butylether was added and the precipitate was isolated and dried overnight at 50° C. under vacuo.

Yield: 700 mg (content 85%, 99% of theory)
Analysis (method E): $R_t$: 1.38 min, (M+H)$^+$: 331/333 (Cl)

Synthesis of 5-chloro-7-[3-methoxy-4-(1-methyl-piperidine-3-yloxy)-phenyl]-[1,6]naphthyridine (6.12) and 5-chloro-7-[3-methoxy-4-(1-methyl-pyrrolidine-2-ylmethoxy)-phenyl]-[1,6]naphthyridine (6.13) (for Examples 105, 106)

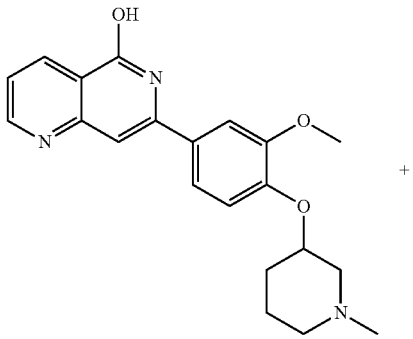

5.3

5.4

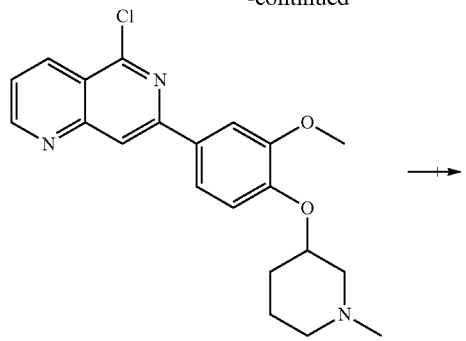

6.12

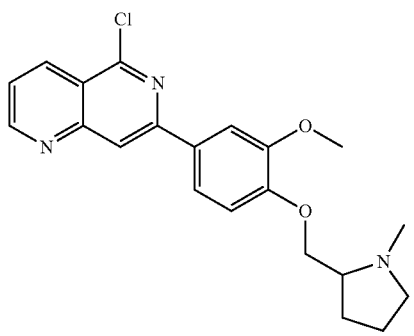

6.13

A mixture of 1.00 g 7-[3-methoxy-4-(1-methyl-piperidine-3-yloxy)-phenyl]-[1,6]naphthyridine-5-ol (5.3) and 7-[3-methoxy-4-(1-methyl-pyrrolidine-2-ylmethoxy)-phenyl]-[1,6]naphthyridine-5-ol (5.4) in 25 mL phosphoryl chloride was heated to 105° C. where it was maintained overnight. After this time the reaction was cooled to ambient temperature and concentrated under reduced pressure. The crude product was partitioned between dichloromethane and 2M sodium carbonate and the organic phase was separated, washed with water, a saturated solution of sodium chloride, dried over sodium sulfate, filtered and the filtrate was concentrated under reduced pressure to give the title compounds as a mixture which was used without further purification.

Yield: 0.80 g (77% of theory)

Analysis: HPLC-MS (Method B): $R_t$: 1.52 min $(M+H)^+=384$

The following compounds were prepared analogously to the method described above (see Table 3).

TABLE 3

Further 5-chloro-[1,6]naphthyridine derivatives

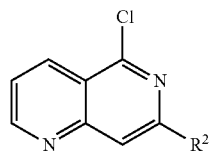

6.14-6.52

| Chloride number | Product number | R² | Analytical data | Conditions |
|---|---|---|---|---|
| 5.6 | 6.14 For Example 2 | ![F, Cl, F substituted phenyl] | HPLC-MS (method E) $R_t$ min = 1.67 $(M + H)^+$ 311/313 | 3 h 120°, overnight 110° C., 3 h 140° C. |
| 5.7 | 6.15 For Example 3 | ![pyridine-CF3] | HPLC-MS (Method B) $R_t$ min = 2.17 $(M + H)^+$ 310 | 110° C. overnight |
| 5.48 | 6.16 For Example 4 | ![OMe, OCF3 phenyl] | HPLC-MS (method E) $R_t$ min = 1.58 $(M + H)^+$ 355/357 | 3 h 120°, overnight 110° C. |

TABLE 3-continued

Further 5-chloro-[1,6]naphthyridine derivatives 6.14-6.52

| Chloride number | Product number | R² | Analytical data | Conditions |
|---|---|---|---|---|
| 5.8 | 6.17 For Example 5 | (2-methoxy-5-* -phenyl with CF₃) | HPLC-MS (Method B) R$_t$ min = 2.39 (M + H)⁺ 339/341 | 4 h 120° C., overnight 25° C. |
| 5.9 | 6.18 For Examples 6, 7, 9 | (3-chloro-4-methoxy-5-methoxyphenyl-*) | HPLC-MS (method E) R$_t$ min = 1.55 (M + H)⁺ 335/337/339 | 4 h 120° |
| 5.49 | 6.19 For Example 8 | (4-chloro-3,5-dimethoxyphenyl-*) | HPLC-MS (method E) R$_t$ min = 1.51 (M + H)⁺ 335/337/339 | overnight 120° C. |
| 5.11 | 6.20 For Example 11 | (4-trifluoromethylphenyl-*) | HPLC-MS (method D) R$_t$ min = 1.89 (M + H)⁺ 309/311 | 1.5 h 80° C., 2.5 h 100° C., |
| 5.12 | 6.21 For Example 12 | (5-methylisoxazol-3-yl-*) | HPLC-MS (Method B) R$_t$ min = 1.87 (M + H)⁺ 246 | 4 h 105° C. |
| 5.13 | 6.22 For Examples 13, 14 | (3,5-difluoro-4-methoxyphenyl-*) | HPLC-MS (Method B) R$_t$ min = 2.35 (M + H)⁺ 307/309 | 5 h 105° C. |
| 5.14 | 6.23 For Example 15 | (2-(tetrahydropyran-4-yloxy)-3-trifluoromethylphenyl-*) | HPLC-MS (Method B) R$_t$ min = 2.52 (M + H)⁺ 409 | 4 h 105° C. overnight 25° C. |
| 5.15 | 6.24 For Example 16 | (3-chloro-4-methoxyphenyl-*) | HPLC-MS (method D) R$_t$ min = 1.78 (M + H)⁺ 305/307/309 | 2 h 80° C., overnight 50° C. |

TABLE 3-continued

Further 5-chloro-[1,6]naphthyridine derivatives

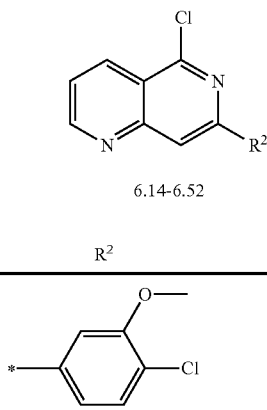

6.14-6.52

| Chloride number | Product number | R² | Analytical data | Conditions |
|---|---|---|---|---|
| 5.16 | 6.25 For Example 17 | 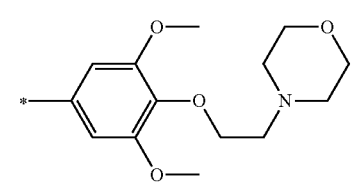 | HPLC-MS (method D) $R_t$ min = 1.89 $(M + H)^+$ 305/307/309 | 2 h 80° C., 3 h 110° C., overnight 80° C. |
| 5.17 | 6.26 For Examples 19-20 | 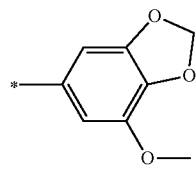 | HPLC-MS (method D) $R_t$ min = 1.32 $(M + H)^+$ 430/432 | 2 h 80° C., 3 h 110° C., overnight 80° C. |
| 5.18 | 6.27 For Example 21 | 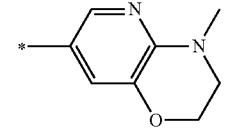 | HPLC-MS (method E) $R_t$ min = 1.45 $(M + H)^+$ 315/317 | 4 h 120° C., overnight 25° C. |
| 5.20 | 6.28 For Example 23 | 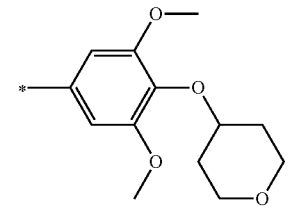 | HPLC-MS (method D) $R_t$ min = 1.24 $(M + H)^+$ 313/315 | 8 h 115° C. |
| 5.21 | 6.29 For Example 44 | 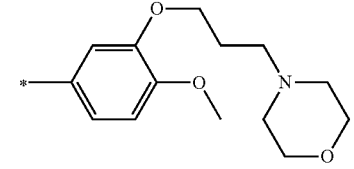 | HPLC-MS (method D) $R_t$ min = 1.50 $(M + H)^+$ 401/403 | overnight 90° C. |
| 5.23 | 6.30 For Example 47 | 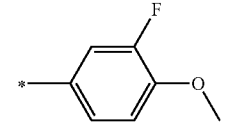 | HPLC-MS (method D) $R_t$ min = 1.33 $(M + H)^+$ 414/416 | 7 h 120° C. |
| 5.24 | 6.31 For Example 48 | 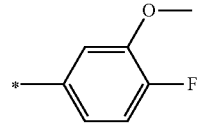 | HPLC-MS (method D) $R_t$ min = 1.70 $(M + H)^+$ 289/291 | 2 h 80° C., overnight 50° C. |
| 5.25 | 6.32 For Example 49 | | HPLC-MS (method D) $R_t$ min = 1.69 $(M + H)^+$ 289/291 | 2 h 80° C., 3 h 110° C. overnight 80° C. |

TABLE 3-continued

Further 5-chloro-[1,6]naphthyridine derivatives

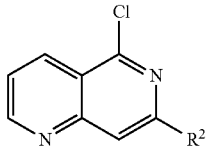

6.14-6.52

| Chloride number | Product number | R² | Analytical data | Conditions |
|---|---|---|---|---|
| 5.27 | 6.33 For Example 56 | 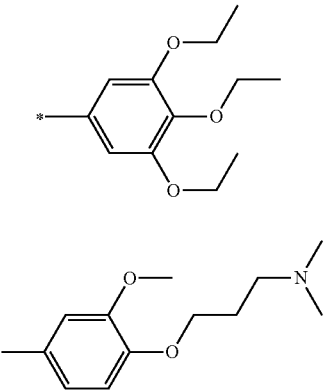 | HPLC-MS (method E) $R_t$ min = 1.58 $(M + H)^+$ 373/375 | 5 h 120° C. |
| 5.28 | 6.34 For Example 57 | 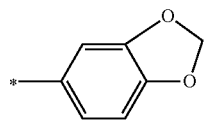 | HPLC-MS (method E) $R_t$ min = $(M + H)^+$ 372/374 | 2 h 80° C., overnight 50° C. |
| 5.29 | 6.35 For Example 58 | 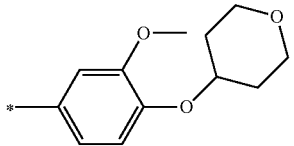 | HPLC-MS (method D) $R_t$ min = 1.66 $(M + H)^+$ 285/287 | 2.75 h 105° C., |
| 5.30 | 6.36 For Examples 60, 63, 65 | 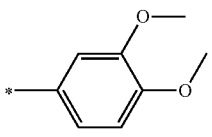 | HPLC-MS (method D) $R_t$ min = 1.59 $(M + H)^+$ 371/373 | 3 h 120° C., overnight 80° C. 5 h 120° C. |
| 5.31 | 6.37 see Examples 69-74, 78, 81-86, 88, 89-92, 93-95, 97-101 | 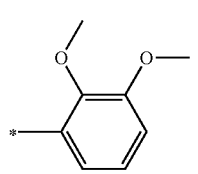 | HPLC-MS (method D) $R_t$ min = 1.56 $(M + H)^+$ 301/303 | 6 h 100° C., overnight 80° C. |
| 5.32 | 6.38 For Example 79 | 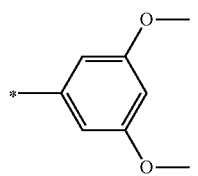 | HPLC-MS (Method B) $R_t$ min = 2.13 $(M + H)^+$ 301/303 | 2 h 105° C. |
| 5.33 | 6.39 For Example 87 |  | HPLC-MS (Method B) $R_t$ min = 2.44 $(M + H)^+$ 301/303 | overnight 110° C. |

TABLE 3-continued

Further 5-chloro-[1,6]naphthyridine derivatives 6.14-6.52

| Chloride number | Product number | R² | Analytical data | Conditions |
|---|---|---|---|---|
| 5.34 | 6.40 For Example 102 | (3-methoxy-4-((tetrahydro-2H-pyran-4-yl)methoxy)phenyl) | HPLC-MS (Method B) R$_t$ min = 2.15 (M + H)⁺ 385/387 | 3 h 105° C. |
| 5.35 | 6.41 For Example 103 | (3-fluoro-4-isopropoxyphenyl) | HPLC-MS (Method B) R$_t$ min = 2.55 (M + H)⁺ 317/319 | 3 h 130° C. |
| 5.36 | 6.42 For Example 104 | (4-((1-methylpiperidin-4-yl)oxy)phenyl) | HPLC-MS (Method B) R$_t$ min = 1.54 (M + H)⁺ 384/386 | |
| 5.37 | 6.43 For Examples 107, 108 | (3,4-dimethoxy-5-methylphenyl) | HPLC-MS (method E) R$_t$ min = 1.51 (M + H)⁺ 315/317 | 3 h 120° C. |
| 5.38 | 6.44 For Example 109 | (2,2-dimethyl-2,3-dihydrobenzo[1,4]dioxin-6-yl) | HPLC-MS (method D) R$_t$ min = 1.70 (M + H)⁺ 329/331 | 2 h 80° C., overnight 50° C. |
| 5.39 | 6.45 For Example 110 | (3-methoxy-4-propoxyphenyl) | HPLC-MS (method D) R$_t$ min = 1.74 (M + H)⁺ 329/331 | 2 h 80° C., overnight 50° C. |
| 5.40 | 6.46 For Examples 111, 112, 113 | (3-methoxy-4-isopropoxyphenyl) | HPLC-MS (method D) R$_t$ min = 1.69 (M + H)⁺ 329/331 | 3 h 120° C., |
| 5.42 | 6.47 For Example 117 | (pyridin-2-yl) | HPLC-MS (method E) R$_t$ min = 1.02 (M + H)⁺ 242/244 | 3 h 120° C., |

TABLE 3-continued

Further 5-chloro-[1,6]naphthyridine derivatives

6.14-6.52

| Chloride number | Product number | R² | Analytical data | Conditions |
|---|---|---|---|---|
| 5.43 | 6.48 For Example 118 | *-C₆H₄-OCH₃ (4-methoxyphenyl) | HPLC-MS (Method B) R$_t$ min = 2.26 (M + H)⁺ 271/273 | 3 h 105° C. |
| 5.44 | 6.49 For Example 119 | *-C₆H₄-OCH(CH₃)₂ (4-isopropoxyphenyl) | HPLC-MS (Method B) R$_t$ min = 2.50 (M + H)⁺ 299/301 | 4 h 105°C. |
| 5.45 | 6.50 For Example 120 | *-(tetrahydroisoquinoline-N-Boc) | HPLC-MS (method D) R$_t$ min = 1.90 (M + H)⁺ 396/398 | 4 h 120° C., |
| 5.5 | 6.51 For Examples 121, 122 | *-C₆H₄-CN (4-cyanophenyl) | HPLC-MS (Method A) R$_t$ min = 4.61 (M + H)⁺ 266/268 | 5 h 120° C. |
| 5.47 | 6.52 For Examples 124, 125, 126 | *-C₆H₅ (phenyl) | HPLC-MS (method D) R$_t$ min = 1.68 (M + H)⁺ 241/243 | 4 h 120° C., |

Synthesis of 5-chloro-7-(6-methoxy-pyridine-3-yl)-1,6-naphthyridine (6.53) and 5-(5-chloro-1,6-naphthyridine-7-yl)pyridine-2(1H)-one (6.54) (For Example 22, 46)

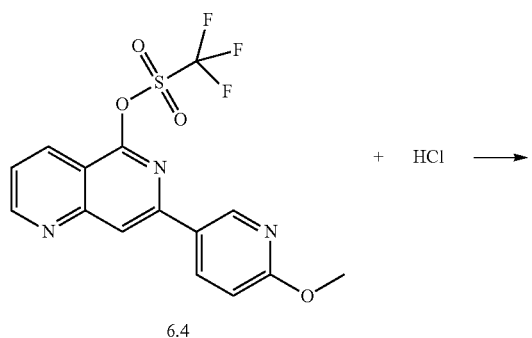

6.4

+ HCl →

-continued

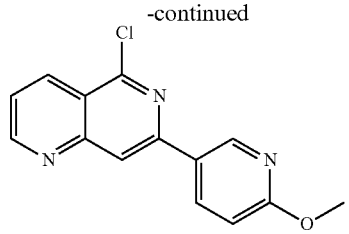

6.53

+

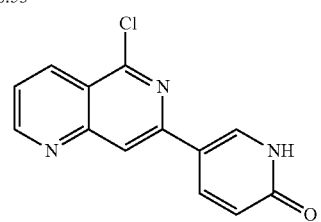

6.54

400 mg Trifluoromethanesulfonic acid 7-(6-methoxy-pyridine-3-yl)[1,6]-naphthyridine-5-yl ester (6.4) in 5 mL acetonitrile was treated with 0.78 mL (4N) hydrogen chloride in dioxane solution at 70° C. After 20 min additional 0.25 mL (4N) hydrogen chloride in dioxane solution was added and the mixture stirred for 10 min. The solvents were evaporated and the residue dried overnight at 50° C. under vacuo. The crude product which was used in the next step was used without further purification contains 72% of 6.53 and 14% of 6.54

Yield: 380 mg

Analysis 6.53

HPLC-MS (method E): $R_t$: 1.40 min, $(M+H)^+$: 272/274 (Cl)

Analysis 6.54

HPLC-MS (method E): $R_t$: 1.09 min, $(M+H)^+$: 258/260 (Cl)

Synthesis of 5-chloro-7-(6-morpholine-4-yl-pyridine-3-yl)-1,6-naphthyridine (6.55) (For Example 45)

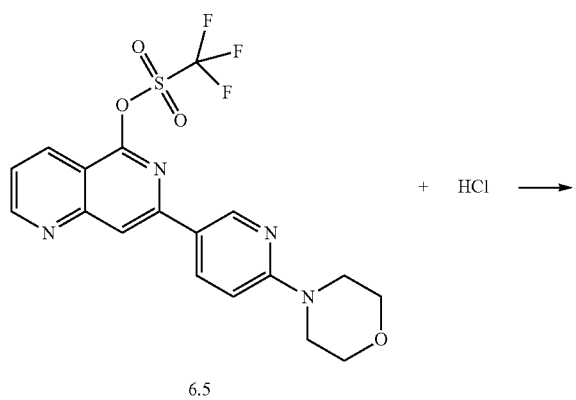

6.5

+ HCl ⟶

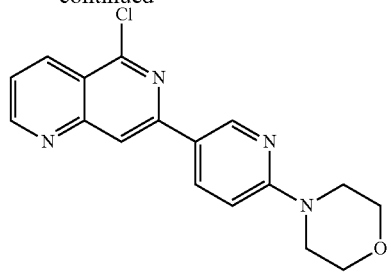

6.55

400 mg Trifluoromethanesulfonic acid 7-(6-morpholine-4-yl-pyridine-3-yl)-[1,6]-naphthyridine-5-yl ester (6.5) in 5 mL N-methyl-2-pyrrolidinone was treated with 1.6 mL (4N) hydrochloric acid in dioxane for 30 min at 70° C. 2 mL dichloromethane, 20 mL ethyl acetate and 10 mL methyl-tert-butylether was added and the precipitate isolated and dried at 50° C. under vacuo.

Yield: 650 mg (content 85%, 92% of theory)

HPLC-MS (method E): $R_t$: 1.05 min, $(M+H)^+$: 327/329 (Cl)

The following compounds were prepared analogously to the method described above (see Table 4).

TABLE 4

Further 5-chloro-[1,6]naphthyridine derivatives

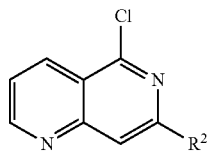

6.56-6.58

| Adduct number | Product number | R² | Analytical data | Conditions |
|---|---|---|---|---|
| 6.9 | 6.56 For Examples 52 | (2-methoxy-phenoxy-cyclohexyl-4-methylpiperazinone) | HPLC-MS (method D) $R_t$ min = 1.32 $(M + H)^+$ 481/483 | 4 h at 80° |
| 6.7 | 6.57 For Example 115 | (2-fluorophenyl) | HPLC-MS (method E) $R_t$ min = 1.47 $(M + H)^+$ 259/261 | 2 h at 70° C.° |
| 6.8 | 6.58 For Example 123 | (cyclopropyl) | HPLC-MS (method E) $R_t$ min = 1.28 $(M + H)^+$ 205/207 | 2 h at 70° C., |

5-Chloro-[1.6]naphthyridine is commercially obtainable: for Example 127

4.4. Synthesis of the Patent Examples of Formula 1

4.4.1. Reaction 3 of Scheme 1 and reaction 4 of Scheme 2

(R)-4-((R)-1-(7-(3-fluoro-4-(trifluoromethoxy)phenyl)-1,6-naphthyridine-5-yloxy)ethyl)pyrrolidine-2-one (Example 1)

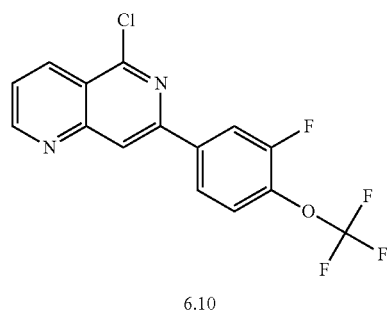
6.10

+

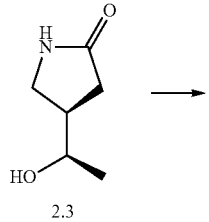
2.3

→

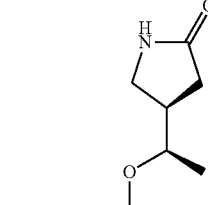
Example 1

40.0 mg (R)-4-((R)-1-hydroxyethyl)pyrrolidine-2-one (2.3) was placed in 1 mL dimethylacetamide and 13 mg sodium hydride (60%) were added and the mixture was stirred for 15 min at ambient temperature. Then 100 mg 6.10 was added and the mixture was stirred for 3 h at 40° C. The reaction mixture was purified by chromatography (RP-HPLC-MS). The corresponding fractions were freeze-dried.

Yield: 26 mg (23% of theory)

Analysis: HPLC-MS (method E): $R_t$: 1.49 min, (M+H)$^+$: 436

Example 5

(R)-4-[7-(3-Fluoro-4-methoxy-phenyl)-[1,6]naphthyridine-5-yloxymethyl]-pyrrolidine-2-one

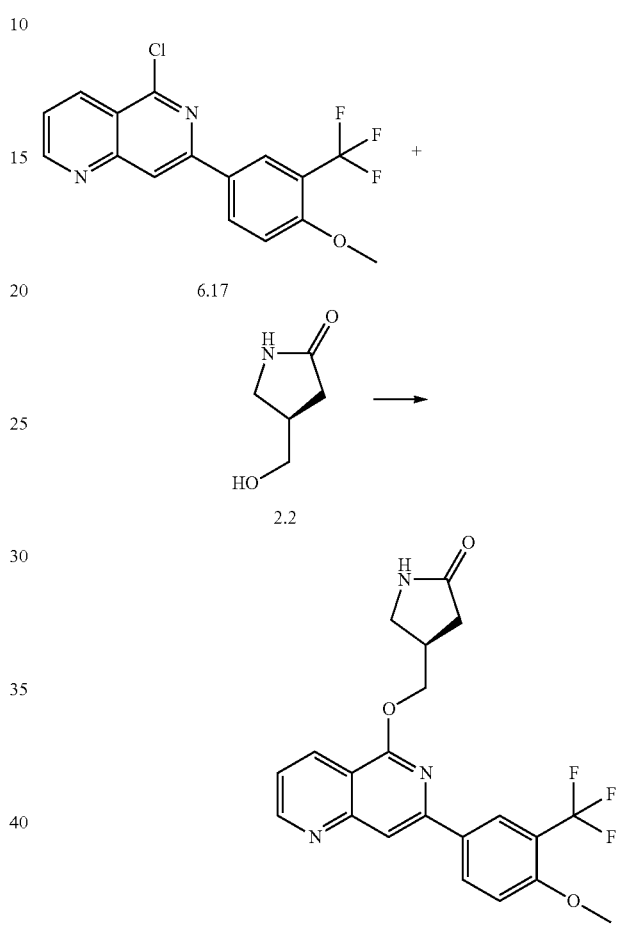
Example 5

61 mg (R)-4-Hydroxymethyl-pyrrolidine-2-one (2.2) was placed in 1.5 mL of dimethylacetamide at ambient temperature under nitrogen and then 24.8 mg sodium hydride (as a 60% dispersion in oil) was added. The reaction was stirred for 10 min and then 150 mg of 5-chloro-7-(4-methoxy-3-trifluoromethyl-phenyl)-[1,6]naphthyridine (6.17) was introduced.

The reaction was heated to 70° C. where it was maintained overnight. After this time, additional sodium hydride was introduced and heating was continued for a further 7 h. The reaction mixture was cooled to ambient temperature and then it was partitioned between ethyl acetate and water. The organic phase was separated, dried over sodium sulfate, filtered and the solvent was removed from the filtrate under reduced pressure. Purification by silica gel chromatography (ethyl acetate/methanol: 100:0 to 90:10), followed by preparative HPLC provided the title compound.

Yield: 26.4 mg (0.063 mmol=14% of theory)

Analysis: $^1$H NMR (250 MHz, chloroform-d) in ppm 2.35-2.50 (1 H, m), 2.59-2.74 (1 H, m), 3.09-3.30 (1 H, m), 3.41-3.51 (1 H, m), 3.64-3.79 (1 H, m), 3.99 (3 H, s), 4.60-4.77 (2

H, m), 6.11 (1 H, br. s.), 7.13 (1 H, d, J=8.68 Hz), 7.44 (1 H, dd, J=8.30, 4.34 Hz), 7.90 (1 H, d, J=0.76 Hz), 8.27 (1 H, dd, J=8.68, 2.13 Hz), 8.40 (1 H, d, J=2.13 Hz), 8.48 (1 H, ddd, J=8.34, 1.71, 0.76 Hz), 9.01 (1 H, dd, J=4.26, 1.52 Hz).

Example 10

(R)-4-((7-(1,1-dioxo-hexahydro-1λa*6*-thiopyran-4-yloxy-3-methoxy-phenyl)-1,6-naphthyridine-5-yloxy)methyl)pyrrolidine-2-one

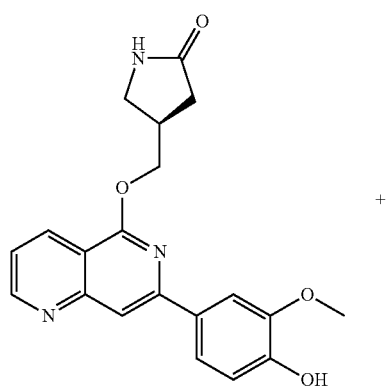

Example 53

+

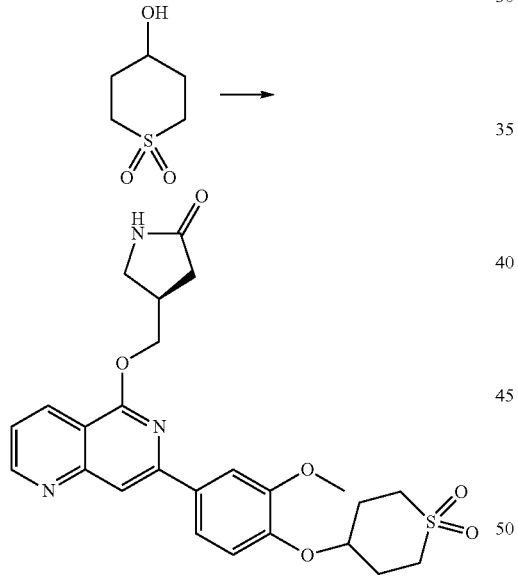

Example 10

78 mg (R)-4-[7-(4-Hydroxy-3-methoxy-phenyl)-[1,6]-naphthyridine-5-yloxymethyl]-pyrrolidine-2-one (Example 53), 38 mg (0.25 mmol) 1,1-dioxo-hexahydro-1λ,*6*-thiopyran-4-ol and 112 mg triphenylphosphine was suspended in 5 mL tetrahydrofuran. 98 mg DBAD and 1 mL dichloromethane was added and the mixture was stirred overnight at ambient temperature. Further 50 mg triphenylphosphine and 40 mg DBAD was added and stirred for further 24 h. The mixture was concentrated, then dissolved in methanol and diluted with water and purified by chromatography (RP-HPLC-MS).

Yield: 16 mg (15% of theory)

Analysis: HPLC-MS (method E): $R_t$: 1.11 min, (M+H)$^+$: 498

Example 15

(R)-4-{7-[4-(Tetrahydro-pyran-4-yloxy)-3-trifluoromethyl-phenyl]-[1,6]naphthyridine-5-yloxymethyl}-pyrrolidine-2-one

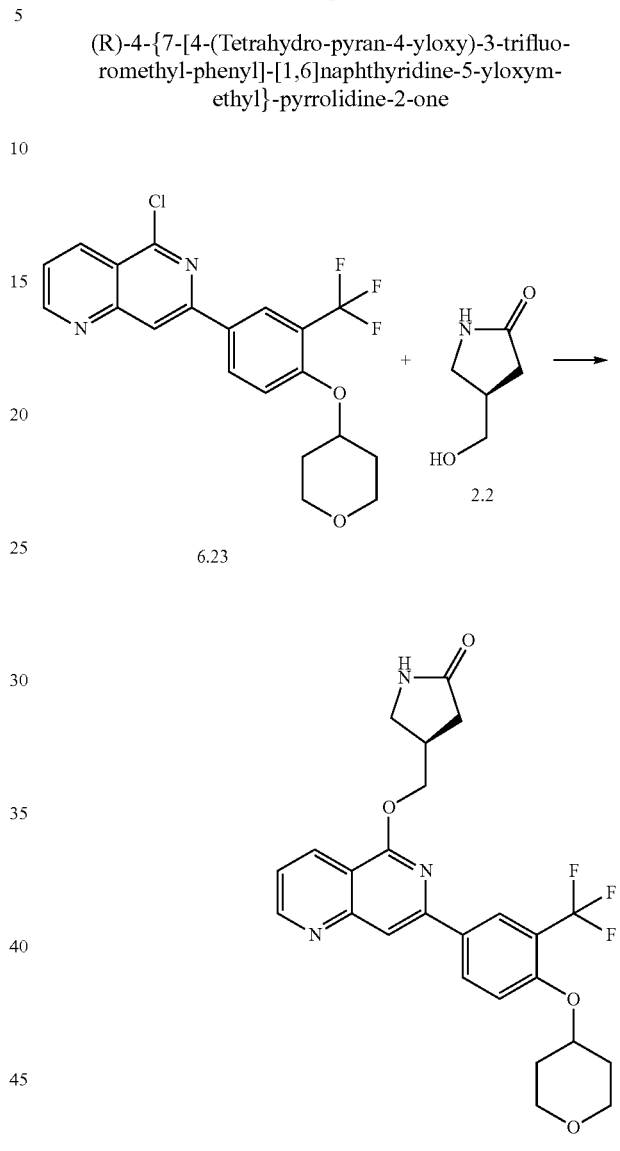

Example 15

50.7 mg (R)-4-Hydroxymethyl-pyrrolidine-2-one (2.2) was placed in 1.5 mL of dimethylacetamide at ambient temperature under nitrogen before 20.5 mg sodium hydride (60% dispersion in oil) was added. The reaction was stirred for 10 min and then 150 mg 5-chloro-7-[4-(tetrahydro-pyran-4-yloxy)-3-trifluoromethyl-phenyl]-[1,6]naphthyridine (6.23) was introduced and the reaction was heated to 70° C. and stirred overnight. After this time the mixture was cooled to ambient temperature and partitioned between ethyl acetate, water and some saturated sodium chloride solution. The organic layer was separated, dried over sodium sulfate, filtered and the solvent was removed from the filtrate under reduced pressure. Purification by chromatography on silica provided the title compound.

Yield: 47.9 mg (27% of theory)

Analysis: HPLC-MS (method B): $R_t$: 2.00 min, (M+H)$^+$: 488

Example 19

(R)-4-((R)-1-(7-(3,5-dimethoxy-4-(2-morpholinoethoxy)phenyl)-1,6-naphthyridine-5-yloxy)ethyl)pyrrolidine-2-one

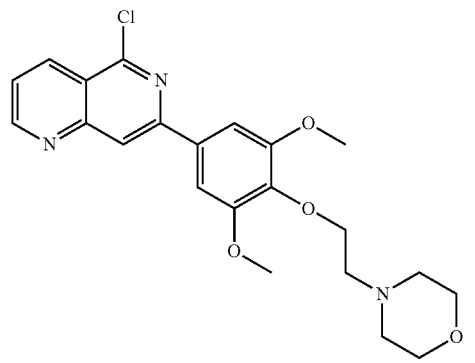

6.26

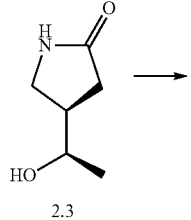

2.3

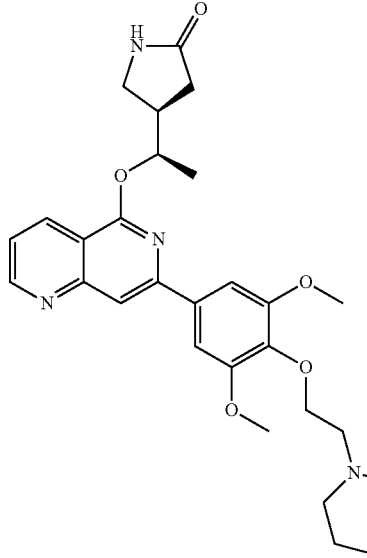

Example 19

46.0 mg (80%) (R)-4-((R)-1-hydroxyethyl)pyrrolidine-2-one (2.3) was placed in 0.5 mL dimethylacetamide and 21 mg sodium hydride (60%) were added and the mixture was stirred for 15 min at ambient temperature. Then 100 mg 6.26 was added and the mixture was stirred for 2 h at 70° C. The reaction mixture was purified by chromatography (RP-HPLC-MS). The corresponding fractions were freeze-dried.

Yield: 35 mg (24% of theory)

Analysis: HPLC-MS (method D): $R_t$: 1.18 min, (M+H)$^+$: 523

Example 22+46

(R)-4-((R)-1-(7-(6-methoxypyridine-3-yl)-1,6-naphthyridine-5-yloxy)ethyl)pyrrolidine-2-one and 5-(5-((R)-1-((R)-5-oxopyrrolidine-3-yl)ethoxy)-1,6-naphthyridine-7-yl)pyridine-2(1H)-one

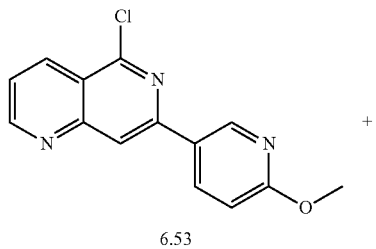

6.53

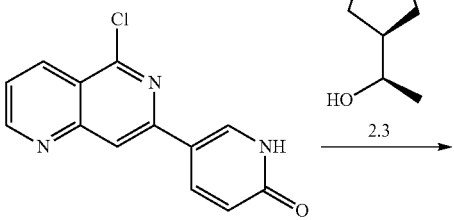

6.54

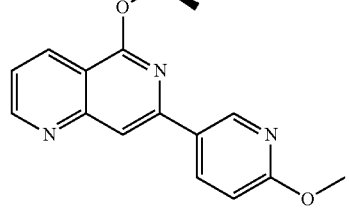

Example 46

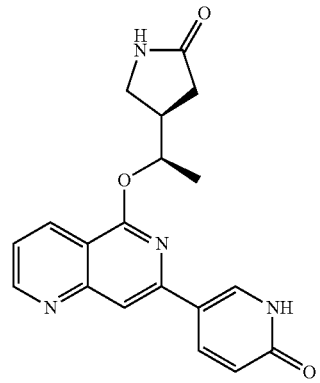

Example 22

115.0 mg (85%) (R)-4-((R)-1-hydroxyethyl)pyrrolidine-2-one (2.3) was placed in 2 mL dimethylacetamide and 70 mg sodium hydride (60%) were added and the mixture was stirred for 1 h at ambient temperature. Then 230 mg of a mixture of 6.53 and 6.54 was added and stirred for 25 min at 70° C. Further 80 mg sodium hydride (60%) was added followed by a third portion (30 mg). After 25 minutes, water and trifluoroacetic acid was added and the reaction mixture was purified by chromatography (RP-HPLC-MS). The corresponding fractions were freeze-dried.

Yield: 52 mg of example 22 (21% of theory)
Analysis: HPLC-MS (method E): $R_t$: 0.90 min, $(M+H)^+$: 351

Yield: 15 mg of example 46 (6% of theory)
Analysis: HPLC-MS (method E): $R_t$: 1.15 min, $(M+H)^+$: 365

Example 24

5-{[7-(3,4,5-Trimethoxy-phenyl)-[1,6]naphthyridine-5-ylamino]-methyl}-3H-[1,3,4]oxadiazole-2-one

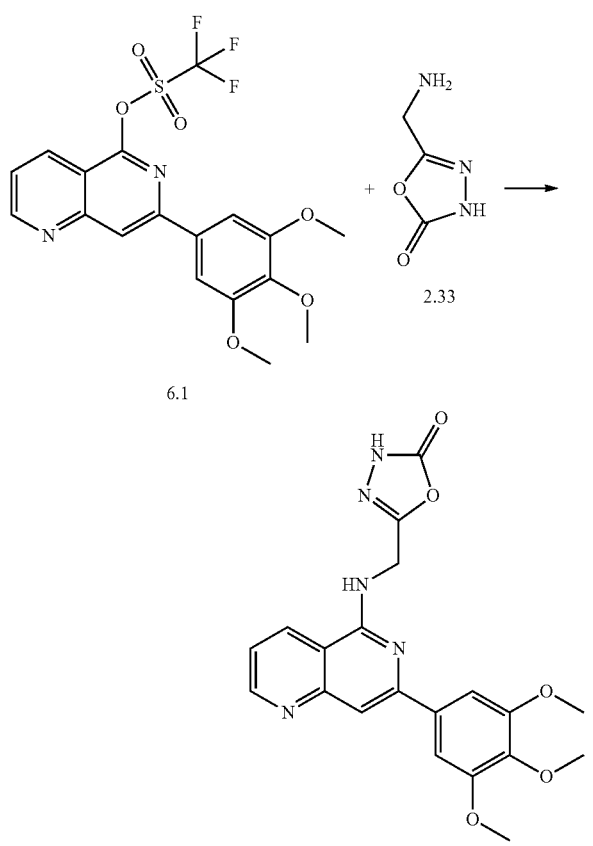

Example 24

104 mg Trifluoro-methanesulfonic acid 7-(3,4,5-trimethoxy-phenyl)-[1,6]naphthyridine-5-yl ester (6.1), 30 mg (0.261 mmol) of 5-aminomethyl-3H-[1,3,4]oxadiazole-2-one (2.33) and 0.132 mL (0.782 mL) N,N-diisopropylamine were placed in dimethylacetamide at ambient temperature. The reaction was then heated to 70° C. where it was maintained overnight and then cooled to ambient temperature. After this time 0.132 mL (0.782 mL) N,N-diisopropylamine was added and the reaction was heated to 90° C. where it was left for 6 h. The reaction was then cooled to ambient temperature and partitioned between water and ethyl acetate. The organic layer was separated and the aqueous phase was extracted with additional ethyl acetate (×2). The combined organic fractions were dried over sodium sulfate, filtered and the solvent was removed from the filtrate under reduced pressure. Purification by silica gel chromatography (ethyl acetate/methanol: 100:0 to 90:10) and then a second purification by silica gel chromatography (dichloromethane/methanol: 100:0 to 95:5) gave the title compound.

Yield: 5.4 mg (5% of theory)
Analysis: HPLC-MS (method A): $R_t$: 4.10 min, $(M+H)^+$: 410

Example 29

(S)-5-((7-(3,4,5-trimethoxyphenyl)-1,6-naphthyridine-5-ylamino)methyl) oxazolidine-2-one

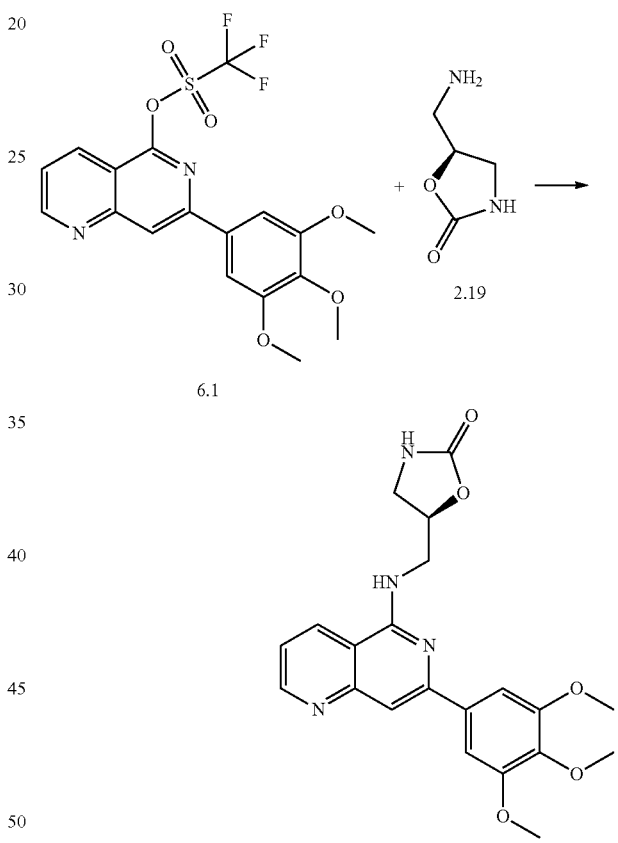

Example 29

100 mg 6.1 and 70 mg of (S)-5-(aminomethyl)oxazolidine-2-one (2.19) (50%) were dissolved in dimethylacetamide. 0.175 mL (1.01 mmol) of diisopropylethylamine was added and the mixture was heated at 70° C. for 30 minutes and overnight at ambient temperature. The mixture was diluted with 20 mL dichloromethane and 20 mL water. The phases were separated and the water phase extracted with additional 10 mL dichloromethane. The combined organic phases were concentrated and the product purified via chromatography (SiO$_2$: dichloromethane → dichloromethane/methanol 90:10). The product was recrystallized from ethyl acetate and methyl-tert-butylether.

Yield: 25 mg (30% of theory)
Analysis: HPLC-MS (method E): $R_t$: 1.00 min, $(M+H)^+$: 411

Example 33

(S)-4-((7-(3,4,5-trimethoxyphenyl)-1,6-naphthyridine-5-ylamino)methyl)pyrrolidine-2-one

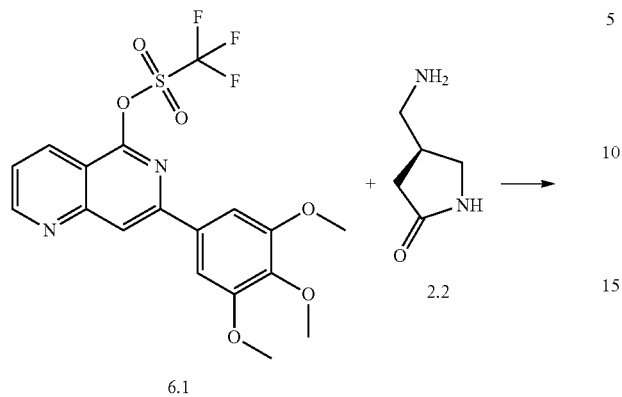

Example 33

100 mg 6.1 and 30 mg of (S)-4-(aminomethyl)pyrrolidin-2-one (2.2) were dissolved in dimethylacetamide. 0.175 mL of diisopropylethylamine was added and the mixture was heated at 70° C. overnight. The mixture was diluted with water and methanol and purified via chromatography (RP-HPLC) and the corresponding fractions were freeze-dried.

Yield: 45 mg (55% of theory)

Analysis: HPLC-MS (method E): $R_t$: 1.03 min, (M+H)$^+$: 409

Example 38

(4R,5R)-5-methyl-4-((7-(3,4,5-trimethoxyphenyl)-1,6-naphthyridine-5-yl amino)methyl)pyrolidine-2-one

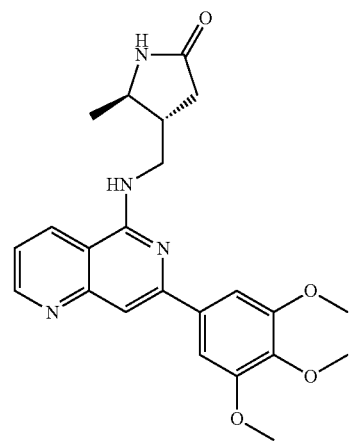

Example 38

100 mg 6.1 and 33 mg (4R,5R)-4-(aminomethyl)-5-methylpyrrolidine-2-one (2.26) were dissolved in dimethylacetamide. 0.175 mL Diisopropylethylamine was added and the mixture was heated at 80° C. for 85 min. The mixture was acidified with trifluoroacetic acid and purified via chromatography (RP-HPLC) and the corresponding fractions were freeze-dried.

Yield: 27 mg (28% of theory)

Analysis: HPLC-MS (method E): $R_t$: 1.12 min, (M+H)$^+$: 423

Example 40

5-{[7-(3,4,5-Trimethoxy-phenyl)-[1,6]naphthyridine-5-ylamino]-methyl}-1H-pyridine-2-one

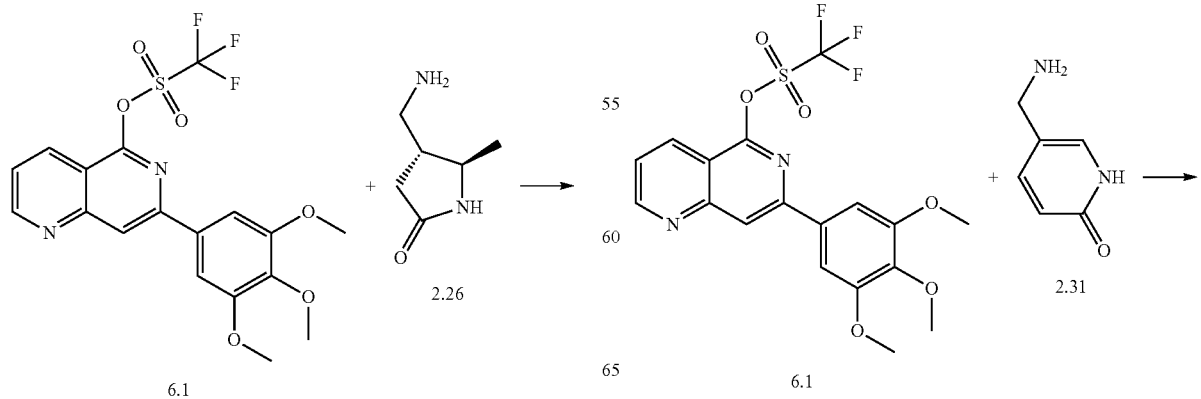

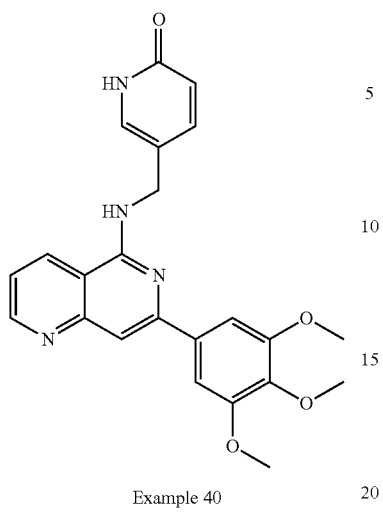

Example 40

100 mg Trifluoro-methanesulfonic acid 7-(3,4,5-trimethoxy-phenyl)-[1,6]naphthyridine-5-yl ester (6.1) was placed in 3 mL dimethylacetamide at ambient temperature before 111 mg 5-amino-1H-pyridine-2-one (2.31) was added. The reaction was heated to 70° C. overnight and then cooled to ambient temperature. 1.3 mL N,N-Diisopropylamine was added and the reaction was heated to 100° C. overnight. After this time, the reaction was heated to 120° C. and stirred overnight. The mixture was then cooled to ambient temperature and water was added. The mixture was extracted into ethyl acetate (×3) and the combined organic fractions were washed with water, separated and the solvent was removed under reduced pressure. Purification by preparative HPLC and then by silica gel chromatography (ethyl acetate containing 1-10% of 7M ammonia in methanol) gave the title compound.

Yield: 4.6 mg (5% of theory)

Analysis: HPLC-MS (Method A): $R_t$: 2.89 min, (M+H)$^+$: 419

Example 53

(R)-4-((7-(4-hydroxy-3-methoxyphenyl)-1,6-naphthyridine-5-yloxy)methyl)pyrrolidine-2-one

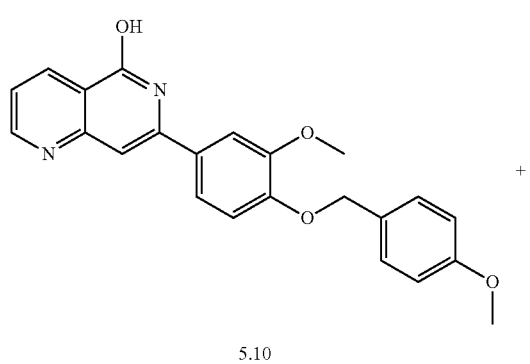

5.10

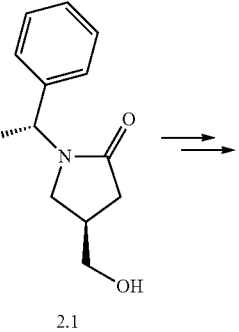

2.1

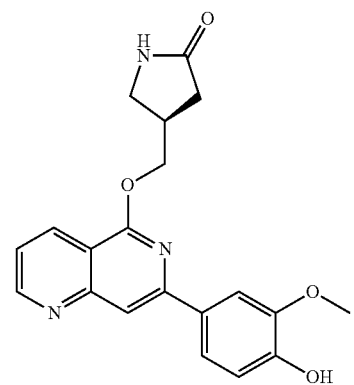

Example 53

Step 1

621 mg (R)-4-(hydroxymethyl)-1-((R)-1-phenylethyl)pyrrolidine-2-one (2.1), 1000 mg of 5.10 and 1.4 g of triphenylphosphine was suspended in 70 mL tetrahydrofuran. A solution was 1.2 g DBAD in 10 mL dichloromethane was added and the mixture stirred overnight at ambient temperature. 50 mL ethyl acetate and 50 mL water was added to the mixture and the phases separated. The water phase was extracted again with 50 mL ethyl acetate. The combined organic phases were washed with 20 mL 1N sodium hydroxide and 20 mL saturated sodium chloride solution and concentrated to yield 2.5 g of an intermediate A which was used without further purification.

Step 2

The intermediate A was dissolved in 8.3 mL trifluoroacetic acid for 5 min at ambient temperature. The mixture was concentrated and dissolved in 25 mL ethyl acetate. After 14 h the precipitate was collected to yield 1022 mg of intermediate B.

Step 3

Intermediate B was dissolved in 4 mL trifluoroacetic acid and heated to 150° C. for 35 min in the microwave. The mixture was concentrated and suspended in methanol and dichloromethane and neutralized with aqueous NH$_3$ and purified via chromotography (SiO$_2$: dichloromethane→ dichloromethane: methanol 90:10) to give Example 53

Yield: 217 mg (0.59 mmol=23% of theory)

Analysis: HPLC-MS (method D): $R_t$: 1.16 min, (M+H)$^+$: 366

Example 60

(R)-4-{7-[3-Methoxy-4-(tetrahydro-pyran-4-yloxy)-phenyl]-[1,6]naphthyridine-5-yloxymethyl}-pyrrolidine-2-one

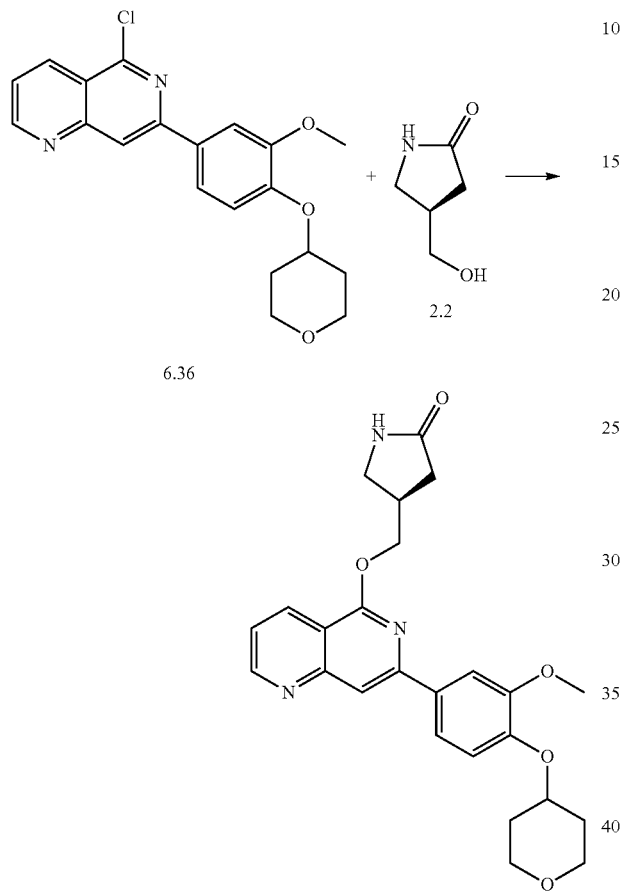

Example 60

91 mg (R)-4-Hydroxymethyl-pyrrolidine-2-one (2.2) was placed in 1 mL of dimethylacetamide at ambient temperature under nitrogen. The reaction was stirred for 10 min before 210 mg 5-chloro-7-[3-methoxy-4-(tetrahydro-pyran-4-yloxy)-phenyl]-[1,6]naphthyridine (6.36) as a solution in 1.5 mL dimethylacetamide was introduced. The reaction was stirred overnight at ambient temperature and then heated to 70° C. where it was maintained for 2 h. After this time the mixture was cooled to ambient temperature and it was partitioned between water and ethyl acetate. The aqueous layer was separated and it was extracted with additional ethyl acetate (×2). The combined organic fractions were dried over sodium sulfate, filtered and the filtrate was concentrated under reduced pressure. Purification by silica gel chromatography (ethyl acetate/methanol: 100:0 to 92:8) gave the title compound.

Yield: 163 mg (I.42 mmol=64% of theory)

Analysis: HPLC-MS (method A): $R_t$: 3.52 min, $(M+H)^+$: 450. $^1H$ NMR (250 MHz, chloroform-d) in ppm 1.89 (2 H, dd, J=8.60, 4.19 Hz), 2.00-2.15 (2 H, m), 2.31-2.48 (1 H, m), 2.56-2.74 (1 H, m), 3.07-3.28 (1 H, m), 3.41-3.50 (1 H, m), 3.56 (2 H, ddd, J=11.73, 8.83, 3.05 Hz), 3.64-3.77 (1 H, m), 3.90-4.12 (5 H, m), 4.53 (1 H, s), 4.69 (2 H, t, J=6.17 Hz), 6.38 (1 H, s), 7.05 (1 H, d, J=8.53 Hz), 7.41 (1 H, dd, J=8.30, 4.34 Hz), 7.66-7.78 (2 H, m), 7.90 (1 H, s), 8.46 (1 H, dd, J=8.22, 1.07 Hz), 8.92-9.11 (1 H, m)

Example 64

5-({7-[3-Methoxy-4-(tetrahydro-pyran-4-yloxy)-phenyl]-[1,6]naphthyridine-5-ylamino}-methyl)-1H-pyridine-2-one

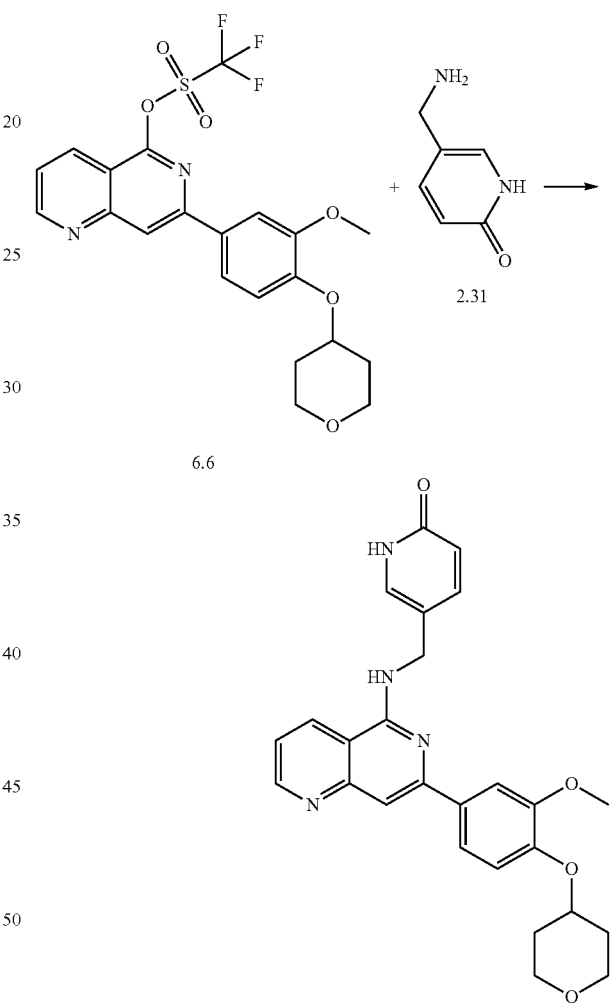

Example 64

200 mg Trifluoro-methanesulfonic acid 7-[3-methoxy-4-(tetrahydro-pyran-4-yloxy)-phenyl]-[1,6]naphthyridine-5-yl ester (6.6) was placed in 3 mL dimethylacetamide at ambient temperature before 51 mg 5-amino-1H-pyridine-2-one (2.31) and 109 mg N,N-diisopropylamine was added. The reaction was heated to 70° C. overnight in a sealed tube and then cooled to ambient temperature. After this time, additional 5-amino-1H-pyridin-2-one was added and the reaction was heated to 100° C. for 6 h, cooled to ambient temperature overnight. The reaction was then heated again at 100° C. for 24 h and then additional N,N-diisopropylamine was added and heating continued for 24 h. The reaction mixture was then cooled to ambient temperature and partitioned between water and ethyl acetate. The organic phase was separated and the aqueous phase was extracted with additional ethyl acetate (×3) and the combined organic fractions were dried, filtered and the solvent was concentrated from the filtrate under reduced pressure. Purification by silica gel chromatography (ethyl acetate/methanol: 95:5) and then by preparative HPLC provided the title compound.

Yield: 9 mg (5% of theory)
Analysis: HPLC-MS (Method A): R$_t$: 2.91 min, (M+H)$^+$: 459

Example 67

5-{[7-(3,4-Dimethoxy-phenyl)-[1,6]naphthyridine-5-ylamino]-methyl}-3H-[1,3,4]oxadiazole-2-one

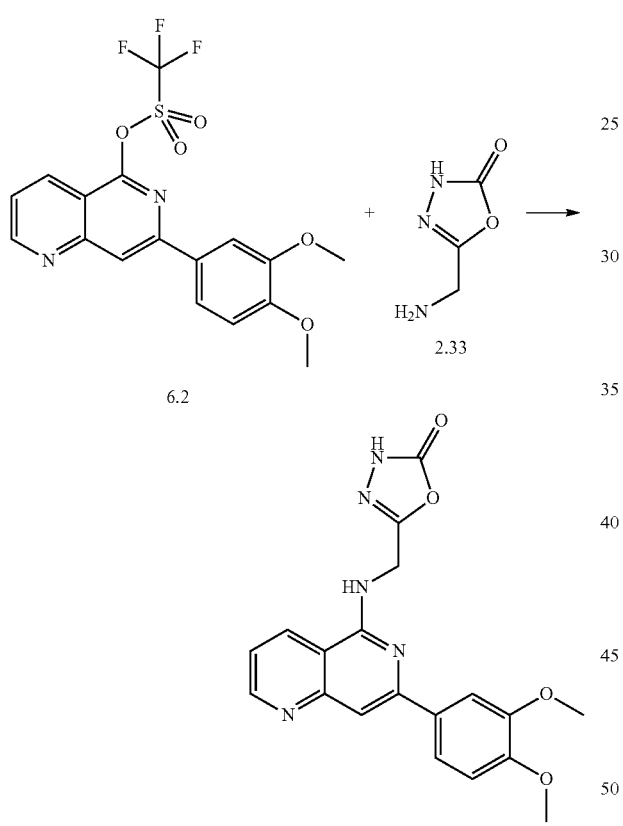

Example 67

97 mg Trifluoromethanesulfonic acid 7-(3,4-dimethoxy-phenyl)-[1,6]-naphthyridine-5-yl ester (6.2), 30 mg 5-aminomethyl-3H-[1,3,4]oxadiazole-2-one (2.33) and 0.132 mL N,N-diisopropylamine were placed in dimethylacetamide at ambient temperature. The reaction was heated to 70° C. overnight. After this time the reaction was cooled to ambient temperature and additional 0.132 mL N,N-diisopropylamine were added. The reaction was heated to 90° C. for 6 h. After this time, the mixture was cooled to ambient temperature and partitioned between water and ethyl acetate. The organic phase was separated and the aqueous phase was extracted with additional ethyl acetate (×3) and the combined organic fractions were dried over sodium sulfate, filtered and the solvent was concentrated from the filtrate under reduced pressure. Purification by and then by silica gel chromatography (ethyl acetate/methanol: 100:0 to 95:5) provided the title compound.

Yield: 4 mg (4% of theory)
Analysis: HPLC-MS (Method A): R$_t$: 2.91 min, (M+H)$^+$: 380

Example 77

Synthesis of (R)-5-[7-(3,4-Dimethoxy-phenyl)-[1,6]naphthyridine-5-yloxymethyl]-1-methyl-imidazolidine-2-one Step 1

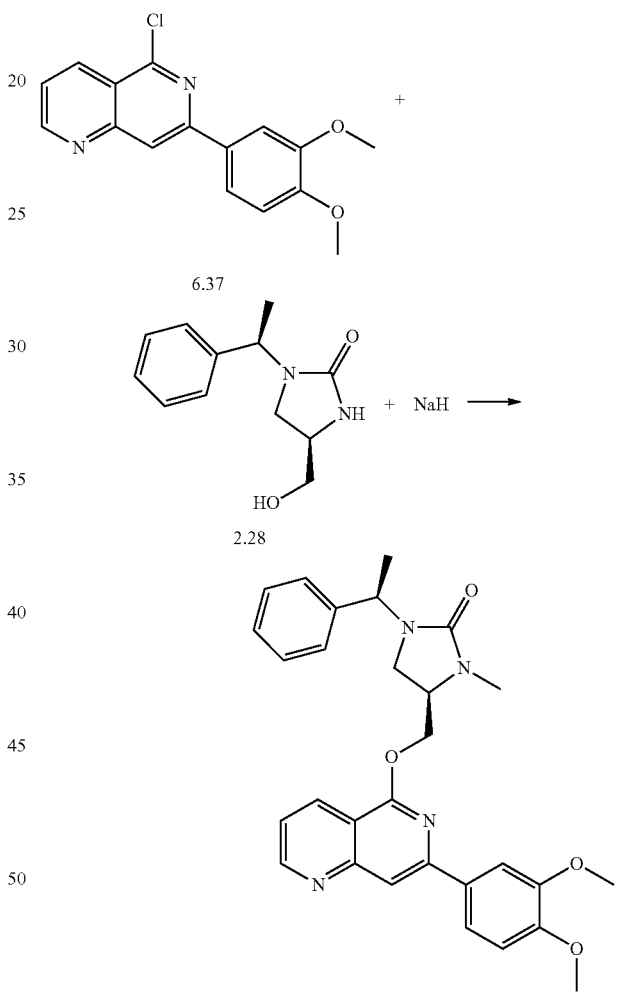

174 mg (R)-4-Hydroxymethyl-1-((R)-1-phenyl-ethyl)-imidazolidine-2-one (2.28) was placed in 2 mL dimethylacetamide under nitrogen at ambient temperature before 37.8 mg sodium hydride (60% dispersion in oil) was added. The reaction was stirred for 10 min and then 296 mg 5-chloro-7-(3,4-dimethoxy-phenyl)-[1,6]naphthyridine (6.37) as a solution in 2 mL dimethylacetamide was added. The mixture was heated to 90° C. where it was maintained for 2 h. After this time additional sodium hydride was added and the reaction was stirred at 90° C. for a further 16 h and then at ambient temperature for 3 d. After this time the reaction was heated to 90° C. for 24 h and then it was cooled to ambient temperature. The reaction was quenched by the addition of 5 mL water and extracted with ethyl acetate (×3). The organic fractions were combined, dried over sodium sulfate, filtered and the solvent was removed from the filtrate under reduced pressure. Purification by silica gel chromatography (ethyl acetate/dichloromethane: 5-7% then switching to methanol/ethyl acetate: 10%) provided the title compound.

Yield: 222 mg (58% of theory)

Analysis: HPLC-MS (Method B): $R_t$=2.18 min (M+H)$^+$=485.

Step 2

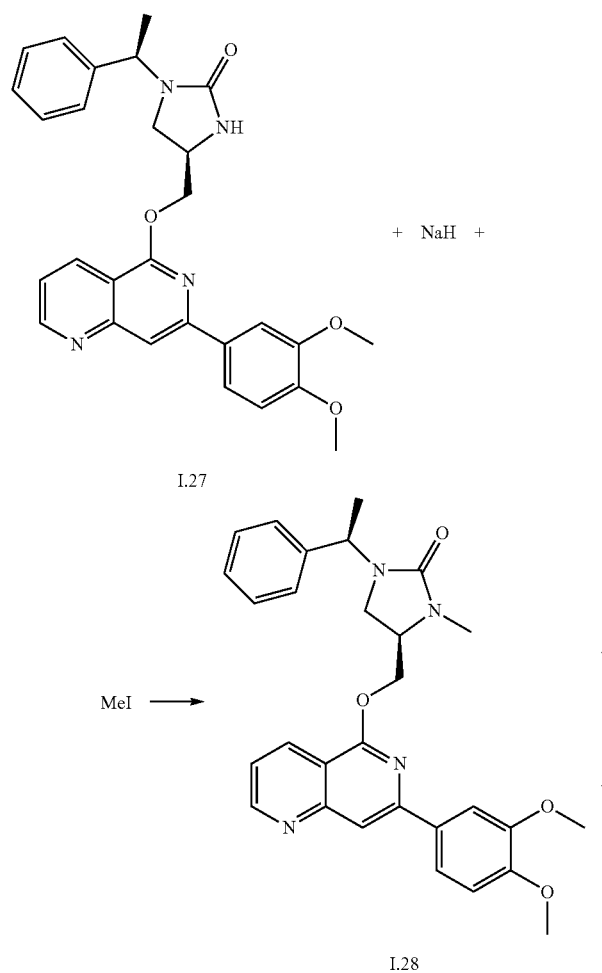

I.27

MeI ⟶

I.28

111 mg (R)-4-[7-(3,4-Dimethoxy-phenyl)-[1,6]-naphthyridine-5-yloxymethyl]-1-((R)-1-phenyl-ethyl)-imidazolidine-2-one (I.27) was placed in N,N-dimethylformamide and cooled to −10° C. before 9.16 mg sodium hydride (60% dispersion in oil) and 0.114 mL methyl iodide were added. The reaction was allowed to warm to ambient temperature where it was maintained for 5 h. After this time the solvent was removed under reduced pressure and the product was partitioned between ethyl acetate and water. The organic phase was separated and the aqueous phase was extracted with additional ethyl acetate (×2). The combined organic fractions were washed with water (×2), a saturated solution of sodium chloride, dried over sodium sulfate, filtered and the solvent was removed from the filtrate under reduced pressure. The crude compound was used without further purification.

Yield: 78.7 mg (69% of theory)

Analysis: HPLC-MS (Method B): $R_t$=2.52 min (M+H)$^+$=499.

Step 3

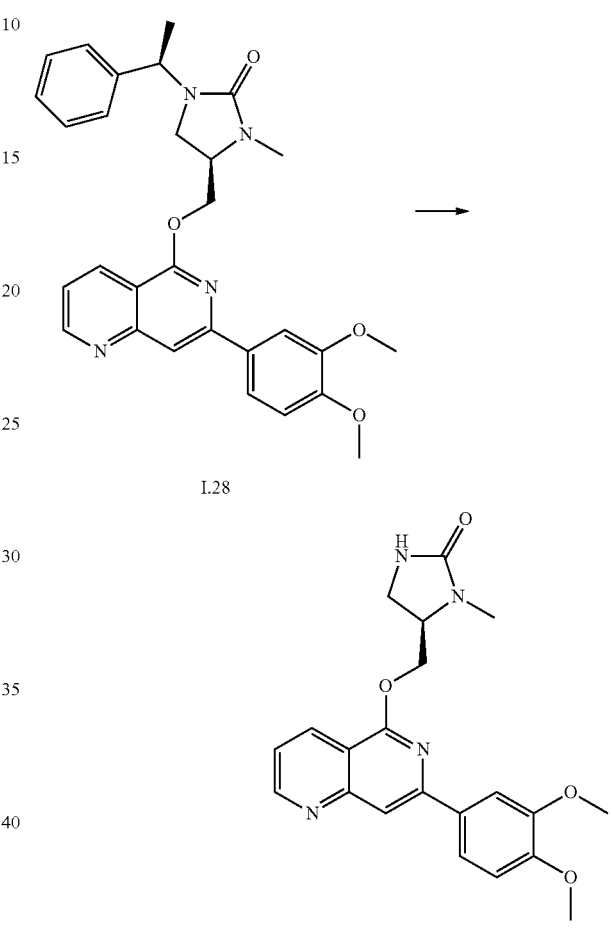

I.28

⟶

Example 77

78 mg (R)-4-[7-(3,4-Dimethoxy-phenyl)-[1,6]-naphthyridine-5-yloxymethyl]-3-methyl-1-((R)-1-phenyl-ethyl)-imidazolidine-2-one (I.28) was placed in 1 mL of trifluoroacetic acid at ambient temperature. The reaction mixture was heated to 160° C. under microwave irradiation where it was maintained for 10 min. After this time the mixture was cooled to ambient temperature and concentrated under reduced pressure. Purification by silica gel chromatography (methanol/dichloromethane: 1-4%) gave the title compound.

Yield: 32.7 mg (53% of theory)

Analysis: HPLC-MS (Method A): $R_t$=3.61 min (M+H)$^+$=396.

Example 74

(R)-4-[7-(3,4-Dimethoxy-phenyl)-[1,6]-naphthyridine-5-yloxymethyl]-imidazolidine-2-one was obtained from (R)-4-[7-(3,4-Dimethoxy-phenyl)-[1,6]naphthyridine- 5-yloxymethyl]-1-((R)-1-phenyl-ethyl)-imidazolidine-2-one using a procedure analogous to the method described for Example 77.

Example 78

(R)-4-((7-(3,4-dimethoxyphenyl)-1,6-naphthyridine-5-yloxy)methyl)pyrrolidine-2-one

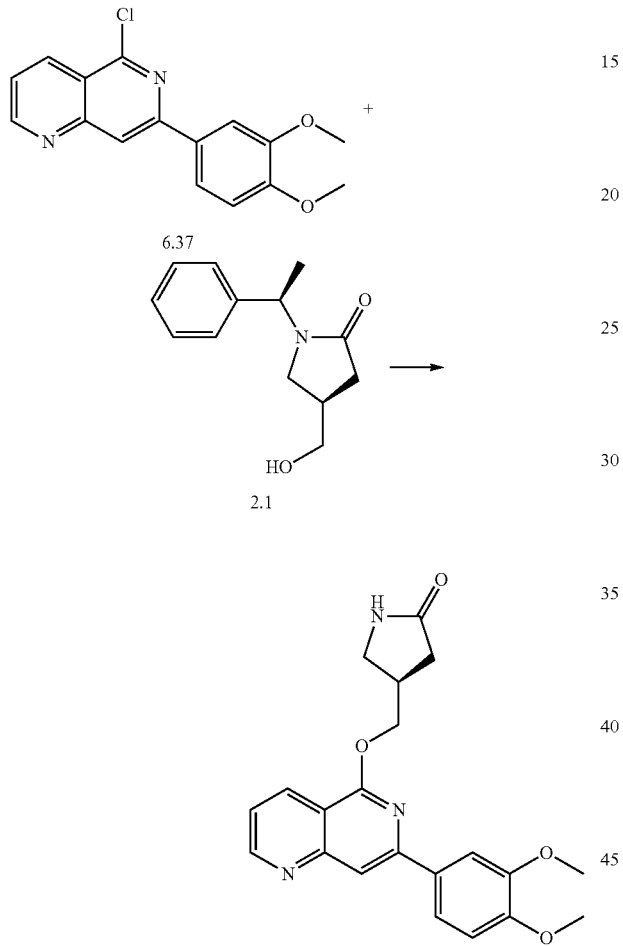

Example 78

100 mg (R)-4-(hydroxymethyl)-1-((R)-1-phenylethyl) pyrrolidine-2-one (2.1) was placed in 2 mL dimethylacetamide and 20 mg sodium hydride (60%) were added and the mixture was stirred for 15 min at ambient temperature. Then 100 mg 6.37 was added and the mixture was stirred for 3 h at 50° C., further 4 h at 80° C. and overnight at 50° C. The reaction mixture was purified by chromatography (RP-HPLC-MS). The corresponding fractions were freeze-dried to provide protected Example 78 as intermediate. The intermediate was then treated with 2 mL of trifluoroacetic acid and heated for 30 min at 160° C. in the microwave. The reaction mixture was diluted with water and acetonitrile and purified by chromatography (RP-HPLC-MS). The corresponding fractions were freeze-fried.

Yield: 15 mg (9% of theory)

Analysis: HPLC-MS (method D): $R_t$: 1.21 min, (M+H)$^+$: 523

Example 91

5-{[7-(3,4-Dimethoxy-phenyl)-[1,6]naphthyridine-5-ylamino]-methyl}-1H-pyridine-2-one

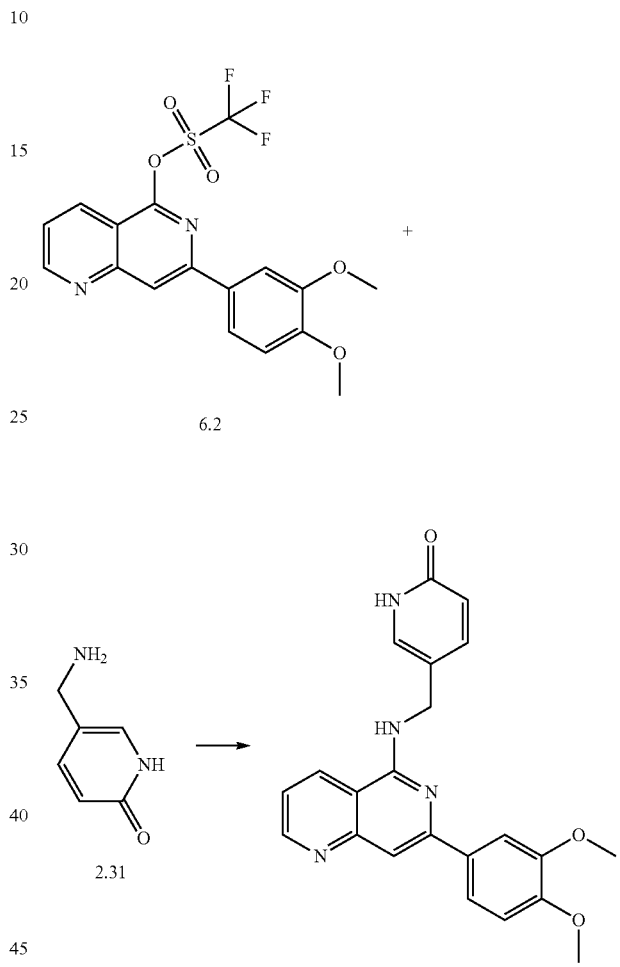

Example 91

100 mg Trifluoromethanesulfonic acid 7-(3,4-dimethoxyphenyl)-[1,6]-naphthyridine-5-yl ester (6.2) was placed in 2 mL dimethylacetamide at ambient temperature before 120 mg 5-amino-1H-pyridine-2-one (2.31) was added. The reaction was heated to 70° C. overnight and then cooled to ambient temperature. After this time, additional 14.9 mg 5-amino-1H-pyridin-2-one (2.31) was added and the reaction was heated to 70° C. for 24 h and then 100° C. for a further 24 h. The solvent was removed under reduced pressure and the crude material was purified twice by silica gel chromatography (ethyl acetate/methanol) and then by preparative chromatography. Finally it was free-based using a SCX column to give the title compound.

Yield: 9 mg (10% of theory)

Analysis: $^1$H NMR (500 MHz, methanol-d$_4$) d ppm 3.89 (6 H, s), 4.70 (2 H, s), 6.53 (1 H, d, J=9.46 Hz), 7.04 (1 H, d, J=8.39 Hz), 7.43 (1 H, dd, J=8.39, 4.43 Hz), 7.47 (1 H, s), 7.52

(1H, d, J=1.83 Hz), 7.68-7.75 (2 H, m), 7.78 (1 H, dd, J=9.31, 2.44 Hz), 8.55 (1 H, d, J=8.24 Hz), 8.83 (1 H, d, J=4.27 Hz)

Analysis: HPLC-MS (method A): R$_t$: 4.24 min, (M+H)$^+$: 396

Example 103

(R)-4-[7-(3-Fluoro-4-isopropoxy-phenyl)-[1,6]naphthyridine-5-yloxymethyl]-pyrrolidine-2-one

Examples 105 and 106

Synthesis of (R)-4-{7-[3-Methoxy-4-(1-methyl-piperidine-3-yloxy)-phenyl]-[1,6]naphthyridine-5-yloxymethyl}-pyrrolidine-2-one and (R)-4-{7-[3-Methoxy-4-(1-methyl-pyrrolidine-2-ylmethoxy)-phenyl]-[1,6]naphthyridine-5-yloxymethyl}-pyrrolidine-2-one

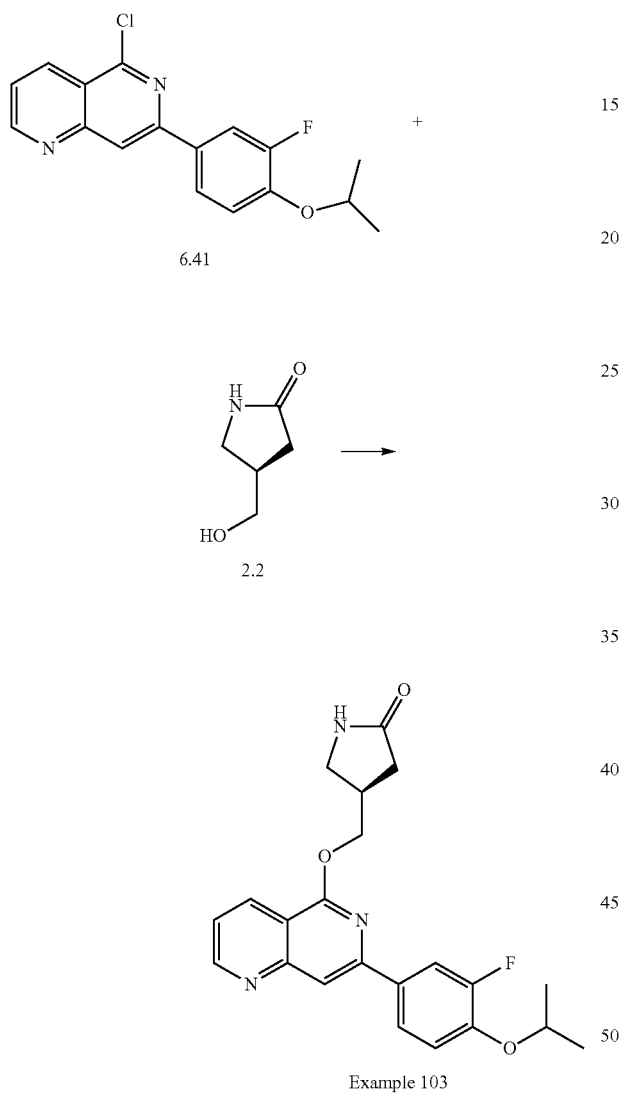

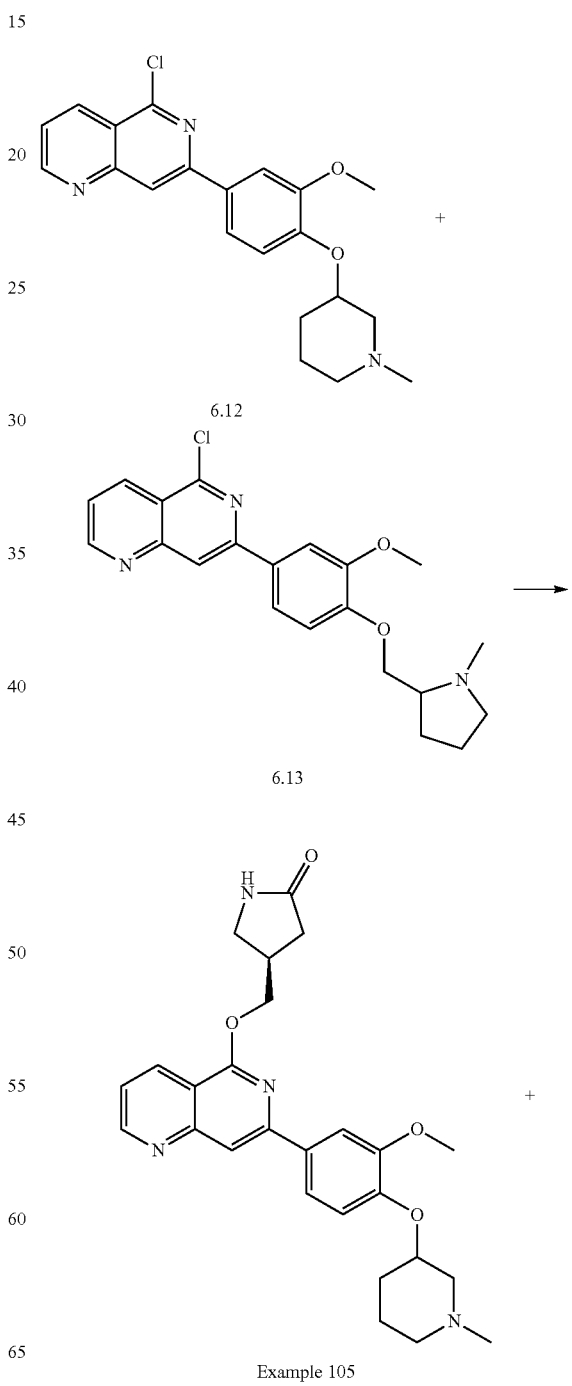

224 mg (R)-4-Hydroxymethyl-pyrrolidine-2-one (2.2) was placed in 1.5 mL of dimethylacetamide at ambient temperature under nitrogen. The reaction was stirred for 10 min before 5-chloro-7-(3-fluoro-4-isopropoxy-phenyl)-[1,6]-naphthyridine (6.41) as a solution in 3 mL dimethylacetamide was introduced. The reaction was heated to 100° C. for 3 h and then cooled to ambient temperature. Water was added and the mixture was extracted with ethyl acetate (×3). The combined organic fractions were dried over sodium sulfate, filtered and the filtrate was concentrated under reduced pressure. Purification by silica gel chromatography (ethyl acetate/methanol: 100:0 to 90:10) gave the title compound.

Yield: 120 mg (43% of theory)

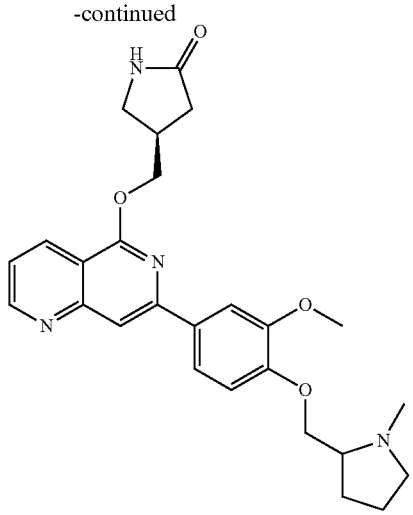

Example 106

21.9 mg sodium hydride (as a 60% dispersion in oil) was added to a solution of 54 mg (R)-4-(hydroxymethyl)pyrrolidine-2-one (2.2) in dimethylacetamide at ambient temperature under nitrogen. The reaction was stirred for 10 min before a mixture of 150 mg 5-chloro-7-[3-methoxy-4-(1-methyl-piperidine-3-yloxy)-phenyl]-[1,6]naphthyridine (6.12) and 5-chloro-7-[3-methoxy-4-(1-methyl-pyrrolidine-2-yl-methoxy)-phenyl]-[1,6]naphthyridine (6.13) as a solution in 1.5 mL dimethylacetamide was added. The reaction was then sealed and heated to 70° C. where it was monitored by HPLC-MS. After the disappearance of starting material the reaction was cooled to ambient temperature and diluted with water. The mixture as extracted with ethyl acetate (×3) and the combined organic fractions were dried over sodium sulfate, filtered and the filtrate was concentrated under reduced pressure. Purification by silica gel chromatography (dichloromethane: 7N ammonia in methanol) and then by preparative HPLC provided the title compounds.

Yield: 31 mg of Example 105 (17% of theory)
Analysis: HPLC-MS (Method F): $R_t$: 4.26 min (M+H)$^+$=463
Yield: 27 mg of Example 106 (15% of theory)
Analysis: HPLC-MS (Method F): $R_t$: 4.40 min (M+H)$^+$=463

4.4.2. Reaction 5 and Ring Formation to R1 of Scheme 3

Example 28

(R/S)-5-[7-(3,4,5-trimethoxy-phenyl)-[1,6]naphthyridine-5-yloxymethyl]-isoxazolidine-3-one Step 1

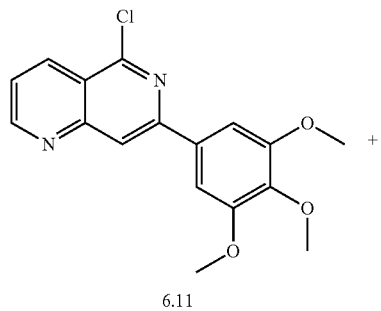

6.11

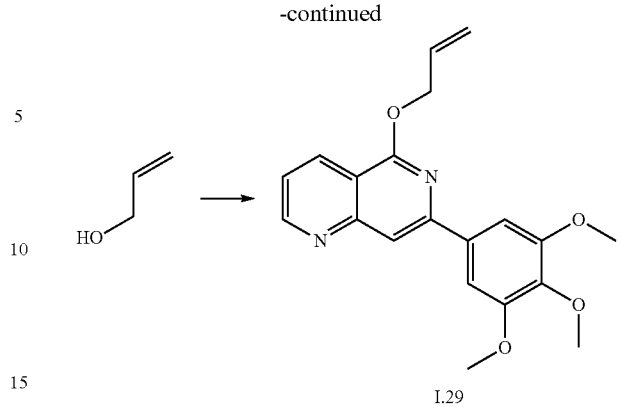

I.29

75 mg Sodium hydride (as a 60% dispersion in oil) was added to 0.212 mL allyl alcohol in 4.68 mL dimethylacetamide at ambient temperature under nitrogen. The reaction was stirred for 10 min before 515 mg 5-chloro-7-(3,4,5-trimethoxy-phenyl)-[1,6]naphthyridine (6.11) in 2 mL dimethylacetamide was added and then the reaction was heated to 90° C. where it was left overnight. After this time, additional 37 mg sodium hydride (as a 60% dispersion in oil) was introduced and the reaction was stirred for a further 1 h at 90° C. The mixture was cooled to ambient temperature and diluted with water and then extracted with ethyl acetate (×3). The combined organic fractions were dried (sodium sulfate), filtered and the filtrate was concentrated under reduced pressure to give the title compound which was used without further purification.

Yield 0.469 g (86% of theory)
Analysis: HPLC-MS (Method B): $R_t$=2.41 min (M+H)$^+$=353.

5-(1-Methyl-allyloxy)-7-(3,4,5-trimethoxy-phenyl)-[1,6]-naphthyridine (for Example 31) was prepared from 5-chloro-7-(3,4,5-trimethoxy-phenyl)-[1,6]-naphthyridine and (R/S)-but-3-en-2-ol using an analogous procedure 5-Allyloxy-7-(3,4-dimethoxy-phenyl)-[1,6]-naphthyridine (for Example 73) was prepared from 5.31 and allyl alcohol using an analogous procedure Synthesis of Dibromoformaldoxime

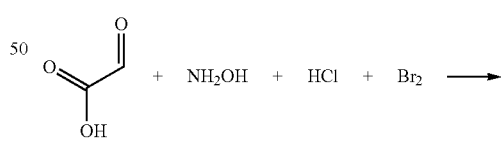

1.30

Dibromoformaldoxime may be synthesised according to the following literature procedure: Vyas, D M; Chiang, Y.; Doyle, T W *Tetrahedron Lett.* (1984), 25(5), 487-490.

Step 2

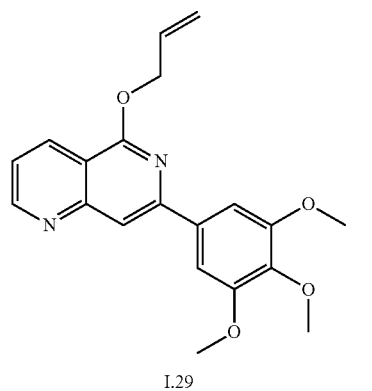

I.29

+

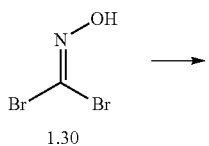

I.30

→

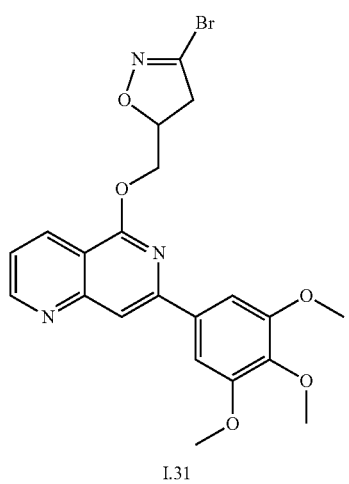

I.31

0.469 g (5-Allyloxy-7-(3,4,5-trimethoxy-phenyl)-[1,6]-naphthyridine (I.29) were placed in 5.40 mL ethyl acetate at ambient temperature, then 0.487 g sodium hydrogen carbonate and 0.405 g dibromoformaldoxime (I.30) were added. The reaction was stirred at ambient temperature for 20 h and then heated to 70° C. where it was maintained for 3 h. After this time the reaction was cooled to ambient temperature and poured onto water. The mixture was extracted with ethyl acetate (×2) and the combined organic fractions were dried with sodium sulfate and the solvent was removed from the filtrate under reduced pressure to provide the title compound as a mixture of enantiomers which was used without further purification.

Yield: 0.634 g (100% of theory)
Analysis: HPLC-MS (Method B): $R_t$=2.23 min (M+H)$^+$=474, 476.

The following compounds were prepared analogously to the methods described (see Table 5).

TABLE 5

Further 5-(3-Bromo-4,5-dihydro-isoxazole-5-ylmethoxy)-[1,6]naphthyridines

| Product number | $R^5$ | $R^2$ | Analytical data |
|---|---|---|---|
| see Example 31 | Me | *-C6H2(OMe)3 (3,4,5-trimethoxyphenyl) | HPLC-MS (method B) $R_t$ min = 2.38 (M + H)$^+$ 488, 490 |
| see Example 73 | H | *-C6H3(OMe)2 (3,4-dimethoxyphenyl) | HPLC-MS (method A) $R_t$ min = 3.48 (M + H)$^+$ 382 |

Step 3

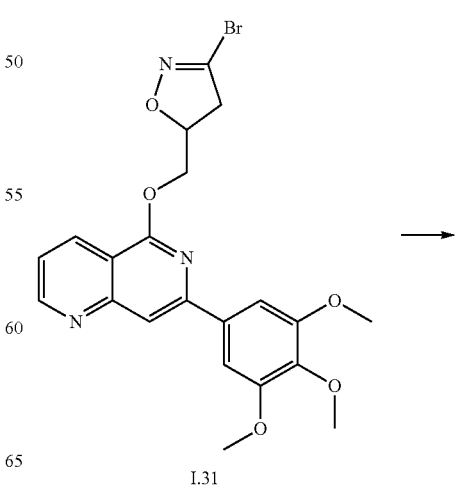

I.31

→

127

-continued

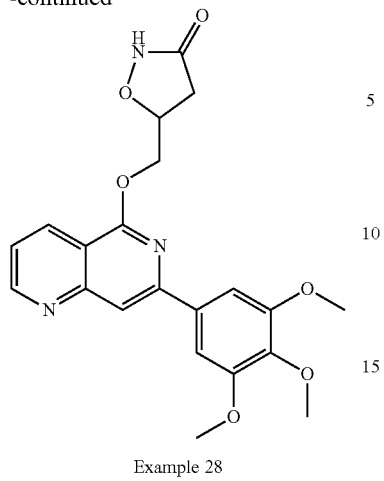

Example 28

0.634 g 5-(3-Bromo-4,5-dihydro-isoxazole-5-yl-methoxy)-7-(3,4,5-trimethoxy-phenyl)-[1,6]naphthyridine (I.31) were placed in 9.34 mL tetrahydrofuran at ambient temperature, then 37.5 mL of 1M sodium hydroxide and 37.2 mg tetrabutylammonium hydrogensulfate were added. The reaction was heated to 80° C. where it was maintained for 26 h. After this time, reaction mixture was cooled to ambient temperature and washed with diethyl ether (×2). The aqueous phase was acidified to pH ~4 using 4M hydrochloric acid and extracted with ethyl acetate (×4). The combined organic fractions were dried with sodium sulfate and the solvent was removed from the filtrate under reduced pressure. Purification by silica gel chromatography (methanol/dichloromethane: 2-4%), followed by trituration with dichloromethane and then a second purification by silica gel chromatography (methanol/dichloromethane: 1.5%) gave the title compound as a mixture of enantiomers.

Yield: 98 mg (18% of theory)

Analysis: HPLC-MS (Method A): $R_t$=3.51 min $(M+H)^+$=412

$^1$H NMR (500 MHz, chloroform-d) δ ppm 2.90 (1 H, dd, J=16.63, 6.87 Hz), 3.05 (1 H, dd, J=16.63, 8.39 Hz), 3.94 (3 H, s), 3.99 (6 H, s), 4.89-4.93 (2 H, m), 5.15-5.22 (1 H, m), 7.39 (2 H, s), 7.45 (1 H, dd, J=8.24, 4.58 Hz), 7.96 (1 H, s), 8.54 (1 H, d, J=8.24 Hz), 9.01 (1 H, dd, J=4.42, 1.68 Hz)

Example 66

Synthesis of 5-[7-(3,4-dimethoxy-phenyl)-[1,6]naphthyridine-5-yloxymethyl]-3H-[1,3,4]oxadiazole-2-one Step 1

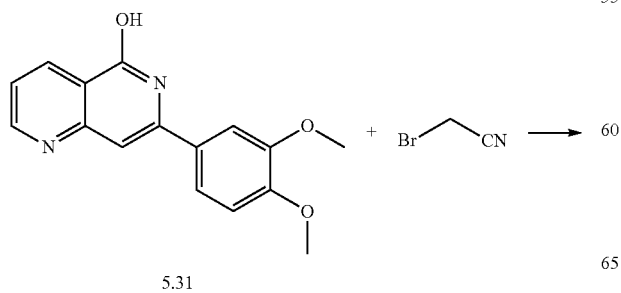

128

-continued

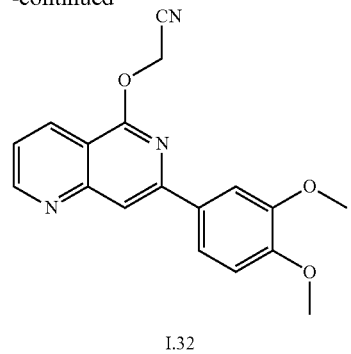

I.32

1 g 7-(3,4-Dimethoxy-phenyl)-[1,6]naphthyridine-5-ol (5.31) was placed in 20 mL N,N-dimethylformamide at ambient temperature before 2.45 g potassium carbonate was added. The reaction was stirred for 10 min at ambient temperature before 0.74 mL bromoacetonitrile was introduced. The reaction was heated to 60° C. under an atmosphere of nitrogen for 4 h. After this time, the reaction was cooled to ambient temperature and water was added. The mixture was extracted with ethyl acetate (×2) and the combined organic fractions were washed with water (×2), saturated sodium chloride solution, dried over sodium sulfate, filtered and the filtrate was concentrated under reduced pressure. Purification by chromatography on silica gel (tert-butyl methyl ether/ethyl acetate: 100:0 to 0:100) provided the title compound.

Yield: 510 mg (45% of theory)

Analysis: HPLC-MS (Method B): $R_t$=1.87 min $(M+H)^+$=322.

Step 2

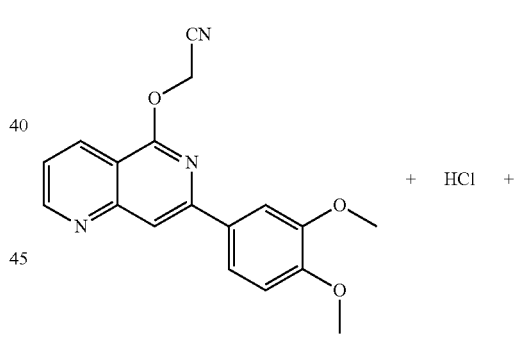

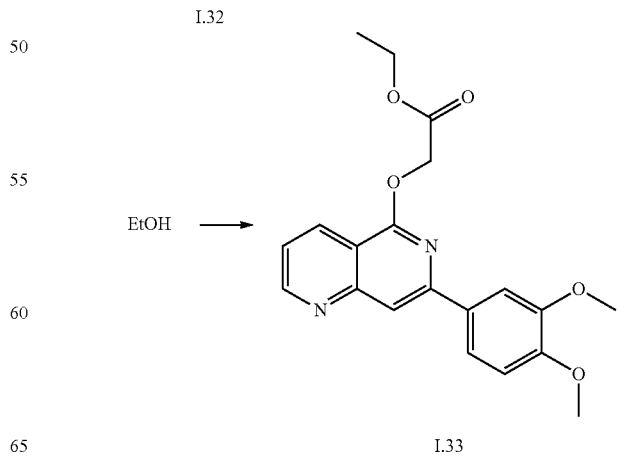

200 mg [7-(3,4-Dimethoxy-phenyl)-[1,6]-naphthyridine-5-yloxy]-acetonitrile (I.32) was placed in 1 mL diethyl ether at ambient temperature before 35.8 mL ethanol was added. The reaction mixture was cooled to 0° C. and 10 mL of 2M hydrogen chloride in diethyl ether was introduced. The reaction was stirred for 1 h at 0° C. and then hydrogen chloride gas was bubbled through the mixture for 20 min. After a further 2 h at 0° C. the reaction was warmed to ambient temperature where it was left for 16 h. The resulting suspension was filtered and the solid filter cake was partitioned between ethyl acetate and a saturated solution of sodium hydrogen carbonate. The organic layer was separated and the aqueous phase was extracted with additional ethyl acetate. The combined organic fractions were dried over sodium sulfate, filtered and concentrated under reduced pressure. Purification by silica gel chromatography (heptanes/ethyl acetate: 50:50 to 0:100 and then ethyl acetate/methanol: 100:0 to 90:10) provided the title compound.

Yield: 80 mg (35% of theory)
Analysis: HPLC-MS (Method A): $R_t$=4.23 min $(M+H)^+$=369.

Step 3:

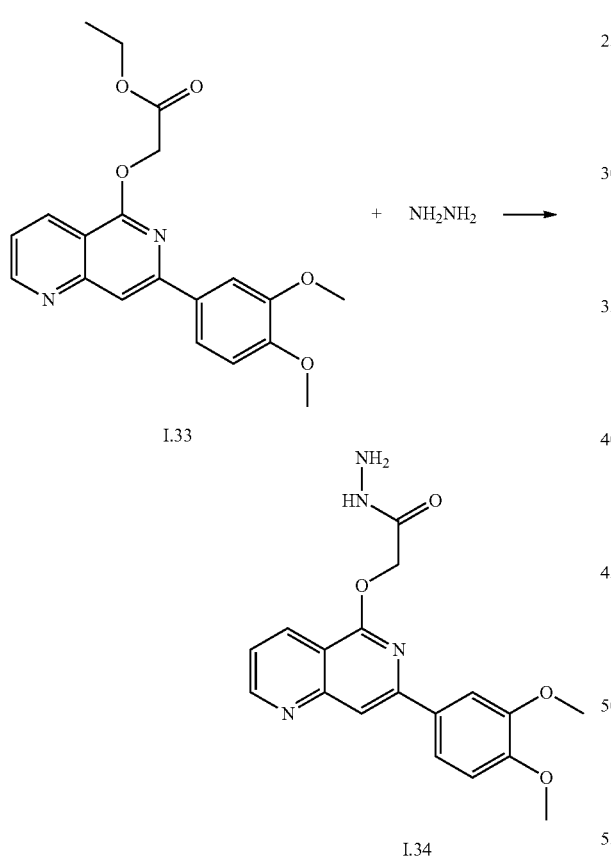

66 mg [7-(3,4-Dimethoxy-phenyl)-[1,6]-naphthyridine-5-yloxy]-acetic acid ethyl ester (I.33) was placed in 5 mL ethanol with 7.68 μl hydrazine hydrate (80%) at ambient temperature. The reaction was stirred at ambient temperature for 3 d before additional hydrazine hydrate was added and the mixture was heated to reflux. The reaction was then cooled to ambient temperature and the solvent was removed under reduced pressure by azeotroping the mixture with toluene. This provided the title compound which was used without further purification.

Yield: 63 mg (99% of theory)
Analysis: HPLC-MS (Method A): $R_t$=2.99 min $(M+H)^+$=355.

Step 4:

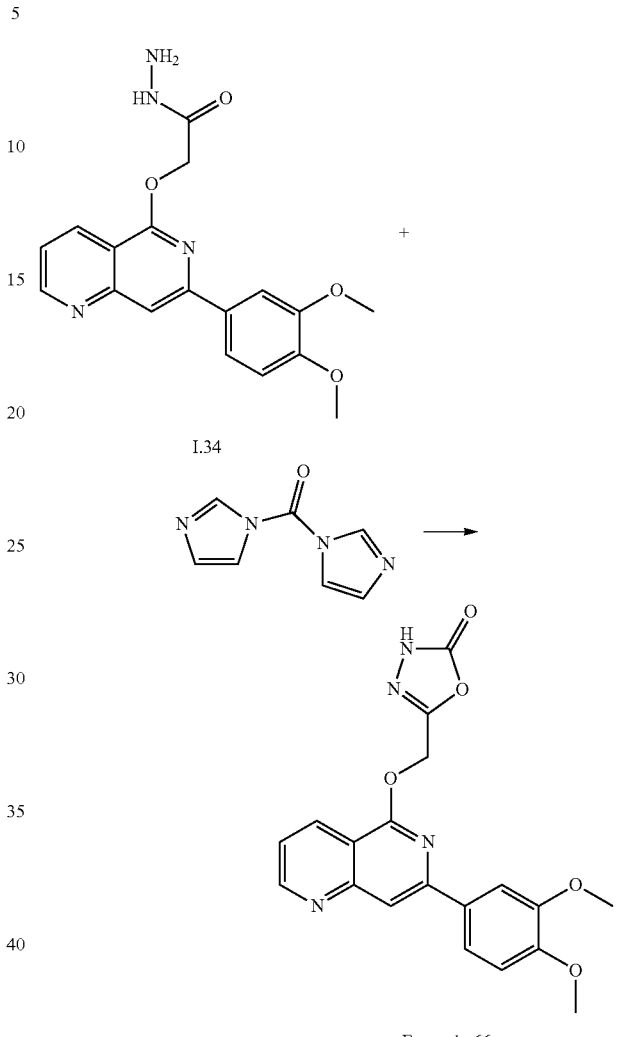

Example 66

54 mg [7-(3,4-Dimethoxy-phenyl)-[1,6]-naphthyridine-5-yloxy]-acetic acid hydrazide (I.34) was placed in tetrahydrofuran (10 mL) and N,N-dimethyl formamide (1 mL) at ambient temperature before 37 mg carbonyl diimidazole and 43 μl triethylamine were added. The reaction mixture was heated to 70° C. where it was maintained for 16 h. After this time additional carbonyl diimidazole and triethylamine were added and the reaction was maintained at 70° C. for a further 5 h. After this time additional carbonyl diimidazole and triethylamine were added and the reaction was maintained at 70° C. for a further 19 h. The solvent was then removed under reduced pressure and the crude product that remained was partitioned between dichloromethane and water. The dichloromethane layer was separated and the aqueous phase was extracted with additional dichloromethane (×2). The combined organic fractions were washed with water, saturated sodium chloride solution and then dried over sodium sulfate, filtered and the solvent was removed from the filtrate under reduced pressure. Purification twice by chromatography on silica gel (methanol/ethyl acetate: 0%-5% and then methanol/ethyl acetate: 0%-2%) followed by trituration with dichloromethane provided the title compound.

Yield: 58 mg (35% of theory)
Analysis: HPLC-MS (Method B): $R_t$=1.78 min $(M+H)^+$=381.

1H NMR (500 MHz, dimethyl sulfoxide-d6) d ppm 3.83 (3 H, s), 3.91 (3 H, s), 5.62 (2 H, s), 7.07 (1 H, d, J=8.54 Hz), 7.60 (1 H, dd, J=8.32, 4.35 Hz), 7.81-7.89 (2 H, m), 8.09 (1 H, s), 8.55 (1 H, d, J=7.78 Hz), 9.08 (1 H, dd, J=4.27, 1.53 Hz), 12.52 (1 H, br. s.).

Example 76

Synthesis of (R/S)-5-{[7-(3,4,Dimethoxy-phenyl)-[1,6]naphthyridine-5-ylamino]-methyl}-isoxazolidine-3-one Step 1

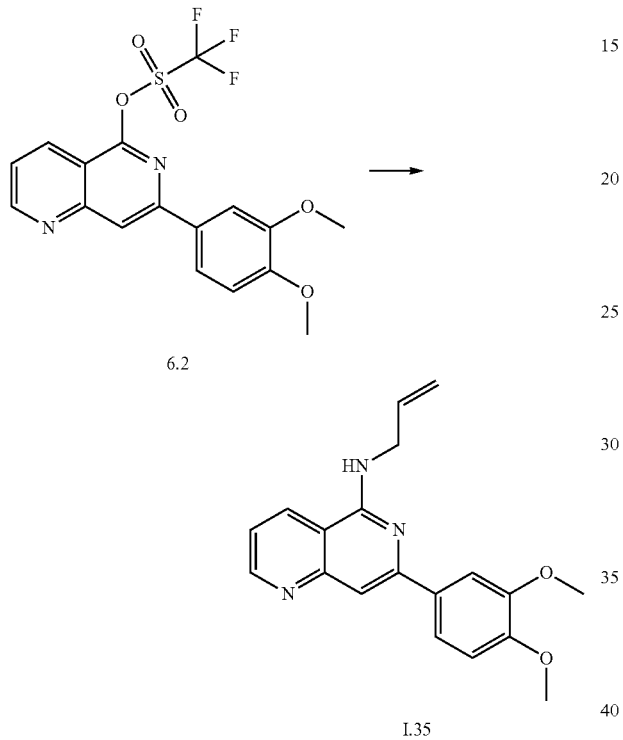

Steps 2&3

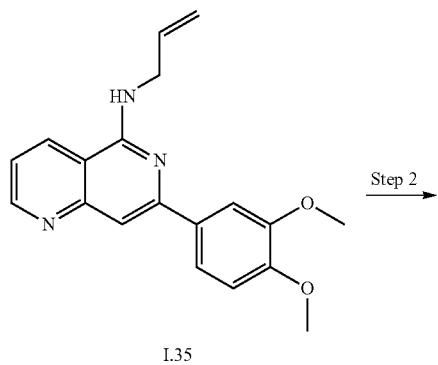

300 mg 7-(3,4-Dimethoxy-phenyl)-[1,6]naphthyridine-5-yl-trifluoromethanesulfonic acid ester (6.2) and 0.163 mL allyl amine in 4 mL dimethylacetamide were heated to 90° C. in sealed tube overnight. After this time, the reaction mixture was cooled to ambient temperature and concentrated under reduced pressure. The crude material was used without further purification.

Yield: 233 mg (100% of theory)

Analysis (Method B): $R_t$: 1.91 min

Steps 2&3

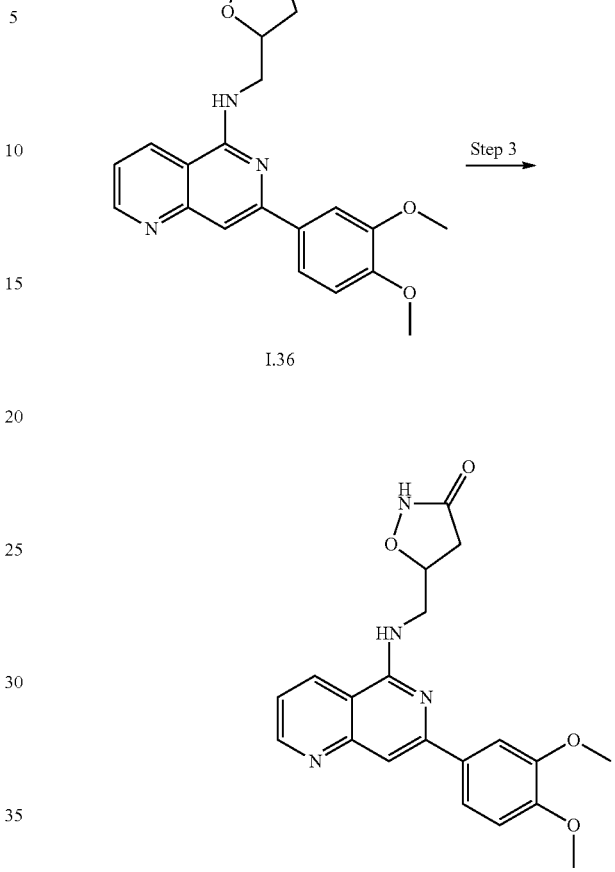

Example 77

0.233 g Allyl-[7-(3,4,dimethoxy-phenyl)-[1,6]-naphthyridin-5-yl]-amine (I.35) were placed in 2.9 mL ethyl acetate at ambient temperature, then 0.265 g sodium hydrogen carbonate and 0.220 g dibromoformaldoxime were added. The reaction was stirred at ambient temperature for 21 h. After this time the reaction was poured onto water and extracted with ethyl acetate (×2). The combined organic fractions were dried with sodium sulfate and the solvent was removed from the filtrate under reduced pressure to provide 1.36 as a mixture of enantiomers which was used without further purification. The crude material was placed in 6 mL tetrahydrofuran at ambient temperature, then 23.9 mL of 1M sodium hydroxide and 23.8 mg tetrabutylammonium hydrogensulfate were added. The reaction was heated to 80° C. where it was maintained for 22 h. After this time, reaction mixture was cooled to ambient temperature and washed with diethyl ether (×2). The aqueous phase was acidified to pH ~6 using 4M hydrochloric acid and extracted with dichloromethane (×4). The combined organic fractions were dried with sodium sulfate, filtered and the solvent was removed from the filtrate under reduced pressure. Purification by silica gel chromatography (methanol/dichloromethane: 2-5%) gave the title compound as a mixture of enantiomers.

Yield: 26.6 mg (8% of theory)

Analysis: HPLC-MS (Method A): $R_t$=2.80 min $(M+H)^+$=381.

4.4.3. Reaction 6 of Scheme 4

Example 9

7-(3,4-dimethoxyphenyl)-5-((R)-3-methoxy-1-((R)-5-oxopyrrolidine-3-yl)propoxy)-1,6-naphthyridine 1-oxide

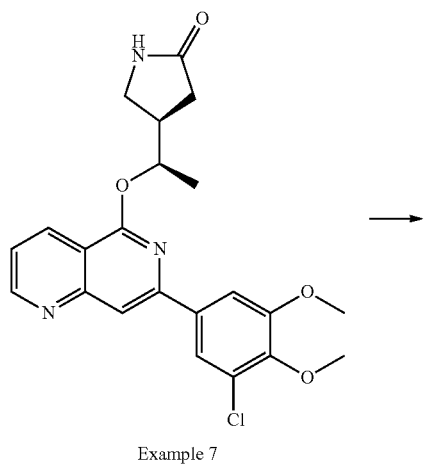

Example 7

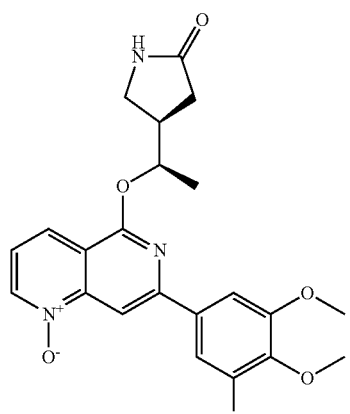

Example 9

12 mg Example 7 was dissolved in dichloromethane. Then 0.6 mg methyltrioxorhenium was added, the solution was cooled to 10° C., 3 μL H₂O₂ (35% in water) was added and the mixture was stirred for 2 h at ambient temperature. The reaction mixture was then diluted with acetonitrile and water purified by chromatography (RP-HPLC-MS). The corresponding fractions were freeze-dried.

Yield: 9 mg (72% of theory)
Analysis: HPLC-MS (method E): $R_t$: 1.29 min, (M+H)⁺: 444/446

Example 37 was prepared in an analogous manner from example 6.

4.4.4. Alternative Syntheses of Example 35

Synthesis of (1'R,3R/S)-1-(1'-(4-Methoxyphenyl-ethyl)-5-oxo-3-pyrrolidine carboxylic acid (mixture of diastereoisomers)

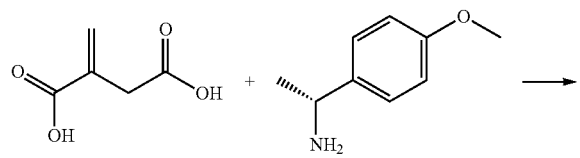

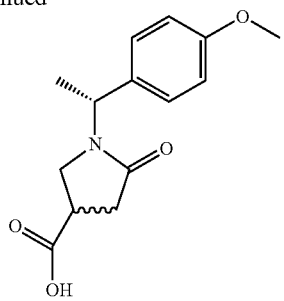

A suspension of 100 g of (R)-1-(4-methoxy-phenyl)-ethylamine and 95 g itaconic acid in 0.5 L 1-methyl-2-pyrrolidinone is heated to 80° C. for 1 hour. The solution is stirred for additional 4 hours at 120° C. The reaction mixture is cooled to 25° C. and poured into 1.5 L of demineralized water. The precipitate is filtered, washed with demineralized water and dried at 50° C.

Yield: 195 g (quantitative yield) solid as a mixture of diastereoisomers
Analysis (method G): $R_t$: 2.6 min and 2.7 min, (M+H)⁺: 264

In analogy is prepared (1'S,3R/S)-1-(1'-(4-Methoxyphenylethyl)-5-oxo-3-pyrrolidine carboxylic acid as a mixture of diastereoisomers
Analysis (method G): $R_t$: 2.6 min and 2.7 min, (M+H)⁺: 264

Synthesis of (R/S)—N-Methoxy-5-oxo-1-[(S)-1-(4-methoxyphenyl)-ethyl]-pyrrolidine-3-carboxamide as a mixture of diastereoisomers

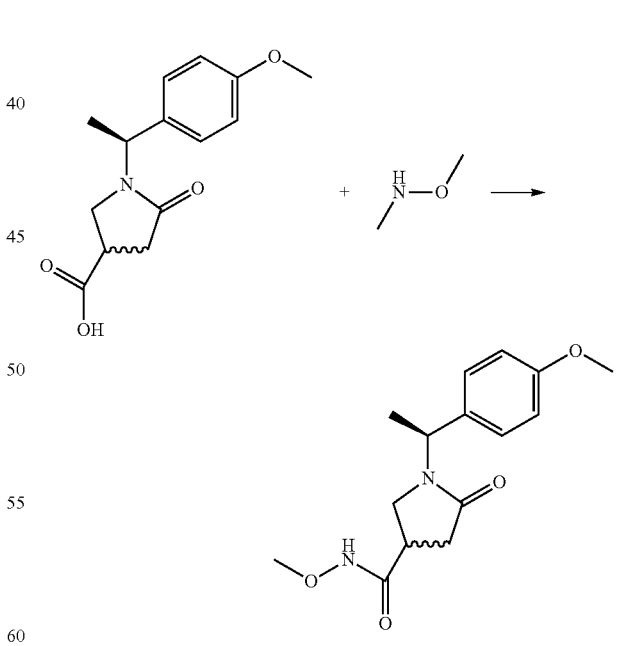

260 g of 1,1'-Carbonyldiimidazole (CDI) are added to a solution of 285 g (1'R,3R/S)-1-(1'-(4-methoxyphenylethyl)-5-oxo-3-pyrrolidine carboxylic acid (mixture of diastereoisomers) in 1.4 L 2-methyltetrahydrofuran at 20° C. The suspension is stirred at 20° C. for 80 minutes. 235 mL ethyldiisopropylamine (DIPEA) and 130 g of N,O-dimethylhydroxylamine hydrochloride are added. The suspension is stirred for 3 hours at 20° C. Under cooling 850 mL 4 N hydrochloric acid is added. The organic phase is separated and washed two times with 500 mL 1 N hydrochloric acid. The aqueous phase is reextracted two times with 500 mL ethyl acetate. The combined organic phases are dried over sodium sulfate. After filtration the solvent is evaporated under reduced pressure.

Yield: 271 g (82% of theory) of (R/S)—N-Methoxy-5-oxo-1-[(S)-1-(4-methoxyphenyl)-ethyl]-pyrrolidine-3-carboxamide (mixture of diastereoisomers) as an oil.

Analysis (method H): $R_t$: 11.1 min (41 area %) and 13.8 min (59 area %), (M+H)$^+$: 307

Synthesis of (R/S)-4-acetyl-1-[(S)-1-(4-methoxyphenyl)-ethyl]-pyrrolidine-2-one as a mixture of diastereoisomers

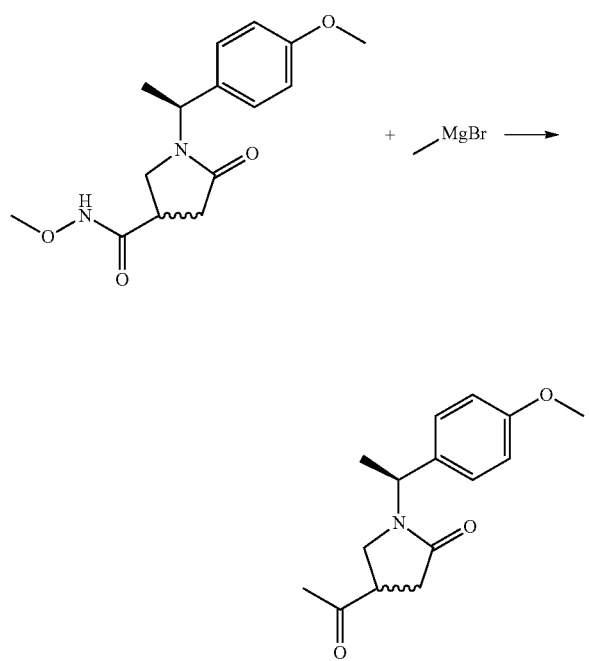

530 mL of a 3 M solution of methylmagnesium bromide in diethylether is added slowly to a cooled solution of 271 g of (R/S)—N-Methoxy-5-oxo-1-[(S)-1-(4-methoxyphenyl)-ethyl]-pyrrolidine-3-carboxamide (mixture of diastereoisomers) in 1.4 L of 2-methyltetrahydrofuran so that the temperature remains under 0° C. After complete addition the temperature is kept for 75 minutes at 0° C. and then warmed up to 20° C. The suspension is stirred 16 hours at 20° C. Under cooling 650 mL of a 4 M hydrochloric acid are added. The organic phase is separated and washed with 500 mL saturated sodium carbonate solution and with 500 mL saturated brine. The organic phase is dried over sodium sulfate. After filtration the solvent is evaporated under reduced pressure.

Yield: 188 g (81% of theory) of (R/S)-4-acetyl-1-[(S)-1-(4-methoxyphenyl)-ethyl]-pyrrolidine-2-one (mixture of diastereoisomers) as an oil.

Analysis (method H): $R_t$: 7.4 min and 9.6 min, (M+H)$^+$: 262

Crystallization of (R)-4-acetyl-1-[(S)-1-(4-methoxyphenyl)-ethyl]pyrrolidine-2-one under base induced epimerization conditions

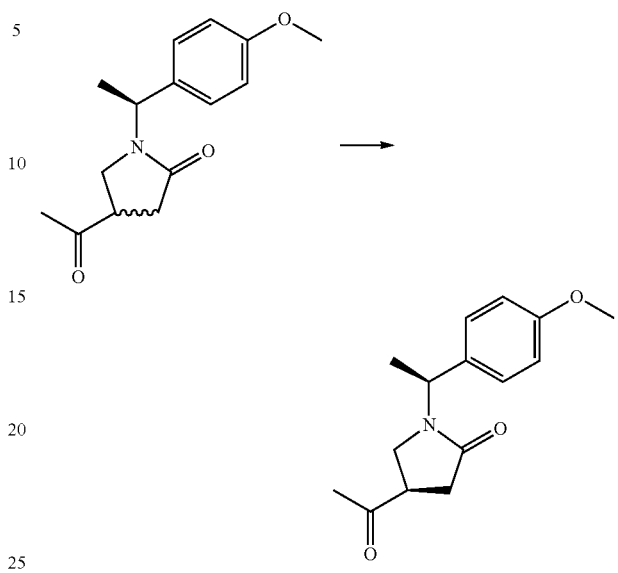

103 g of a mixture of diastereoisomers (R/S)-4-acetyl-1-[(S)-1-(4-methoxyphenyl)-ethyl]-pyrrolidine-2-one is dissolved in 155 mL 1-butanol at 25° C. 18 mL benzyltrimethylammonium hydroxide (40% solution in methanol) is added. The solution is stirred for 30 minutes at 25° C. The solution is cooled to 0° C. Precipitation starts. The suspension is stirred for 15 minutes at 0° C. 100 mL n-heptane is added slowly and the suspension is stirred for 30 minutes at 0° C. The addition of 100 mL portions of n-heptane is repeated 4 times with subsequent stirring of the suspension at 0° C. for 30 minutes. The precipitate is isolated, washed with n-heptane and dried at 50° C.

Yield: 77.1 g of a beige solid (75% of theory) with a diastereoisomeric purity of ~95:5 (method H).

For further purification the crude product is dissolved in 310 mL 2-methyl-2-butanol at 40° C. (temperature<50° C.). The solution is slowly cooled to 0° C. Precipitation starts. At 0° C. 385 mL of n-heptane is added and the suspension is stirred for 1 hour. The precipitate is filtrated, washed with n-heptane and dried at 50° C.

Yield: 68.7 g (67% of theory) of a colorless solid with a diastereoisomeric purity of >99:1.

Analysis (method H): $R_t$: 6.8 min, (M+H)$^+$: 262

Synthesis of (R)-4-[(S)-1-hydroxyethyl]-1-[(S)-1-(4-methoxyphenyl)-ethyl]-pyrrolidin-2-one

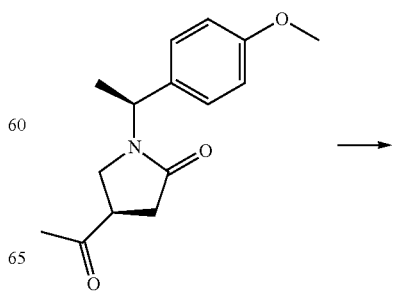

-continued

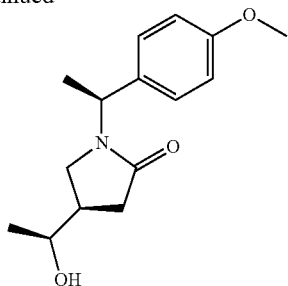

2.4 g of Dichloro-(pentamethylcyclopentadienyl)-rhodium-(III)-dimer and 2.8 g (R,R)—N-(p-toluenesulfonyl)-1,2-diphenylethylendiamine [(R,R)-TsDPEN] is added to a solution of 50 g (R)-4-acetyl-1-[(S)-1-(4-methoxyphenyl)-ethyl]pyrrolidine-2-one in acetonitril at 25° C. The solution is cooled to −15° C. At this temperature a mixture of 22 mL formic acid and 135 mL triethylamine is added. The reaction mixture is stirred for 22 hours at −15° C. and then warmed up to 20° C. 230 mL of a 4 molar hydrochloric acid is added under cooling. The aqueous phase is extracted 3 times with ethyl acetate. The organic phase is washed with diluted and concentrated brine and treated with activated carbon. The organic phase is dried over sodium sulfate. The solvent is evaporated under reduced pressure to obtain 57.1 g of a beige solid with a diastereomeric purity of ~97:3.

For further purification the crude product is crystallized from isopropyl acetate.

Yield: 37.8 g (75% of theory) of a beige solid with a diastereoisomeric purity of >99:1.

Analysis (method I): $R_t$: 12.9 min, (M+H)$^+$: 264

The transfer hydrogenation reaction can also be performed in 2-propanol at 20° C.

Synthesis of 1-[(S)-1-(4-Methoxy-phenyl)-ethyl]-(R)-4-[(R)-1-[7-(3,4,5-trimethoxy-phenyl)-[1,6]naphthyridin-5-yloxy]-ethyl]-pyrrolidin-2-one

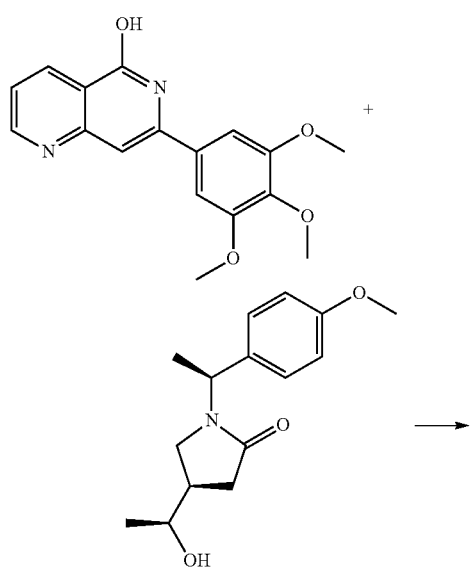

-continued

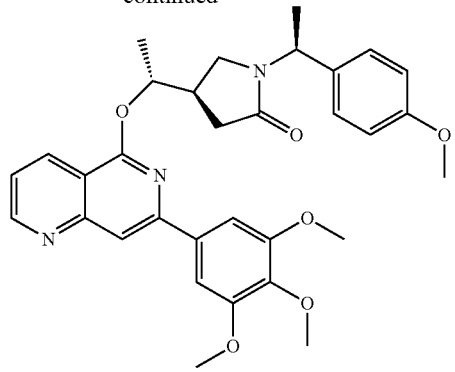

114.6 g of powdered 7-(3,4,5-trimethoxy-phenyl)-[1.6]naphthyridine-5-ol is suspended in 900 mL tetrahydrofurane. A solution of 115.9 g of (R)-4-[(S)-1-hydroxyethyl]-1-[(S)-1-(4-methoxyphenyl)-ethyl]-pyrrolidin-2-one and 136 g triphenylphosphine in 1000 mL tetrahydrofurane is added. The suspension is cooled to 0° C. During 40 minutes a solution of 105 mL diisopropylazodicarboxylate [DIAD] in 400 mL tetrahydrofurane is added at 0° C. to 2° C. The suspension is stirred for 3.5 hours at this temperature and then warmed up to 20° C. The solvent is evaporated under reduced pressure. The residue is suspended in 680 mL of tert-butylmethylether. Seeding crystals of triphenylphosphinoxid are added and the mixture is stirred 16 hours at 20° C. The precipitate is filtered and washed with tert.-butylmethylether. The filtrate is evaporated under reduced pressure. The crude product is dissolved in a mixture of 220 mL of 2-propanol and 1100 mL of isopropyl acetate at 40° C. 48 mL of trimethylchlorosilane are added during 15 minutes. The suspension is stirred for 2 hours at 20° C. The precipitate is filtered and washed with isopropyl acetate and dried at 60° C.

Yield: 185.7 g (84% of theory) yellow solid as hydrochloride salt

Analysis (method K): $R_t$: 5.4 min, (M+H)$^+$: 558

Synthesis of (R)-4-[(R)-1-[7-(3,4,5-Trimethoxy-phenyl)-[1,6]naphthyridin-5-yloxy]-ethyl]-pyrrolidin-2-one (example 35)

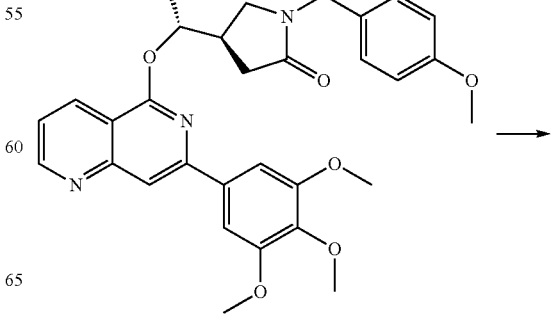

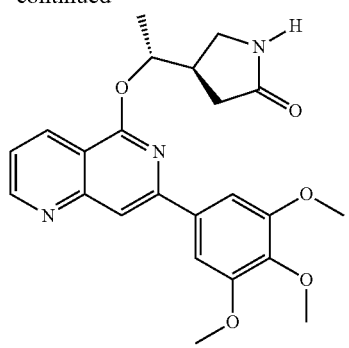

example 35

152 g 1-[(S)-1-(4-Methoxy-phenyl)-ethyl]-(R)-4-[(R)-1-[7-(3,4,5-trimethoxy-phenyl)-[1,6]naphthyridin-5-yloxy]-ethyl]-pyrrolidin-2-one is suspended in 1.5 L of toluene. At 20° C. 0.86 L of 1 N sodium hydroxide solution is added under vigorous mixing. The toluene phase is separated and the solvent is evaporated. 1.5 L toluene are added to the residue and evaporation is repeated. 176 g of the free base is obtained as an oil.

Under inert gas atmosphere the oil is dissolved in 0.5 L trifluoroacetic acid. The solution is stirred for 40 hours at 55° C. to 60° C. 2.8 L tert.-butylmethylether is added at 45° C. to 50° C. The suspension is stirred for 1 hour at 20° C. and 3 hours at 0° C. The precipitate is filtered, washed with 2 L of tert.-butylmethylether and dried at 40° C.

Yield. 165 g (quantitative) crude product as trifluoroacetic acid salt.

326 g of the trifluoroacetic acid salt are suspended in 2.6 L 2-methyltetrahydrofurane. 0.6 L of a 2 N sodium hydroxide solution is added under vigorous mixing. The organic phase is separated and the aqueous phase is extracted twice with 0.4 L of 2-methyltetrahydrofurane. The combined organic phases were washed several times with 0.6 L of sodium hydroxide solution. The organic phase is dried and the solvent is evaporated under reduced pressure.

Yield: 240 g (94% of theory) of the free base as a foam.

240 g of the base is dissolved in 1 L of ethanol at 40° C. to 45° C. After clarification 72.3 mL of chlorotrimethylsilane is added. Crystallization starts. After 5 minutes 1 L of tert.-butylmethylether is added. The suspension is stirred for 2 hours at 20° C. The precipitate is filtered, washed with tert.-butylmethylether and dried at 50° C.

Yield. 204 g (73% of theory) yellow solid as hydrochloride salt.

Analysis (method L): $R_t$: 12.3 min, $(M+H)^+$: 424

4.5 Chromatographic Methods (HPLC-MS Methods)

The Example compounds prepared according to the foregoing synthesis scheme were characterised by the following chromatographic methods, which—if they were carried out—are specified individually in Table 6.

Method A:
Waters ZQ, Agilent G1312A HPLC pump, Waters 2996 PDA detector, Waters 2420 ancillary detector

| Eluent A: Water (0.1% formic acid) | | | |
|---|---|---|---|
| Eluent B: Acetonitrile (0.1% formic acid) | | | |
| Time [min] | % A | % B | Flow rate [mL/min] |
| 0.00 | 95 | 5 | 0.60 |
| 5.00 | 0 | 100 | 0.60 |
| 5.40 | 0 | 100 | 0.60 |
| 5.42 | 95 | 5 | 0.60 |
| 7.00 | 95 | 5 | 0.60 |

The stationary phase used was a Waters Atlantis dC18 2.1 mm×100 mm, 3 μm, injection volume 3 μL (column temperature: constant at 40° C.).

Detector at a wavelength range 215 nm (nominal).

Method B:
Shimadzu LCMS2010EV, Shimadzu LC-20AB pump, SPD-M20A PDA detector, PL2100 ancillary

| Eluent A: Water (0.1% formic acid) | | | |
|---|---|---|---|
| Eluent B: Acetonitrile (0.1% formic acid) | | | |
| Time [min] | % A | % B | Flow rate [mL/min] |
| 0.00 | 95 | 5 | 1.00 |
| 2.50 | 0 | 100 | 1.00 |
| 2.70 | 0 | 100 | 1.00 |
| 2.71 | 95 | 5 | 1.00 |
| 3.50 | 95 | 5 | 1.00 |

The stationary phase used was a Waters Atlantis dC18 2.1 mm×50 mm, 3 μm, injection volume 3 μL (column temperature: constant at 40° C.).

Detector at a wavelength range 215 nm (nominal).

Method C:
Waters ZQ, Agilent G1312A HPLC pump, Waters 2996 PDA detector, Waters 2420 ancillary detector

| Eluent A: Water (0.1% formic acid) | | | |
|---|---|---|---|
| Eluent B: Acetonitrile (0.1% formic acid) | | | |
| Time [min] | % A | % B | Flow rate [mL/min] |
| 0.00 | 95 | 5 | 1.00 |
| 1.50 | 0 | 100 | 1.00 |
| 1.60 | 0 | 100 | 1.00 |
| 1.61 | 95 | 5 | 1.00 |

The stationary phase used was a Waters Atlantis dC18 2.1 mm×30 mm, 3 μm, injection volume 3 μL (column temperature: constant at 40° C.).

Detector at a wavelength range 215 nm (nominal).

Method D
Waters ZMD, Alliance 2690/2695 HPLC, Waters 996/2996 diode array detector The mobile phase used was:

| A: water with 0.10% TFA | | | |
|---|---|---|---|
| B: acetonitrile with 0.10% TFA | | | |
| time in min | % A | % B | flow rate in mL/min |
| 0.00 | 95 | 5 | 2.80 |
| 0.30 | 95 | 5 | 2.80 |

-continued

| A: water with 0.10% TFA<br>B: acetonitrile with 0.10% TFA | | | |
|---|---|---|---|
| time in min | % A | % B | flow rate in mL/min |
| 1.60 | 2 | 98 | 2.80 |
| 1.90 | 2 | 98 | 2.80 |
| 2.00 | 95 | 5 | 2.50 |

The stationary phase used was a Merck Chromolith™ Flash RP-18e column, 3 mm×100 mm (column temperature: constant at 25° C.).

Diode array detection took place in the wavelength range 210-400 nm.

Method E

Waters ZMD, Alliance 2690/2695 HPLC, Waters 996/2996 diode array detector

The mobile phase used was:

| A: water with 0.10% TFA<br>D: methanol with 0.10% TFA | | | |
|---|---|---|---|
| time in min | % A | % D | flow rate in mL/min |
| 0.00 | 95 | 5 | 4.00 |
| 0.20 | 95 | 5 | 4.00 |
| 1.60 | 0 | 100 | 4.00 |
| 2.10 | 0 | 100 | 4.00 |

The stationary phase used was a Waters XBridge™ C18 3.5 μM, 4.6×20 mm IS™ (column temperature: constant at 40° C.).

Diode array detection took place in the wavelength range 210-400 nm.

Method F:

Waters ZQ, Agilent G1312A HPLC pump, Waters 2996 PDA detector, Waters 2420 ancillary detector

| Eluent A: 2 mM Ammonium bicarbonate, buffered to pH10<br>Eluent B: Acetonitrile | | | |
|---|---|---|---|
| Time [min] | % A | % B | Flow rate [mL/min] |
| 0.00 | 95 | 5 | 1.00 |
| 5.50 | 0 | 100 | 1.00 |
| 5.90 | 0 | 100 | 1.00 |
| 5.92 | 95 | 5 | 1.00 |

The stationary phase used was a Phenomenex Gemini C18 2.0×100 mm, 3 μm, injection volume 3 μL (column temperature: constant at 50° C.).

Detector at a wavelength range 215 nm (nominal).

Method G:

| Eluent A: Water/0.2% KH$_2$PO$_4$ pH = 3<br>Eluent B: Acetonitrile | | | |
|---|---|---|---|
| Time [min] | % A | % B | Flow rate [mL/min] |
| 0.00 | 80 | 20 | 1.50 |
| 5.00 | 20 | 80 | 1.50 |
| 8.00 | 20 | 80 | 1.50 |

The stationary phase used was a Inertsil C8-3 (GL Sciences), 5 μm; dimension: 100×4.0 mm, (column temperature: constant at 30° C.).

Detection UV 220 nm.

Method H:

| Eluent A: Hexane<br>Eluent B: 2-Propanol | | | |
|---|---|---|---|
| Time [min] | % A | % B | Flow rate [mL/min] |
| 00.00 | 90 | 10 | 1.0 |
| 20.00 | 90 | 10 | 1.0 |

The stationary phase used was a Chiralpak AD-H (Daicel), 5 μm; dimension: 150×4.6 mm, (column temperature: constant at 10° C.).

Detection DAD 225 nm.

Method I:

| Eluent A: Hexane<br>Eluent B: 2-Propanol | | | |
|---|---|---|---|
| Time [min] | % A | % B | Flow rate [mL/min] |
| 00.00 | 90 | 10 | 1.0 |
| 25.00 | 90 | 10 | 1.0 |

The stationary phase used was a Chiralpak AD-H (Daicel), 5 μm; dimension: 150×4.6 mm, (column temperature: constant at 10° C.).

Detection DAD 225 nm.

Method K:

| Eluent A: Water/0.2% KH$_2$PO$_4$ pH = 3<br>Eluent B: Acetonitrile | | | |
|---|---|---|---|
| Time [min] | % A | % B | Flow rate [mL/min] |
| 0.00 | 70 | 30 | 1.00 |
| 10.00 | 20 | 80 | 1.00 |

The stationary phase used was a Zorbax Eclipse XDB-C18 (Agilent), 1.8 μm; dimension: 50×4.6 mm, (column temperature: constant at 20° C.).

Detection UV 200 nm.

Method L:

| Eluent A: Water/0.2% KH$_2$PO$_4$ pH = 3<br>Eluent B: Acetonitrile | | | |
|---|---|---|---|
| Time [min] | % A | % B | Flow rate [mL/min] |
| 0.00 | 75 | 25 | 0.70 |
| 14.00 | 70 | 30 | 0.70 |
| 15.00 | 20 | 80 | 0.70 |
| 20.00 | 20 | 80 | 0.70 |

The stationary phase used was an Ascentis Express C18 (Supelco), 2.7 μm; dimension: 150×3.0 mm, (column temperature: constant at 10° C.).

Detection UV 200 nm.

4.6 NMR Methods

Configuration of the Bruker DRX 500 MHz NMR

High performance digital NMR spectrometer, 2-channel microbay console and Windows XP host workstation running Topspin version 1.3.

Equipped with:
Oxford instruments magnet 11.74 Tesla (500 MHz proton resonance frequency)
B-VT 3000 temperature controller
GRASP II gradient spectroscopy accessory for fast acquisition of 2D pulse sequences
Deuterium lock switch for gradient shimming
5 mm Broad Band Inverse geometry double resonance probe with automated tuning and matching (BBI ATMA). Allows $^1$H observation with pulsing/decoupling of nuclei in the frequency range $^{15}$N and $^{31}$P with $^2$H lock and shielded z-gradient coils.

Configuration of the Bruker DPX 250 MHz NMR

High performance one bay Bruker 250 MHz digital two channel NMR spectrometer console and Windows XP host workstation running XwinNMR version 3.5.

Equipped with:
Oxford instruments magnet 5.87 Tesla (250 MHz proton resonance frequency)
B-VT 3300 variable temperature controller unit
Four nucleus (QNP) switchable probe for observation of $^1$H, $^{13}$C, $^{19}$F and $^{31}$P with $^2$H lock

5. EXAMPLES

The following Examples were prepared analogously to the methods of synthesis described above. These compounds are suitable as SYK inhibitors and have $IC_{50}$-values of less than or equal to 1 μmol. The $IC_{50}$-values of the individual example substances are shown in the following Table 6 and were experimentally determined as follows:

Syk Kinase Test

Recombinant human Syk (amino acids 342-635) was expressed as a fusion protein with an N-terminal GST tag, affinity-purified and deep-frozen at a concentration of approx. 50-100 μM in test buffer (25 mM HEPES pH7.5; 25 mM $MgCl_2$; 5 mM $MnCl_2$; 50 mM KCl; 0.2% BSA; 0.01% CHAPS; 100 μM $Na_3VO_4$; 0.5 mM DTT) and 10% glycerol at −80° C. until use.

The catalytic activity of the GST-Syk kinase fusion protein was determined using the Kinase Glo® Luminescence Kinase test (Promega; V6712). In this homogeneous test the amount of ATP remaining after the kinase reaction is quantified by a luciferin-luciferase reaction using luminescence. The luminescence signal obtained correlates with the amount of ATP still present and thus correlates inversely with the activity of the protein kinase.

Method

The test compounds were dissolved in 100% DMSO at a concentration of 10 mM and diluted in DMSO to a concentration of 1 mM. All further dilutions of the substances were carried out with 7.5% DMSO in test buffer until a concentration was reached which was 7.5 times above the final test concentration (final concentration of the compounds: 30 μM to 1 nM). 2 μl aliquots of these dilutions were transferred into a 384-well Optiplate (Perkin Elmer, #6007290). GST-Syk was diluted to 6.0 nM in the test buffer and 10 μl of this dilution were used in the kinase test (final concentration of Syk=4 nM in a total volume of 15 μl). After 15 minutes incubation at room temperature 3 μl of a mixture of 750 nM ATP and 100 μg/ml poly (L-Glutamic acid L-Tyrosine 4:1), Fluka #81357) in test buffer were added to each well and the incubation was continued for a further 60 minutes at room temperature.

Positive controls are the reaction mixtures that contain no test substance; negative controls (blanks) are reaction mixtures that contain no kinase.

After 60 minutes, 10 μl Kinase-Glo® solution (Promega, Cat. # V6712) (heated to room temperature) were added to each well and incubation was continued for a further 15 minutes. The plates were read in a Microplate Scintillation and Luminescence Counter (Canberra Packard GmbH).

Data Evaluation and Calculation:

The output file of the "Counter" is a text file that contains the well number and measured counts in two columns. For data evaluation and calculation, the measurement of the negative control was set as 100% inhibition and the measurement of the positive control was set as 0% inhibition. Based on this values the % inherent value for the measurement of each substance concentration was calculated using an "MS-Excel—VB macro". Normally, the % inhibition values calculated are between 100% and 0% inhibition values but may also occur outside these limits in individual cases. The $IC_{50}$ values were calculated from the % inhibition values using "GraphPadPrism" software (Version 5) (GraphPad Software Inc.).

The following Examples of formula 1

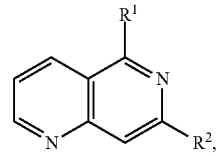

having the following properties were prepared according to the methods of synthesis described above, wherein $X_1$ denotes the point where the group $R^1$ is linked to the structure of formula 1, and wherein $X_2$ denotes the point where the group $R^2$ is linked to the structure of formula 1:

TABLE 5

Examples

| Example No. | Structure | R¹ | R² | Analytical data | Method of preparation | IC$_{50}$-value (μM) |
|---|---|---|---|---|---|---|
| 1 | Chiral | | | HPLC-MS: method E Rt = 1.49 min | see description 4.4.1 | 0.0131 |
| 2 | Chiral | | | HPLC-MS: method E Rt = 1.51 min | analogous to Example 1 | 0.0124 |

TABLE 5-continued

Examples

| Example No. | Structure | R¹ | R² | Analytical data | Method of preparation | IC$_{50}$-value (μM) |
|---|---|---|---|---|---|---|
| 3 | Chiral structure with pyrrolidinone, naphthyridine, and 2-(trifluoromethyl)pyridine | pyrrolidinone-CH(CH₃)-O-X₁ | X₂-pyridine-CF₃ | HPLC-MS: method B Rt = 1.84 min | analogous to Example 19 | 0.0037 |
| 4 | Chiral structure with pyrrolidinone, naphthyridine, and 3-methoxy-4-(trifluoromethoxy)phenyl | pyrrolidinone-CH(CH₃)-O-X₁ | X₂-phenyl-OCH₃, OCF₃ | HPLC-MS: method E Rt = 1.44 min | analogous to Example 1 | 0.0019 |

TABLE 5-continued

Examples

| Example No. | Structure | R¹ | R² | Analytical data | Method of preparation | IC$_{50}$-value (μM) |
|---|---|---|---|---|---|---|
| 5 | Chiral; quinoline-pyridine core with 4-methoxy-3-(trifluoromethyl)phenyl substituent and (pyrrolidin-2-one-4-yl)methoxy group | X₁–O–CH₂–(pyrrolidin-2-on-4-yl) | 4-methoxy-3-(trifluoromethyl)phenyl–X₂ | HPLC-MS: method B Rt = 2.46 min | see description 4.4.1. | 0.0121 |
| 6 | Chiral; structure with 3-chloro-4,5-dimethoxyphenyl substituent and (pyrrolidin-2-on-4-yl)methoxy group | (pyrrolidin-2-on-4-yl)–CH₂–O–X₁ | 3,4-dimethoxy-5-chlorophenyl–X₂ | HPLC-MS: method E Rt = 1.30 min | analogous to Example 1 | 0.0253 |

TABLE 5-continued

Examples

| Example No. | Structure | R¹ | R² | Analytical data | Method of preparation | IC$_{50}$-value (μM) |
|---|---|---|---|---|---|---|
| 7 | Chiral; pyrrolidinone-CH(CH₃)-O-linked to 8-position of 2-(3-chloro-4,5-dimethoxyphenyl)-1,7-naphthyridine | pyrrolidinone-CH(CH₃)-O-X₁ | 3-Cl-4,5-(OCH₃)₂-C₆H₂-X₂ | HPLC-MS: method E Rt = 1.37 min | analogous to Example 1 | 0.0005 |
| 8 | Chiral; pyrrolidinone-CH(CH₃)-O-linked to 8-position of 2-(4-chloro-3,5-dimethoxyphenyl)-1,7-naphthyridine | pyrrolidinone-CH(CH₃)-O-X₁ | 4-Cl-3,5-(OCH₃)₂-C₆H₂-X₂ | HPLC-MS: method E Rt = 1.34 min | analogous to Example 1 | 0.0030 |

TABLE 5-continued

Examples

| Example No. | Structure | R¹ | R² | Analytical data | Method of preparation | IC$_{50}$-value (µM) |
|---|---|---|---|---|---|---|
| 9 | Chiral structure with pyrrolidinone, pyridine N-oxide, chloro-dimethoxyphenyl | pyrrolidinone-CH(CH₃)-O-X₁ | 3-chloro-4,5-dimethoxyphenyl-X₂ | HPLC-MS: method E Rt = 1.29 min | see description 4.4.3. | 0.0050 |
| 10 | Chiral structure with pyrrolidinone, naphthyridine, methoxyphenyl-tetrahydrothiopyran dioxide | pyrrolidinone-CH₂-O-X₁ | methoxyphenyl-O-(1,1-dioxothian-4-yl)-X₂ | HPLC-MS: method E Rt = 1.11 min | see description 4.4.1. | 0.0010 |

TABLE 5-continued

Examples

| Example No. | Structure | R¹ | R² | Analytical data | Method of preparation | IC₅₀-value (μM) |
|---|---|---|---|---|---|---|
| 11 | Chiral; pyrrolidinone-CH₂-O-linked to 1,7-naphthyridine substituted with 4-(trifluoromethyl)phenyl | pyrrolidinone-CH₂-O-X₁ | 4-(trifluoromethyl)phenyl-X₂ | HPLC-MS: method D Rt = 1.42 min | analogous to Example 79 | 0.0347 |
| 12 | Chiral; pyrrolidinone-CH₂-O-linked to 1,7-naphthyridine substituted with 5-methylisoxazol-3-yl | pyrrolidinone-CH₂-O-X₁ | 5-methylisoxazol-3-yl-X₂ | HPLC-MS: method A Rt = 3.29 min | analogous to Example 19 | 0.2078 |

TABLE 5-continued

Examples

| Example No. | Structure | R¹ | R² | Analytical data | Method of preparation | IC$_{50}$-value (µM) |
|---|---|---|---|---|---|---|
| 13 | Chiral; quinoline fused with pyridine bearing 3,5-difluoro-4-methoxyphenyl and O-CH₂-(pyrrolidin-2-one) substituent | X₁-O-CH₂-(pyrrolidin-2-one) | 3,5-difluoro-4-methoxyphenyl with X₂ | HPLC-MS: method A Rt = 4.04 min | analogous to Example 19 | 0.0223 |
| 14 | Chiral; naphthyridine bearing 3,5-difluoro-4-methoxyphenyl and O-CH(CH₃)-(pyrrolidin-2-one) substituent | (pyrrolidin-2-one)-CH(CH₃)-O-X₁ | 3,5-difluoro-4-methoxyphenyl with X₂ | HPLC-MS: method A Rt = 4.14 min | analogous to Example 5 | 0.0007 |

TABLE 5-continued

Examples

| Example No. | Structure | R¹ | R² | Analytical data | Method of preparation | IC$_{50}$-value (μM) |
|---|---|---|---|---|---|---|
| 15 | Chiral; quinoline with trifluoromethyl-(tetrahydropyran-4-yloxy)phenyl and pyrrolidinone-methoxy substituents | X₁—O—CH₂—(pyrrolidin-2-one) | 4-(tetrahydropyran-4-yloxy)-3-(trifluoromethyl)phenyl—X₂ | HPLC-MS: method B Rt = 2.00 min | see description 4.4.1. | 0.0101 |
| 16 | Chiral; naphthyridine with chloro-methoxyphenyl and pyrrolidinone-methoxy substituents | (pyrrolidin-2-one)—CH₂—O—X₁ | 3-chloro-4-methoxyphenyl—X₂ | HPLC-MS: method D Rt = 1.33 min | analogous to Example 1 | 0.0072 |

TABLE 5-continued

Examples

| Example No. | Structure | R¹ | R² | Analytical data | Method of preparation | IC$_{50}$-value (μM) |
|---|---|---|---|---|---|---|
| 17 | Chiral | | | HPLC-MS: method D Rt = 1.39 min | analogous to Example 1 | 0.0145 |
| 18 | Chiral | | | HPLC-MS: method D Rt = 1.33 min | analogous to Example 1 | 0.0136 |

TABLE 5-continued

Examples

| Example No. | Structure | R¹ | R² | Analytical data | Method of preparation | IC$_{50}$-value (µM) |
|---|---|---|---|---|---|---|
| 19 | Chiral structure with quinoline, pyrrolidinone, and trimethoxyphenyl-morpholinoethoxy groups | Pyrrolidinone with CH(CH₃)-O-X₁ substituent | Trimethoxyphenyl with morpholinoethoxy and X₂ | HPLC-MS: method D Rt = 1.18 min | see description 4.4.1. | 0.0008 |
| 20 | Chiral structure with quinoline, pyrrolidinone, and trimethoxyphenyl-morpholinoethoxy groups | Pyrrolidinone with CH(CH₂CH₃)-O-X₁ substituent | Trimethoxyphenyl with morpholinoethoxy and X₂ | HPLC-MS: method D Rt = 1.21 min | analogous to Example 19 | 0.0007 |

TABLE 5-continued

Examples

| Example No. | Structure | R¹ | R² | Analytical data | Method of preparation | IC$_{50}$-value (μM) |
|---|---|---|---|---|---|---|
| 21 | Chiral structure | | | HPLC-MS: method E Rt = 1.22 min | analogous to Example 19 | 0.0007 |
| 22 | Chiral structure | | | HPLC-MS: method E Rt = 0.90 min | see description 4.4.1. | 0.0010 |
| 23 | Chiral structure | | | HPLC-MS: method D Rt = 1.12 min | analogous to Example 78 | 0.0172 |

TABLE 5-continued

Examples

| Example No. | Structure | R¹ | R² | Analytical data | Method of preparation | IC$_{50}$-value (μM) |
|---|---|---|---|---|---|---|
| 24 | (quinoline-pyridine with trimethoxyphenyl and oxadiazolone-methylamino substituent) | oxadiazol-2(3H)-one-CH$_2$-N-X$_1$ | 3,4,5-trimethoxyphenyl-X$_2$ | HPLC-MS: method A Rt = 3.07 min | see description 4.4.1. | 0.0050 |
| 25 | (quinoline-pyridine with trimethoxyphenyl and triazolone-methylamino substituent) | 1,2,4-triazol-3(2H)-one-CH$_2$-N-X$_1$ | 3,4,5-trimethoxyphenyl-X$_2$ | HPLC-MS: method A Rt = 2.74 min | analogous to Example 33 | 0.0103 |

TABLE 5-continued
Examples
| Example No. | Structure | R¹ | R² | Analytical data | Method of preparation | IC$_{50}$-value (μM) |
|---|---|---|---|---|---|---|
| 26 | 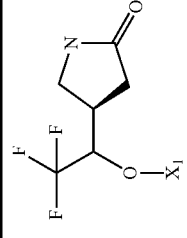 | 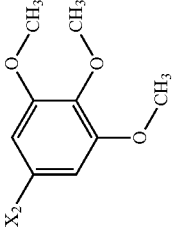 | 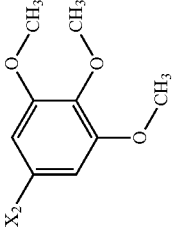 | HPLC-MS: method E Rt = 1.36 min | analogous to Example 19 | 0.0041 |
| 27 | 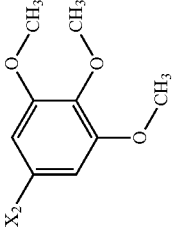 | 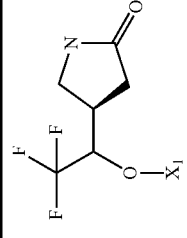 | 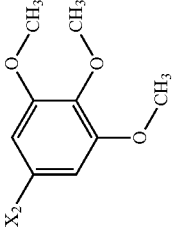 | HPLC-MS: method E Rt = 1.10 min | analogous to Example 19 | 0.0012 |

TABLE 5-continued

Examples

| Example No. | Structure | R¹ | R² | Analytical data | Method of preparation | IC$_{50}$-value (µM) |
|---|---|---|---|---|---|---|
| 28 | (structure with isoxazolidinone-CH2-O-quinoline-trimethoxyphenyl) | isoxazolidin-3-one-CH2-O-X1 | 3,4,5-trimethoxyphenyl-X2 | HPLC-MS: method A Rt = 3.51 min | see description 4.4.2. | 0.0671 |
| 29 | Chiral (structure with oxazolidinone-CH2-NH-quinoline-trimethoxyphenyl) | oxazolidin-2-one-CH2-N-X1 | 3,4,5-trimethoxyphenyl-X2 | HPLC-MS: method E Rt = 1.00 min | see description 4.4.1. | 3.3328 |

TABLE 5-continued

Examples

| Example No. | Structure | R¹ | R² | Analytical data | Method of preparation | IC$_{50}$-value (μM) |
|---|---|---|---|---|---|---|
| 30 | (structure: isoxazolone-CH₂-NH-quinoline-pyridine-trimethoxyphenyl) | (isoxazolone-CH₂-N-X₁) | (X₂-trimethoxyphenyl) | HPLC-MS: method A Rt = 3.15 min | analogous to Example 33 | 0.1052 |
| 31 | (structure: isoxazolone-CH(CH₃)-O-quinoline-pyridine-trimethoxyphenyl) | (isoxazolone-CH(CH₃)-O-X₁) | (X₂-trimethoxyphenyl) | HPLC-MS: method A Rt = 4.13 min | analogous to Example 28 | 0.0173 |

TABLE 5-continued

Examples

| Example No. | Structure | R¹ | R² | Analytical data | Method of preparation | IC$_{50}$-value (µM) |
|---|---|---|---|---|---|---|
| 32 | Chiral | | | HPLC-MS: method D Rt = 1.25 min | analogous to Example 19 | 0.0071 |
| 33 | Chiral | | | HPLC-MS: method E Rt = 1.03 min | see description 4.4.1. | |

TABLE 5-continued

Examples

| Example No. | Structure | R¹ | R² | Analytical data | Method of preparation | IC$_{50}$-value (μM) |
|---|---|---|---|---|---|---|
| 34 | Chiral (structure shown) | (structure shown) | (structure shown) | HPLC-MS: method E Rt = 1.18 min | analogous to Example 19 | 0.0124 |
| 35 | Chiral (structure shown) | (structure shown) | (structure shown) | HPLC-MS: method D Rt = 1.29 min | analogous to Example 19 | 0.0002 |

TABLE 5-continued

Examples

| Example No. | Structure | R¹ | R² | Analytical data | Method of preparation | IC$_{50}$-value (µM) |
|---|---|---|---|---|---|---|
| 36 | (Chiral structure) | (3-methyl-pyrrolidin-2-one with CH₂O-X₁) | (3,4,5-trimethoxyphenyl-X₂) | HPLC-MS: method A Rt = 3.69 min | analogous to Example 5 | 0.0174 |
| 37 | (Chiral structure with N-oxide) | (pyrrolidinone with CH(CH₃)O-X₁) | (3,4,5-trimethoxyphenyl-X₂) | HPLC-MS: method E Rt = 1.16 min | analogous to Example 9 | 0.0043 |

TABLE 5-continued

Examples

| Example No. | Structure | R¹ | R² | Analytical data | Method of preparation | IC$_{50}$-value (μM) |
|---|---|---|---|---|---|---|
| 38 | (structure with trimethoxyphenyl-isoquinoline-pyrrolidinone) | H₃C-pyrrolidinone-CH₂-N-X₁ | trimethoxyphenyl-X₂ | HPLC-MS: method E Rt = 1.12 min | see description 4.4.1. | 0.2515 |
| 39 | Chiral (structure with trimethoxyphenyl-isoquinoline-pyrrolidinone) | H₃C-CH(pyrrolidinone)-N-X₁ | trimethoxyphenyl-X₂ | HPLC-MS: method E Rt = 1.10 min | analogous to Example 33 | 0.0133 |

TABLE 5-continued

Examples

| Example No. | Structure | R¹ | R² | Analytical data | Method of preparation | IC$_{50}$-value (μM) |
|---|---|---|---|---|---|---|
| 40 | (quinoline-pyridine with trimethoxyphenyl and pyridinone-CH$_2$-NH linker) | pyridinone-CH$_2$-NH-X$_1$ | 3,4,5-trimethoxyphenyl-X$_2$ | HPLC-MS: method A Rt = 2.89 min | see description 4.4.1. | 0.4108 |
| 41 | Chiral (quinoline with trimethoxyphenyl and pyrrolidinone-ether linker) | pyrrolidinone with CH(CH$_3$)-O-X$_1$ | 3,4,5-trimethoxyphenyl-X$_2$ | HPLC-MS: method D Rt = 1.33 min | analogous to Example 19 | 0.0003 |

TABLE 5-continued

Examples

| Example No. | Structure | R¹ | R² | Analytical data | Method of preparation | IC$_{50}$-value (μM) |
|---|---|---|---|---|---|---|
| 42 | Chiral | | | HPLC-MS: method A Rt = 3.87 min | analogous to Example 15 | 0.0117 |
| 43 | Chiral | | | HPLC-MS: method D Rt = 1.12 min | analogous to Example 38 | 1.5250 |

TABLE 5-continued

Examples

| Example No. | Structure | R¹ | R² | Analytical data | Method of preparation | IC$_{50}$-value (μM) |
|---|---|---|---|---|---|---|
| 44 | Chiral | | | HPLC-MS: method E Rt = 1.20 min | analogous to Example 1 | 0.0161 |
| 45 | Chiral | | | HPLC-MS: method E Rt = 0.97 min | analogous to Example 19 | 0.0001 |

TABLE 5-continued

Examples

| Example No. | Structure | R¹ | R² | Analytical data | Method of preparation | IC$_{50}$-value (µM) |
|---|---|---|---|---|---|---|
| 46 | Chiral | | | HPLC-MS: method E Rt = 1.15 min | see description 4.4.1. | 0.0004 |
| 47 | 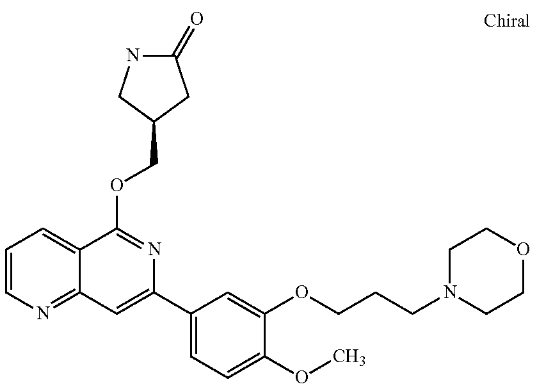 [SMILES: COc1ccc(-c2cc3ncccc3c(OC[C@H]3CNC(=O)C3)n2)cc1OCCCN1CCOCC1] | | | HPLC-MS: method D Rt = 1.16 min | analogous to Example 19 | 0.0107 |

TABLE 5-continued
Examples
| Example No. | Structure | R¹ | R² | Analytical data | Method of preparation | IC$_{50}$-value (µM) |
|---|---|---|---|---|---|---|
| 48 | 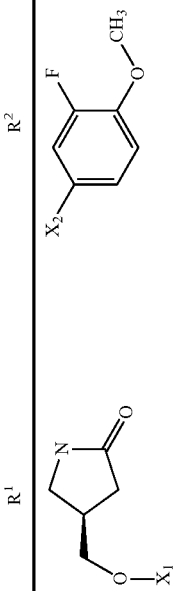 | 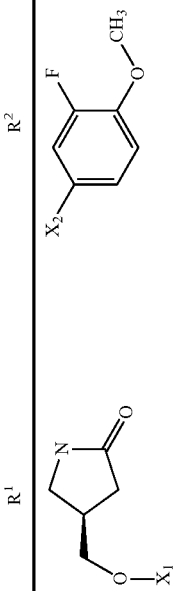 | 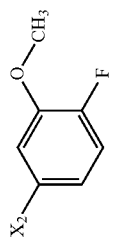 | HPLC-MS: method D Rt = 1.69 min | analogous to Example 1 | 0.0063 |
| 49 | 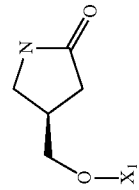 | 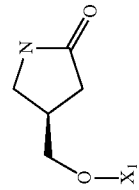 | 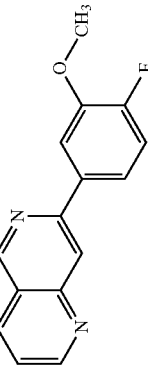 | HPLC-MS: method D Rt = 1.31 min | analogous to Example 1 | 0.0140 |

TABLE 5-continued

Examples

| Example No. | Structure | R¹ | R² | Analytical data | Method of preparation | IC$_{50}$-value (μM) |
|---|---|---|---|---|---|---|
| 50 | Chiral structure | pyrrolidinone-CH₂-O-X₁ | X₂-aryl-OCH₃, O-CH(CH₃)-CH₂-OCH₃ | HPLC-MS: method D Rt = 1.28 min | analogous to Example 10 | 0.0027 |
| 51 | Chiral structure | pyrrolidinone-CH₂-O-X₁ | X₂-aryl-OCH₃, O-CH(CH₃)-CH₂-OCH₃ | HPLC-MS: method D Rt = 1.27 min | analogous to Example 10 | 0.0023 |

TABLE 5-continued

Examples

| Example No. | Structure | R¹ | R² | Analytical data | Method of preparation | IC$_{50}$-value (μM) |
|---|---|---|---|---|---|---|
| 52 | Chiral (structure shown) | (structure shown) | (structure shown) | HPLC-MS: method D Rt = 1.14 min | analogous to Example 19 | 0.0009 |
| 53 | Chiral (structure shown) | (structure shown) | (structure shown) | HPLC-MS: method D Rt = 1.16 min | see description 4.4.1. | |

TABLE 5-continued

Examples

| Example No. | Structure | R¹ | R² | Analytical data | Method of preparation | IC$_{50}$-value (μM) |
|---|---|---|---|---|---|---|
| 54 | Chiral structure | pyrrolidinone-CH₂-O-X₁ | X₂-phenyl(OCH₃)-O-tetrahydrofuran | HPLC-MS: method D Rt = 1.22 min | analogous to Example 10 | 0.0014 |
| 55 | Chiral structure | pyrrolidinone-CH₂-O-X₁ | X₂-phenyl(OCH₃)-O-tetrahydrofuran | HPLC-MS: method D Rt = 1.22 min | analogous to Example 10 | 0.0010 |

TABLE 5-continued

Examples

| Example No. | Structure | R¹ | R² | Analytical data | Method of preparation | IC$_{50}$-value (μM) |
|---|---|---|---|---|---|---|
| 56 | Chiral structure with quinoline, pyrrolidinone, and trimethoxyphenyl groups | pyrrolidinone-CH(CH₃)-O-X₁ | 3,4,5-tri(OCH₃ via OCH₂CH₃/OCH₃)phenyl-X₂ | HPLC-MS: method E Rt = 1.41 min | analogous to Example 19 | 0.0007 |
| 57 | Chiral structure with quinoline, pyrrolidinone, and dimethylaminopropoxy-methoxyphenyl groups | pyrrolidinone-CH₂-O-X₁ | 3-OCH₃-4-O(CH₂)₃N(CH₃)₂-phenyl-X₂ | HPLC-MS: method D Rt = 1.15 min | analogous to Example 19 | 0.0137 |

TABLE 5-continued

Examples

| Example No. | Structure | R¹ | R² | Analytical data | Method of preparation | IC$_{50}$-value (μM) |
|---|---|---|---|---|---|---|
| 58 | (Chiral) | | | HPLC-MS: method D Rt = 1.26 min | analogous to Example 19 | 0.0153 |
| 59 | 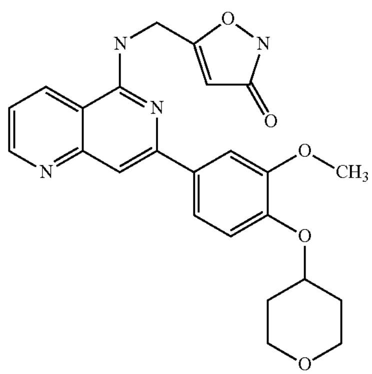 [SMILES: COc1cc(-c2cc3ncccc3c(NCc3cc(=O)[nH]o3)n2)ccc1OC1CCOCC1] | | | HPLC-MS: method E Rt = 3.12 min | analogous to Example 33 | 0.0782 |

TABLE 5-continued

Examples

| Example No. | Structure | R¹ | R² | Analytical data | Method of preparation | IC$_{50}$-value (μM) |
|---|---|---|---|---|---|---|
| 60 | Chiral structure with pyrrolidinone, naphthyridine, methoxyphenyl, and tetrahydropyran | pyrrolidinone-CH₂-O-X₁ | X₂-phenyl(OCH₃)-O-tetrahydropyran | HPLC-MS: method B Rt = 1.99 min | see description 4.4.1. | 0.0005 |
| 61 | Chiral structure with pyrrolidinone, naphthyridine, methoxyphenyl, and (S)-tetrahydropyran | pyrrolidinone-CH₂-O-X₁ | X₂-phenyl(OCH₃)-O-(S)-tetrahydropyran | HPLC-MS: method D Rt = 1.27 min | analogous to Example 10 | 0.0007 |

TABLE 5-continued

Examples

| Example No. | Structure | R¹ | R² | Analytical data | Method of preparation | IC$_{50}$-value (μM) |
|---|---|---|---|---|---|---|
| 62 | Chiral structure with pyrrolidinone, quinoline, methoxy-phenoxy-tetrahydropyran | pyrrolidinone-CH₂-O-X₁ | methoxy-phenoxy-(tetrahydropyran-3-yl)-X₂ | HPLC-MS: method D Rt = 1.28 min | analogous to Example 10 | 0.0018 |
| 63 | Chiral structure with pyrrolidinone, quinoline, methoxy-phenoxy-tetrahydropyran | pyrrolidinone-CH(CH₃)-O-X₁ | methoxy-phenoxy-(tetrahydropyran-4-yl)-X₂ | HPLC-MS: method D Rt = 1.29 min | analogous to Example 19 | <0.0001 |

TABLE 5-continued

Examples

| Example No. | Structure | R¹ | R² | Analytical data | Method of preparation | IC$_{50}$-value (μM) |
|---|---|---|---|---|---|---|
| 64 | 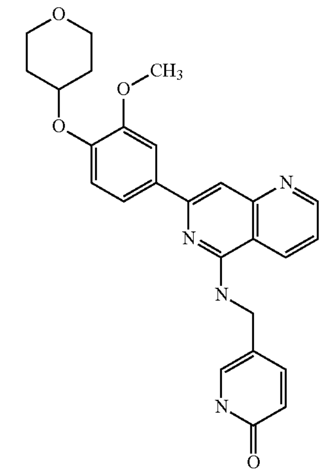 [SMILES: COc1cc(-c2cc3ncccc3c(NCc3ccc(=O)[nH]c3)n2)ccc1OC1CCOCC1] | | | HPLC-MS: method A Rt = 2.91 min | see description 4.4.1. | 0.0063 |
| 65 | Chiral | | | HPLC-MS: method D Rt = 1.32 min | analogous to Example 19 | 0.0001 |

TABLE 5-continued

Examples

| Example No. | Structure | R[1] | R[2] | Analytical data | Method of preparation | IC$_{50}$-value (μM) |
|---|---|---|---|---|---|---|
| 66 | (structure) | (oxadiazolone-CH$_2$-O-X$_1$) | (3,4-dimethoxyphenyl-X$_2$) | HPLC-MS: method B Rt = 1.78 min | see description 4.4.2. | 0.0041 |
| 67 | (structure) | (oxadiazolone-CH$_2$-N-X$_1$) | (3,4-dimethoxyphenyl-X$_2$) | HPLC-MS: method A Rt = 2.89 min | see description 4.4.1. | 0.0004 |

TABLE 5-continued

Examples

| Example No. | Structure | R¹ | R² | Analytical data | Method of preparation | IC$_{50}$-value (µM) |
|---|---|---|---|---|---|---|
| 68 | (1,2,4-triazol-3-one-CH$_2$-NH-naphthyridine with 3,4-dimethoxyphenyl) | triazolone-CH$_2$-NH-X$_1$ | X$_2$-(3,4-dimethoxyphenyl) | HPLC-MS: method B Rt = 1.25 min | analogous to Example 33 | 0.0007 |
| 69 | Chiral (pyrrolidinone-CHF$_3$CH-O-naphthyridine with 3,4-dimethoxyphenyl) | pyrrolidinone-CH(CF$_3$)-O-X$_1$ | X$_2$-(3,4-dimethoxyphenyl) | HPLC-MS: method E Rt = 1.32 min | analogous to Example 19 | 0.0001 |

TABLE 5-continued

Examples

| Example No. | Structure | R¹ | R² | Analytical data | Method of preparation | IC$_{50}$-value (μM) |
|---|---|---|---|---|---|---|
| 70 | Chiral | | | HPLC-MS: method E Rt = 1.32 min | analogous to Example 19 | 0.0048 |
| 71 | Chiral | | | HPLC-MS: method E Rt = 1.31 min | analogous to Example 19 | 0.0002 |

TABLE 5-continued

Examples

| Example No. | Structure | R¹ | R² | Analytical data | Method of preparation | IC$_{50}$-value (µM) |
|---|---|---|---|---|---|---|
| 72 | Chiral; oxazolidinone-CH₂-O-pyridine-quinoline with 3,4-dimethoxyphenyl | oxazolidinone-CH₂-O-X₁ | X₂-(3,4-dimethoxyphenyl) | HPLC-MS: method E Rt = 1.03 min | analogous to Example 19 | 0.0003 |
| 73 | isoxazolidinone-CH₂-O-pyridine-quinoline with 3,4-dimethoxyphenyl | isoxazolidin-3-one-CH₂-O-X₁ | X₂-(3,4-dimethoxyphenyl) | HPLC-MS: method A Rt = 3.48 min | analogous to Example 28 | 0.0100 |

TABLE 5-continued

Examples

| Example No. | Structure | R¹ | R² | Analytical data | Method of preparation | IC$_{50}$-value (μM) |
|---|---|---|---|---|---|---|
| 74 | Chiral structure with oxazolidinone-CH₂-O linked to quinoline-pyridine-3,4-dimethoxyphenyl | oxazolidin-2-one-CH₂-O-X₁ (imidazolidinone) | 3,4-dimethoxyphenyl-X₂ | HPLC-MS: method A Rt = 3.59 min | analogous to Example 77 | 0.0273 |
| 75 | Chiral structure with oxazolidinone-CH₂-NH linked to quinoline-pyridine-3,4-dimethoxyphenyl | oxazolidin-2-one-CH₂-N-X₁ | 3,4-dimethoxyphenyl-X₂ | HPLC-MS: method E Rt = 0.90 min | analogous to Example 33 | 0.0567 |

TABLE 5-continued

Examples

| Example No. | Structure | R¹ | R² | Analytical data | Method of preparation | IC$_{50}$-value (μM) |
|---|---|---|---|---|---|---|
| 76 | (structure shown, Chiral) | isoxazolidin-3-one-CH$_2$-NH-X$_1$ | 3,4-dimethoxyphenyl-X$_2$ | HPLC-MS: method A Rt = 2.80 min | see description 4.4.2. | 0.0386 |
| 77 | (structure shown) | 3-methylimidazolidin-2-one-CH$_2$-O-X$_1$ | 3,4-dimethoxyphenyl-X$_2$ | HPLC-MS: method A Rt = 3.61 min | see description 4.4.1. | 0.0463 |

TABLE 5-continued

Examples

| Example No. | Structure | R¹ | R² | Analytical data | Method of preparation | IC$_{50}$-value (μM) |
|---|---|---|---|---|---|---|
| 78 | Chiral structure with pyrrolidinone, naphthyridine, and 3,4-dimethoxyphenyl groups | pyrrolidinone-CH₂-O-X₁ | 3,4-dimethoxyphenyl-X₂ | HPLC-MS: method D Rt = 1.21 min | see description 4.4.1. | 0.0041 |
| 79 | Chiral structure with pyrrolidinone, naphthyridine, and 2,3-dimethoxyphenyl groups | pyrrolidinone-CH₂-O-X₁ | 2,3-dimethoxyphenyl-X₂ | HPLC-MS: method A Rt = 3.48 min | analogous to Example 19 | 7.9380 |
| 80 | Chiral structure with pyrrolidinone, naphthyridine, and 3,4-dimethoxyphenyl groups | pyrrolidinone-CH₂-N-X₁ | 3,4-dimethoxyphenyl-X₂ | HPLC-MS: method E Rt = 0.99 min | analogous to Example 33 | 0.0118 |

TABLE 5-continued

Examples

| Example No. | Structure | R[1] | R[2] | Analytical data | Method of preparation | IC$_{50}$-value (µM) |
|---|---|---|---|---|---|---|
| 81 | Chiral structure with pyrrolidinone, quinoline, dimethoxyphenyl | (pyrrolidinone-CH(O-X$_1$)-CH$_2$-CH$_2$-O-CH$_3$) | 3,4-dimethoxyphenyl-X$_2$ | HPLC-MS: method D Rt = 1.23 min | analogous to Example 19 | 0.0055 |
| 82 | Chiral structure with pyrrolidinone, quinoline, dimethoxyphenyl | (pyrrolidinone-CH(O-X$_1$)-CH$_2$-CH$_2$-O-CH$_3$) | 3,4-dimethoxyphenyl-X$_2$ | HPLC-MS: method E Rt = 1.11 min | analogous to Example 19 | 0.0002 |

TABLE 5-continued

Examples

| Example No. | Structure | R¹ | R² | Analytical data | Method of preparation | IC$_{50}$-value (μM) |
|---|---|---|---|---|---|---|
| 83 | Chiral structure with quinoline, pyrrolidinone, and dimethoxyphenyl groups | pyrrolidinone with H₃C-CH(O-X₁)- substituent | 3,4-dimethoxyphenyl with X₂ | HPLC-MS: method D Rt = 1.24 min | analogous to Example 19 | 0.0003 |
| 84 | Chiral structure with quinoline, pyrrolidinone, and dimethoxyphenyl groups | pyrrolidinone with H₃C-CH(O-X₁)- substituent | 3,4-dimethoxyphenyl with X₂ | HPLC-MS: method D Rt = 1.25 min | analogous to Example 19 | 0.1964 |
| 85 | Chiral structure with quinoline, pyrrolidinone, and dimethoxyphenyl groups | pyrrolidinone with H₃C-CH(O-X₁)- substituent | 3,4-dimethoxyphenyl with X₂ | HPLC-MS: method D Rt = 1.24 min | analogous to Example 19 | 0.0001 |

TABLE 5-continued

Examples

| Example No. | Structure | R¹ | R² | Analytical data | Method of preparation | IC$_{50}$-value (μM) |
|---|---|---|---|---|---|---|
| 86 | Chiral | | | HPLC-MS: method A Rt = 3.62 min | analogous to Example 5 | 0.0060 |
| 87 | Chiral | | | HPLC-MS: method A Rt = 3.89 min | analogous to Example 15 | 0.0005 |

TABLE 5-continued

Examples

| Example No. | Structure | R¹ | R² | Analytical data | Method of preparation | IC$_{50}$-value (μM) |
|---|---|---|---|---|---|---|
| 88 | (structure with pyrrolidinone-ethoxy-naphthyridine-dimethoxyphenyl) | pyrrolidin-2-one with ethyleneoxy-X₁ | 3,4-dimethoxyphenyl-X₂ | HPLC-MS: method D Rt = 1.25 min | analogous to Example 19 | 0.0081 |
| 89 | (structure with piperidinone-methyleneoxy-naphthyridine-dimethoxyphenyl) | piperidin-2-one with methyleneoxy-X₁ | 3,4-dimethoxyphenyl-X₂ | HPLC-MS: method D Rt = 1.29 min | analogous to Example 19 | 0.0400 |

TABLE 5-continued

Examples

| Example No. | Structure | R¹ | R² | Analytical data | Method of preparation | IC$_{50}$-value (μM) |
|---|---|---|---|---|---|---|
| 90 | (structure with pyrrolidinone, methylene-linked naphthyridine, and 3,4-dimethoxyphenyl) | H$_3$C-pyrrolidinone-CH$_2$-N-X$_1$ | 3,4-dimethoxyphenyl-X$_2$ | HPLC-MS: method E Rt = 1.04 min | analogous to Example 33 | 0.0227 |
| 91 | (structure with pyridinone, methylene-linked naphthyridine, and 3,4-dimethoxyphenyl) | pyridin-2(1H)-one-CH$_2$-N-X$_1$ | 3,4-dimethoxyphenyl-X$_2$ | HPLC-MS: method A Rt = 2.80 min | see description 4.4.1. | 0.0160 |

TABLE 5-continued

Examples

| Example No. | Structure | R¹ | R² | Analytical data | Method of preparation | IC$_{50}$-value (µM) |
|---|---|---|---|---|---|---|
| 92 | Chiral structure with pyrrolidinone, quinoline, and dimethoxyphenyl groups | pyrrolidinone-CH(CH₃)-O-X₁ | 3,4-dimethoxyphenyl-X₂ | HPLC-MS: method D Rt = 1.28 min | analogous to Example 19 | 0.0003 |
| 93 | Chiral structure with pyrrolidinone, quinoline, and dimethoxyphenyl groups | pyrrolidinone-CH(CH₃)-O-X₁ | 3,4-dimethoxyphenyl-X₂ | HPLC-MS: method D Rt = 1.31 min | analogous to Example 19 | 0.1213 |
| 94 | Chiral structure with pyrrolidinone, quinoline, and dimethoxyphenyl groups | pyrrolidinone-CH(CH₃)-O-X₁ | 3,4-dimethoxyphenyl-X₂ | HPLC-MS: method D Rt = 1.29 min | analogous to Example 19 | 0.0001 |

TABLE 5-continued

Examples

| Example No. | Structure | R¹ | R² | Analytical data | Method of preparation | IC$_{50}$-value (μM) |
|---|---|---|---|---|---|---|
| 95 | Chiral | | | HPLC-MS: method A Rt = 3.82 min | analogous to Example 5 | 0.0057 |
| 96 | Chiral | | | HPLC-MS: method E Rt = 1.09 min | analogous to Example 33 | 0.8047 |

TABLE 5-continued

Examples

| Example No. | Structure | R¹ | R² | Analytical data | Method of preparation | IC$_{50}$-value (μM) |
|---|---|---|---|---|---|---|
| 97 | Chiral | | | HPLC-MS: method D Rt = 1.27 min | analogous to Example 19 | 0.0043 |
| 98 | Chiral | | | HPLC-MS: method D Rt = 1.35 min | analogous to Example 19 | 0.0017 |
| 99 | Chiral | | | HPLC-MS: method E Rt = 1.28 min | analogous to Example 19 | 0.0047 |

TABLE 5-continued
Examples
| Example No. | Structure | R¹ | R² | Analytical data | Method of preparation | IC$_{50}$-value (μM) |
|---|---|---|---|---|---|---|
| 100 | 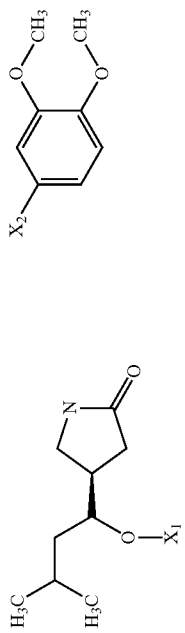 | 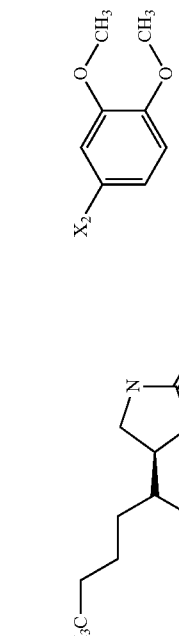 | 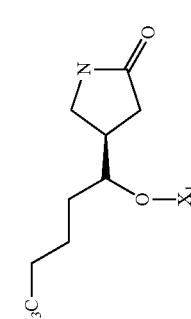 | HPLC-MS: method D Rt = 1.38 min | analogous to Example 19 | 0.0073 |
| 101 | 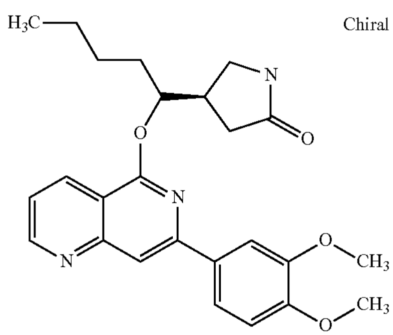 [SMILES: CCCCC(Oc1nc(-c2ccc(OC)c(OC)c2)cc2ncccc12)[C@H]1CNC(=O)C1] | | | HPLC-MS: method D Rt = 1.39 min | analogous to Example 19 | 0.0038 |

TABLE 5-continued

Examples

| Example No. | Structure | R¹ | R² | Analytical data | Method of preparation | IC$_{50}$-value (μM) |
|---|---|---|---|---|---|---|
| 102 | Chiral | | | HPLC-MS: method A Rt = 3.73 min | analogous to Example 19 | 0.0009 |
| 103 | Chiral | | | HPLC-MS: method A Rt = 4.25 min | see description 4.4.1. | 0.0047 |

TABLE 5-continued

Examples

| Example No. | Structure | R¹ | R² | Analytical data | Method of preparation | IC$_{50}$-value (μM) |
|---|---|---|---|---|---|---|
| 104 | Chiral structure with pyrrolidinone, quinoline core, methoxyphenyl-O-(N-methylpiperidin-4-yl) | pyrrolidinone-CH$_2$-O-X$_1$ | X$_2$-phenyl(OCH$_3$)-O-(N-methylpiperidin-4-yl) | HPLC-MS: method A Rt = 2.70 min | analogous to Example 19 | 0.0021 |
| 105 | Chiral structure with pyrrolidinone, quinoline core, methoxyphenyl-O-(N-methylpiperidin-3-yl) | pyrrolidinone-CH$_2$-O-X$_1$ | X$_2$-phenyl(OCH$_3$)-O-(N-methylpiperidin-3-yl) | HPLC-MS: method A Rt = 4.26 min | see description 4.4.1. | 0.0051 |

TABLE 5-continued

Examples

| Example No. | Structure | R¹ | R² | Analytical data | Method of preparation | IC$_{50}$-value (μM) |
|---|---|---|---|---|---|---|
| 106 | Chiral structure with pyrrolidinone-CH$_2$-O- linked to quinoline bearing 3-methoxy-4-(N-methylpyrrolidin-2-ylmethoxy)phenyl | pyrrolidinone-CH$_2$-O-X$_1$ | 2-OCH$_3$, 4-X$_2$-phenyl with O-CH$_2$-(N-methylpyrrolidin-2-yl) | HPLC-MS: method A Rt = 4.40 min | see description 4.4.1. | 0.0062 |
| 107 | Chiral structure with pyrrolidinone-CH$_2$-O- linked to quinoline bearing 3,4-dimethoxy-5-methylphenyl | pyrrolidinone-CH$_2$-O-X$_1$ | 3,4-di-OCH$_3$, 5-CH$_3$, X$_2$-phenyl | HPLC-MS: method E Rt = 1.19 min | analogous to Example 19 | 0.0045 |

TABLE 5-continued

Examples

| Example No. | Structure | R¹ | R² | Analytical data | Method of preparation | IC$_{50}$-value (μM) |
|---|---|---|---|---|---|---|
| 108 | Chiral structure with pyrrolidinone, chiral CH(CH₃)O linker, naphthyridine, and 3,4-dimethoxy-5-methylphenyl group | pyrrolidinone-CH(CH₃)-O-X₁ | 3,4-dimethoxy-5-methylphenyl with X₂ | HPLC-MS: method E Rt = 1.26 min | analogous to Example 19 | 0.0001 |
| 109 | Chiral structure with pyrrolidinone, CH₂O linker, naphthyridine, and 3-(1-methoxyethoxy)-4-methoxyphenyl group | pyrrolidinone-CH₂-O-X₁ | 3-(1-methoxyethoxy)-4-methoxyphenyl with X₂ | HPLC-MS: method D Rt = 1.29 min | analogous to Example 19 | 0.0204 |

TABLE 5-continued

Examples

| Example No. | Structure | R¹ | R² | Analytical data | Method of preparation | IC$_{50}$-value (μM) |
|---|---|---|---|---|---|---|
| 110 | Chiral structure with pyrrolidinone-CH₂-O-quinoline-phenyl-OCH₃/OCH₂CH₃ | pyrrolidinone-CH₂-O-X₁ | phenyl with OCH₃ and OCH₂CH₃, X₂ | HPLC-MS: method D Rt = 1.33 min | analogous to Example 19 | 0.0047 |
| 111 | Chiral structure with pyrrolidinone-CH₂-O-quinoline-phenyl-OCH₃/OCH(CH₃)₂ | pyrrolidinone-CH₂-O-X₁ | phenyl with OCH₃ and OCH(CH₃), X₂ | HPLC-MS: method A Rt = 3.85 min | analogous to Example 19 | 0.0007 |

TABLE 5-continued

Examples

| Example No. | Structure | R¹ | R² | Analytical data | Method of preparation | IC$_{50}$-value (μM) |
|---|---|---|---|---|---|---|
| 112 | Chiral | | | HPLC-MS: method D Rt = 1.34 min | analogous to Example 19 | 0.0001 |
| 113 | Chiral | | | HPLC-MS: method D Rt = 1.38 min | analogous to Example 19 | 0.0001 |

TABLE 5-continued

Examples

| Example No. | Structure | R[1] | R[2] | Analytical data | Method of preparation | IC$_{50}$-value (μM) |
|---|---|---|---|---|---|---|
| 114 | Chiral | | | HPLC-MS: method D Rt = 1.42 min | analogous to Example 10 | 0.0178 |
| 115 | Chiral | | | HPLC-MS: method E Rt = 1.26 min | analogous to Example 19 | 0.0134 |

TABLE 5-continued

Examples

| Example No. | Structure | R¹ | R² | Analytical data | Method of preparation | IC$_{50}$-value (μM) |
|---|---|---|---|---|---|---|
| 116 | Chiral; pyrrolidinone-CH$_2$-O-quinoline-phenyl(OCH$_3$)(O-cyclohexyl) | pyrrolidinone-CH$_2$-O-X$_1$ | X$_2$-phenyl-(OCH$_3$)-O-cyclohexyl | HPLC-MS: method D Rt = 1.46 min | analogous to Example 10 | 0.0074 |
| 117 | Chiral; pyrrolidinone-CH(CH$_3$)-O-naphthyridine-pyridine | H$_3$C-CH(pyrrolidinone)-O-X$_1$ | X$_2$-pyridine | HPLC-MS: method E Rt = 0.90 min | analogous to Example 19 | 0.0072 |

TABLE 5-continued

Examples

| Ex-ample No. | Structure | R¹ | R² | Analytical data | Method of preparation | IC₅₀-value (μM) |
|---|---|---|---|---|---|---|
| 118 | Chiral; pyrrolidinone-CH₂-O-naphthyridine-phenyl-OCH₃ | pyrrolidinone-CH₂-O-X₁ | X₂-C₆H₄-OCH₃ | HPLC-MS: method A Rt = 3.53 min | analogous to Example 19 | 0.0021 |
| 119 | Chiral; pyrrolidinone-CH₂-O-naphthyridine-phenyl-O-CH(CH₃)₂ | pyrrolidinone-CH₂-O-X₁ | X₂-C₆H₄-OCH(CH₃)H₃C | HPLC-MS: method C Rt = 1.93 min | analogous to Example 19 | 0.0037 |

TABLE 5-continued
Examples
| Example No. | Structure | R¹ | R² | Analytical data | Method of preparation | IC$_{50}$-value (μM) |
|---|---|---|---|---|---|---|
| 120 | 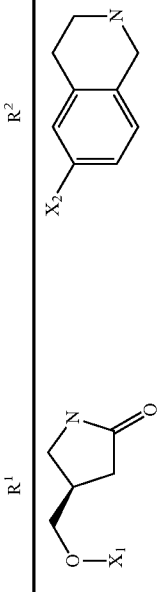 | 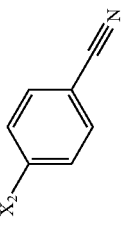 | 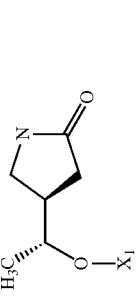 | HPLC-MS: method E Rt = 1.07 min | analogous to Example 78 | 0.0575 |
| 121 | 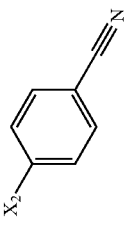 | 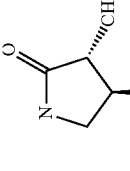 | 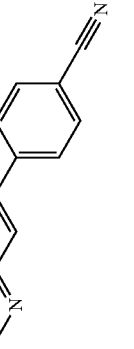 | HPLC-MS: method E Rt = 1.22 min | analogous to Example 19 | 0.0004 |
| 122 | 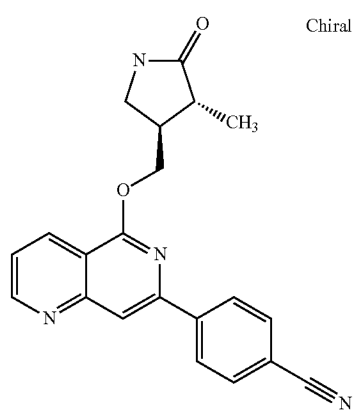 [SMILES: C[C@H]1C(=O)NC[C@@H]1COc1nc(-c2ccc(C#N)cc2)cc2ncccc12] | | | HPLC-MS: method A Rt = 3.84 min | analogous to Example 15 | 0.1187 |

TABLE 5-continued
Examples
| Ex-ample No. | Structure | R¹ | R² | Analytical data | Method of preparation | IC₅₀-value (µM) |
|---|---|---|---|---|---|---|
| 123 | 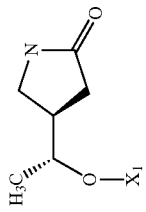 |  | 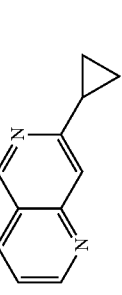 | HPLC-MS: method E Rt = 1.02 min | analogous to Example 19 | 1.900 |
| 124 | 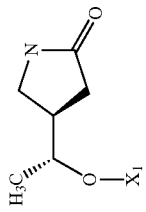 | 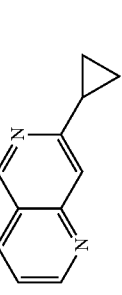 |  | HPLC-MS: method D Rt = 1.24 min | analogous to Example 19 | 0.0075 |

| Example No. | Structure | R¹ | R² | Analytical data | Method of preparation | IC₅₀-value (µM) |
|---|---|---|---|---|---|---|
| 125 | (Chiral) pyrrolidinone-CH(CH₃)-O-linked to 3-phenyl-[1,7]naphthyridine | H₃C-CH(-O-X₁)- pyrrolidinone | X₂-phenyl | HPLC-MS: method D Rt = 1.29 min | analogous to Example 19 | >1000 |
| 126 | (Chiral) pyrrolidinone-CH(CH₃)-O-linked to 3-phenyl-[1,7]naphthyridine | H₃C-CH(-O-X₁)- pyrrolidinone | X₂-phenyl | HPLC-MS: method D Rt = 1.29 min | analogous to Example 19 | 0.0002 |
| 127 | (Chiral) pyrrolidinone-CH(CH₃)-O-linked to [1,7]naphthyridine | H₃C-CH(-O-X₁)- pyrrolidinone | H | HPLC-MS: method D Rt = 1.02 min | analogous to Example 19 | 2156 |

6. INDICATIONS

As has been found, the compounds of formula 1 are characterised by their range of applications in the therapeutic field. Particular mention should be made of those applications for which the compounds of formula 1 according to the invention are preferably used on the basis of their pharmaceutical activity as SYK-inhibitors. Examples include respiratory complaints, allergic diseases, osteoporosis, gastrointestinal diseases or complaints, immune or autoimmune diseases, allergic diseases, inflammatory diseases, e.g. inflammatory diseases of the joints, skin and eyes and diseases of the peripheral or central nervous system.

Particular mention should be made of the prevention and treatment of respiratory tract and pulmonary diseases which are accompanied by increased mucus production, inflammation and/or obstructive diseases of the airways. Examples of these include asthma, paediatric asthma, ARDS (Adult Respiratory Distress Syndrome), acute, allergic or chronic bronchitis, autoimmune haemolytic anemia, chronic obstructive bronchitis (COPD) (including the treatment of Rhinovirus-induced exacerbations), coughs, allergic rhinitis or sinusitis, allergic rhinoconjunctivitis, chronic rhinitis or sinusitis, alveolitis, farmers' lung, hyperreactive airways, infectious bronchitis or pneumonitis, bronchiectasis, pulmonary fibrosis, bronchial oedema, pulmonary oedema, pneumonia or interstitial pneumonia triggered by various causes such as aspiration, inhalation of toxic gases or bronchitis, pneumonia or interstitial pneumonia triggered by cardiac insufficiency, radiation, chemotherapy, cystic fibrosis or mucoviscidosis, alpha1-antitrypsin deficiency.

The compounds according to the invention are preferably also suitable for the treatment of allergic diseases such as for example allergic rhinitis, allergic rhinoconjunctivitis, allergic conjunctivitis, and contact dermatitis, urticaria/angiooedema and allergic dermatitis.

Mention should also preferably be made of the treatment of inflammatory diseases of the gastrointestinal tract. Examples of these are Crohn's disease and ulcerative colitis.

The compounds according to the invention are preferably also suitable for the treatment of inflammatory diseases of the joints or inflammatory diseases of the skin and eyes. Examples of these are rheumatoid arthritis, antibody-based glomerulonephritis, psoriasis, Kawasaki syndrome, coeliac disease (sprue) and Wegener's granulomatosis.

The compounds according to the invention are preferably also suitable for the treatment of autoimmune diseases. Examples of these are hepatitis (autoimmune-based), lupus erythematodes, anti-phospholipid syndrome, Berger's disease, Evans's syndrome, immunohaemolytic anaemia, ITP (idiopathic thrombocytopenic purpura; adult, neonatal and paediatric), myasthenia gravis, Sjögren's syndrome and sclerodermy.

The compounds according to the invention are preferably also suitable for the treatment of B-cell lymphomas, like chronic lymphocytic leukaemia and non Hodgkin's lymphomas or T cell lymphomas.

Mention may preferably also be made of the prevention and treatment of diseases of the peripheral or central nervous system. Examples of these are acute and chronic multiple sclerosis or non-familial lateral sclerosis.

Mention may preferably also be made of the prevention and treatment of osteoporotic diseases such as for example disease-associated osteopenia, osteoporosis and osteolytic diseases.

The present invention relates particularly preferably to the use of compounds of formula 1 for preparing a pharmaceutical composition for the treatment of diseases selected from among asthma, COPD, allergic rhinitis, Adult Respiratory Distress Syndrome, bronchitis, allergic dermatitis, contact dermatitis, ITP, rheumatoid arthritis and allergic rhinoconjunctivitis.

Most preferably, the compounds of formula 1 may be used for the treatment of a disease selected from among asthma, allergic rhinitis, rheumatoid arthritis, allergic dermatitis and COPD.

7. COMBINATIONS

The compounds of formula 1 may be used on their own or in conjunction with other active substances of formula 1 according to the invention. The compounds of formula 1 may optionally also be used in conjunction with other pharmacologically active substances. Preferably the active substances used here may be selected for example from among the betamimetics, anticholinergics, corticosteroids, PDE4-inhibitors, LTD4-antagonists, EGFR-inhibitors, MRP4-inhibitors, dopamine agonists, H1-antihistamines, PAF-antagonists, iNos-inhibitors, HMG-CoA reductase inhibitors (statins), PI3-kinase-inhibitors, CCR3-antagonists, CCR2-antagonists, CCR1-antagonists, IKK2-inhibitors, A2a agonists, alpha-4-integrin-inhibitors, CRTH2-antagonists, histamine 1, combined H1/H3-antagonists, p38 kinase inhibitors, methylxanthines, ENaC-inhibitors, CXCR1-antagonists, CXCR2-antagonists, ICE-inhibitors, LTB4-antagonists, 5-LO antagonists, FLAP-antagonists. LTB4-antagonists; cromoglycine, dissociated glucocorticoid mimetics, anti-TNF-antibodies, anti-GM-CSF antibodies, anti-CD46-antibodies, anti-IL-1-antibodies, anti-IL-2-antibodies, anti-IL-4-antibodies, anti-IL-5-antibodies, anti-IL-13-antibodies, anti-IL-4/IL-13-antibodies, or double or triple combinations thereof, such as for example combinations of one, two or three compounds selected from among the

- SYK-inhibitors of formula 1, betamimetics, corticosteroids, EGFR-inhibitors and PDE4-antagonists,
- SYK-inhibitors of formula 1, anticholinergics, betamimetics, corticosteroids, EGFR-inhibitors and PDE4-antagonists,
- SYK-inhibitors of formula 1, PDE4-inhibitors, corticosteroids and EGFR-inhibitors,
- SYK-inhibitors of formula 1, EGFR-inhibitors and PDE4-inhibitors,
- SYK-inhibitors of formula 1 and EGFR-inhibitors,
- SYK-inhibitors of formula 1, betamimetics and anticholinergics
- SYK-inhibitors of formula 1, anticholinergics, betamimetics, corticosteroids and PDE4-inhibitors,
- SYK-inhibitors of formula 1, anticholinergics, betamimetics, corticosteroids, iNOS inhibitors, HMG-CoA reductase inhibitors.

Combinations of three active substances each taken from one of the above-mentioned categories of compounds are also an object of the invention.

Suitable betamimetics used are preferably compounds selected from among arformoterol, carmoterol, formoterol, indacaterol, salmeterol, albuterole, bambuterol, bitolterol, broxaterol, carbuterol, clenbuterol, fenoterol, hexoprenalin, ibuterol, isoetharin, isoprenalin, levosalbutamol, mabuterol, meluadrin, metaproterenol, milveterol, orciprenalin, pirbuterol, procaterol, reproterol, rimiterol, ritodrin, salmefamol, soterenol, sulphonterol, terbutalin, tiaramide, tolubuterol, zinterol, 6-Hydroxy-8-{11-hydroxy-2-[2-(4-methoxy-phenyl)-1,1-dimethyl-ethylamino]-ethyl}-4H-benzo[1,4]oxazine-3-one; 8-{2-[2-(2,4-Difluor-phenyl)-1,1- dimethyl-ethylamino]-1-hydroxy-ethyl}-6-hydroxy-4H-benzo[1,4]oxazine-3-one; 8-{2-[2-(3,5-Difluor-phenyl)-1,1-dimethyl-ethylamino]-1-hydroxy-ethyl}-6-hydroxy-4H-benzo[1,4]oxazine-3-one; 8-{2-[2-(4-Ethoxy-phenyl)-1,1-dimethyl-ethylamino]-1-hydroxy-ethyl}-6-hydroxy-4H-benzo[1,4]oxazine-3-one; 8-{2-[2-(4-Fluor-phenyl)-1,1-dimethyl-ethylamino]-1-hydroxy-ethyl}-6-hydroxy-4H-benzo[1,4]oxazine-3-one; N-(5-{2-[3-(4,4-Diethyl-2-oxo-4H-benzo[d][1,3]oxazine-1-yl)-1,1-dimethyl-propylamino]-1-hydroxy-ethyl}-2-hydroxy-phenyl)-methansulfonamide; N-(5-{2-[3-(4,4-Diethyl-6-fluoro-2-oxo-4H-benzo[d][1,3]oxazine-1-yl)-1,1-dimethyl-propylamino]-1-hydroxy-ethyl}-2-hydroxy-phenyl)-methansulfonamide; N-(5-{2-[3-(4,4-Diethyl-6-methoxy-2-oxo-4H-benzo[d][1,3]oxazine-1-yl)-1,1-dimethyl-propylamino]-1-hydroxy-ethyl}-2-hydroxy-phenyl)-methansulfonamide; N-(5-{2-[1,1-Dimethyl-3-(2-oxo-4,4-dipropyl-4H-benzo[d][1,3]oxazine-1-yl)-propylamino]-1-hydroxy-ethyl}-2-hydroxy-phenyl)-methansulfonamide; 8-{2-[1,1-Dimethyl-3-(2-oxo-2,3-dihydro-benzoimidazol-1-yl)-propylamino]-1-hydroxy-ethyl}-6-hydroxy-4H-benzo[1,4]oxazine-3-one; 8-{2-[1,1-Dimethyl-3-(6-methyl-2-oxo-2,3-dihydro-benzoimidazole-1-yl)-propylamino]-1-hydroxy-ethyl}-6-hydroxy-4H-benzo[1,4]oxazine-3-one; 8-{2-[1,1-Dimethyl-3-(2-oxo-5-trifluormethyl-2,3-dihydro-benzoimidazol-1-yl)-propylamino]-1-hydroxy-ethyl}-6-hydroxy-4H-benzo[1,4]oxazine-3-one; 8-{2-[1,1-Dimethyl-3-(3-methyl-2-oxo-2,3-dihydro-benzoimidazol-1-yl)-propylamino]-1-hydroxy-ethyl}-6-hydroxy-4H-benzo[1,4]oxazine-3-one; N-[2-Hydroxy-5-((1R)-1-hydroxy-2-{2-[4-(2-hydroxy-2-phenyl-ethylamino)-phenyl]-ethylamino}-ethyl)-phenyl]-formamide; 8-Hydroxy-5-((1R)-1-hydroxy-2-{2-[4-(6-methoxy-biphenyl-3-ylamino)-phenyl]-ethylamino}-ethyl)-1H-quinoline-2-one; 8-Hydroxy-5-[(1R)-1-hydroxy-2-(6-phenethylamino-hexylamino)-ethyl]-1H-quinoline-2-one; 5-[(1R)-2-(2-{4-[4-(2-Amino-2-methyl-propoxy)-phenylamino]-phenyl}-ethylamino)-1-hydroxy-ethyl]-8-hydroxy-1H-quinoline-2-one; [3-(4-{6-[(2R)-2-Hydroxy-2-(4-hydroxy-3-hydroxymethyl-phenyl)-ethylamino]-hexyloxy}-butyl)-5-methylphenyl]-urea; 4-((1R)-2-{6-[2-(2,6-Dichlor-benzyloxy)-ethoxy]-hexylamino}-1-hydroxy-ethyl)-2-hydroxymethyl-phenol; 3-(4-{6-[(2R)-2-Hydroxy-2-(4-hydroxy-3-hydroxymethyl-phenyl)-ethylamino]-hexyloxy}-butyl)-benzenesulfonamide; 3-(3-{7-[(2R)-2-Hydroxy-2-(4-hydroxy-3-hydroxymethyl-phenyl)-ethylamino]-heptyloxy}-propyl)-benzenesulfonamide; 4-((1R)-2-{6-[4-(3-Cyclopentanesulfonyl-phenyl)-butoxy]-hexylamino}-1-hydroxy-ethyl)-2-hydroxymethyl-phenol, 4-(2-{6-[2-(2,6-dichloro-benzyloxy)-ethoxy]-hexylamino}-1-hydroxy-ethyl)-2-hydroxymethyl-phenol; Vilanterol; N-1-Adamantanyl-2-{3-[(2R)-2-({(2R)-2-hydroxy-2-[4-hydroxy-3-(hydroxymethyl)phenyl]ethyl}amino)propyl]phenyl}acetamide; 2-(3-{2-[2-hydroxy-3-methanesulfonylamino-phenyl)-ethylamino]-propyl}-phenyl)-N-[4-(4-hydroxy-phenyl)-2-vinyl-penta-2,4-dienyl]-acetamide; (1R)-5-{2-[6-(2,2-Difluor-2-phenyl-ethoxy)-hexylamino]-1-hydroxy-ethyl}-8-hydroxy-1H-quinoline-2-one; (R,S)-4-(2-{[6-(2,2-Difluor-4-phenylbutoxy)hexyl]amino}-1-hydroxy-ethyl)-2-(hydroxymethyl)phenol; (R,S)-4-(2-{[6-(2,2-Difluor-2-phenylethoxy)hexyl]amino}-1-hydroxy-ethyl)-2-(hydroxymethyl)phenol; (R,S)-4-(2-{[4,4-Difluor-6-(4-phenylbutoxy)hexyl]amino}-1-hydroxy-ethyl)-2-(hydroxymethyl)phenol; (R,S)-4-(2-{[6-(4,4-Difluor-4-phenylbutoxy)hexyl]amino}-1-hydroxy-ethyl)-2-(hydroxymethyl)phenol; (R,S)-5-(2-{[6-(2,2-Difluor-2-phenylethoxy)hexyl]amino}-1-hydroxy-ethyl)-8-hydroxyquinoline-2(1H)-one; (R,S)-[2-({6-[2,2-Difluor-2-(3-methylphenyl)ethoxy]hexyl}amino)-1-hydroxyethyl]-2-(hydroxymethyl)phenol; 4-(1R)-2-{[6-(2,2-Difluor-2-phenylethoxy)hexyl]amino}-1-hydroxyethyl)-2-(hydroxymethyl)phenol; (R,S)-2-(Hydroxymethyl)-4-(1-hydroxy-2-{[4,4,5I.5-tetrafluor-6-(3-phenylpropoxy)-hexyl]amino}ethyl)phenol; (R,S)-[5-(2-{[6-(2,2-Difluor-2-phenylethoxy)hexyl]amino}-1-hydroxy-ethyl)-2-hydroxyphenyl]formamide; (R,S)-4-[2-({6-[2-(3-Bromophenyl)-2,2-difluoroethoxy]hexyl}amino)-1-hydroxyethyl]-2-(hydroxymethyl)phenol; (R,S)—N-[3-(1,1-Difluor-2-{[6-({2-hydroxy-2-[4-hydroxy-3-(hydroxymethyl)phenyl]-ethyl}amino)hexyl]oxy}ethyl)phenyl]-urea; 3-[3-(1,1-Difluor-2-{[6-({2-hydroxy-2-[4-hydroxy-3-(hydroxymethyl)phenyl]ethyl}amino)hexyl]oxy}ethyl)phenyl]imidazolidine-2,4-dione; (R,S)-4-[2-({6-[2,2-Difluor-2-(3-methoxyphenyl)ethoxy]hexyl}amino)-1-hydroxyethyl]-2-(hydroxymethyl)phenol; 5-((1R)-2-{[6-(2,2-Difluor-2-phenylethoxy)hexyl]amino}-1-hydroxyethyl)-8-hydroxyquinoline-2(1H)-one; 4-((1R)-2-{[4,4-Difluor-6-(4-phenylbutoxy)hexyl]amino}-1-hydroxy-ethyl)-2-(hydroxymethyl)phenol; (R,S)-4-(2-{[6-(3,3-Difluor-3-phenylpropoxy)hexyl]amino}-1-hydroxy-ethyl)-2-(hydroxymethyl)phenol; (R,S)-4-(2-{[6-(2,2-Difluor-2-phenylethoxy)-4,4-difluorohexyl]amino}-1-hydroxyethyl)-2-(hydroxymethyl)phenol; (R,S)-4-(2-{[6-(2,2-Difluor-3-phenylpropoxy)hexyl]amino}-1-hydroxy ethyl)-2-(hydroxymethyl)phenol; 3-[2-(3-Chlor-phenyl)-ethoxy]-N-(2-diethylamino-ethyl)-N-{2-[2-(4-hydroxy-2-oxo-2,3-dihydro-benzothiazol-7-yl)-ethylamino]-ethyl}-propionamide; N-(2-Diethylamino-ethyl)-N-{2-[2-(4-hydroxy-2-oxo-2,3-dihydro-benzothiazol-7-yl)-ethylamino]-ethyl}-3-(2-naphthalen-1-yl-ethoxy)-propionamide; 7-[2-(2-{3-[2-(2-Chlor-phenyl)-ethylamino]-propylsulfanyl}-ethylamino)-1-hydroxy-ethyl]-4-hydroxy-3H-benzothiazol-2-one, optionally in the form of the racemates, enantiomers, diastereomers and optionally in the form of the pharmacologically acceptable acid addition salts, solvates or hydrates thereof. According to the invention the acid addition salts of the betamimetics are preferably selected from among the hydrochloride, hydrobromide, hydroiodide, hydrosulphate, hydrophosphate, hydromethanesulphonate, hydronitrate, hydromaleate, hydroacetate, hydrocitrate, hydrofumarate, hydrotartrate, hydrooxalate, hydrosuccinate, hydrobenzoate and hydro-p-toluenesulphonate, preferably the hydrochloride, hydrobromide, hydrosulphate, hydrophosphate, hydrofumarate and hydromethanesulphonate. Of the above-mentioned acid addition salts the salts of hydrochloric acid, methanesulphonic acid, benzoic acid and acetic acid are particularly preferred according to the invention.

The anticholinergics used are preferably compounds selected from among tiotropium salts, particularly the bromide salt, oxitropium salts, particularly the bromide salt, flutropium salts, particularly the bromide salt, ipratropium salts, particularly the bromide salt, Aclidinium salts, particularly the bromide salt, glycopyrronium salts, particularly the bromide salt, trospium salts, particularly the chloride salt, tolterodin, (3R)-1-Phenethyl-3-(9H-xanthene-9-carbonyloxy)-1-azoniabicyclo[2.2.2]octan-salts; 2,2-Diphenyl propionic acid tropenole ester-methobromide; 2,2-Diphenyl propionic acid scopine ester-methobromide; 2-Fluor-2,2-Diphenyl acetic acid scopine ester-methobromide; 2-Fluor-2,2-Diphenyl acetic acid tropenole ester-methobromide; 3,3',4,4'-Tetrafluor benzilic acid tropenole ester-methobromide; 3,3',4,4'-Tetrafluor benzilic acid scopine ester-methobromide; 4,4'-Difluor benzilic acid tropenole ester-methobromide; 4,4'-Difluor benzilic acid scopine ester-methobromide;

3,3'-Difluor benzilic acid tropenole ester-methobromide; 3,3'-Difluor benzilic acid scopine ester-methobromide; 9-Hydroxy-fluorene-9-carboxylic acid tropenole ester-methobromide; 9-Fluor-fluorene-9-carboxylic acid tropenole ester-methobromide; 9-Hydroxy-fluorene-9-carboxylic acid scopine ester-methobromide; 9-Fluor-fluorene-9-carboxylic acid scopine ester-methobromide; 9-Methyl-fluorene-9-carboxylic acid tropenole ester-methobromide; 9-Methyl-fluorene-9-carboxylic acid scopine ester-methobromide; Benzilic acid cyclopropyl tropine ester-methobromide; 2,2-Diphenyl propionic acid cyclopropyltropine ester-methobromide; 9-Hydroxy-xanthene-9-carboxylic acid cyclopropyltropine ester-methobromide; 9-Methyl-fluorene-9-carboxylic acid cyclopropyltropine ester-methobromide; 9-Methyl-xanthene-9-carboxylic acid cyclopropyltropine ester-methobromide; 9-Hydroxy-fluorene-9-carboxilic acid cyclopropyltropine ester-methobromide; 4,4'-Difluor benzilic acid methyl ester cyclopropyltropine ester-methobromide; 9-Hydroxy-xanthene-9-carboxylic acid tropenole ester-methobromide; 9-Hydroxy-xanthene-9-carboxylic acid scopine ester-methobromide; 9-Methyl-xanthene-9-carboxylic acid tropenole ester-methobromide; 9-Methyl-xanthene-9-carboxylic acid scopine ester-methobromide; 9-Ethyl-xanthene-9-carboxylic acid tropenole ester-methobromide; 9-Difluormethyl-xanthene-9-carboxylic acid tropenole ester-methobromide; 9-Hydroxymethyl-xanthene-9-carboxylic acid scopine ester-methobromide;
3-[2-(3-Chloro-phenyl)-ethoxy]-N-(2-diethylamino-ethyl)-N-{2-[2-(4-hydroxy-2-oxo-2,3-dihydro-benzothiazol-7-yl)-ethylamino]-ethyl}-propionamide;
N-(2-Diethylamino-ethyl)-N-{2-[2-(4-hydroxy-2-oxo-2,3-dihydro-benzothiazol-7-yl)-ethylamino]-ethyl}-3-(2-naphthalen-1-yl-ethoxy)-propionamide;
7-[2-(2-{3-[2-(2-Chloro-phenyl)-ethylamino]-propylsulfanyl}-ethylamino)-1-hydroxy-ethyl]-4-hydroxy-3H-benzothiazol-2-one and Darotropium;
optionally in the form of the solvates or hydrates thereof.

In the above-mentioned salts the cations tiotropium, oxitropium, flutropium, ipratropium, glycopyrronium, aclidinium and trospium are the pharmacologically active ingredients. As anions, the above-mentioned salts may preferably contain chloride, bromide, iodide, sulphate, phosphate, methanesulphonate, nitrate, maleate, acetate, citrate, fumarate, tartrate, oxalate, succinate, benzoate or p-toluenesulphonate, while chloride, bromide, iodide, sulphate, methanesulphonate or p-toluenesulphonate are preferred as counter-ions. Of all the salts, the chlorides, bromides, iodides and methanesulphonate are particularly preferred.

Of particular importance is tiotropium bromide. In the case of tiotropium bromide the pharmaceutical combinations according to the invention preferably contain it in the form of the crystalline tiotropium bromide monohydrate, which is known from WO 02/30928. If the tiotropium bromide is used in anhydrous form in the pharmaceutical combinations according to the invention, it is preferable to use anhydrous crystalline tiotropium bromide, which is known from WO 03/000265.

Corticosteroids used here are preferably compounds selected from among beclomethasone, betamethasone, budesonide, butixocort, ciclesonide, deflazacort, dexamethasone, etiprednole, flunisolide, fluticasone, loteprednole, mometasone, prednisolone, prednisone, rofleponide, triamcinolone, tipredane; Pregna-1,4-diene-3,20-dione, 6-fluoro-11-hydroxy-16,17-[[(1-methylethylidene)bis(oxy)]-21-[[4-[(nitrooxy)methyl]benzoyl]oxy]-, (6-alpha,11-beta,16-alpha)-(9Cl); 16,17-butylidenedioxy-6,9-difluoro-11-hydroxy-17-(methylthio)androst-4-en-3-one; 6,9-Difluor-17-[(2-furanylcarbonyl)oxy]-11-hydroxy-16-methyl-3-oxo-androsta-1,4-dien-17-carbothione acid (S)-fluoromethylester; (S)-fluoromethyl 6,9-difluoro-17-[(2-furanylcarbonyl)oxy]-11-hydroxy-16-methyl-3-oxo-androsta-1,4-diene-17-carbothionate; 6-alpha,9-alpha-difluoro-11-beta-hydroxy-16alpha-methyl-3-oxo-17alpha-(2,2,3,3-tetramethylcyclopropylcarbonyl)oxy-androsta-1,4-diene-17beta-carboxylic acid cyanomethyl ester, each optionally in the form of the racemates, enantiomers or diastereomers thereof and optionally in the form of the salts and derivatives, solvates and/or hydrates thereof.

Particularly preferably the steroid is selected from among budesonide, fluticasone, mometasone, ciclesonide and (S)-fluoromethyl 6,9-difluoro-17-[(2-furanylcarbonyl)oxy]-11-hydroxy-16-methyl-3-oxo-androsta-1,4-diene-17-carbothionate, optionally in the form of the racemates, enantiomers or diastereomers thereof and optionally in the form of the salts and derivatives, solvates and/or hydrates thereof.

Any reference to steroids includes a reference to any salts or derivatives, hydrates or solvates thereof which may exist. Examples of possible salts and derivatives of the steroids may be: alkali metal salts, such as for example sodium or potassium salts, sulfobenzoates, phosphates, isonicotinates, acetates, propionates, dihydrogen phosphates, palmitates, pivalates or furoates thereof.

PDE4 inhibitors which may be used are preferably compounds selected from among enprofyllin, theophyllin, roflumilast, ariflo (cilomilast), tofimilast, pumafentrin, lirimilast, apremilast, arofyllin, atizoram, oglemilast, tetomilast; 5-[(N-(2,5-dichloro-3-pyridinyl)-carboxamide]-8-methoxy-Quinoline (D-4418); 5-[N-(3,5-dichloro-1-oxido-4-pyridinyl)-carboxamide]-8-methoxy-2-(trifluoromethyl)-Quinoline (D-4396 (Sch-351591)); N-(3,5-dichloropyrid-4-yl)-[1-(4-fluorobenzyl)-5-hydroxy-indol-3-yl]glyoxylic acid amide (AWD-12-281 (GW-842470)); 9-[(2-fluorophenyl)methyl]-N-methyl-2-(trifluoromethyl)-9H-Purin-6-amine (NCS-613); 4-[(2R)-2-[3-(cyclopentyloxy)-4-methoxyphenyl]-2-phenylethyl]-Pyridine (CDP-840); N-[(3R)-3,4,6,7-tetrahydro-9-methyl-4-oxo-1-phenylpyrrolo[3,2,1-jk][1,4]benzodiazepin-3-yl]-4-Pyridinecarboxamide (PD-168787); 4-[6,7-diethoxy-2,3-bis(hydroxymethyl)-1-naphthalenyl]-1-(2-methoxyethyl)-2(1H)-Pyridinone (T-440); 2-[4-[6,7-diethoxy-2,3-bis(hydroxymethyl)-1-naphthalenyl]-2-pyridinyl]-4-(3-pyridinyl)-1(2H)-Phthalazinone (T-2585); (3-(3-cyclopenyloxy-4-methoxybenzyl)-6-ethylamino-8-isopropyl-3H-purine (V-11294A); beta-[3-(cyclopentyloxy)-4-methoxyphenyl]-1,3-dihydro-1,3-dioxo-2H-Isoindole-2-propanamide (CDC-801); Imidazo[1,5-a]pyrido[3,2-e]pyrazine-6(5H)-one, 9-ethyl-2-methoxy-7-methyl-5-propyl-(D-22888); 5-[3-(cyclopentyloxy)-4-methoxyphenyl]-3-[(3-methylphenyl)methyl]-, (3S,5S)-2-Piperidinon (HT-0712); 4-[1-[3,4-bis(difluoromethoxy)phenyl]-2-(3-methyl-1-oxido-4-pyridinyl)ethyl]-alpha,alpha-bis(trifluoromethyl)-Benzenemethanol (L-826141); N-(3,5-Dichloro-1-oxo-pyridin-4-yl)-4-difluormethoxy-3-cyclopropylmethoxybenzamide; (−)p-[(4aR*,10bS*)-9-Ethoxy-1,2,3,4,4a,10b-hexahydro-8-methoxy-2-methylbenzo[s][1,6]naphthyridin-6-yl]-N,N-diisopropylbenzamide; (R)-(+)-1-(4-Brombenzyl)-4-[(3-cyclopentyloxy)-4-methoxyphenyl]-2-pyrrolidon; 3-(Cyclopentyloxy-4-methoxyphenyl)-1-(4-N'-[N-2-cyano-S-methyl-isothioureido]benzyl)-2-pyrrolidon; cis[4-Cyano-4-(3-cyclopentyloxy-4-methoxyphenyl)cyclohexan-1-carboxylic acid]; 2-carbomethoxy-4-cyano-4-(3-cyclopropylmethoxy-4-difluoromethoxyphenyl) cyclohexan-1-one; cis[4-Cyano-4-(3-cyclopropylmethoxy-4-difluormethoxyphenyl)cyclohexan-1-ol]; (R)-(+)-Ethyl[4-

(3-cyclopentyloxy-4-methoxyphenyl)pyrrolidin-2-yliden] acetat; (S)-(−)-Ethyl[4-(3-cyclopentyloxy-4-methoxyphenyl)pyrrolidin-2-yliden]acetat; 9-Cyclopentyl-5,6-dihydro-7-ethyl-3-(2-thienyl)-9H-pyrazolo[3,4-c]-1,2,4-triazolo[4,3-a]pyridin; 9-Cyclopentyl-5,6-dihydro-7-ethyl-3-(tert-butyl)-9H-pyrazolo[3,4-c]-1,2,4-triazolo[4,3-a]pyridin, optionally in the form of the racemates, enantiomers or diastereomers and optionally in the form of the pharmacologically acceptable acid addition salts, solvates and/or hydrates thereof.

By acid addition salts with pharmacologically acceptable acids which the above-mentioned PDE4-inhibitors might be in a position to form are meant, for example, salts selected from among the hydrochloride, hydrobromide, hydroiodide, hydrosulphate, hydrophosphate, hydromethanesulphonate, hydronitrate, hydromaleate, hydroacetate, hydrobenzoate, hydrocitrate, hydrofumarate, hydrotartrate, hydrooxalate, hydrosuccinate, hydrobenzoate and hydro-p-toluenesulphonate, preferably hydrochloride, hydrobromide, hydrosulphate, hydrophosphate, hydrofumarate and hydromethanesulphonate.

LTD4-antagonists which may be used are preferably compounds selected from among montelukast, pranlukast, zafirlukast; (E)-8-[2-[4-[4-(4-Fluorophenyl)butoxy]phenyl]ethenyl]-2-(1H-tetrazol-5-yl)-4H-1-benzopyran-4-one (MEN-91507); 4-[6-Acetyl-3-[3-(4-acetyl-3-hydroxy-2-propylphenylthio)propoxy]-2-propylphenoxy]-butyric acid (MN-001); 1-(((R)-3-(2-(6,7-Difluor-2-quinolinyl)ethenyl)phenyl)-3-(2-(2-hydroxy-2-propyl)phenyl)thio)methylcyclopropane-acetic acid; 1-(((1(R)-3(3-(2-(2,3-Dichlorthieno[3,2-b]pyridin-5-yl)-(E)-ethenyl)phenyl)-3-(2-(1-hydroxy-1-methylethyl)phenyl) propyl)thio)methyl)cyclopropane acetic acid; [2-[[2-(4-tert-Butyl-2-thiazolyl)-5-benzofuranyl]oxymethyl]phenyl]acetic acid, optionally in the form of the racemates, enantiomers or diastereomers, optionally in the form of the pharmacologically acceptable acid addition salts and optionally in the form of the salts and derivatives, solvates and/or hydrates thereof.

By acid addition salts with pharmacologically acceptable acids which the LTD4-antagonists may be capable of forming are meant, for example, salts selected from among the hydrochloride, hydrobromide, hydroiodide, hydrosulphate, hydrophosphate, hydromethanesulphonate, hydronitrate, hydromaleate, hydroacetate, hydrobenzoate, hydrocitrate, hydrofumarate, hydrotartrate, hydrooxalate, hydrosuccinate, hydrobenzoate and hydro-p-toluenesulphonate, preferably hydrochloride, hydrobromide, hydrosulphate, hydrophosphate, hydrofumarate and hydromethanesulphonate. By salts or derivatives which the LTD4-antagonists may be capable of forming are meant, for example: alkali metal salts, such as, for example, sodium or potassium salts, alkaline earth metal salts, sulphobenzoates, phosphates, isonicotinates, acetates, propionates, dihydrogen phosphates, palmitates, pivalates or furoates.

The EGFR-inhibitors used are preferably compounds selected from among 4-[(3-chloro-4-fluorophenyl)amino]-6-{[4-(morpholine-4-yl)-1-oxo-2-butene-1-yl]amino}-7-cyclopropylmethoxy-quinazoline, 4-[(3-chloro-4-fluorophenyl)amino]-6-{[4-(N,N-diethylamino)-1-oxo-2-butene-1-yl]amino}-7-cyclopropylmethoxy-quinazoline, 4-[(3-chloro-4-fluorophenyl)amino]-6-{[4-(N,N-dimethylamino)-1-oxo-2-butene-1-yl]amino}-7-cyclopropylmethoxy-quinazoline, 4-[(R)-(1-phenyl-ethyl)amino]-6-{[4-(morpholine-4-yl)-1-oxo-2-butene-1-yl]amino}-7-cyclopentyloxy-quinazoline, 4-[(3-chloro-4-fluoro-phenyl)amino]-6-{[4-((R)-6-methyl-2-oxo-morpholine-4-yl)-1-oxo-2- butene-1-yl]amino}-7-cyclopropylmethoxy-quinazoline, 4-[(3-chloro-4-fluoro-phenyl)amino]-6-{[4-((R)-6-methyl-2-oxo-morpholine-4-yl)-1-oxo-2-butene-1-yl]amino}-7-[(S)-(tetrahydrofuran-3-yl)oxy]-quinazoline, 4-[(3-chloro-4-fluoro-phenyl)amino]-6-{[4-((R)-2-methoxymethyl-6-oxo-morpholine-4-yl)-1-oxo-2-butene-1-yl]amino}-7-cyclopropylmethoxy-quinazoline, 4-[(3-chloro-4-fluorophenyl)amino]-6-[2-((S)-6-methyl-2-oxo-morpholine-4-yl)-ethoxy]-7-methoxy-quinazoline, 4-[(3-chloro-4-fluorophenyl)amino]-6-({4-[N-(2-methoxy-ethyl)-N-methyl-amino]-1-oxo-2-butene-1-yl}amino)-7-cyclopropylmethoxy-quinazoline, 4-[(3-chloro-4-fluorophenyl)amino]-6-{[4-(N,N-dimethylamino)-1-oxo-2-butene-1-yl]amino}-7-cyclopentyloxy-quinazoline, 4-[(R)-(1-phenyl-ethyl)amino]-6-{[4-(N,N-bis-(2-methoxy-ethyl)-amino)-1-oxo-2-butene-1-yl]amino}-7-cyclopropylmethoxy-quinazoline, 4-[(R)-(1-phenyl-ethyl)amino]-6-({1-[4N-(2-methoxy-ethyl)-N-ethylamino]-1-oxo-2-butene-1-yl}amino)-7-cyclopropylmethoxy-quinazoline, 4-[(R)-(1-phenyl-ethyl)amino]-6-({4-[N-(2-methoxy-ethyl)-N-methyl-amino]-1-oxo-2-butene-1-yl}amino)-7-cyclopropylmethoxy-quinazoline, 4-[(R)-(1-phenyl-ethyl)amino]-6-({4-[N-(tetrahydropyran-4-yl)-N-methyl-amino]-1-oxo-2-butene-1-yl}amino)-7-cyclopropylmethoxy-quinazoline, 4-[(R)-(1-Phenyl-ethyl)amino]-6-({4-[N-(2-methoxy-ethyl)-N-methyl-amino]-1-oxo-2-butene-1-yl}amino)-7-cyclopropylmethoxy-quinazoline, 4-[(R)-(1-Phenyl-ethyl)amino]-6-({4-[N-(tetrahydropyran-4-yl)-N-methyl-amino]-1-oxo-2-butene-1-yl}amino)-7-cyclopropylmethoxy-quinazoline, 4-[(3-chloro-4-fluorophenyl)amino]-6-{[4-(N,N-dimethylamino)-1-oxo-2-butene-1-yl]amino}-7-((R)-tetrahydrofuran-3-yloxy)-quinazoline, 4-[(3-chloro-4-fluorophenyl)amino]-6-{[4-(N,N-dimethylamino)-1-oxo-2-butene-1-yl]amino}-7-((S)-tetrahydrofuran-3-yloxy)-quinazoline, 4-[(3-chloro-4-fluorophenyl)amino]-6-({4-[N-(2-methoxy-ethyl)-N-methyl-amino]-1-oxo-2-butene-1-yl}amino)-7-cyclopentyloxy-quinazoline, 4-[(3-chloro-4-fluorophenyl)amino]-6-{[4-(N-cyclopropyl-N-methyl-amino)-1-oxo-2-butene-1-yl]amino}-7-cyclopentyloxy-quinazoline, 4-[(3-chloro-4-fluorophenyl)amino]-6-{[4-(N,N-dimethylamino)-1-oxo-2-butene-1-yl]amino}-7-[(R)-(tetrahydrofuran-2-yl)methoxy]-quinazoline, 4-[(3-chloro-4-fluorophenyl)amino]-6-{[4-(N,N-dimethylamino)-1-oxo-2-butene-1-yl]amino}-7-[(S)-(tetrahydrofuran-2-yl)methoxy]-quinazoline, 4-[(3-ethynyl-phenyl)amino]-6,7-bis-(2-methoxy-ethoxy)-quinazoline, 4-[(3-chloro-4-fluorophenyl)amino]-7-[3-(morpholine-4-yl)-propyloxy]-6-[(vinylcarbonyl)amino]-quinazoline, 4-[(R)-(1-phenyl-ethyl)amino]-6-(4-hydroxy-phenyl)-7H-pyrrolo[2,3-d]pyrimidine, 3-cyano-4-[(3-chloro-4-fluorophenyl)amino]-6-{[4-(N,N-dimethylamino)-1-oxo-2-butene-1-yl]amino}-7-ethoxy-quinoline, 4-{[3-chloro-4-(3-fluoro-benzyloxy)-phenyl]amino}-6-(5-{[(2-methanesulphonyl-ethyl)amino]methyl}-furan-2-yl) quinazoline, 4-[(R)-(1-phenyl-ethyl)amino]-6-{[4-((R)-6-methyl-2-oxo-morpholine-4-yl)-1-oxo-2-butene-1-yl]amino}-7-methoxy-quinazoline, 4-[(3-chloro-4-fluorophenyl)amino]-6-{[4-(morpholine-4-yl)-1-oxo-2-butene-1-yl]-amino}-7-[(tetrahydrofuran-2-yl)methoxy]-quinazoline, 4-[(3-chloro-4-fluorophenyl)amino]-6-({4-[N,N-bis-(2-methoxy-ethyl)-amino]-1-oxo-2-butene-1-yl}amino)-7-[(tetrahydrofuran-2-yl)methoxy]-quinazoline, 4-[(3-ethynyl-phenyl)amino]-6-{[4-(5,5-dimethyl-2-oxo-morpholine-4-yl)-1-oxo-2-butene-1-yl]amino}-quinazoline, 4-[(3-chloro-4-fluoro-phenyl)amino]-6-[2-(2,2-dimethyl-6-oxo-morpholine-4-yl)-ethoxy]-7-methoxy-quinazoline, 4-[(3-chloro-4-fluoro-phenyl)amino]-6-[2-(2,2-dimethyl-6-oxo-morpholine-4-yl)-ethoxy]-7-[(R)-(tetrahydrofuran-2-yl)methoxy]-quinazoline, 4-[(3-chloro-4-fluoro-phenyl)

amino]-7-[2-(2,2-dimethyl-6-oxo-morpholine-4-yl)-ethoxy]-6-[(S)-(tetrahydrofuran-2-yl)methoxy]-quinazoline, 4-[(3-chloro-4-fluoro-phenyl)amino]-6-{2-[4-(2-oxo-morpholine-4-yl)-piperidine-1-yl]-ethoxy}-7-methoxy-quinazoline, 4-[(3-chloro-4-fluoro-phenyl)amino]-6-[1-(tert.-butyloxycarbonyl)-piperidine-4-yloxy]-7-methoxy-quinazoline, 4-[(3-chloro-4-fluoro-phenyl)amino]-6-(trans-4-amino-cyclohexan-1-yloxy)-7-methoxy-quinazoline, 4-[(3-chloro-4-fluoro-phenyl)amino]-6-(trans-4-methanesulphonylamino-cyclohexan-1-yloxy)-7-methoxy-quinazoline, 4-[(3-chloro-4-fluoro-phenyl)amino]-6-(tetrahydropyran-3-yloxy)-7-methoxy-quinazoline, 4-[(3-chloro-4-fluoro-phenyl)amino]-6-(1-methyl-piperidine-4-yloxy)-7-methoxy-quinazoline, 4-[(3-chloro-4-fluoro-phenyl)amino]-6-{1-[(morpholine-4-yl)carbonyl]-piperidine-4-yloxy}-7-methoxy-quinazoline, 4-[(3-chloro-4-fluoro-phenyl)amino]-6-{1-[(methoxymethyl)carbonyl]-piperidine-4-yloxy}-7-methoxy-quinazoline, 4-[(3-chloro-4-fluoro-phenyl)amino]-6-(piperidine-3-yloxy)-7-methoxy-quinazoline, 4-[(3-chloro-4-fluoro-phenyl)amino]-6-[1-(2-acetylamino-ethyl)-piperidine-4-yloxy]-7-methoxy-quinazoline, 4-[(3-chloro-4-fluoro-phenyl)amino]-6-(tetrahydropyran-4-yloxy)-7-ethoxy-quinazoline, 4-[(3-chloro-4-fluoro-phenyl)amino]-6-((S)-tetrahydrofuran-3-yloxy)-7-hydroxy-quinazoline, 4-[(3-chloro-4-fluoro-phenyl)amino]-6-(tetrahydropyran-4-yloxy)-7-(2-methoxy-ethoxy)-quinazoline, 4-[(3-chloro-4-fluoro-phenyl)amino]-6-{trans-4-[(dimethylamino)sulphonylamino]-cyclohexan-1-yloxy}-7-methoxy-quinazoline, 4-[(3-chloro-4-fluoro-phenyl)amino]-6-{trans-4-[(morpholine-4-yl)carbonylamino]-cyclohexan-1-yloxy}-7-methoxy-quinazoline, 4-[(3-chloro-4-fluoro-phenyl)amino]-6-{trans-4-[(morpholine-4-yl)sulphonylamino]-cyclohexan-1-yloxy}-7-methoxy-quinazoline, 4-[(3-chloro-4-fluoro-phenyl)amino]-6-(tetrahydropyran-4-yloxy)-7-(2-acetylamino-ethoxy)-quinazoline, 4-[(3-chloro-4-fluoro-phenyl)amino]-6-(tetrahydropyran-4-yloxy)-7-(2-methanesulphonylamino-ethoxy)-quinazoline, 4-[(3-chloro-4-fluoro-phenyl)amino]-6-{1-[(piperidine-1-yl)carbonyl]-piperidine-4-yloxy}-7-methoxy-quinazoline, 4-[(3-chloro-4-fluoro-phenyl)amino]-6-(1-aminocarbonylmethyl-piperidine-4-yloxy)-7-methoxy-quinazoline, 4-[(3-chloro-4-fluoro-phenyl)amino]-6-cis-4-{N-[(tetrahydropyran-4-yl)carbonyl]-N-methyl-amino}-cyclohexan-1-yloxy)-7-methoxy-quinazoline, 4-[(3-chloro-4-fluoro-phenyl)amino]-6-(cis-4-{N-[(morpholine-4-yl)carbonyl]-N-methyl-amino}-cyclohexan-1-yloxy)-7-methoxy-quinazolin; 4-{2-[4-(3-chloro-4-fluoro-phenylamino)-7-methoxy-quinazolin-6-yloxy]-ethyl}-6-methyl-morpholine-2-one, 4-{4-[4-(3-chloro-2-fluoro-phenylamino)-7-methoxy-quinazolin-6-yloxy]-cyclohexyl}-1-methyl-piperazine-2-one, 4-[(3-chloro-4-fluoro-phenyl)amino]-6-(cis-4-{N-[(morpholine-4-yl)sulphonyl]-N-methyl-amino}-cyclohexan-1-yloxy)-7-methoxy-quinazoline, 4-[(3-chloro-4-fluoro-phenyl)amino]-6-(trans-4-ethansulphonylamino-cyclohexan-1-yloxy)-7-methoxy-quinazoline, 4-[(3-chloro-4-fluoro-phenyl)amino]-6-(1-methanesulphonyl-piperidine-4-yloxy)-7-ethoxy-quinazoline, 4-[(3-chloro-4-fluoro-phenyl)amino]-6-(1-methanesulphonyl-piperidine-4-yloxy)-7-(2-methoxy-ethoxy)-quinazoline, 4-[(3-chloro-4-fluoro-phenyl)amino]-6-[1-(2-methoxy-acetyl)-piperidine-4-yloxy]-7-(2-methoxy-ethoxy)-quinazoline, 4-[(3-chloro-4-fluoro-phenyl)amino]-6-(cis-4-acetylamino-cyclohexan-1-yloxy)-7-methoxy-quinazoline, 4-[(3-ethynyl-phenyl)amino]-6-[1-(tert.-butyloxycarbonyl)-piperidine-4-yloxy]-7-methoxy-quinazoline, 4-[(3-ethynyl-phenyl)amino]-6-(tetrahydropyran-4-yloxy)-7-methoxy-quinazoline, 4-[(3-chloro-4-fluoro-phenyl)amino]-6-(cis-4-{N-[(piperidine-1-yl)carbonyl]-N-methyl-amino}-cyclohexan-1-yloxy)-7-methoxy-quinazoline, 4-[(3-chloro-4-fluoro-phenyl)amino]-6-(cis-4-{N-[(4-methyl-piperazine-1-yl)carbonyl]-N-methyl-amino}-cyclohexan-1-yloxy)-7-methoxy-quinazoline, 4-[(3-chloro-4-fluoro-phenyl)amino]-6-{cis-4-[(morpholine-4-yl)carbonylamino]-cyclohexan-1-yloxy}-7-methoxy-quinazoline, 4-[(3-chloro-4-fluoro-phenyl)amino]-6-{1-[2-(2-oxopyrrolidin-1-yl)ethyl]-piperidine-4-yloxy}-7-methoxy-quinazoline, 4-[(3-chloro-4-fluoro-phenyl)amino]-6-{1-[(morpholine-4-yl)carbonyl]-piperidine-4-yloxy}-7-(2-methoxy-ethoxy)-quinazoline, 4-[(3-ethynyl-phenyl)amino]-6-(1-acetyl-piperidine-4-yloxy)-7-methoxy-quinazoline, 4-[(3-ethynyl-phenyl)amino]-6-(1-methyl-piperidine-4-yloxy)-7-methoxy-quinazoline, 4-[(3-ethynyl-phenyl)amino]-6-(1-methanesulphonyl-piperidine-4-yloxy)-7-methoxy-quinazoline, 4-[(3-chloro-4-fluoro-phenyl)amino]-6-(1-methyl-piperidine-4-yloxy)-7(2-methoxy-ethoxy)-quinazoline, 4-[(3-chloro-4-fluoro-phenyl)amino]-6-(1-isopropyloxycarbonyl-piperidine-4-yloxy)-7-methoxy-quinazoline, 4-[(3-chloro-4-fluoro-phenyl)amino]-6-(cis-4-methylamino-cyclohexan-1-yloxy)-7-methoxy-quinazoline, 4-[(3-chloro-4-fluoro-phenyl)amino]-6-{cis-4-[N-(2-methoxy-acetyl)-N-methyl-amino]-cyclohexan-1-yloxy}-7-methoxy-quinazoline, 4-[(3-ethynyl-phenyl)amino]-6-(piperidine-4-yloxy)-7-methoxy-quinazoline, 4-[(3-ethynyl-phenyl)amino]-6-[1-(2-methoxy-acetyl)-piperidine-4-yloxy]-7-methoxy-quinazoline, 4-[(3-ethynyl-phenyl)amino]-6-{1-[(morpholine-4-yl)carbonyl]-piperidine-4-yloxy}-7-methoxy-quinazoline, 4-[(3-chloro-4-fluoro-phenyl)amino]-6-{1-[(cis-2,6-dimethyl-morpholine-4-yl)carbonyl]-piperidine-4-yloxy}-7-methoxy-quinazoline, 4-[(3-chloro-4-fluoro-phenyl)amino]-6-{1-[(2-methyl-morpholine-4-yl)carbonyl]-piperidine-4-yloxy}-7-methoxy-quinazoline, 4-[(3-chloro-4-fluoro-phenyl)amino]-6-{1-[(S,S)-(2-oxa-5-aza-bicyclo[2,2,1]hept-5-yl)carbonyl]-piperidine-4-yloxy}-7-methoxy-quinazoline, 4-[(3-chloro-4-fluoro-phenyl)amino]-6-{1-[(N-methyl-N-2-methoxyethyl-amino)carbonyl]-piperidine-4-yloxy}-7-methoxy-quinazoline, 4-[(3-chloro-4-fluoro-phenyl)amino]-6-(1-ethyl-piperidine-4-yloxy)-7-methoxy-quinazoline, 4-[(3-chloro-4-fluoro-phenyl)amino]-6-{1-[(2-methoxyethyl)carbonyl]-piperidine-4-yloxy}-7-methoxy-quinazoline, 4-[(3-chloro-4-fluoro-phenyl)amino]-6-{1-[(3-methoxypropyl-amino)-carbonyl]-piperidine-4-yloxy}-7-methoxy-quinazoline, 4-[(3-chloro-4-fluoro-phenyl)amino]-6-[cis-4-(N-methanesulphonyl-N-methyl-amino)-cyclohexan-1-yloxy]-7-methoxy-quinazoline, 4-[(3-chloro-4-fluoro-phenyl)amino]-6-[cis-4-(N-acetyl-N-methyl-amino)-cyclohexan-1-yloxy]-7-methoxy-quinazoline, 4-[(3-chloro-4-fluoro-phenyl)amino]-6-(trans-4-methylamino-cyclohexan-1-yloxy)-7-methoxy-quinazoline, 4-[(3-chloro-4-fluoro-phenyl)amino]-6-[trans-4-(N-methanesulphonyl-N-methyl-amino)-cyclohexan-1-yloxy]-7-methoxy-quinazoline, 4-[(3-chloro-4-fluoro-phenyl)amino]-6-(trans-4-dimethylamino-cyclohexan-1-yloxy)-7-methoxy-quinazoline, 4-[(3-chloro-4-fluoro-phenyl)amino]-6-(trans-4-{N-[(morpholine-4-yl)carbonyl]-N-methyl-amino}-cyclohexan-1-yloxy)-7-methoxy-quinazoline, 4-[(3-chloro-4-fluoro-phenyl)amino]-6-[2-(2,2-dimethyl-6-oxo-morpholine-4-yl)-ethoxy]-7-[(S)-(tetrahydrofuran-2-yl)methoxy]-quinazoline, 4-[(3-chloro-4-fluoro-phenyl)amino]-6-(1-methanesulphonyl-piperidine-4-yloxy)-7-methoxy-quinazoline, 4-[(3-chloro-4-fluoro-phenyl)amino]-6-(1-cyano-piperidine-4-yloxy)-7-methoxy-quinazoline, 3-Cyano-4-[(3-chlor-4-fluorphenyl)amino]-6-{[4-(N,N-dimethylamino)-1-oxo-2-buten-1-yl]amino}-7-ethoxy-quinoline, [44(3-chloro-4-fluoro-phenyl)amino]-6-{[4-(homomorpholine-4-yl)-1-oxo-2-butene-1-yl]amino}-7-[(S)-(tetrahydrofuran-3-yl)oxy]-quinazoline, 4-[(3-chloro-4-fluoro-phenyl)amino]-7-(2-{4-[(S)-(2-oxo-tetrahydrofuran-5-yl)carbonyl]-piperazine-1-yl}-ethoxy)-6-[(vinylcarbonyl)amino]-quinazoline, 4-[(3-chloro-4-fluoro-phenyl)amino]-7-[2-((S)-6-methyl-2-oxo-morpholine-4-yl)-ethoxy]-6-[(vinylcarbonyl)amino]-quinazoline, 4-[(3-chloro-4-fluoro-phenyl)amino]-7-[4-((R)-6-methyl-2-oxo-morpholine-4-yl)-butyloxy]-6-[(vinylcarbonyl)amino]-quinazoline, 4-[(3-chloro-4-fluoro-phenyl)amino]-7-[4-((S)-6-methyl-2-oxo-morpholine-4-yl)-butyloxy]-6-[(vinylcarbonyl)amino]-quinazoline, 4-[(3-chloro-4-fluoro-phenyl)amino]-7-(2-{4-[(S)-(2-oxo-tetrahydrofuran-5-yl)carbonyl]-piperazine-1-yl}-ethoxy)-6-[(vinylcarbonyl)amino]-quinazoline, 4-[(3-chloro-4-fluoro-phenyl)amino]-7-[2-((S)-6-methyl-2-oxo-morpholine-4-yl)-ethoxy]-6-[(vinylcarbonyl)amino]-quinazoline, 4-[(3-chloro-4-fluoro-phenyl)amino]-7-[4-((R)-6-methyl-2-oxo-morpholine-4-yl)-butyloxy]-6-[(vinylcarbonyl)amino]-quinazoline, 4-[(3-chloro-4-fluoro-phenyl)amino]-7-[4-((S)-6-methyl-2-oxo-morpholine-4-yl)-butyloxy]-6-[(vinylcarbonyl)amino]-quinazoline, cetuximab, trastuzumab, panitumumab (=ABX-EGF), Mab ICR-62, gefitinib, pelitinib, canertinib and erlotinib, optionally in the form of the racemates, enantiomers or diastereomers thereof, optionally in the form of the pharmacologically acceptable acid addition salts thereof, the solvates and/or hydrates thereof.

By acid addition salts with pharmacologically acceptable acids which the EGFR-inhibitors may be capable of forming are meant, for example, salts selected from among the hydrochloride, hydrobromide, hydroiodide, hydrosulphate, hydrophosphate, hydromethanesulphonate, hydronitrate, hydromaleate, hydroacetate, hydrobenzoate, hydrocitrate, hydrofumarate, hydrotartrate, hydrooxalate, hydrosuccinate, hydrobenzoate and hydro-p-toluenesulphonate, preferably hydrochloride, hydrobromide, hydrosulphate, hydrophosphate, hydrofumarate and hydromethanesulphonate.

Examples of dopamine agonists which may be used preferably include compounds selected from among bromocriptine, cabergoline, alpha-dihydroergocryptine, lisuride, pergolide, pramipexol, roxindol, ropinirol, talipexol, terguride and viozan. Any reference to the above-mentioned dopamine agonists within the scope of the present invention includes a reference to any pharmacologically acceptable acid addition salts and optionally hydrates thereof which may exist. By the physiologically acceptable acid addition salts which may be formed by the above-mentioned dopamine agonists are meant, for example, pharmaceutically acceptable salts which are selected from the salts of hydrochloric acid, hydrobromic acid, sulphuric acid, phosphoric acid, methanesulphonic acid, acetic acid, fumaric acid, succinic acid, lactic acid, citric acid, tartaric acid and maleic acid.

Examples of H1-antihistamines preferably include compounds selected from among epinastine, cetirizine, azelastine, fexofenadine, levocabastine, loratadine, mizolastine, ketotifen, emedastine, dimetinden, clemastine, bamipin, cexchlorpheniramine, pheniramine, doxylamine, chlorophenoxamine, dimenhydrinate, diphenhydramine, promethazine, ebastine, olopatadine, desloratidine and meclozine. Any reference to the above-mentioned H1-antihistamines within the scope of the present invention includes a reference to any pharmacologically acceptable acid addition salts which may exist.

Examples of PAF-antagonists preferably include compounds selected from among lexipafant, 4-(2-chlorophenyl)-9-methyl-2-[3(4-morpholinyl)-3-propanon-1-yl]-6H-thieno-[3,2-f]-[1,2,4]triazolo[4,3-a][1,4]diazepines, 6-(2-chlorophenyl)-8,9-dihydro-1-methyl-8-[(4-morpho-linyl)carbonyl]-4H,7H-cyclo-penta-[4,5]thieno-[3,2-f][1,2,4]triazolo[4,3-a][1,4]diazepines. Any reference to the abovementioned above-mentioned PAF-antagonists includes within the scope of the present invention a reference to any pharmacologically acceptable acid addition salts thereof which may exist.

MRP4-inhibitors used are preferably compounds selected from among N-acetyl-dinitrophenyl-cysteine, cGMP, cholate, diclofenac, dehydroepiandrosterone 3-glucuronide, dehydroepiandrosterone 3-sulphate, dilazep, dinitrophenyl-s-glutathione, estradiol 17-beta-glucuronide, estradiol 3,17-disulphate, estradiol 3-glucuronide, estradiol 3-sulphate, estrone 3-sulphate, flurbiprofen, folate, N5-formyl-tetrahydrofolate, glycocholate, glycolithocholic acid sulphate, ibuprofen, indomethacin, indoprofen, ketoprofen, lithocholic acid sulphate, methotrexate, ((E)-3-[[[3-[2-(7-chloro-2-quinolinyl)ethenyl]phenyl]-[[3-dimethylamino)-3-oxopropyl]thio]methyl]thio]-propanoic acid), alpha-naphthyl-beta-D-glucuronide, nitrobenzyl mercaptopurine riboside, probenecid, sildenafil, sulfinpyrazone, taurochenodeoxycholate, taurocholate, taurodeoxycholate, taurolithocholate, taurolithocholic acid sulphate, topotecan, trequinsin and zaprinast, dipyridamole, optionally in the form of the racemates, enantiomers, diastereomers and the pharmacologically acceptable acid addition salts and hydrates thereof.

The invention relates more preferably to the use of MRP4-inhibitors for preparing a pharmaceutical composition for treating respiratory complaints, containing the SYK-inhibitors of formula 1 and MRP4-inhibitors according to the invention, the MRP4-inhibitors preferably being selected from among dehydroepiandrosterone 3-sulphate, estradiol 3,17-disulphate, flurbiprofen, indomethacin, indoprofen, taurocholate, optionally in the form of the racemates, enantiomers, diastereomers and the pharmacologically acceptable acid addition salts and hydrates thereof. The separation of enantiomers from the racemates can be carried out using methods known from the art (e.g. chromatography on chiral phases, etc.).

By acid addition salts with pharmacologically acceptable acids are meant, for example, salts selected from among the hydrochlorides, hydrobromides, hydroiodides, hydrosulphates, hydrophosphates, hydromethanesulphonates, hydronitrates, hydromaleates, hydroacetates, hydrobenzoates, hydrocitrates, hydrofumarates, hydrotartrates, hydrooxalates, hydrosuccinates, hydrobenzoates and hydro-p-toluenesulphonates, preferably the hydrochlorides, hydrobromides, hydrosulphates, hydrophosphates, hydrofumarates and hydromethanesulphonates.

The invention further relates to pharmaceutical preparations which contain a triple combination of the SYK-inhibitors of formula 1, MRP4-inhibitors and another active substance according to the invention, such as, for example, an anticholinergic, a PDE4 inhibitor, a steroid, an LTD4-antagonist or a betamimetic, and the preparation thereof and the use thereof for treating respiratory complaints.

Compounds which may be used as iNOS inhibitors are compounds selected from among: S-(2-aminoethyl)isothiourea, aminoguanidine, 2-aminomethylpyridine, 5,6-dihydro-6-methyl-4H-1,3-Thiazine-2-amine (=AMT), L-canavanine, 2-iminopiperidine, S-isopropylisothiourea, S-methylisothiourea, S-ethylisothiourea, S-methyltiocitrullin, S-ethylthiocitrulline, L-NA (Nw-nitro-L-arginine), L-NAME (N$^\omega$-nitro-L-argininemethylester), L-NMMA (N$^G$-monomethyl-L-arginine), L-NIO (N$^\omega$-iminoethyl-L-ornithine), L-NIL (N$^\omega$-iminoethyl-lysine), (S)-6-acetimidoylamino-2-aminohexanoic acid (1H-tetrazol-5-yl)-amide (SC-51) (*J. Med.*

*Chem.* 2002, 45, 1686-1689), N-[[3-(aminomethyl)phenyl]methyl]-Ethanimidamide (=1400 W), (S)-4-(2-acetimidoylamino-ethylsulphanyl)-2-amino-butyric acid (GW274150) (*Bioorg. Med. Chem. Lett.* 2000, 10, 597-600), 2-[2-(4-methoxy-pyridin-2-yl)-ethyl]-3H-imidazo[4,5-b]pyridine (BYK191023) (*Mol. Pharmacol.* 2006, 69, 328-337), 2-((R)-3-amino-1-phenyl-propoxy)-4-chloro-5-fluorobenzonitrile (WO 01/62704), 2-((1R,3S)-3-amino-4-hydroxy-1-thiazol-5-yl-butylsulphanyl)-6-trifluoromethyl-nicotinonitrile (WO 2004/041794), 2-((1R.3S)-3-amino-4-hydroxy-1-thiazol-5-yl-butylsulphanyl)-4-chloro-benzonitrile (WO 2004/041794), 2-((1R.3S)-3-amino-4-hydroxy-1-thiazol-5-yl-butylsulphanyl)-5-chloro-benzonitrile (WO 2004/041794), (2S,4R)-2-amino-4-(2-chloro-5-trifluoromethyl-phenylsulphanyl)-4-thiazol-5-yl-butan-1-ol (WO 2004/041794), 2-((1R.3S)-3-amino-4-hydroxy-1-thiazol-5-yl-butylsulphanyl)-5-chloro-nicotinonitrile (WO 2004/041794), 4-((S)-3-amino-4-hydroxy-1-phenyl-butylsulphanyl)-6-methoxy-nicotinonitrile (WO 02/090332), substituted 3-phenyl-3,4-dihydro-1-isoquinolinamine such as e.g. (1S,5S,6R)-7-chloro-5-methyl-2-aza-bicyclo[4.1.0]hept-2-en-3-ylamine (ONO-1714) (*Biochem. Biophys. Res. Commun.* 2000, 270, 663-667), (4R,5R)-5-ethyl-4-methyl-thiazolidin-2-ylideneamine (*Bioorg. Med. Chem.* 2004, 12, 4101), (4R,5R)-5-ethyl-4-methyl-selenazolidin-2-ylideneamine (*Bioorg. Med. Chem. Lett.* 2005, 15, 1361), 4-aminotetrahydrobiopterine (*Curr. Drug Metabol.* 2002, 3, 119-121), (E)-3-(4-chlorophenyl)-N-(1-{2-oxo-2-[4-(6-trifluoromethyl-pyrimidin-4-yloxy)-piperidine-1-yl]-ethylcarbamoyl}-2-pyridin-2-yl-ethyl)-acrylamide (FR260330) (*Eur. J. Pharmacol.* 2005, 509, 71-76), 3-(2,4-difluoro-phenyl)-6-[2-(4-imidazol-1-yl-methyl-phenoxy)-ethoxy]-2-phenyl-pyridine (PPA250) (*J. Pharmacol. Exp. Ther.* 2002, 303, 52-57), 3-{[(benzo[1,3]dioxol-5-ylmethyl)-carbamoyl]-methyl}-4-(2-imidazol-1-yl-pyrimidin-4-yl)-piperazine-1-carboxylate (BBS-1) (*Drugs Future* 2004, 29, 45-52), (R)-1-(2-imidazol-1-yl-6-methyl-pyrimidin-4-yl)-pyrrolidine-2-carboxylic acid (2-benzo[1,3]dioxol-5-yl-ethyl)-amide (BBS-2) (*Drugs Future* 2004, 29, 45-52) and the pharmaceutical salts, prodrugs or solvates thereof.

Examples of iNOS-inhibitors within the scope of the present invention may also include antisense oligonucleotides, particularly those antisense oligonucleotides which bind iNOS-coding nucleic acids. For example, WO 01/52902 describes antisense oligonucleotides, particularly antisense oligonucleotides, which bind iNOS coding nucleic acids, for modulating the expression of iNOS. iNOS-antisense oligonucleotides as described particularly in WO 01/52902 may therefore also be combined with the PDE4-inhibitors of the present invention on account of their similar effect to the iNOS-inhibitors.

Suitable HMG-CoA reductase inhibitors (also called statins) which may be preferably used in double or triple combinations with the compounds of formula 1 are selected from among Atorvastatin, Cerivastatin, Flurvastatin, Lovastatin, Pitavastatin, Pravastatin, Rosuvastatin, Simvastatin, optionally in form of their pharmaceutically available acid addition salts, prodrugs, solvates or hydrates thereof.

8. FORMULATIONS

Suitable forms for administration are for example tablets, capsules, solutions, syrups, emulsions or inhalable powders or aerosols. The content of the pharmaceutically effective compound(s) in each case should be in the range from 0.1 to 90 wt. %, preferably 0.5 to 50 wt. % of the total composition, i.e. in amounts which are sufficient to achieve the dosage range specified hereinafter.

The preparations may be administered orally in the form of a tablet, as a powder, as a powder in a capsule (e.g. a hard gelatine capsule), as a solution or suspension. When administered by inhalation the active substance combination may be given as a powder, as an aqueous or aqueous-ethanolic solution or using a propellant gas formulation.

Preferably, therefore, pharmaceutical formulations are characterised by the content of one or more compounds of formula 1 according to the preferred embodiments above.

It is particularly preferable if the compounds of formula 1 are administered orally, and it is also particularly preferable if they are administered once or twice a day. Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number of layers to achieve delayed release, possibly using the excipients mentioned above for the tablets.

Syrups containing the active substances or combinations thereof according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Capsules containing one or more active substances or combinations of active substances may for example be prepared by mixing the active substances with inert carriers such as lactose or sorbitol and packing them into gelatine capsules. Suitable suppositories may be made for example by mixing with carriers provided for this purpose, such as neutral fats or polyethyleneglycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose), emulsifiers (e.g. lignin, spent sulphite liquors, methylcellulose, starch and polyvinylpyrrolidone) and lubricants (e.g. magnesium stearate, talc, stearic acid and sodium lauryl sulphate).

For oral administration the tablets may, of course, contain, apart from the abovementioned carriers, additives such as sodium citrate, calcium carbonate and dicalcium phosphate together with various additives such as starch, preferably potato starch, gelatine and the like. Moreover, lubricants such as magnesium stearate, sodium lauryl sulphate and talc may be used at the same time for the tabletting process. In the case of aqueous suspensions the active substances may be combined with various flavour enhancers or colourings in addition to the excipients mentioned above.

It is also preferred if the compounds of formula 1 are administered by inhalation, particularly preferably if they are administered once or twice a day. For this purpose, the compounds of formula 1 have to be made available in forms suitable for inhalation. Inhalable preparations include inhalable powders, propellant-containing metered-dose aerosols or propellant-free inhalable solutions, which are optionally present in admixture with conventional physiologically acceptable excipients.

Within the scope of the present invention, the term propellant-free inhalable solutions also includes concentrates or sterile ready-to-use inhalable solutions. The preparations which may be used according to the invention are described in more detail in the next part of the specification.

Inhalable Powders

If the active substances of formula 1 are present in admixture with physiologically acceptable excipients, the following physiologically acceptable excipients may be used to prepare the inhalable powders according to the invention: monosaccharides (e.g. glucose or arabinose), disaccharides (e.g. lactose, saccharose, maltose), oligo- and polysaccharides (e.g. dextran), polyalcohols (e.g. sorbitol, mannitol, xylitol), salts (e.g. sodium chloride, calcium carbonate) or mixtures of these excipients with one another. Preferably, mono- or disaccharides are used, while the use of lactose or glucose is preferred, particularly, but not exclusively, in the form of their hydrates. For the purposes of the invention, lactose is the particularly preferred excipient, while lactose monohydrate is most particularly preferred. Methods of preparing the inhalable powders according to the invention by grinding and micronising and by finally mixing the components together are known from the prior art.

Propellant-Containing Inhalable Aerosols

The propellant-containing inhalable aerosols which may be used according to the invention may contain the compounds of formula 1 dissolved in the propellant gas or in dispersed form. The propellant gases which may be used to prepare the inhalation aerosols according to the invention are known from the prior art. Suitable propellant gases are selected from among hydrocarbons such as n-propane, n-butane or isobutane and halohydrocarbons such as preferably fluorinated derivatives of methane, ethane, propane, butane, cyclopropane or cyclobutane. The propellant gases mentioned above may be used on their own or in mixtures thereof. Particularly preferred propellant gases are fluorinated alkane derivatives selected from TG134a (1,1,1,2-tetrafluoroethane), TG227 (1,1,1,2,3,3,3-heptafluoropropane) and mixtures thereof. The propellant-driven inhalation aerosols used within the scope of the use according to the invention may also contain other ingredients such as co-solvents, stabilisers, surfactants, antioxidants, lubricants and pH adjusters. All these ingredients are known in the art.

Propellant-Free Inhalable Solutions

The compounds of formula 1 according to the invention are preferably used to prepare propellant-free inhalable solutions and inhalable suspensions. Solvents used for this purpose include aqueous or alcoholic, preferably ethanolic solutions. The solvent may be water on its own or a mixture of water and ethanol. The solutions or suspensions are adjusted to a pH of 2 to 7, preferably 2 to 5, using suitable acids. The pH may be adjusted using acids selected from inorganic or organic acids. Examples of particularly suitable inorganic acids include hydrochloric acid, hydrobromic acid, nitric acid, sulphuric acid and/or phosphoric acid. Examples of particularly suitable organic acids include ascorbic acid, citric acid, malic acid, tartaric acid, maleic acid, succinic acid, fumaric acid, acetic acid, formic acid and/or propionic acid etc. Preferred inorganic acids are hydrochloric and sulphuric acids. It is also possible to use the acids which have already formed an acid addition salt with one of the active substances. Of the organic acids, ascorbic acid, fumaric acid and citric acid are preferred. If desired, mixtures of the above acids may also be used, particularly in the case of acids which have other properties in addition to their acidifying qualities, e.g. as flavourings, antioxidants or complexing agents, such as citric acid or ascorbic acid, for example. According to the invention, it is particularly preferred to use hydrochloric acid to adjust the pH.

Co-solvents and/or other excipients may be added to the propellant-free inhalable solutions used for the purpose according to the invention. Preferred co-solvents are those which contain hydroxyl groups or other polar groups, e.g. alcohols—particularly isopropyl alcohol, glycols—particularly propyleneglycol, polyethyleneglycol, polypropyleneglycol, glycolether, glycerol, polyoxyethylene alcohols and polyoxyethylene fatty acid esters. The terms excipients and additives in this context denote any pharmacologically acceptable substance which is not an active substance but which can be formulated with the active substance or substances in the pharmacologically suitable solvent in order to improve the qualitative properties of the active substance formulation. Preferably, these substances have no pharmacological effect or, in connection with the desired therapy, no appreciable or at least no undesirable pharmacological effect. The excipients and additives include, for example, surfactants such as soya lecithin, oleic acid, sorbitan esters, such as polysorbates, polyvinylpyrrolidone, other stabilisers, complexing agents, antioxidants and/or preservatives which guarantee or prolong the shelf life of the finished pharmaceutical formulation, flavourings, vitamins and/or other additives known in the art. The additives also include pharmacologically acceptable salts such as sodium chloride as isotonic agents. The preferred excipients include antioxidants such as ascorbic acid, for example, provided that it has not already been used to adjust the pH, vitamin A, vitamin E, tocopherols and similar vitamins or provitamins occurring in the human body. Preservatives may be used to protect the formulation from contamination with pathogens. Suitable preservatives are those which are known in the art, particularly cetyl pyridinium chloride, benzalkonium chloride or benzoic acid or benzoates such as sodium benzoate in the concentration known from the prior art.

For the treatment forms described above, ready-to-use packs of a medicament for the treatment of respiratory complaints are provided, containing an enclosed description including for example the words respiratory disease, COPD or asthma, together with a naphthyridine according to formula 1 and one or more combination partners selected from those described above.

The invention claimed is:

1. A method of treating a disease comprising administering a therapeutically effective amount of a compound of formula 1, to a patient in need thereof, wherein:

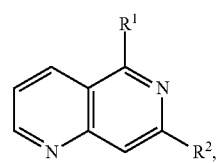

$R^1$ is selected from among —O—$R^3$ or —$NR^3R^4$
  wherein $R^3$ is $C_{1-6}$-alkyl which is substituted by $R^5$ and $R^6$
  wherein $R^5$ is selected from hydrogen, branched or linear $C_{1-6}$-alkyl, $C_{2-6}$-alkenyl, —$C_{1-6}$-alkylen-O—$C_{1-3}$-alkyl, $C_{1-3}$-haloalkyl,
  wherein $R^6$ is ring X

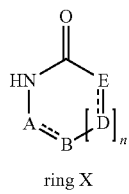

ring X wherein n is either 0 or 1,
wherein === is a either a single or a double bond and
wherein A, B, D and E are each independently from one another selected from $CH_2$, CH, C, N, NH, O or S and
wherein ring X is attached to the molecule either via position A, B, D or E,
wherein said ring X may optionally be further substituted by one, two or three residues each selected individually from the group consisting of -oxo, hydroxy, —$C_{1-3}$-alkyl, —$C_{1-3}$-haloalkyl, —O—$C_{1-3}$-alkyl, —$C_{1-3}$-alkanol and halogen,
$R^4$ is selected from the group consisting of hydrogen and $C_{1-6}$-Alkyl,
$R^2$ is selected from the group consisting of hydrogen; 5- to 10-membered aryl; 5- to 10-membered heteroaryl comprising 1, 2 or 3 heteroatoms each individually selected from among N, O and S; 5- to 10-membered, saturated or partially unsaturated heterocyclus comprising 1, 2 or 3 heteroatoms each individually selected from among N, O and S; 3- to 10-membered saturated or partially unsaturated cycloalkyl,
  wherein—in case that $R^2$ is not hydrogen—said $R^2$ may optionally be substituted by 1, 2, 3 or 4 residues each individually selected from the group consisting of hydrogen, -oxo, halogen, —$C_{1-6}$-alkyl, —$C_{2-6}$-alkenyl, —$C_{1-6}$-alkylene-COOH, —COOH, —CO—$NR^9R^{10}$, —$C_{1-6}$-alkylene-CO—$NR^9R^{10}$, —$C_{1-6}$-alkylene-$NR^9R^{10}$, —$C_{1-6}$-alkylene-CO-Q, —CO-Q, —$C_{1-6}$-alkylene-CO—$NR^9Q$, —CO—$NR^9Q$, —$C_{1-6}$-alkylene-$NR^{11}$—CO—$NR^9R^{10}$, —$C_{1-6}$-alkylene-$NR^{11}$—CO-Q, —$C_{1-6}$-alkylene-$NR^{11}$—$SO_2R^9$, —$C_{1-6}$-alkylene-O—CO—$R^9$, —$C_{1-6}$-alkylene-O—CO—$NR^9R^{10}$, —$C_{1-6}$-alkylene-O—$R^9$, —$C_{1-6}$-alkylene-SO—$NR^9R^{10}$, —$C_{1-6}$-alkylene-$SO_2R^9$, —$C_{1-6}$-alkylene-$SOR^9$, —$C_{1-6}$-alkinylene-O—$R^9$, —$C_{1-6}$-alkinylene-O, —$C_{1-6}$-alkinylene-$NR^9R^{10}$, $C_{5-10}$-aryl, -Q, —$C_{3-8}$-cycloalkyl, —O—$R^7$, —O—$C_{1-6}$-alkylene-$R^7$, —O—$C_{1-6}$-alkylene-O—$R^7$, —$C_{1-3}$-haloalkyl, cyanide,
—$NR^{11}R^7$, —$NR^{11}(C_{1-6}$-alkylene-$R^7$), —S(O)—$C_{1-6}$-alkyl, —$SO_2$—$C_{1-6}$-alkyl, —S—$C_{1-6}$-alkyl, —$SO_2$—$NR^9R^{10}$, —$SO_2$—$NR^{11}Q$, 5- to 10-membered heteroaryl comprising 1, 2 or 3 heteroatoms each individually selected from among N, O and S, —$NR^{11}$—CO—$R^7$ and —O—CO—$R^7$,
  wherein $R^7$ is selected from the group consisting of hydrogen; branched or linear —$C_{1-6}$-alkyl; —$C_{1-6}$-haloalkyl; —$C_{1-6}$-alkylene-COOH; —$C_{1-6}$-alkylen-CO—$NR^9R^{10}$; —$C_{1-6}$-alkylene-CO-Q; —$C_{2-6}$-alkylene-$NR^{11}$—CO—$NR^9R^{10}$; —$C_{2-6}$-alkylene-$NR^{11}$—CO-Q; —$C_{2-6}$-alkylene-$NR^{11}$—$SO_2R^9$; —$C_{2-6}$-alkylene-$NR^9R^{10}$; —$C_{2-6}$-alkylene-Q; —$C_{2-6}$-alkylene-O—CO—$R^9$, —$C_{2-6}$-alkylene-O—CO—$NR^9R^{10}$, —$C_{2-6}$-alkylene-SO—$NR^9R^{10}$, —$C_{2-6}$-alkylene-$SO_2$—$R^9$, —$C_{2-6}$-alkylene-SO—$R^9$, —$SO_2$—$R^9$, —SO—$R^9$, —$SO_2$—$NR^9R^{10}$, —$SO_2$—$NR^{11}Q$, —$SO_2$-Q, —$C_{1-6}$-alkylene-O—$R^9$; —CO—$NR^9R^{10}$, —CO—$NR^9Q$, —CO—$R^9$, —CO-Q, —$C_{1-6}$-alkylene-Q, —$C_{5-10}$-aryl, -Q, 3- to 8-membered saturated or partially unsaturated cycloalkyl; 5- to 10-membered heteroaryl comprising 1, 2 or 3 heteroatoms each individually selected from among N, O and S; —$C_{1-6}$-alkylene-heteroaryl wherein this heteroaryl is 5- to 10-membered and comprises 1, 2 or 3 heteroatoms each individually selected from among N, O and S;
whereby—in case that $R^7$ is not hydrogen—$R^7$ may optionally be substituted by 1, 2 or 3 residues $R^8$ that are individually selected from the group consisting of hydrogen; -oxo; hydroxy; —$C_{1-6}$-alkyl; —$C_{1-6}$-haloalkyl; —$NR^9R^{10}$, -Q, —$NR^9Q$, 3- to 6-membered saturated or partially unsaturated cycloalkyl;
whereby—in case that $R^8$ is not hydrogen—$R^8$ may optionally be substituted by 1, 2 or 3 residues selected from hydrogen, -oxo, hydroxy, —$C_{1-6}$-alkyl, halogen, —$C_{1-6}$-haloalkyl, —O—$C_{1-6}$-alkyl, —$C_{1-3}$-alkylene-O—$C_{1-3}$-alkyl,
wherein each of $R^9$, $R^{10}$ and $R^{11}$ is individually from one another selected from the group consisting of hydrogen, —$C_{1-6}$-alkyl, —$C_{3-8}$-cycloalkyl, —$C_{1-6}$-alkyl-$C_{3-8}$-cycloalkyl and phenyl,
and wherein each Q is individually selected either from a 5- to 10-membered saturated or partially unsaturated heterocyclus comprising 1, 2 or 3 heteroatoms each individually selected from among N, O or S or from a 5- to 10-membered heteroaryl comprising 1, 2 or 3 heteroatoms each individually selected from among N, O and S;
whereby Q is attached to the rest of the molecule either via a carbon atom or via an nitrogen atom,
the N-oxides of the aforementioned compounds, particularly the 1-naphthyridinyl-oxides of the aforementioned compounds, and the pharmaceutically acceptable salts of the aforementioned compounds wherein said disease is selected from asthma, COPD, allergic rhinitis, allergic dermatitis and rheumatoid arthritis.

2. The method according to claim 1 wherein said disease is mediated by SYK enzyme.

* * * * *